(12) United States Patent
Curtiss, III et al.

US011766475B2

(10) Patent No.: US 11,766,475 B2
(45) Date of Patent: *Sep. 26, 2023

(54) **FOOD SAFETY VACCINE TO CONTROL *SALMONELLA ENTERICA* AND REDUCE *CAMPYLOBACTER* IN POULTRY**

(71) Applicant: UNIVERSITY OF FLORIDA RESEARCH FOUNDATION, INCORPORATED, Gainesville, FL (US)

(72) Inventors: Roy Curtiss, III, Gainesville, FL (US); Soo-Young Wanda, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 246 days.

This patent is subject to a terminal disclaimer.

(21) Appl. No.: 17/207,948

(22) Filed: Mar. 22, 2021

(65) Prior Publication Data

US 2021/0283235 A1    Sep. 16, 2021

Related U.S. Application Data

(63) Continuation of application No. 16/480,904, filed as application No. PCT/US2018/015438 on Jan. 26, 2018, now Pat. No. 11,000,583.

(60) Provisional application No. 62/451,146, filed on Jan. 27, 2017.

(51) Int. Cl.
| | | |
|---|---|---|
| *A61K 39/02* | (2006.01) | |
| *A61K 39/112* | (2006.01) | |
| *A61K 39/205* | (2006.01) | |
| *C07K 14/205* | (2006.01) | |
| *C12N 1/36* | (2006.01) | |
| *C12N 15/74* | (2006.01) | |
| *A61K 39/00* | (2006.01) | |

(52) U.S. Cl.
CPC ........ *A61K 39/0275* (2013.01); *A61K 39/105* (2013.01); *A61K 39/205* (2013.01); *C07K 14/205* (2013.01); *C12N 1/36* (2013.01); *C12N 15/74* (2013.01); *A61K 2039/522* (2013.01); *A61K 2039/523* (2013.01); *A61K 2039/58* (2013.01); *A61K 2039/70* (2013.01)

(58) Field of Classification Search
CPC .......... A61K 39/0275; A61K 2039/522; A61K 2039/523; A61K 39/105; C12N 1/36; C07K 14/205

See application file for complete search history.

(56) References Cited

U.S. PATENT DOCUMENTS

| | | | |
|---|---|---|---|
| 5,614,195 A * | 3/1997 | Bumstead | ............... A61P 33/02 424/191.1 |
| 8,465,755 B2 | 6/2013 | Curtiss, III et al. | |
| 11,000,583 B2 * | 5/2021 | Curtiss, III | .......... A61K 39/205 |
| 2011/0033501 A1 | 2/2011 | Curtiss, III et al. | |
| 2013/0266604 A1 | 10/2013 | Szymanski et al. | |
| 2014/0273163 A1 | 9/2014 | Fisher et al. | |
| 2016/0184422 A1 | 6/2016 | Joens et al. | |
| 2016/0199467 A1 | 7/2016 | Curtiss, III et al. | |
| 2016/0326563 A1 | 11/2016 | Aebi et al. | |
| 2019/0382717 A1 | 12/2019 | Curtiss, III et al. | |

FOREIGN PATENT DOCUMENTS

| | | |
|---|---|---|
| CN | 1315871 A | 10/2001 |
| CN | 1906210 A | 1/2007 |
| CN | 102317439 A | 1/2012 |
| CN | 105307677 A | 2/2016 |
| WO | WO-2010/108682 A1 | 9/2010 |
| WO | WO-2011/091291 A1 | 7/2011 |
| WO | WO-2012/027850 A1 | 3/2012 |

OTHER PUBLICATIONS

U.S. Appl. No. 16/480,904, filed Jul. 25, 2019, U.S. Pat. No. 11,000,583, Granted.
Curtiss et al., New technologies in using recombinant attenuated *Salmonella* vaccine vectors. Crit Rev Immunol. 2010;30(3):255-70.
Laniewski et al., Evaluation of the immunogenicity of *Campylobacter jejuni* CjaA protein delivered by *Salmonella enterica* sv. *Typhimurium* strain with regulated delayed attenuation in chickens. World J Microbiol Biotechnol. Jan. 2014;30(1):281-92.
International Preliminary Report on Patentability for Application No. PCT/US2018/015438, dated Aug. 8, 2019, 9 pages.
International Search Report and Written Opinion for Application No. PCT/US2018/015438, dated May 8, 2018, 11 pages.

* cited by examiner

*Primary Examiner* — Mary Maille Lyons
(74) *Attorney, Agent, or Firm* — McCarter & English, LLP; Marcie B. Clarke

(57) ABSTRACT

Described herein are compositions and methods for making and using recombinant bacteria that are capable of regulated attenuation, regulated expression of one or more antigens of interest, and/or N-glycan modification of secreted/surface antigens.

13 Claims, 12 Drawing Sheets

Specification includes a Sequence Listing.

G1- BSG
G2-χ11840(pYA3342) non-lysis ΔsifA strain
G3-χ11442(pYA5301) non-lysis strain + SO7
G4-χ11840(pYA5301) non-lysis ΔsifA strain + SO7
G5-χ11791(pYA3681) lysis ΔsifA strain
G6-χ11730(pYA5293) lysis strain + SO7
G7-χ11791(pYA5293) ) lysis ΔsifA strain + SO7

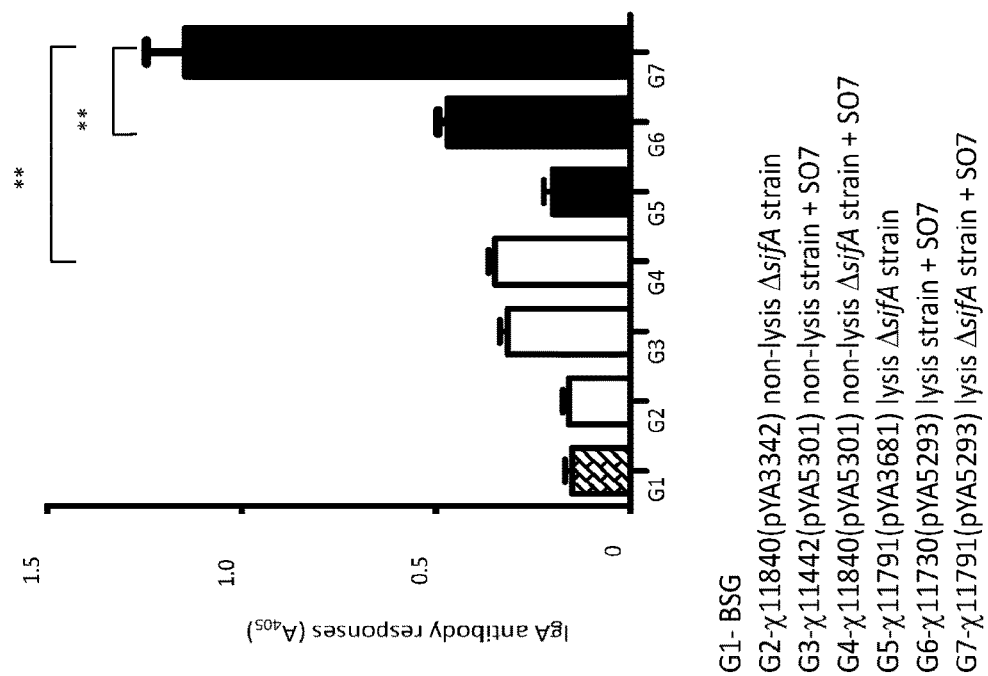
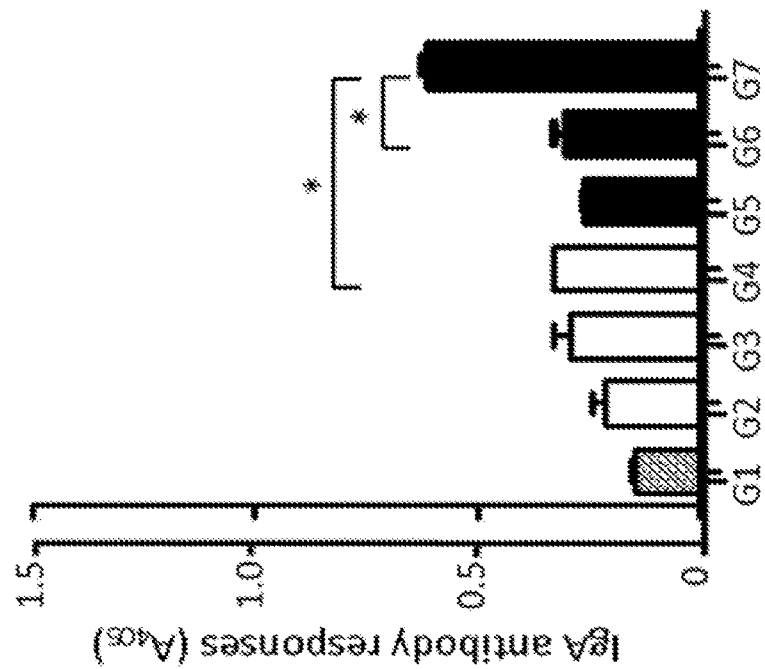

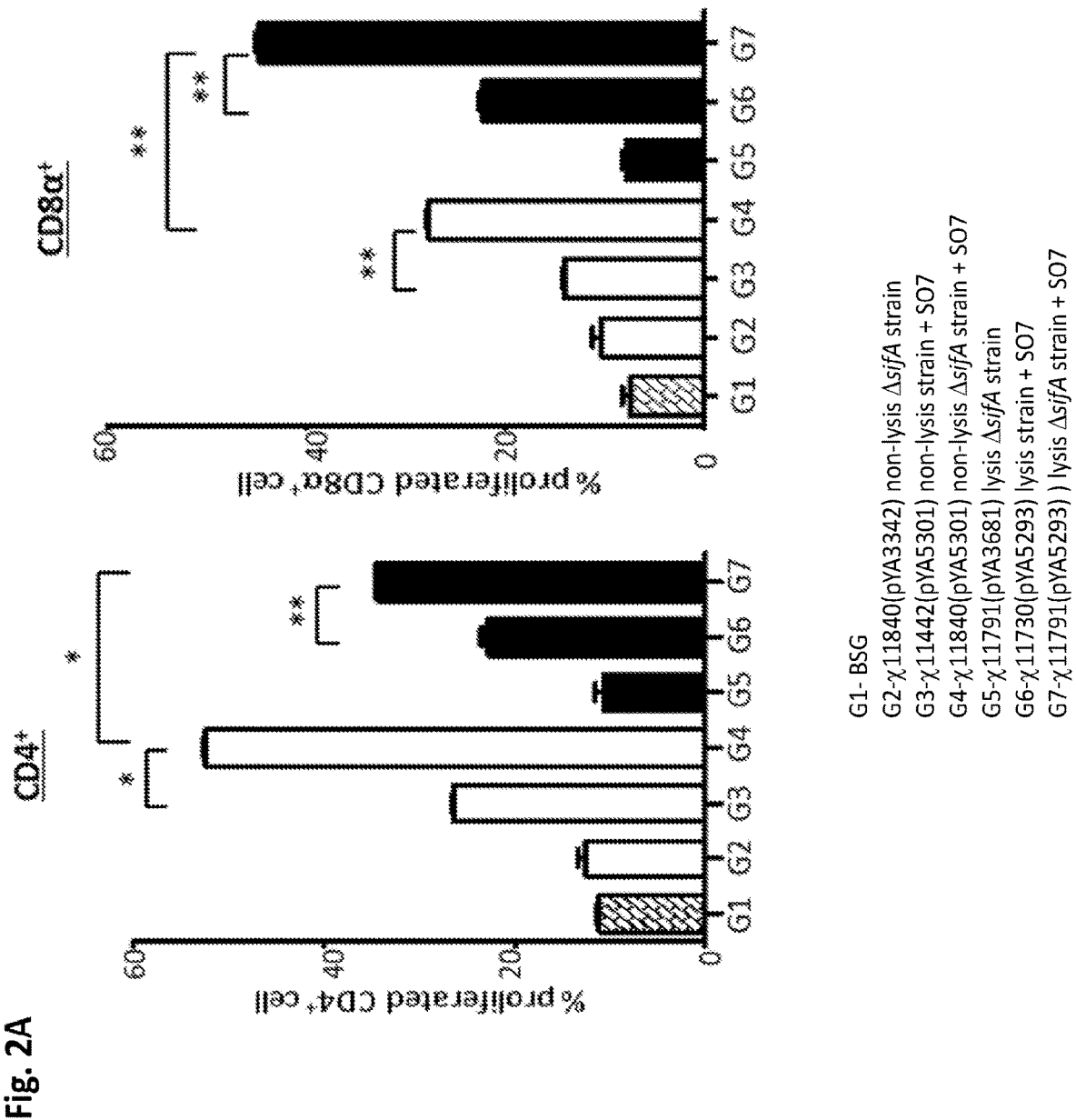

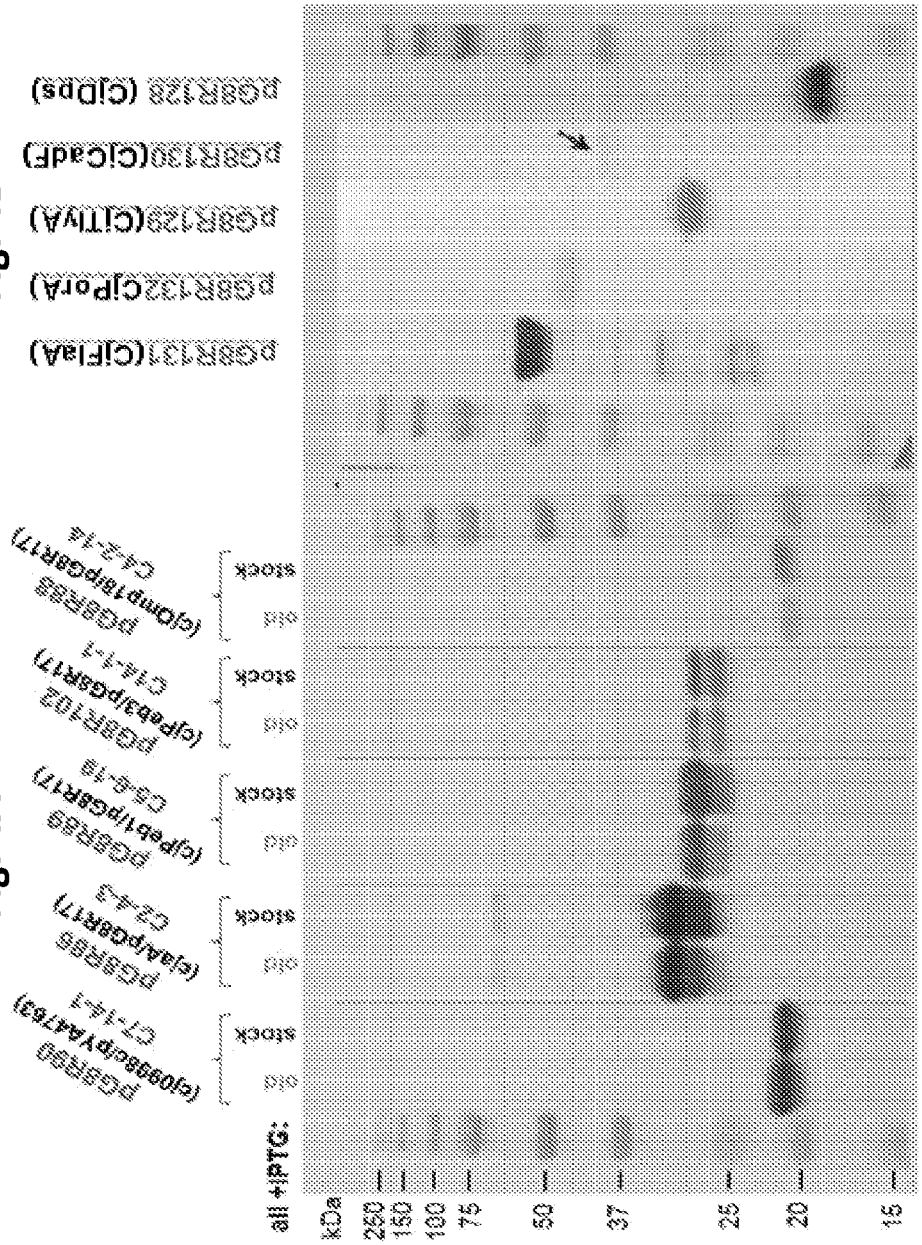

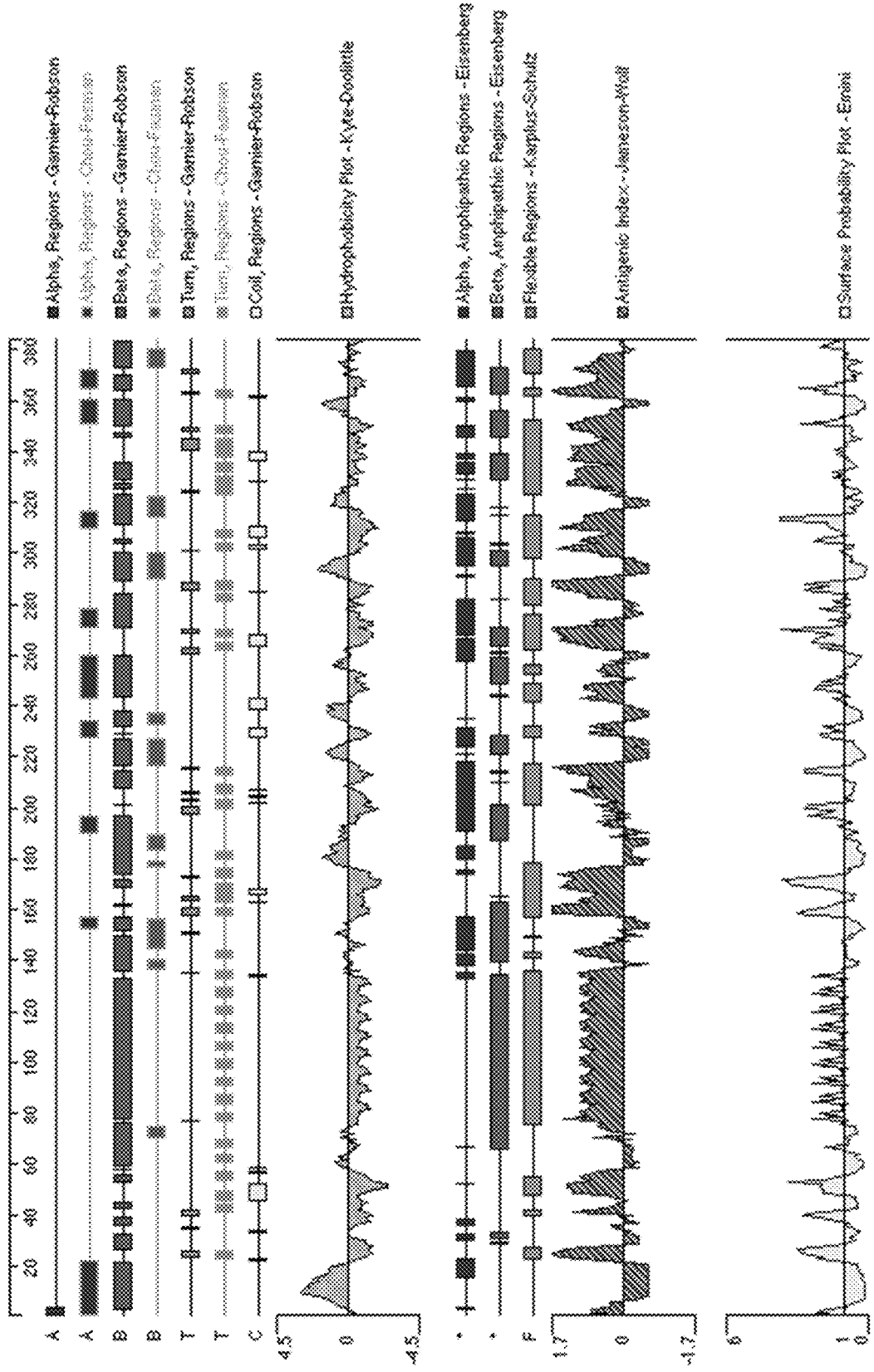
Fig. 8A: OmpA Δaa70-107 + Cj1443c (aa21-86) insertion
2 beta barrels (3 and 4) of OmpA deleted Predicted Structural Class of the Whole Protein: Alpha
Deléage & Roux Modification of Nishikawa & Ooi 1987

| Analysis | Whole Protein |
|---|---|
| Molecular Weight | 41323.30 m.w. |
| Length | 382 |
| 1 microgram = | 24.199 pMoles |
| Molar Extinction coefficient | 38640±5% |
| 1 A(280) = | 1.07 mg/ml |
| Isoelectric Point | 5.45 |
| Charge at pH 7 | -5.31 |

Whole Protein Composition Analysis

| Amino Acid(s) | Number count | % by weight | % by frequency |
|---|---|---|---|
| Charged (RKHYCDE) | 100 | 31.66 | 26.18 |
| Acidic (DE) | 44 | 12.63 | 11.52 |
| Basic (KR) | 38 | 12.53 | 9.95 |
| Polar (NCQSTY) | 113 | 30.88 | 29.58 |
| Hydrophobic (AILFWV) | 128 | 32.32 | 33.51 |
| A Ala | 32 | 5.50 | 8.38 |
| C Cys | 2 | 0.50 | 0.52 |
| D Asp | 33 | 9.19 | 8.64 |
| E Glu | 11 | 3.44 | 2.88 |
| F Phe | 9 | 3.21 | 2.36 |
| G Gly | 31 | 4.28 | 8.12 |
| H His | 5 | 1.66 | 1.31 |
| I Ile | 26 | 7.12 | 6.81 |
| K Lys | 27 | 8.37 | 7.07 |
| L Leu | 30 | 8.22 | 7.85 |
| M Met | 3 | 0.95 | 0.79 |
| N Asn | 34 | 9.39 | 8.90 |
| P Pro | 20 | 4.70 | 5.24 |
| Q Gln | 17 | 5.27 | 4.45 |
| R Arg | 11 | 4.16 | 2.88 |
| S Ser | 18 | 3.79 | 4.71 |
| T Thr | 31 | 7.58 | 8.12 |
| V Val | 27 | 6.48 | 7.07 |
| W Trp | 4 | 1.80 | 1.05 |
| Y Tyr | 11 | 4.34 | 2.88 |
| B Asx | 0 | 0.00 | 0.00 |
| Z Glx | 0 | 0.00 | 0.00 |
| X Xxx | 0 | 0.00 | 0.00 |
| . Ter | 1 | 0.00 | 0.26 |

Fig. 8B

SEQUENCE LISTING

```
<160> NUMBER OF SEQ ID NOS: 82

<210> SEQ ID NO 1
<211> LENGTH: 5
<212> TYPE: PRT
<213> ORGANISM: Campylobacter jejuni
<220> FEATURE:
<221> NAME/KEY: MOD_RES
<222> LOCATION: (1)..(1)
<223> OTHER INFORMATION: Asp or Glu
```

```
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (5)..(5)
<223> OTHER INFORMATION: Ser or Thr

<400> SEQUENCE: 1

Xaa Xaa Asn Tyr Xaa
1               5

<210> SEQ ID NO 2
<211> LENGTH: 4
<212> TYPE: PRT
<213> ORGANISM: Campylobacter jejuni

<400> SEQUENCE: 2

Asp Gly Gly Lys
1

<210> SEQ ID NO 3
<211> LENGTH: 702
<212> TYPE: DNA
<213> ORGANISM: Campylobacter jejuni

<400> SEQUENCE: 3
atgaaaacaa ataatatctt tatggcttta gccatagttt tggcaagttt gattctagct     60
tttggattta caaggctttt aagtgatttt aaaacacttg aagaagtgt aagtgtaaag    120 ggtttaagtc aaaagaagt cgaagcggat actttgatac ttcctataaa attcacaaga    180
tcaaacaaca atcttacaaa tttatacgaa gaactagaac aagataaaga aaatatcatc    240 aaattttttag aaaaacaagg cataaaagaa gatgagatca gctacaactc gccaaatatc    300
atagatcgtt taagcgatcc ttatagcaac gacactcaag ctgcataccg atacataggc    360
actgcgaatt tactcatcta tactcaaaat gtaaagcttg gaaaaagcat actagaaaac    420
atttcaagtc ttgcaaaatt tggtatagta acaaaaatcg atgattatga tatagaatac    480
ctttacacca agctaaatga tataaaacca caaatgatag aagaagcaac gctcaatgct    540
agaaatgcag cgataaaatt cgcacaagac tcaaacagcc atctaggcaa gataaaaaag    600
gcttctcaag acaatttag cattagcaac agagataaaa cacccctta tatcaaaacc    660 ataagagtgg tttctactat agaatactac ttaaaagact ga                       702

<210> SEQ ID NO 4
<211> LENGTH: 233
<212> TYPE: PRT
<213> ORGANISM: Campylobacter jejuni

<400> SEQUENCE: 4

Met Lys Thr Asn Asn Ile Phe Met Ala Leu Ala Ile Val Leu Ala Ser
1               5                   10                  15

Leu Ile Leu Ala Phe Gly Phe Asn Lys Ala Leu Ser Asp Phe Lys Thr
                20                  25                  30

Leu Glu Arg Ser Val Ser Val Lys Gly Leu Ser Gln Lys Glu Val Glu
            35                  40                  45

Ala Asp Thr Leu Ile Leu Pro Ile Lys Phe Thr Arg Ser Asn Asn Asn
        50                  55                  60

Leu Thr Asn Leu Tyr Glu Glu Leu Glu Gln Asp Lys Glu Asn Ile Ile
65                  70                  75                  80
```

```
Lys Phe Leu Glu Lys Gln Gly Ile Lys Glu Asp Glu Ile Ser Tyr Asn
                85                  90                  95

Ser Pro Asn Ile Ile Asp Arg Leu Ser Asp Pro Tyr Ser Asn Asp Thr
            100                 105                 110

Gln Ala Ala Tyr Arg Tyr Ile Gly Thr Ala Asn Leu Leu Ile Tyr Thr
        115                 120                 125

Gln Asn Val Lys Leu Gly Lys Ser Ile Leu Glu Asn Ile Ser Ser Leu
    130                 135                 140

Ala Lys Phe Gly Ile Val Thr Lys Ile Asp Asp Tyr Asp Ile Glu Tyr
145                 150                 155                 160

Leu Tyr Thr Lys Leu Asn Asp Ile Lys Pro Gln Met Ile Glu Glu Ala
                165                 170                 175

Thr Leu Asn Ala Arg Asn Ala Ala Ile Lys Phe Ala Gln Asp Ser Asn
            180                 185                 190

Ser His Leu Gly Lys Ile Lys Lys Ala Ser Gln Gly Gln Phe Ser Ile
        195                 200                 205

Ser Asn Arg Asp Lys Asn Thr Pro Tyr Ile Lys Thr Ile Arg Val Val
    210                 215                 220

Ser Thr Ile Glu Tyr Tyr Leu Lys Asp
225                 230

<210> SEQ ID NO 5
<211> LENGTH: 573
<212> TYPE: DNA
<213> ORGANISM: Campylobacter jejuni

<400> SEQUENCE: 5
atgaaaaaag ttttattgag ttcattggtt gcggtgtctt tgttaagcac aggtttgttt      60
gctaaagaat atactttaga taaagcacat acagatgtag gttttaaaat caaacattta     120
caaattagca atgtaaaagg aaatttcaaa gattattctg cggtgattga ttttgatcct     180
gcgagtgctg aatttaaaaa gcttgatgta actataaaaa tcgcatctgt aaatacagaa     240
aatcaaacaa gagataatca cttacaacaa gatgattttt tcaaagcaaa aaaatatcct     300
gatatgactt ttacaatgaa aaaatatgaa aaaatcgata tgaaaaaagg caaaatgaca     360
ggaactttaa ctatagctgg agtttctaaa gatatcgttt tagatgctga atcggcggt      420 gtagctaaag gcaaagatgg aaaagaaaaa ataggatttc tttaaatgg aaaaatcaaa     480 cgctctgatt ttaaatttgc aacaagtact tcaactatta ctttaagtga tgatattaat     540
ttaaatatcg aagttgaagc gaacgaaaaa taa                                  573

<210> SEQ ID NO 6
<211> LENGTH: 190
<212> TYPE: PRT
<213> ORGANISM: Campylobacter jejuni

<400> SEQUENCE: 6

Met Lys Lys Val Leu Leu Ser Ser Leu Val Ala Val Ser Leu Leu Ser
1               5                   10                  15

Thr Gly Leu Phe Ala Lys Glu Tyr Thr Leu Asp Lys Ala His Thr Asp
            20                  25                  30

Val Gly Phe Lys Ile Lys His Leu Gln Ile Ser Asn Val Lys Gly Asn
        35                  40                  45

Phe Lys Asp Tyr Ser Ala Val Ile Asp Phe Asp Pro Ala Ser Ala Glu
    50                  55                  60
```

```
Phe Lys Lys Leu Asp Val Thr Ile Lys Ile Ala Ser Val Asn Thr Glu
 65                  70                  75                  80

Asn Gln Thr Arg Asp Asn His Leu Gln Gln Asp Asp Phe Phe Lys Ala
                 85                  90                  95

Lys Lys Tyr Pro Asp Met Thr Phe Thr Met Lys Lys Tyr Glu Lys Ile
            100                 105                 110

Asp Asn Glu Lys Gly Lys Met Thr Gly Thr Leu Thr Ile Ala Gly Val
        115                 120                 125

Ser Lys Asp Ile Val Leu Asp Ala Glu Ile Gly Gly Val Ala Lys Gly
    130                 135                 140

Lys Asp Gly Lys Glu Lys Ile Gly Phe Ser Leu Asn Gly Lys Ile Lys
145                 150                 155                 160

Arg Ser Asp Phe Lys Phe Ala Thr Ser Thr Ser Thr Ile Thr Leu Ser
                165                 170                 175

Asp Asp Ile Asn Leu Asn Ile Glu Val Glu Ala Asn Glu Lys
            180                 185                 190

<210> SEQ ID NO 7
<211> LENGTH: 168
<212> TYPE: DNA
<213> ORGANISM: Campylobacter jejuni

<400> SEQUENCE: 7
atgaaaaaag ttgtactaat ctcagcatta ctaggtgctt tcgcagctaa tgtttttgca    60
gctaatactc caagcgatgt aaatcaaaca catacaaaag ctaaagctga taaaaaacat   120
gaagctaaaa ctcacaaaaa aacaaaagag caaacaccag ctcaataa               168

<210> SEQ ID NO 8
<211> LENGTH: 55
<212> TYPE: PRT
<213> ORGANISM: Campylobacter jejuni

<400> SEQUENCE: 8

Met Lys Lys Val Val Leu Ile Ser Ala Leu Leu Gly Ala Phe Ala Ala
  1               5                  10                  15

Asn Val Phe Ala Ala Asn Thr Pro Ser Asp Val Asn Gln Thr His Thr
             20                  25                  30

Lys Ala Lys Ala Asp Lys Lys His Glu Ala Lys Thr His Lys Lys Thr
         35                  40                  45

Lys Glu Gln Thr Pro Ala Gln
     50                  55

<210> SEQ ID NO 9
<211> LENGTH: 858
<212> TYPE: DNA
<213> ORGANISM: Campylobacter jejuni

<400> SEQUENCE: 9
atgattggag atatgaatga gcttttatta aaaagcgttg aagtattgcc acctttacct    60
gatactgtaa gtaagttaag aaaatatgtg agcgaggcta attcaaatat agaaactatg   120
aaagttgctg aaatcatttc aagcgatccg ttgatgacgg ctaagctttt gcaattagca   180
aattctcctt attatggttt tacaagagaa attacaacca taaatcaagt gattacttta   240
ttaggcgttg gtaatatcat caatatagtt atggctgact ccattagaga taattttaaa   300
atagacgttt cacctatgg tttaaatact caaaattttt taaaaacgtg caatgaagag   360
gcaactttta tcgcaaattg gcttaatgat gaagataaaa actttctca tcttttagtt   420
```

-continued

```
ccttgtgcaa tgcttttaag gcttggtatt gttattttt caaatttct tatacaaaat    480 cataaggata aggatttttt agctttttta aataaaaatg aaaatcttgc tttagcggag    540
aatgaatttt taggcgtaga tcatatttct ttcttgggat ttttgttaca tcgttggaat    600
tttgatgatg ttttgattga aagtatatgt tttgttcgca ctcctcatgc tgctcgcgaa    660
aaagtgaaaa aatccgctta tgctttagca ataacagatc atcttttgc tccgcatgat     720 ggttcttctc catttaacgc aaaagctgca gttgctttac ttaaagaggc aaaaactcaa    780
ggaattaatt ttgatttaaa caatctttta tctaagcttc ctaacaaagc taaggaaaat    840
ttaaacaaag aagattaa                                                   858
```

<210> SEQ ID NO 10
<211> LENGTH: 285
<212> TYPE: PRT
<213> ORGANISM: Campylobacter jejuni

<400> SEQUENCE: 10

```
Met Ile Gly Asp Met Asn Glu Leu Leu Lys Ser Val Glu Val Leu
1               5                   10                  15

Pro Pro Leu Pro Asp Thr Val Ser Lys Leu Arg Lys Tyr Val Ser Glu
            20                  25                  30

Ala Asn Ser Asn Ile Glu Thr Met Lys Val Ala Glu Ile Ser Ser
        35                  40                  45

Asp Pro Leu Met Thr Ala Lys Leu Leu Gln Leu Ala Asn Ser Pro Tyr
    50                  55                  60

Tyr Gly Phe Thr Arg Glu Ile Thr Thr Ile Asn Gln Val Ile Thr Leu
65                  70                  75                  80

Leu Gly Val Gly Asn Ile Ile Asn Ile Val Met Ala Asp Ser Ile Arg
                85                  90                  95

Asp Asn Phe Lys Ile Asp Val Ser Pro Tyr Gly Leu Asn Thr Gln Asn
            100                 105                 110

Phe Leu Lys Thr Cys Asn Glu Glu Ala Thr Phe Ile Ala Asn Trp Leu
        115                 120                 125

Asn Asp Glu Asp Lys Lys Leu Ser His Leu Leu Val Pro Cys Ala Met
    130                 135                 140

Leu Leu Arg Leu Gly Ile Val Ile Phe Ser Asn Phe Leu Ile Gln Asn
145                 150                 155                 160

His Lys Asp Lys Asp Phe Leu Ala Phe Leu Asn Lys Asn Glu Asn Leu
                165                 170                 175

Ala Leu Ala Glu Asn Glu Phe Leu Gly Val Asp His Ile Ser Phe Leu
            180                 185                 190

Gly Phe Leu Leu His Arg Trp Asn Phe Asp Asp Val Leu Ile Glu Ser
        195                 200                 205

Ile Cys Phe Val Arg Thr Pro His Ala Ala Arg Glu Lys Val Lys Lys
    210                 215                 220

Ser Ala Tyr Ala Leu Ala Ile Thr Asp His Leu Phe Ala Pro His Asp
225                 230                 235                 240

Gly Ser Ser Pro Phe Asn Ala Lys Ala Ala Val Ala Leu Leu Lys Glu
                245                 250                 255

Ala Lys Thr Gln Gly Ile Asn Phe Asp Leu Asn Asn Leu Leu Ser Lys
            260                 265                 270

Leu Pro Asn Lys Ala Lys Glu Asn Leu Asn Lys Glu Asp
        275                 280                 285
```

<210> SEQ ID NO 11
<211> LENGTH: 753
<212> TYPE: DNA
<213> ORGANISM: Campylobacter jejuni

<400> SEQUENCE: 11

| | | |
|---|---|---|
| atgaaaaaaa ttattacttt atttggtgca tgtgccttag cttttagtat ggcaaatgca | 60 |
| gacgtgaacc tgtacggccc gggcggcccg cacacggccc tgaaagacat cgcaaacaaa | 120 |
| tatagcgaaa aaaccggcgt gaaagtgaac gtgaactttg ccccgcaggc gacctggttt | 180 |
| gaaaaagcga aaaaagacgc ggacatcctg tttggcgcgt cagaccagtc cgctctggct | 240 |
| atcgcgagcg actttggcaa agactttaac gtgagcaaaa tcaaaccgct gtattttcgt | 300 |
| gaagccatca tcctgaccca gaaaggcaac ccgctgaaaa tcaaaggcct gaaagacctg | 360 |
| gcgaacaaaa aagtgcgtat cgtggtgccg gaaggcgcgg gcaaaagcaa cacctctggc | 420 |
| accggcgtgt gggaagacat gatcggccgt acccaggaca tcaaaccat ccagaacttt | 480 |
| cgtaacaaca tcgtggcctt tgtgccgaac agcggtagcg cgcgtaaact gttcgcgcag | 540 |
| gaccaggccg acgcttggat cacttggatc gactggtcaa aaagcaaccc ggacatcggc | 600 |
| actgccgtgg ctatcgaaaa agacctggtg gtgtatcgta cttttaacgt gatcgcgaaa | 660 |
| gaaggcgcga gcaaagaaac acaggacttt atcgcttatc tgagttctaa agaagcgaaa | 720 |
| gaaatcttta aaaaatacgg ctggcgtgaa taa | 753 |

<210> SEQ ID NO 12
<211> LENGTH: 250
<212> TYPE: PRT
<213> ORGANISM: Campylobacter jejuni

<400> SEQUENCE: 12

Met Lys Lys Ile Ile Thr Leu Phe Gly Ala Cys Ala Leu Ala Phe Ser
1               5                   10                  15

Met Ala Asn Ala Asp Val Asn Leu Tyr Gly Pro Gly Pro His Thr
            20                  25                  30

Ala Leu Lys Asp Ile Ala Asn Lys Tyr Ser Glu Lys Thr Gly Val Lys
        35                  40                  45

Val Asn Val Asn Phe Gly Pro Gln Ala Thr Trp Phe Glu Lys Ala Lys
    50                  55                  60

Lys Asp Ala Asp Ile Leu Phe Gly Ala Ser Asp Gln Ser Ala Leu Ala
65                  70                  75                  80

Ile Ala Ser Asp Phe Gly Lys Asp Phe Asn Val Ser Lys Ile Lys Pro
                85                  90                  95

Leu Tyr Phe Arg Glu Ala Ile Ile Leu Thr Gln Lys Gly Asn Pro Leu
            100                 105                 110

Lys Ile Lys Gly Leu Lys Asp Leu Ala Asn Lys Lys Val Arg Ile Val
        115                 120                 125

Val Pro Glu Gly Ala Gly Lys Ser Asn Thr Ser Gly Thr Gly Val Trp
    130                 135                 140

Glu Asp Met Ile Gly Arg Thr Gln Asp Ile Lys Thr Ile Gln Asn Phe
145                 150                 155                 160

Arg Asn Asn Ile Val Ala Phe Val Pro Asn Ser Gly Ser Ala Arg Lys
                165                 170                 175

Leu Phe Ala Gln Asp Gln Ala Asp Ala Trp Ile Thr Trp Ile Asp Trp
            180                 185                 190

Ser Lys Ser Asn Pro Asp Ile Gly Thr Ala Val Ala Ile Glu Lys Asp

```
                195               200               205
Leu Val Val Tyr Arg Thr Phe Asn Val Ile Ala Lys Glu Gly Ala Ser
        210               215               220

Lys Glu Thr Gln Asp Phe Ile Ala Tyr Leu Ser Ser Lys Glu Ala Lys
225               230               235               240

Glu Ile Phe Lys Lys Tyr Gly Trp Arg Glu
                245               250

<210> SEQ ID NO 13
<211> LENGTH: 1479
<212> TYPE: DNA
<213> ORGANISM: Campylobacter jejuni

<400> SEQUENCE: 13
atgaataaaa taatttcaat tagtgctata gcaagtttta ctcttttgat ttcagcttgc        60
tctttaagtc caaatttaaa tattcccgaa gcaaactata gcattgataa taagcttgga       120
gccttatctt gggaaaaaga aaacaatagc tctatcacaa aaaattggtg aaagactttt       180
gatgatgaaa atttaaataa agtggttgat ttagcactta aaaataataa tgatttaaaa       240
cttgctttca tacacatgga acaagctgct gctcaattag gtatagattt tagcagtttg       300
ttgccaaaat tgatggtag cgcaagcgga agtcgtgcaa aaacagctat aaatgctcca        360
agcaatcgaa ctggggaagt aagttacggt aatgatttta aatgggact taatttaagc       420 tatgaaatcg atctttgggg aaaatatcgc gatacatatc gcgcctcaaa atcaggcttt       480
aaagcaagtg agtatgatta tgaagctgca agactttctg ttatttcaaa tacagttcaa       540
acttatttta atcttgtaaa tgcttatgaa atgaaaatg ctcttaaaga agcctataaa        600
tctgcaaaag aaatttatag gattaatgat gaaaaatttc aagttggtgc tgtaggtgaa       660
tatgaacttg ctcaagcaag agccaactta gaaagtatgg ctttgcaata taatgaagca       720
aagttaaata agaaaaatta ccttaaagct ttaaaaattt taacttcaaa tgatttaaat       780
gacatacttt acaaaaatca aagctatcaa gttttttaatc ttaaagaatt tgacattcca      840
actggaattt caagtaccat cttgcttcaa cgtccagata ttggctcttc tttagaaaaa       900
ttaactcagc aaaattatct tgttggagta gctcgcacgg ctttcttacc tagccttttct     960 ttaacaggat tattgggatt tgaaagcggg gatttagata ccttggttaa aggaggttct      1020
aagacttgga atataggtgg aaactttact ctgcctattt tcattggggg tgaaatttac      1080
caaaatgtaa atttagccaa gcttaataaa gatgaagctt tgtaaatta tcaaaatact      1140 ttgattactg cttttggaga aattcgctat gctttagtag ctagaaaaac tatacgctta      1200
caatacgata tgcacaagc aagcgaacaa tcttacaaaa gaatctatga aattgctaaa       1260
gaacgctatg atataggaga atgtctttg caagattatt tagaggcacg tcaaaattgg       1320
cttaatgctg cggttgcttt taataatatt aaatattctt atgccaattc catagtagat      1380
gtaatcaaag catttggtgg aggatttgag caaagtgaag atacgagtaa aaatataaaa      1440
gaagaatcaa aaaatttaga tatgtctttt agagaatag                             1479

<210> SEQ ID NO 14
<211> LENGTH: 492
<212> TYPE: PRT
<213> ORGANISM: Campylobacter jejuni

<400> SEQUENCE: 14

Met Asn Lys Ile Ile Ser Ile Ser Ala Ile Ala Ser Phe Thr Leu Leu
1               5                   10                  15
```

```
Ile Ser Ala Cys Ser Leu Ser Pro Asn Leu Asn Ile Pro Glu Ala Asn
                20              25                  30

Tyr Ser Ile Asp Asn Lys Leu Gly Ala Leu Ser Trp Glu Lys Glu Asn
            35              40                  45

Asn Ser Ser Ile Thr Lys Asn Trp Trp Lys Asp Phe Asp Asp Glu Asn
50                      55                  60

Leu Asn Lys Val Val Asp Leu Ala Leu Lys Asn Asn Asn Asp Leu Lys
65                      70                  75                  80

Leu Ala Phe Ile His Met Glu Gln Ala Ala Gln Leu Gly Ile Asp
                    85                  90                  95

Phe Ser Ser Leu Leu Pro Lys Phe Asp Gly Ser Ala Ser Gly Ser Arg
                100                 105                 110

Ala Lys Thr Ala Ile Asn Ala Pro Ser Asn Arg Thr Gly Glu Val Ser
            115                 120                 125

Tyr Gly Asn Asp Phe Lys Met Gly Leu Asn Leu Ser Tyr Glu Ile Asp
    130                 135                 140

Leu Trp Gly Lys Tyr Arg Asp Thr Tyr Arg Ala Ser Lys Ser Gly Phe
145                 150                 155                 160

Lys Ala Ser Glu Tyr Asp Tyr Glu Ala Ala Arg Leu Ser Val Ile Ser
                165                 170                 175

Asn Thr Val Gln Thr Tyr Phe Asn Leu Val Asn Ala Tyr Glu Asn Glu
            180                 185                 190

Asn Ala Leu Lys Glu Ala Tyr Lys Ser Ala Lys Glu Ile Tyr Arg Ile
        195                 200                 205

Asn Asp Glu Lys Phe Gln Val Gly Ala Val Gly Glu Tyr Glu Leu Ala
    210                 215                 220

Gln Ala Arg Ala Asn Leu Glu Ser Met Ala Leu Gln Tyr Asn Glu Ala
225                 230                 235                 240

Lys Leu Asn Lys Glu Asn Tyr Leu Lys Ala Leu Lys Ile Leu Thr Ser
                245                 250                 255

Asn Asp Leu Asn Asp Ile Leu Tyr Lys Asn Gln Ser Tyr Gln Val Phe
            260                 265                 270

Asn Leu Lys Glu Phe Asp Ile Pro Thr Gly Ile Ser Ser Thr Ile Leu
        275                 280                 285

Leu Gln Arg Pro Asp Ile Gly Ser Ser Leu Glu Lys Leu Thr Gln Gln
    290                 295                 300

Asn Tyr Leu Val Gly Val Ala Arg Thr Ala Phe Leu Pro Ser Leu Ser
305                 310                 315                 320

Leu Thr Gly Leu Leu Gly Phe Glu Ser Gly Asp Leu Asp Thr Leu Val
                325                 330                 335

Lys Gly Gly Ser Lys Thr Trp Asn Ile Gly Gly Asn Phe Thr Leu Pro
            340                 345                 350

Ile Phe His Trp Gly Glu Ile Tyr Gln Asn Val Asn Leu Ala Lys Leu
    355                 360                 365

Asn Lys Asp Glu Ala Phe Val Asn Tyr Gln Asn Thr Leu Ile Thr Ala
        370                 375                 380

Phe Gly Glu Ile Arg Tyr Ala Leu Val Ala Arg Lys Thr Ile Arg Leu
385                 390                 395                 400

Gln Tyr Asp Asn Ala Gln Ala Ser Glu Gln Ser Tyr Lys Arg Ile Tyr
                405                 410                 415

Glu Ile Ala Lys Glu Arg Tyr Asp Ile Gly Glu Met Ser Leu Gln Asp
            420                 425                 430
```

```
Tyr Leu Glu Ala Arg Gln Asn Trp Leu Asn Ala Ala Val Ala Phe Asn
            435                 440                 445

Asn Ile Lys Tyr Ser Tyr Ala Asn Ser Ile Val Asp Val Ile Lys Ala
        450                 455                 460

Phe Gly Gly Phe Glu Gln Ser Glu Asp Thr Ser Lys Asn Ile Lys
465                 470                 475                 480

Glu Glu Ser Lys Asn Leu Asp Met Ser Phe Arg Glu
                485                 490

<210> SEQ ID NO 15
<211> LENGTH: 837
<212> TYPE: DNA
<213> ORGANISM: Campylobacter jejuni

<400> SEQUENCE: 15
atggaaaatc aaaaaaatga atttgatgat attattttag aaaaaagtaa taaaagtgaa      60
aaagtaaaaa aaattctttt acgagttatt gctttagtta ttttgttttt agctatcatg     120
atagttatga agcttattaa tggtagtggt gatgaaaata cgcaaaatca agtgtattg      180 ccaagtgaac ctatagcaac tcaagacaat aacaatgata cttcttttga agtatgcca     240 attacagata atacttcagc agaagatcaa tttgaggcat taagaaaaca atttcaagat    300
gaacaaaata caactcaaaa tacaacaacc tctagttcaa ataacaatga tactacaaat    360
tttgctatgc ctgatcaaga agttccagca gaaccaacag caactacttc agcaaatacc    420
actccacaag caagtactcc taaacaagaa gtaacacaaa ctgcaaaatc taagaagaa     480 gcaaaaaaac aaacagctgt aaaaaaagaa aagaaagtg caaacaaac ccctaaaaaa      540 gaacaaaatg caaatgattt atttaaaaat gttgatgcta aacctgtaca tccaagtggt    600
ttagcatcgg gtatttatgt gcaaattttc tcagtaagta atttggatca aaatcaaaa     660 gaacttgctt ctgtaaagca aaaggttat gattataaac tttataaaac tacagttgga     720
agtaaagaaa ttaccaaggt tttaatagga ccatttgaaa aggcagatat tgcagcagaa    780
cttgctaaaa tccgtaagga tattgcaaaa gatgcttttt cttttacttt aaaatga       837

<210> SEQ ID NO 16
<211> LENGTH: 278
<212> TYPE: PRT
<213> ORGANISM: Campylobacter jejuni

<400> SEQUENCE: 16

Met Glu Asn Gln Lys Asn Glu Phe Asp Asp Ile Ile Leu Glu Lys Ser
1               5                   10                  15

Asn Lys Ser Glu Lys Val Lys Lys Ile Leu Leu Arg Val Ile Ala Leu
            20                  25                  30

Val Ile Leu Phe Leu Ala Ile Met Ile Val Met Lys Leu Ile Asn Gly
        35                  40                  45

Ser Gly Asp Glu Asn Thr Gln Asn Gln Ser Val Leu Pro Ser Glu Pro
    50                  55                  60

Ile Ala Thr Gln Asp Asn Asn Asn Asp Thr Ser Phe Glu Ser Met Pro
65                  70                  75                  80

Ile Thr Asp Asn Thr Ser Ala Glu Asp Gln Phe Glu Ala Leu Arg Lys
                85                  90                  95

Gln Phe Gln Asp Glu Gln Asn Thr Thr Gln Asn Thr Thr Ser Ser
            100                 105                 110

Ser Asn Asn Asn Asp Thr Thr Asn Phe Ala Met Pro Asp Gln Glu Val
        115                 120                 125
```

```
Pro Ala Glu Pro Thr Ala Thr Thr Ser Ala Asn Thr Thr Pro Gln Ala
    130                 135                 140
Ser Thr Pro Lys Gln Glu Val Thr Gln Thr Ala Lys Ser Lys Glu Glu
145                 150                 155                 160
Ala Lys Lys Gln Thr Ala Val Lys Lys Glu Lys Glu Ser Ala Lys Gln
                165                 170                 175
Thr Pro Lys Lys Glu Gln Asn Ala Asn Asp Leu Phe Lys Asn Val Asp
            180                 185                 190
Ala Lys Pro Val His Pro Ser Gly Leu Ala Ser Gly Ile Tyr Val Gln
        195                 200                 205
Ile Phe Ser Val Ser Asn Leu Asp Gln Lys Ser Lys Glu Leu Ala Ser
    210                 215                 220
Val Lys Gln Lys Gly Tyr Asp Tyr Lys Leu Tyr Lys Thr Thr Val Gly
225                 230                 235                 240
Ser Lys Glu Ile Thr Lys Val Leu Ile Gly Pro Phe Glu Lys Ala Asp
                245                 250                 255
Ile Ala Ala Glu Leu Ala Lys Ile Arg Lys Asp Ile Ala Lys Asp Ala
            260                 265                 270
Phe Ser Phe Thr Leu Lys
        275

<210> SEQ ID NO 17
<211> LENGTH: 573
<212> TYPE: DNA
<213> ORGANISM: Campylobacter jejuni

<400> SEQUENCE: 17
atgaaaaaag ttttattgag ttcattggtt gcggtgtctt tgttaagcac aggtttgttt    60
gctaaagaat atactttaga taaagcacat acagatgtag gttttaaaat caaacattta   120
caaattagca atgtaaaagg aaatttcaaa gattattctg cggtgattga ttttgatcct   180
gcgagtgctg aatttaaaaa gcttgatgta actataaaaa tcgcatctgt aaatacagaa   240
aatcaaacaa gagataatca cttacaacaa gatgattttt tcaaagcaaa aaaatatcct   300
gatatgactt ttacaatgaa aaaatatgaa aaaatcgata tgaaaaagg caaaatgaca   360 ggaactttaa ctatagctgg agtttctaaa gatatcgttt tagatgctga atcggcggt    420 gtagctaaag gcaaagatgg aaaagaaaaa ataggatttc ctttaaatgg aaaaaatcaaa   480 cgctctgatt ttaaatttgc aacaagtact tcaactatta ctttaagtga tgatattaat   540
ttaaatatcg aagttgaagc gaacgaaaaa taa                                573

<210> SEQ ID NO 18
<211> LENGTH: 190
<212> TYPE: PRT
<213> ORGANISM: Campylobacter jejuni

<400> SEQUENCE: 18

Met Lys Lys Val Leu Leu Ser Ser Leu Val Ala Val Ser Leu Leu Ser
1               5                   10                  15

Thr Gly Leu Phe Ala Lys Glu Tyr Thr Leu Asp Lys Ala His Thr Asp
            20                  25                  30

Val Gly Phe Lys Ile Lys His Leu Gln Ile Ser Asn Val Lys Gly Asn
        35                  40                  45

Phe Lys Asp Tyr Ser Ala Val Ile Asp Phe Asp Pro Ala Ser Ala Glu
    50                  55                  60
```

```
Phe Lys Lys Leu Asp Val Thr Ile Lys Ile Ala Ser Val Asn Thr Glu
 65                  70                  75                  80

Asn Gln Thr Arg Asp Asn His Leu Gln Gln Asp Asp Phe Phe Lys Ala
                 85                  90                  95

Lys Lys Tyr Pro Asp Met Thr Phe Thr Met Lys Lys Tyr Glu Lys Ile
            100                 105                 110

Asp Asn Glu Lys Gly Lys Met Thr Gly Thr Leu Thr Ile Ala Gly Val
        115                 120                 125

Ser Lys Asp Ile Val Leu Asp Ala Glu Ile Gly Val Ala Lys Gly
130                 135                 140

Lys Asp Gly Lys Glu Lys Ile Gly Phe Ser Leu Asn Gly Lys Ile Lys
145                 150                 155                 160

Arg Ser Asp Phe Lys Phe Ala Thr Ser Thr Ser Thr Ile Thr Leu Ser
                165                 170                 175

Asp Asp Ile Asn Leu Asn Ile Glu Val Glu Ala Asn Glu Lys
            180                 185                 190
```

<210> SEQ ID NO 19
<211> LENGTH: 336
<212> TYPE: DNA
<213> ORGANISM: Campylobacter jejuni

<400> SEQUENCE: 19

```
atgatggcta aatttagaat tcaatacagc gcaggttttg ggcactatac gcaaaatcac      60
aagggttttg gacctacgat ttatatagaa gaggtcgtag agtttgataa tggcaaggat     120
tattttgact atatagattt ttataaaact tattcaaaga gcgatgatac ttatttcat     180
atcagttttt tagaagatag acctctaagc gataaagaaa tcaccattcg caatgaatac     240
cgcaaaatgc gtgatgaaaa ctgtaaaaaa gccaaggagg aatttatagc caacaatgag     300
cttgatgtgg agcatttgcc tactcaccat gattaa                              336
```

<210> SEQ ID NO 20
<211> LENGTH: 111
<212> TYPE: PRT
<213> ORGANISM: Campylobacter jejuni

<400> SEQUENCE: 20

```
Met Met Ala Lys Phe Arg Ile Gln Tyr Ser Ala Gly Phe Gly His Tyr
  1               5                  10                  15

Thr Gln Asn His Lys Gly Phe Gly Pro Thr Ile Tyr Ile Glu Glu Val
             20                  25                  30

Val Glu Phe Asp Asn Gly Lys Asp Tyr Phe Asp Tyr Ile Asp Phe Tyr
         35                  40                  45

Lys Thr Tyr Ser Lys Ser Asp Asp Thr Tyr Phe His Ile Ser Phe Leu
 50                  55                  60

Glu Asp Arg Pro Leu Ser Asp Lys Glu Ile Thr Ile Arg Asn Glu Tyr
 65                  70                  75                  80

Arg Lys Met Arg Asp Glu Asn Cys Lys Lys Ala Lys Glu Glu Phe Ile
                 85                  90                  95

Ala Asn Asn Glu Leu Asp Val Glu His Leu Pro Thr His His Asp
            100                 105                 110
```

<210> SEQ ID NO 21
<211> LENGTH: 384
<212> TYPE: DNA
<213> ORGANISM: Campylobacter jejuni

<400> SEQUENCE: 21

```
atgcaggtaa attatagaac gattagctcg tatgaatacg atgctattag tggtcagtat      60
aaacaggtgg ataaacagat tgaagattat tcttcatctg gagattctga ttttatggat     120
atgttaaata aggcggatga gaagtcaagc ggagatgctt taaattctag cagtagtttt     180
caaagcaatg cgcaaaactc aaattcaaat ttaagtaatt atgctcaaat gtcaaatgtt     240
tacgcttatc gttttagaca aaatgaaggc gagctgtcta tgagagctca aagtgctagc     300
gttcataatg atcttacaca acaaggtgca aatgaacaaa gtaagaataa tactttgtta     360
aatgatttat tgaacgcaat ttaa                                             384
```

<210> SEQ ID NO 22
<211> LENGTH: 127
<212> TYPE: PRT
<213> ORGANISM: Campylobacter jejuni

<400> SEQUENCE: 22

```
Met Gln Val Asn Tyr Arg Thr Ile Ser Ser Tyr Glu Tyr Asp Ala Ile
1               5                   10                  15
Ser Gly Gln Tyr Lys Gln Val Asp Lys Gln Ile Glu Asp Tyr Ser Ser
            20                  25                  30
Ser Gly Asp Ser Asp Phe Met Asp Met Leu Asn Lys Ala Asp Glu Lys
        35                  40                  45
Ser Ser Gly Asp Ala Leu Asn Ser Ser Ser Ser Phe Gln Ser Asn Ala
    50                  55                  60
Gln Asn Ser Asn Ser Asn Leu Ser Asn Tyr Ala Gln Met Ser Asn Val
65                  70                  75                  80
Tyr Ala Tyr Arg Phe Arg Gln Asn Glu Gly Glu Leu Ser Met Arg Ala
                85                  90                  95
Gln Ser Ala Ser Val His Asn Asp Leu Thr Gln Gln Gly Ala Asn Glu
            100                 105                 110
Gln Ser Lys Asn Asn Thr Leu Leu Asn Asp Leu Leu Asn Ala Ile
        115                 120                 125
```

<210> SEQ ID NO 23
<211> LENGTH: 674
<212> TYPE: DNA
<213> ORGANISM: Campylobacter jejuni

<400> SEQUENCE: 23

```
atgcgtttcg acttcttcgt gtccaaacgt ctgaacatca gccgtaacaa agcgctggag      60
ctgatcgaaa acgaagagat cctgctgaac ggcaaaagct tcaaagcgtc cttcgacgtg     120
aaaaacttcc tggaaaaacct gaaaaaaacc caggacctga cccgggaaga catcctgctg     180
gcgaacgagc tgaaactgga cctgctgagc gaaatctacg tgtcccgtgc ggcgctgaaa     240
ctgaaaaaat tcctggaaga aaacgacatc gaaatcaaac acaaaaactg tctggacatc     300
ggctccagca ccggcggctt cgtgcagatc ctgctgaaaa ccaggcgct gaaaatcacc      360
gcgctggacg tgggcagcaa ccagctgcac ccgagcctgc gtgtgaacga aaaaatcatc     420
ctgcacgaaa acaccgacct gcgtgcgttc aaaagcgaag aaaaattcga actggtgacc     480
tgcgacgtga gcttcatctc cctgatcaac ctgctgtact acatcgacaa cctggcgctg     540
aaagaaatca tcctgctgtt caaaccgcag ttcgaagtgg caaaaacat caaacgtgac      600
aaaaaaggcg tgctgaaaga cgacaaagcg atcctgaaag cgcgtatgga cttcgaaaaa     660
gcgtgcgcga aact                                                        674
```

```
<210> SEQ ID NO 24
<211> LENGTH: 253
<212> TYPE: PRT
<213> ORGANISM: Campylobacter jejuni

<400> SEQUENCE: 24

Met Arg Phe Asp Phe Val Ser Lys Arg Leu Asn Ile Ser Arg Asn
1               5                   10                  15

Lys Ala Leu Glu Leu Ile Glu Asn Glu Ile Leu Leu Asn Gly Lys
                20                  25                  30

Ser Phe Lys Ala Ser Phe Asp Val Lys Asn Phe Leu Glu Asn Leu Lys
            35                  40                  45

Lys Thr Gln Asp Leu Asn Pro Glu Asp Ile Leu Leu Ala Asn Glu Leu
    50                  55                  60

Lys Leu Asp Leu Leu Ser Glu Ile Tyr Val Ser Arg Ala Ala Leu Lys
65                  70                  75                  80

Leu Lys Lys Phe Leu Glu Glu Asn Asp Ile Glu Ile Lys His Lys Asn
                85                  90                  95

Cys Leu Asp Ile Gly Ser Ser Thr Gly Gly Phe Val Gln Ile Leu Leu
            100                 105                 110

Glu Asn Gln Ala Leu Lys Ile Thr Ala Leu Asp Val Gly Ser Asn Gln
        115                 120                 125

Leu His Pro Ser Leu Arg Val Asn Glu Lys Ile Ile Leu His Glu Asn
    130                 135                 140

Thr Asp Leu Arg Ala Phe Lys Ser Glu Glu Lys Phe Glu Leu Val Thr
145                 150                 155                 160

Cys Asp Val Ser Phe Ile Ser Leu Ile Asn Leu Leu Tyr Tyr Ile Asp
                165                 170                 175

Asn Leu Ala Leu Lys Glu Ile Ile Leu Leu Phe Lys Pro Gln Phe Glu
            180                 185                 190

Val Gly Lys Asn Ile Lys Arg Asp Lys Lys Gly Val Leu Lys Asp Asp
        195                 200                 205

Lys Ala Ile Leu Lys Ala Arg Met Asp Phe Glu Lys Ala Cys Ala Lys
    210                 215                 220

Leu Gly Trp Leu Leu Lys Asn Thr Gln Lys Ser Ser Ile Lys Gly Lys
225                 230                 235                 240

Glu Gly Asn Val Glu Tyr Phe Tyr Tyr Ile Lys Asn
                245                 250

<210> SEQ ID NO 25
<211> LENGTH: 780
<212> TYPE: DNA
<213> ORGANISM: Campylobacter jejuni

<400> SEQUENCE: 25
atggttttta gaaatctttt gttaaagttg gcagttttg ctctaggtgc ttgtgttgca      60
tttagcaatg ctaatgcagc agaaggcaaa ctggagtcca tcaaatccaa aggccagctg    120
atcgtgggcg tgaaaaacga cgtgccgcac tacgctctgc tggaccaggc aaccggcgaa    180
atcaaaggct cgaagtggga cgtggccaaa ctgctggcta aaagcatcct ggggacgac     240 aaaaaaatca aactggtggc agtgaacgcc aaaacccgtg gcccgctgct ggacaacggc    300
agcgtggacg cggtgatcgc aaccttcacc atcacccccgg agcgcaaacg tatctataac   360
ttctccgagc cgtattatca ggacgctatc ggcctgctgg ttctgaaaga aaaaaaatat    420
```

-continued

```
aaatctctgg ctgacatgaa aggtgcaaac atcggcgtgg ctcaagctgc aactacaaaa        480
aaagctatcg gcgaagctgc taaaaaaatc ggcatcgacg tgaaattcag cgaattcccg        540
gactatccga gcatcaaagc tgctctggac gctaaacgtg tggacgcgtt ctctgtggac        600
aaatccatcc tgctgggcta tgtggacgac aaaagcgaaa tcctgccgga cagcttcgaa        660
ccgcagagct atggcatcgt gaccaaaaaa gacgacccgg ctttcgcaaa atatgtggac        720
gacttcgtga agaacacaa aaacgaaatc gacgctctgg cgaaaaaatg gggcctgtaa        780
```

<210> SEQ ID NO 26
<211> LENGTH: 259
<212> TYPE: PRT
<213> ORGANISM: Campylobacter jejuni

<400> SEQUENCE: 26

```
Met Val Phe Arg Lys Ser Leu Leu Lys Leu Ala Val Phe Ala Leu Gly
1               5                   10                  15

Ala Cys Val Ala Phe Ser Asn Ala Asn Ala Ala Glu Gly Lys Leu Glu
            20                  25                  30

Ser Ile Lys Ser Lys Gly Gln Leu Ile Val Gly Val Lys Asn Asp Val
        35                  40                  45

Pro His Tyr Ala Leu Leu Asp Gln Ala Thr Gly Glu Ile Lys Gly Phe
    50                  55                  60

Glu Val Asp Val Ala Lys Leu Leu Ala Lys Ser Ile Leu Gly Asp Asp
65                  70                  75                  80

Lys Lys Ile Lys Leu Val Ala Val Asn Ala Lys Thr Arg Gly Pro Leu
                85                  90                  95

Leu Asp Asn Gly Ser Val Asp Ala Val Ile Ala Thr Phe Thr Ile Thr
            100                 105                 110

Pro Glu Arg Lys Arg Ile Tyr Asn Phe Ser Pro Tyr Tyr Gln Asp
        115                 120                 125

Ala Ile Gly Leu Leu Val Leu Lys Glu Lys Tyr Lys Ser Leu Ala
    130                 135                 140

Asp Met Lys Gly Ala Asn Ile Gly Val Ala Gln Ala Ala Thr Thr Lys
145                 150                 155                 160

Lys Ala Ile Gly Glu Ala Ala Lys Lys Ile Gly Ile Asp Val Lys Phe
                165                 170                 175

Ser Glu Phe Pro Asp Tyr Pro Ser Ile Lys Ala Ala Leu Asp Ala Lys
            180                 185                 190

Arg Val Asp Ala Phe Ser Val Asp Lys Ser Ile Leu Leu Gly Tyr Val
        195                 200                 205

Asp Asp Lys Ser Glu Ile Leu Pro Asp Ser Phe Glu Pro Gln Ser Tyr
    210                 215                 220

Gly Ile Val Thr Lys Lys Asp Asp Pro Ala Phe Ala Lys Tyr Val Asp
225                 230                 235                 240

Asp Phe Val Lys Glu His Lys Asn Glu Ile Asp Ala Leu Ala Lys Lys
                245                 250                 255

Trp Gly Leu
```

<210> SEQ ID NO 27
<211> LENGTH: 836
<212> TYPE: DNA
<213> ORGANISM: Campylobacter jejuni

<400> SEQUENCE: 27

```
atgaaaaaaa tacttctaag tgttttaacg gcctttgttg cagtagtatt ggctgcggcg         60
```

```
gcaactccga ctccaaaacc ctgaactccc tggacaaaat caaacagaac ggcgtggtgc    120
gtatcggcgt gtttggcgac aaaccgccgt ttggctatgt ggacgaaaaa ggcaacaacc    180
agggctatga catcgctctg gctaaacgta tcgcgaaaga actgtttggc gacgaaaaca    240
aagtgcagtt tgtgctggtg aagctgcgaa ccgtgtgga gtttctgaaa tccaacaaag    300
tggacatcat cctggctaac tttacccaga ccccgcagcg tgcggagcag gtggactttt    360 gctcccccgta tatgaaagtg gctctgggcg tggctgtgcc gaaagacagc aacatcacca    420
gcgtggaaga cctgaaagac aaaaccctgc tgctgaacaa aggcaccacc gcggacgctt    480
attttaccca gaactatccg aacatcaaaa ccctgaaata tgaccagaac accgaaacct    540 tgcggctct gatggacaaa cgtggcgacg ctctgagcca cgacaacacc ctgctgtttg    600
cttgggtgaa agaccacccg gactttaaaa tgggcatcaa agagctgggc aacaaagacg    660
tgatcgcgcc ggcggtgaaa aaaggcgaca agaactgaa agaatttatc gacaacctga    720
tcatcaaact gggccaggag cagtttttc acaaagctta tgacgaaacc ctgaaagctc    780
actttggcga cgacgtgaaa gcggacgacg tggtgatcga aggcggcaaa atctaa       836

<210> SEQ ID NO 28
<211> LENGTH: 279
<212> TYPE: PRT
<213> ORGANISM: Campylobacter jejuni

<400> SEQUENCE: 28

Met Lys Lys Ile Leu Leu Ser Val Leu Thr Ala Phe Val Ala Val Val
1               5                   10                  15

Leu Ala Ala Cys Gly Gly Asn Ser Asp Ser Lys Thr Leu Asn Ser Leu
                20                  25                  30

Asp Lys Ile Lys Gln Asn Gly Val Val Arg Ile Gly Val Phe Gly Asp
            35                  40                  45

Lys Pro Pro Phe Gly Tyr Val Asp Glu Lys Gly Asn Asn Gln Gly Tyr
        50                  55                  60

Asp Ile Ala Leu Ala Lys Arg Ile Ala Lys Glu Leu Phe Gly Asp Glu
65                  70                  75                  80

Asn Lys Val Gln Phe Val Leu Val Glu Ala Ala Asn Arg Val Glu Phe
                85                  90                  95

Leu Lys Ser Asn Lys Val Asp Ile Ile Leu Ala Asn Phe Thr Gln Thr
            100                 105                 110

Pro Gln Arg Ala Glu Gln Val Asp Phe Cys Ser Pro Tyr Met Lys Val
        115                 120                 125

Ala Leu Gly Val Ala Val Pro Lys Asp Ser Asn Ile Thr Ser Val Glu
    130                 135                 140

Asp Leu Lys Asp Lys Thr Leu Leu Leu Asn Lys Gly Thr Thr Ala Asp
145                 150                 155                 160

Ala Tyr Phe Thr Gln Asn Tyr Pro Asn Ile Lys Thr Leu Lys Tyr Asp
                165                 170                 175

Gln Asn Thr Glu Thr Phe Ala Ala Leu Met Asp Lys Arg Gly Asp Ala
            180                 185                 190

Leu Ser His Asp Asn Thr Leu Leu Phe Ala Trp Val Lys Asp His Pro
        195                 200                 205

Asp Phe Lys Met Gly Ile Lys Glu Leu Gly Asn Lys Asp Val Ile Ala
    210                 215                 220

Pro Ala Val Lys Lys Gly Asp Lys Glu Leu Lys Glu Phe Ile Asp Asn
225                 230                 235                 240
```

Leu Ile Ile Lys Leu Gly Gln Glu Gln Phe Phe His Lys Ala Tyr Asp
            245                 250                 255

Glu Thr Leu Lys Ala His Phe Gly Asp Asp Val Lys Ala Asp Asp Val
            260                 265                 270

Val Ile Glu Gly Gly Lys Ile
        275

<210> SEQ ID NO 29
<211> LENGTH: 573
<212> TYPE: DNA
<213> ORGANISM: Campylobacter jejuni

<400> SEQUENCE: 29

| | | | | |
|---|---|---|---|---|
| atgaaaaaaa ttcttgtaag tgttttaagt tcttgcttgt tagcttcggc tttaagtgcg | 60 |
| gtgtccttca aagaagacag cctgaaaatc tccttcgaag gctacaaaac caaagacatg | 120 |
| atcggcacca aaggcgaatt caaaaacgtg aatacaaat tctccaaaaa catcaaagac | 180 |
| ctggcgagct acctgaaagg cgcgaaagcg accatcaaac cgagcaacgc gttcatgggc | 240 |
| gaaggcaacg acatcatcac caacaacatc accaaagtgt tcttcccggc gctgctgggc | 300 |
| gacacggaca tcaaagtggt gtttcaggac gtgatcgcgg gcgaaaacaa aggcgtgatc | 360 |
| tccgcgaaaa tcaccatgga caaaaaaagc accatcgtgc cgctgaccta taccatcaaa | 420 |
| gacaacaaat ttgaagcgaa aggccagctg gacctgcaca cctttaaaaa cggctccaaa | 480 |
| gcgctgaaag cgctgagcga cgtggctgca ggccacggcg gcatctcctg ccgctggtg | 540 |
| gacatcagct ttaacgcgga cctggcggaa taa | 573 |

<210> SEQ ID NO 30
<211> LENGTH: 190
<212> TYPE: PRT
<213> ORGANISM: Campylobacter jejuni

<400> SEQUENCE: 30

Met Lys Lys Ile Leu Val Ser Val Leu Ser Ser Cys Leu Leu Ala Ser
1               5                   10                  15

Ala Leu Ser Ala Val Ser Phe Lys Glu Asp Ser Leu Lys Ile Ser Phe
            20                  25                  30

Glu Gly Tyr Lys Thr Lys Asp Met Ile Gly Thr Lys Gly Glu Phe Lys
        35                  40                  45

Asn Val Glu Tyr Lys Phe Ser Lys Asn Ile Lys Asp Leu Ala Ser Tyr
    50                  55                  60

Leu Lys Gly Ala Lys Ala Thr Ile Lys Pro Ser Asn Ala Phe Met Gly
65                  70                  75                  80

Glu Gly Asn Asp Ile Ile Thr Asn Asn Ile Thr Lys Val Phe Phe Pro
            85                  90                  95

Ala Leu Leu Gly Asp Thr Asp Ile Lys Val Val Phe Gln Asp Val Ile
            100                 105                 110

Ala Gly Glu Asn Lys Gly Val Ile Ser Ala Lys Ile Thr Met Asp Lys
            115                 120                 125

Lys Ser Thr Ile Val Pro Leu Thr Tyr Thr Ile Lys Asp Asn Lys Phe
    130                 135                 140

Glu Ala Lys Gly Gln Leu Asp Leu His Thr Phe Lys Asn Gly Ser Lys
145                 150                 155                 160

Ala Leu Lys Ala Leu Ser Asp Val Ala Ala Gly His Gly Gly Ile Ser
            165                 170                 175

```
Trp Pro Leu Val Asp Ile Ser Phe Asn Ala Asp Leu Ala Glu
            180                 185                 190
```

<210> SEQ ID NO 31
<211> LENGTH: 1275
<212> TYPE: DNA
<213> ORGANISM: Campylobacter jejuni

<400> SEQUENCE: 31

| | | | | | |
|---|---|---|---|---|---|
| atgaaactag | ttaaacttag | tttagttgca | gctcttgctg | caggtgcttt | ttcagcagct       60 |
| aacgctaccc | cgctggaaga | agcgatcaaa | gacgtggacg | tgtccggcgt | gctgcgttac     120 |
| cgttacgaca | ccggcaactt | tgacaaaaac | ttcgtgaaca | actccaacct | gaacaacagc     180 |
| aaacaggacc | acaaatatcg | tgcacaggtg | aacttcagtg | ctgctatcgc | tgacaacttc     240 |
| aaagcttttg | tgcagtttga | ctataacgct | gctgacggtg | gctatggcgc | taacggcatc     300 |
| aaaaacgacc | agaaaggcct | gtttgtgcgt | cagctgtacc | tgacttatac | caacgaagac     360 |
| gtggctacca | gtgtgatcgc | tggtaaacag | cagctgaacc | tgatctggac | ggacaacgct     420 |
| atcgacggtc | tggtgggcac | cggtgtgaaa | gtggtgaaca | acagcatcga | cggtctgact     480 |
| ctggctgctt | ttgctgtgga | cagcttcatg | gctgcggagc | agggtgcgga | cctgctggaa     540 |
| cacagtaaca | tctccaccac | ctccaaccag | gctccgttta | agtggactc  | cgtgggcaac     600 |
| ctgtacggtg | ctgctgctgt | gggttcttat | gacctggctg | gtggccagtt | caacccgcag     660 |
| ctgtggctgg | cttattggga | ccaggtggca | ttcttctatg | ctgtggacgc | agcttatagc     720 |
| acaactatct | tgacggcat  | caactggaca | ctggaaggcg | cttacctggg | aaacagcctg     780 |
| gacagcgaac | tggacgacaa | acacacgct  | aacggcaacc | tgtttgctct | gaaaggcagc     840 |
| atcgaagtga | acggctggga | cgctagcctg | ggtggtctgt | actacggcga | caagaaaaaa     900 |
| gcttctacag | tggtgatcga | agaccagggt | aacctgggtt | ctctgctggc | aggtgaggaa     960 |
| atcttctata | ctactggctc | acgcctgaac | ggtgacactg | gtcgtaacat | cttcggttat    1020 |
| gtgactggtg | gatatacttt | caacgaaaca | gtgcgcgtgg | gtgctgactt | cgtgtatggt    1080 |
| ggaacaaaaa | cagaagctgc | taaccacctg | ggtggtggta | aaaaactgga | agctgtggca    1140 |
| cgcgtggact | acaaatactc | tccgaaactg | aacttctcag | cattctattc | ttatgtgaac    1200 |
| ctggaccagg | gtgtgaacac | taacgaaagt | gctgaccaca | gcactgtgcg | tctgcaggct    1260 |
| ctgtacaaat | tctaa      |            |            |            |                1275 |

<210> SEQ ID NO 32
<211> LENGTH: 424
<212> TYPE: PRT
<213> ORGANISM: Campylobacter jejuni

<400> SEQUENCE: 32

```
Met Lys Leu Val Lys Leu Ser Leu Val Ala Ala Leu Ala Ala Gly Ala
1               5                   10                  15

Phe Ser Ala Ala Asn Ala Thr Pro Leu Glu Glu Ala Ile Lys Asp Val
            20                  25                  30

Asp Val Ser Gly Val Leu Arg Tyr Arg Tyr Asp Thr Gly Asn Phe Asp
        35                  40                  45

Lys Asn Phe Val Asn Asn Ser Asn Leu Asn Asn Ser Lys Gln Asp His
    50                  55                  60

Lys Tyr Arg Ala Gln Val Asn Phe Ser Ala Ala Ile Ala Asp Asn Phe
65                  70                  75                  80

Lys Ala Phe Val Gln Phe Asp Tyr Asn Ala Ala Asp Gly Gly Tyr Gly
```

|       |       |       |       | 85    |       |       |       |       | 90    |       |       |       |       | 95    |       |
|-------|-------|-------|-------|-------|-------|-------|-------|-------|-------|-------|-------|-------|-------|-------|-------|

Ala Asn Gly Ile Lys Asn Asp Gln Lys Gly Leu Phe Val Arg Gln Leu
            100          105          110

Tyr Leu Thr Tyr Thr Asn Glu Asp Val Ala Thr Ser Val Ile Ala Gly
     115          120          125

Lys Gln Gln Leu Asn Leu Ile Trp Thr Asp Asn Ala Ile Asp Gly Leu
 130         135          140

Val Gly Thr Gly Val Lys Val Val Asn Asn Ser Ile Asp Gly Leu Thr
145         150          155         160

Leu Ala Ala Phe Ala Val Asp Ser Phe Met Ala Ala Glu Gln Gly Ala
         165          170         175

Asp Leu Leu Glu His Ser Asn Ile Ser Thr Thr Ser Asn Gln Ala Pro
     180          185          190

Phe Lys Val Asp Ser Val Gly Asn Leu Tyr Gly Ala Ala Ala Val Gly
         195          200         205

Ser Tyr Asp Leu Ala Gly Gly Gln Phe Asn Pro Gln Leu Trp Leu Ala
 210         215          220

Tyr Trp Asp Gln Val Ala Phe Phe Tyr Ala Val Asp Ala Ala Tyr Ser
225         230          235         240

Thr Thr Ile Phe Asp Gly Ile Asn Trp Thr Leu Glu Gly Ala Tyr Leu
         245          250         255

Gly Asn Ser Leu Asp Ser Glu Leu Asp Asp Lys Thr His Ala Asn Gly
     260          265          270

Asn Leu Phe Ala Leu Lys Gly Ser Ile Glu Val Asn Gly Trp Asp Ala
         275          280         285

Ser Leu Gly Gly Leu Tyr Tyr Gly Asp Lys Glu Lys Ala Ser Thr Val
 290         295          300

Val Ile Glu Asp Gln Gly Asn Leu Gly Ser Leu Ala Gly Glu Glu
305         310          315         320

Ile Phe Tyr Thr Thr Gly Ser Arg Leu Asn Gly Asp Thr Gly Arg Asn
         325          330         335

Ile Phe Gly Tyr Val Thr Gly Gly Tyr Thr Phe Asn Glu Thr Val Arg
     340          345          350

Val Gly Ala Asp Phe Val Tyr Gly Gly Thr Lys Thr Glu Ala Ala Asn
         355          360         365

His Leu Gly Gly Gly Lys Lys Leu Glu Ala Val Ala Arg Val Asp Tyr
 370         375          380

Lys Tyr Ser Pro Lys Leu Asn Phe Ser Ala Phe Tyr Ser Tyr Val Asn
385         390          395         400

Leu Asp Gln Gly Val Asn Thr Asn Glu Ser Ala Asp His Ser Thr Val
         405          410         415

Arg Leu Gln Ala Leu Tyr Lys Phe
     420

<210> SEQ ID NO 33
<211> LENGTH: 1718
<212> TYPE: DNA
<213> ORGANISM: Campylobacter jejuni

<400> SEQUENCE: 33

```
atgggttttc gtatcaacac caacgtggcg gctctgaacg caaaagcaaa cgcggatctg      60
aacagcaaaa gcctggatgc ttctctgagc cgtctgagct ccggcctgcg tatcaactcc     120
gcagcagatg atgcttccgg gatggcgatc gcagatagcc tgcgttctca ggctaacact     180
```

```
ctgggccagg ctatctctaa cggcaacgat gctctgggca tcctgcagac tgctgataaa    240
gctatggacg agcagctgaa aatcctggat accatcaaaa ctaaagcaac ccaggcggct    300
caggatggcc agagcctgaa acccgtacc atgctgcagg cagatatcaa ccgtctgatg     360
gaagaactgg acaacatcgc aaacactact tcctttaacg gtaaacagct gctgagcggc    420
aactttatca accaggaatt tcagatcggc gcaagctcca accagactgt gaaagctact    480
atcggcgcaa ctcagtcttc taaaatcggt ctgacccgct ttgaaaccgg cggccgtatc    540
tccactagcg gcgaagtgca gtttactctg aaaaactaca acggtatcga tgattttcag    600
tttcagaaag tggtgatctc cacttccgtg ggcaccggcc tgggcgctct ggcagatgag    660
atcaacaaaa acgctgataa aaccggtgtg cgtgctactt ttacagtgga aactcgtggt    720
atcgctgcag tgcgtgcagg cgctacttca gatactttg ctatcaacgg ggtgaaaatc     780
ggcaaagtgg attacaaaga tggcgatgct aacgcgccc tggtggctgc aatcaactcg     840
gtgaaagata ccaccggcgt ggaagcttcg atcgatgcta acggccagct gctgctgact    900
tcccgtgaag gccgtggcat caaaatcgat ggtaacatcg gtggcggtgc ctttatcaac    960
gctgatatga agaaaaacta tggccgcctg tctctggtga aaaacgatgg taaagatatc   1020
ctgatcagcg gtagcaacct gtcttctgca ggttttggtg caacccagtt tatctctcag   1080
gcttctgtgt ctctgcgtga gtccaaaggc cagatcgatg ctaacatcgc tgatgctatg   1140
ggctttggct ctgcaaacaa aggcgtggtg ctgggtggtt attcttctgt gagcgcctat   1200
atgagcagcg caggcagcgg cttttcttcc ggttccggtt attctgtggg tagcggcaaa   1260
aactattcca ccggttttgc aaacgctatc gctatctccg ctgcttcgca gctgtctacg   1320
gtgtataacg tgtctgcagg ctcaggtttt tcaagcggtt ccaccctgtc tcagtttgcc   1380
actatgaaaa ccactgcttt tggcgtgaaa gatgaaaccg caggtgtgac caccctgaaa   1440
ggcgctatgg ctgtgatgga tatcgctgaa accgctatca ccaacctgga tcagatccgt   1500
gccgacatcg gctcggtgca gaaccaggtg acatccacta tcaacaacat caccgtgact   1560
caggtgaacg tgaaagcagc agaatcgcag atccgtgatg tggactttgc agccgagagc   1620
gcaaactact ctaaagcaaa catcctggct cagagcggct cttatgccat ggcacaggct   1680
aactctgtgc agcagaacgt gctgcgtctg ctgcagta                            1718
```

<210> SEQ ID NO 34
<211> LENGTH: 571
<212> TYPE: PRT
<213> ORGANISM: Campylobacter jejuni

<400> SEQUENCE: 34

```
Met Gly Phe Arg Ile Asn Thr Asn Val Ala Ala Leu Asn Ala Lys Ala
1               5                   10                  15

Asn Ala Asp Leu Asn Ser Lys Ser Leu Asp Ala Ser Leu Ser Arg Leu
                20                  25                  30

Ser Ser Gly Leu Arg Ile Asn Ser Ala Ala Asp Asp Ala Ser Gly Met
            35                  40                  45

Ala Ile Ala Asp Ser Leu Arg Ser Gln Ala Asn Thr Leu Gly Gln Ala
        50                  55                  60

Ile Ser Asn Gly Asn Asp Ala Leu Gly Ile Leu Gln Thr Ala Asp Lys
65                  70                  75                  80

Ala Met Asp Glu Gln Leu Lys Ile Leu Asp Thr Ile Lys Thr Lys Ala
                85                  90                  95

Thr Gln Ala Ala Gln Asp Gly Gln Ser Leu Lys Thr Arg Thr Met Leu
```

```
                100                 105                 110
Gln Ala Asp Ile Asn Arg Leu Met Glu Glu Leu Asp Asn Ile Ala Asn
            115                 120                 125
Thr Thr Ser Phe Asn Gly Lys Gln Leu Leu Ser Gly Asn Phe Ile Asn
130                 135                 140
Gln Glu Phe Gln Ile Gly Ala Ser Ser Asn Gln Thr Val Lys Ala Thr
145                 150                 155                 160
Ile Gly Ala Thr Gln Ser Ser Lys Ile Gly Leu Thr Arg Phe Glu Thr
                165                 170                 175
Gly Gly Arg Ile Ser Thr Ser Gly Glu Val Gln Phe Thr Leu Lys Asn
            180                 185                 190
Tyr Asn Gly Ile Asp Asp Phe Gln Phe Gln Lys Val Val Ile Ser Thr
        195                 200                 205
Ser Val Gly Thr Gly Leu Gly Ala Leu Ala Asp Glu Ile Asn Lys Asn
    210                 215                 220
Ala Asp Lys Thr Gly Val Arg Ala Thr Phe Thr Val Glu Thr Arg Gly
225                 230                 235                 240
Ile Ala Ala Val Arg Ala Gly Ala Thr Ser Asp Thr Phe Ala Ile Asn
                245                 250                 255
Gly Val Lys Ile Gly Lys Val Asp Tyr Lys Asp Gly Asp Ala Asn Gly
            260                 265                 270
Ala Leu Val Ala Ala Ile Asn Ser Val Lys Asp Thr Thr Gly Val Glu
        275                 280                 285
Ala Ser Ile Asp Ala Asn Gly Gln Leu Leu Leu Thr Ser Arg Glu Gly
    290                 295                 300
Arg Gly Ile Lys Ile Asp Gly Asn Ile Gly Gly Ala Phe Ile Asn
305                 310                 315                 320
Ala Asp Met Lys Glu Asn Tyr Gly Arg Leu Ser Leu Val Lys Asn Asp
                325                 330                 335
Gly Lys Asp Ile Leu Ile Ser Gly Ser Asn Leu Ser Ser Ala Gly Phe
            340                 345                 350
Gly Ala Thr Gln Phe Ile Ser Gln Ala Ser Val Ser Leu Arg Glu Ser
        355                 360                 365
Lys Gly Gln Ile Asp Ala Asn Ile Ala Asp Ala Met Gly Phe Gly Ser
    370                 375                 380
Ala Asn Lys Gly Val Val Leu Gly Gly Tyr Ser Ser Val Ser Ala Tyr
385                 390                 395                 400
Met Ser Ser Ala Gly Ser Gly Phe Ser Ser Gly Ser Gly Tyr Ser Val
                405                 410                 415
Gly Ser Gly Lys Asn Tyr Ser Thr Gly Phe Ala Asn Ala Ile Ala Ile
            420                 425                 430
Ser Ala Ala Ser Gln Leu Ser Thr Val Tyr Asn Val Ser Ala Gly Ser
        435                 440                 445
Gly Phe Ser Ser Gly Ser Thr Leu Ser Gln Phe Ala Thr Met Lys Thr
    450                 455                 460
Thr Ala Phe Gly Val Lys Asp Glu Thr Ala Gly Val Thr Thr Leu Lys
465                 470                 475                 480
Gly Ala Met Ala Val Met Asp Ile Ala Glu Thr Ala Ile Thr Asn Leu
                485                 490                 495
Asp Gln Ile Arg Ala Asp Ile Gly Ser Val Gln Asn Gln Val Thr Ser
            500                 505                 510
Thr Ile Asn Asn Ile Thr Val Thr Gln Val Asn Val Lys Ala Ala Glu
        515                 520                 525
```

Ser Gln Ile Arg Asp Val Asp Phe Ala Ala Glu Ser Ala Asn Tyr Ser
    530                 535                 540

Lys Ala Asn Ile Leu Ala Gln Ser Gly Ser Tyr Ala Met Ala Gln Ala
545                 550                 555                 560

Ser Val Gln Gln Asn Val Leu Arg Leu Leu Gln
            565                 570

<210> SEQ ID NO 35
<211> LENGTH: 960
<212> TYPE: DNA
<213> ORGANISM: Campylobacter jejuni

<400> SEQUENCE: 35

```
atgaaaaaaa tcttcctgtg tctgggcctg gcgagcgtgc tgtttggcgc tgacaacaac     60
gtgaaatttg aaatcacccc gaccctgaac tataactact tgaaggcaa cctggacatg    120
gacaaccgtt atgcgccggg gatccgtctg ggctatcact ttgacgactt ttggctggac    180
cagctggaat ttgggctgga gcactattct gacgtgaaat ataccaacac caacaaaacc    240
accgacatca cccgtaccta tctgagcgct atcaaaggca tcgacgtggg tgagaaattt    300
tatttctatg gcctggcagg cggcggctat gaggacttt ccaacgctgc gtatgacaac    360
aaaagcggcg gctttggcca ctatggcgcg ggcgtgaaat ccgtctgag cgactctctg    420
gctctgcgtc tggaaacccg tgaccagatc aacttcaacc acgcaaacca caactgggtg    480
tccactctgg gcatcagctt tggctttggc ggcaaaaaag aaaagctgt ggaagaagtg    540
gctgacaccc gtgcaactcc gcaggccaaa tgtccggtgg aaccgcgtga aggcgctctg    600
ctggacgaaa acggctgcga aaaaaccatc tctctggaag ccactttgg ctttgacaaa    660
accaccatca cccgactttt caggaaaaa atcaaagaaa tcgcaaaagt gctggacgaa    720
aacgaacgtt atgacactat cctggaaggc acaccgaca catcggctc cgtgcttat    780
aaccagaaac tgtccgaacg tcgtgctaaa gcgtggcta acgaactgga aaatatggc    840
gtggaaaaaa gccgcatcaa acagtgggc tatggccagg acaacccgcg ctccagcaac    900
gacaccaaag aaggccgcgc ggacaaccgt cgcgtggacg ctaaatttat cctgcgctaa    960
```

<210> SEQ ID NO 36
<211> LENGTH: 319
<212> TYPE: PRT
<213> ORGANISM: Campylobacter jejuni

<400> SEQUENCE: 36

Met Lys Lys Ile Phe Leu Cys Leu Gly Leu Ala Ser Val Leu Phe Gly
1               5                   10                  15

Ala Asp Asn Asn Val Lys Phe Glu Ile Thr Pro Thr Leu Asn Tyr Asn
            20                  25                  30

Tyr Phe Glu Gly Asn Leu Asp Met Asp Asn Arg Tyr Ala Pro Gly Ile
        35                  40                  45

Arg Leu Gly Tyr His Phe Asp Asp Phe Trp Leu Asp Gln Leu Glu Phe
    50                  55                  60

Gly Leu Glu His Tyr Ser Asp Val Lys Tyr Thr Asn Thr Asn Lys Thr
65                  70                  75                  80

Thr Asp Ile Thr Arg Thr Tyr Leu Ser Ala Ile Lys Gly Ile Asp Val
                85                  90                  95

Gly Glu Lys Phe Tyr Phe Tyr Gly Leu Ala Gly Gly Gly Tyr Glu Asp
            100                 105                 110

```
Phe Ser Asn Ala Ala Tyr Asp Asn Lys Ser Gly Phe Gly His Tyr
            115                 120                 125

Gly Ala Gly Val Lys Phe Arg Leu Ser Asp Ser Leu Ala Leu Arg Leu
130                 135                 140

Glu Thr Arg Asp Gln Ile Asn Phe Asn His Ala Asn His Asn Trp Val
145                 150                 155                 160

Ser Thr Leu Gly Ile Ser Phe Gly Phe Gly Gly Lys Lys Glu Lys Ala
                165                 170                 175

Val Glu Glu Val Ala Asp Thr Arg Ala Thr Pro Gln Ala Lys Cys Pro
            180                 185                 190

Val Glu Pro Arg Glu Gly Ala Leu Leu Asp Glu Asn Gly Cys Glu Lys
            195                 200                 205

Thr Ile Ser Leu Glu Gly His Phe Gly Phe Asp Lys Thr Thr Ile Asn
            210                 215                 220

Pro Thr Phe Gln Glu Lys Ile Lys Glu Ile Ala Lys Val Leu Asp Glu
225                 230                 235                 240

Asn Glu Arg Tyr Asp Thr Ile Leu Glu Gly His Thr Asp Asn Ile Gly
                245                 250                 255

Ser Arg Ala Tyr Asn Gln Lys Leu Ser Glu Arg Arg Ala Lys Ser Val
            260                 265                 270

Ala Asn Glu Leu Glu Lys Tyr Gly Val Glu Lys Ser Arg Ile Lys Thr
            275                 280                 285

Val Gly Tyr Gly Gln Asp Asn Pro Arg Ser Ser Asn Asp Thr Lys Glu
            290                 295                 300

Gly Arg Ala Asp Asn Arg Arg Val Asp Ala Lys Phe Ile Leu Arg
305                 310                 315

<210> SEQ ID NO 37
<211> LENGTH: 450
<212> TYPE: DNA
<213> ORGANISM: Campylobacter jejuni

<400> SEQUENCE: 37
atgtccgtga ccaaacagct gctgcagatg caggcggacg cgcaccacct gtgggtgaaa      60
ttccacaact accactggaa cgtgaaaggc ctgcagttct tctccatcca cgagtacacc     120
gaaaaagcgt acgaagaaat ggcagaactg ttcgacagct gtgcggaacg tgtgctgcag     180
ctgggcgaaa aagcgatcac ctgccagaaa gtgctgatgg aaaacgcgaa agcccgaaa      240
gtggcgaaag actgcttcac cccgctggaa gtgatcgaac tgatcaaaca ggactacgaa     300
tacctgctgg cggaattcaa aaaactgaac gaagcggcag aaaagaaag cgacaccacc      360
accgctgctt cgcgcagga aaacatcgcg aaatatgaaa aagtctgtg atgatcggc        420
gctaccctgc agggcgcttg caaaatgtaa                                      450

<210> SEQ ID NO 38
<211> LENGTH: 149
<212> TYPE: PRT
<213> ORGANISM: Campylobacter jejuni

<400> SEQUENCE: 38

Met Ser Val Thr Lys Gln Leu Leu Gln Met Gln Ala Asp Ala His His
1               5                   10                  15

Leu Trp Val Lys Phe His Asn Tyr His Trp Asn Val Lys Gly Leu Gln
                20                  25                  30

Phe Phe Ser Ile His Glu Tyr Thr Glu Lys Ala Tyr Glu Glu Met Ala
            35                  40                  45
```

```
Glu Leu Phe Asp Ser Cys Ala Glu Arg Val Leu Gln Leu Gly Glu Lys
 50                  55                  60

Ala Ile Thr Cys Gln Lys Val Leu Met Glu Asn Ala Lys Ser Pro Lys
 65                  70                  75                  80

Val Ala Lys Asp Cys Phe Thr Pro Leu Glu Val Ile Glu Leu Ile Lys
                 85                  90                  95

Gln Asp Tyr Glu Tyr Leu Leu Ala Glu Phe Lys Lys Leu Asn Glu Ala
            100                 105                 110

Ala Glu Lys Glu Ser Asp Thr Thr Ala Ala Phe Ala Gln Glu Asn
        115                 120                 125

Ile Ala Lys Tyr Glu Lys Ser Leu Trp Met Ile Gly Ala Thr Leu Gln
    130                 135                 140

Gly Ala Cys Lys Met
145
```

<210> SEQ ID NO 39
<211> LENGTH: 183
<212> TYPE: DNA
<213> ORGANISM: Campylobacter jejuni

<400> SEQUENCE: 39

```
atggtttcag atgtttctat gggtaatgtt aatttaatga ctgctgttaa tacttcagtt    60
ttgaaaaaat ctatggacac aaacgaggca ttgatgaatg aactcatcga aggtatggaa   120
ggtgtctctc aagcctccgc tccacaagct tctagctcta gtggtttgga tatttacgct   180
taa                                                                 183
```

<210> SEQ ID NO 40
<211> LENGTH: 60
<212> TYPE: PRT
<213> ORGANISM: Campylobacter jejuni

<400> SEQUENCE: 40

```
Met Val Ser Asp Val Ser Met Gly Asn Val Asn Leu Met Thr Ala Val
  1               5                  10                  15

Asn Thr Ser Val Leu Lys Lys Ser Met Asp Thr Asn Glu Ala Leu Met
             20                  25                  30

Asn Glu Leu Ile Glu Gly Met Glu Gly Val Ser Gln Ala Ser Ala Pro
         35                  40                  45

Gln Ala Ser Ser Ser Ser Gly Leu Asp Ile Tyr Ala
     50                  55                  60
```

<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Glu or Asp
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:

```
<221> NAME/KEY: MOD_RES
<222> LOCATION: (5)..(5)
<223> OTHER INFORMATION: Ser or Thr

<400> SEQUENCE: 41

Xaa Xaa Asn Xaa Xaa
1               5

<210> SEQ ID NO 42
<211> LENGTH: 15612
<212> TYPE: DNA
<213> ORGANISM: Campylobacter jejuni

<400> SEQUENCE: 42
ggattacaaa tggcaaaaaa tgaaggttat atttgtgttt ttgattgtga gagtgtgcca      60
gatgttgagc ttatccgcaa aactttgggt tttgaaggaa gtgatttaga ggtaagttta    120
aaagcacttc agtggcaaaa agaacaaagt gggagtgagt ttttgccttt gccttatcat    180
aaaattatca gtatttgtgc ggttttaagt gataattttg gaaaatttat caaagtgaat    240
aaaattgatg acaaaatgaa aaagaaatg attgagaatt ttttcaattt tatagaaaat    300
tatgagccaa aattagtcag ttttaatggt aaaaatttcg atatgcctgt tcttgtttta    360
agggctttaa atacaatttt aaaagcagca acttatttgg atactcaaag tgataaatgg    420
aataattata aaacaagatt ttcagaatta aaacattgtg atttattaga atccttagga    480
tctaacgggc gtggaataaa gcttgataca ctttgttcta tggtgggttt gccaggaaaa    540
tatgatgtgc atggcgatga ggtaatgaaa ctttttttatg aaaataaact tgaaaaaatc    600
cacgaatatt gtgaaagtga tgtttttaaac acctatatgc ttttttttaaa atatgaactt    660 attaaagcta atgttgatga agaagattat gttggttttc tttcttatat gagagatttc    720
ttgtgtgcaa aaaaatcaga tcgttcttat acagaagttt ttgcaaaagc ttgtgagagt    780
gaaatttcaa aagttcgatc ttaagtattt aagaaaatat attaaaattt atttttgaca    840
tttttaaaaa aaggaatgat gatgaaaatt cttattagcg gtggtgcagg ttatataggt    900
tctcatactt taagacaatt tttaaaaaca gatcatgaaa tttgtgtttt agataatctt    960
tctaagggtt ctaaaatcgc aatagaagat ttgcaaaaaa caagagcttt taaattttc   1020 gaacaagatt taagtgattt tcaaggcgta aaagcattgt ttgagagaga aaatttgac    1080 gctattgtgc attttgcagc aagcattgaa gttttttgaaa gtatgcaaaa tcctttaaaa    1140
tattatatga caacactgt taatacgaca atctcatcg aaacttgttt gcaaactgga    1200
gtgaataaat ttatattttc ttcaacggcg gccactttatg gcgaaccaca aactcccgtt    1260
gtgagcgaaa caagtccttt agcacctatt aatccttatg ggcgtagtaa gcttatgagt    1320
gaagaagttt tgcgtgatgc aagtatggca atcctgaatt ttaagcattg tatttttaaga    1380 tattttaatg ttgcaggtgc ttgtatggat tatactttag acaacgcta tccaaaagcg    1440 actttgctta taaagttgc agctgaatgt gccgcaggaa aacgtgataa acttttcata    1500
tttggcgatg attatgatac aaaagatggt acttgcataa gagatttatt ccatgtagat    1560
gatatttcaa gtgcacattt agcggctttg gattatttaa aagagaatga agcaatgtt    1620 tttaatgtag ttatggaca tggttttagc gtaaagaag tgattgaagc gatgaaaaaa    1680
gttagcggag tggattttaa agtagaactt gccccacgcc gtgcgggtga tcctagtgta    1740
ttgatttctg atgcaagtaa aatcagaaat cttacttctt ggcagcctaa atatgatgat    1800
ttagagctta tttgtaaatc tgcttttgat tgggaaaaac agtgttaaaa aaactttttt    1860
```

```
ttatttttaag taaggaagat aaaaatttttt tattttttctt gcttgttttt tcagtattta   1920
tttcttttat agaaacttttt gcaatttctt tggtaatgcc ttttatcact ttggctagtg   1980 attttttctta ttttgatcgt aataaatatt taatcagcct aaaagaatat cttaatatcc   2040
ctgtttttga aatcattgtt tattttggag tggggcttat tgtttttat gtgtttagag    2100 ctttgttaaa tgcgtattat tttcatcttt tggcaagatt ttctaaaggg cgttatcatg   2160
cgatcgctta taaggttttt tctaaatttt taaatattaa ttatgaaaaa tttactcaaa   2220
aaaatcaatc tgaaatttta aagtccatta caggggaagt ttataatcta agcactatga   2280
tttcatcatt tttacttttg atgagtgaaa ttttttgtagt acttttgctt tatgcttttaa  2340 tgcttttgat taattataaa atcactttgt ttttaagtat ttttatggtg ttaaatgcct   2400
ttattttagt gaaaatttta agccctatca ttaaaaaagc aggagtaaga cgcgaagaag   2460
cgatgaaaaa tttctttgaa attttaaata caaatttaaa taatttcaaa tttattaagc   2520
ttaaaaccaa agaagatgga gtattaagtc ttttttaaagc gcaaagtgaa gcttttctta   2580
aagcaaatat taccaacgaa agcgtagctg cggtgcctag aatttatctt gaaggaatag   2640
gcttttgcgt acttgttttt atcgtggtat ttttggttttt gaaaaatgaa agtgatattt   2700
caggtatttt atccacgatt tctattttttg ttttagcgct ttatcgctta atgccaagtg   2760
caaatcgtat tattacaagt tatcatgatt tgctttatta tcattcttct ttggatatta   2820
tttatcaaaa tttaagacaa gaagaagaaa atttgggcga ggaaaaatta agctttaatc   2880
aagagcttaa aatttgcaat cttagctttg gttatgaggg aaaaaaatat ttatttaaaa   2940
atcttaactt aaatattaaa aaaggcgaaa aaatcgcttt tataggggag agtggttgtg   3000 gaaaagtac cttagtagat cttatcatag gacttttaaa accaaaagaa gggcaaattt   3060
taattgatga gcaagaatta aatgcaaata atacaaaaaa ttatcgccaa aaaataggct   3120
atatcccgca aaatatctat cttttttaatg acagtatagc taaaaatatc acttttggag   3180
atgcggttga tgaagaaaaa cttaataggg ttatcaaaca agcaaattta gagcatttta   3240
taaaaatttt acctcaagga gtgcaaacaa agtgggcga tgggggagt aatttaagcg   3300 ggggacaaaa acaacgcata gctatagcaa gagctttata tttagagcct gaaatgttag   3360
tgcttgatga agcaacttct gcgcttgata ctcaaagtga agcaaaaatt atggatgaaa   3420
tttataaaat ttctaaagat aaaaccatga ttattatcgc acatcgcctt tctacgataa   3480
cacaatgtga taaggtttat cgtttagaac acggtaagct taaagaggag aaatgatgaa   3540
aataagcttt attatcgcaa cttttaaattc aggaggtgct gagcgtgctt tagtaacctt   3600
agctaatgca ctttgcaaag agcatgaagt aagtattatt aaatttcatg caggagaatc   3660 ttttttataag cttgaaaatg aagttaaagt tacaagtttg gaacaattta gatttgacac   3720
gctttatcat aaaatcgcaa gtcgttttaa gaaatttttt gctttaagaa aggctttgaa   3780
agaaagtaag tctgatgttt ttatttcttt tttggatacg actaatattg cttgtattgc   3840
tgcgaaaata gggcttaaaa ctccactcat tataagtgag catagcaatg aagcgtattt   3900
aaaacctaaa atttggcgtt ttttaagaag ggtaagctat ccttttttgtg atgctttaag   3960 tgtgcttgga agcagtgata aggtgtatta tgaaagattt gtaaaaaggg ttaagctttt   4020 attaaacccct tgtcatttta gcgatgaaat ttcttttgat tctagttttg aaaaggaaaa   4080
tttggttctt tttatagggc gtttagatca caacaaaaac cctgtaatgt ttttaaaagc   4140
tatagcgcat ttggataaaa atttacaaga aaattataaa tttgttatag caggagatgg   4200
acagttaaga caagaacttg aatataaggt aaaatcttta ggaataaaag ttgatttttt   4260
```

-continued

```
aggacgcgtt gaaaatgtca aggctcttta tgaaaaagca aaagtgcttt gcctttgttc    4320
ttttgtagag ggtttgccaa cggttttaat tgaaagtttg tattttgagg tttgtagaat    4380
ttcaagttct tattataatg gtgctaagga tttaatcaaa gataatcatg atgggctttt    4440
ggtaggttgt gatgatgaaa tagcacttgc taaaaaactt gaacttgttt taaatgatga    4500
aaattttaga aaagaacttg taaataatgc caaacaaagg tgtaaagact ttgaaatttc    4560
tcatatcaaa gaagaatggc ttaagcttat agccgaggtt aaaaatgcct aaactttctg    4620
ttatagtacc aacttttaat cgtcaagttt tgttagaaaa ggctattaaa agcatacaaa    4680
atcaagattt taaagattta gaaattattg taagcgatga taattctagc gatgatacta    4740
aaagtgtggt gcaaaattta caaaagatg atgatcgcat taagtatttt ttaaatcaaa    4800
attacaaaca aggtccaaat ggcaataaaa acaatggctt agatcaagca agtggcgagt    4860
ttgtaacttt tttagatgat gatgatgagc ttttatccgg ggctttaagt accttgatgc    4920
aaaaagcaaa tgagggttat gctcatgttt ttggaaattg tttgatagaa aaagaaggaa    4980
atttaagcaa ggaatttagc ggcaagggct tggaaaaaga tagtgaaatt tctaaaaaag    5040
attttttaat ggctaaattt agcggagagt tttttttctgt ttttaaaaaa tccctacttg    5100
aaaataagcg ttttaatgaa gaattttatg gcaatgaagc cacgctttgg gtaaatttat    5160
acaaagaaaa aagttttttat atccataagg cttttaggat ttatagaatt tttaggcaag    5220
atagcgtgac tttaggggcg agtaaaaatg cttatagggt gtatttggga tatttagagc    5280
ttgctaaaat tttagaaaat gaacttagaa tgagtaagga taagattat aaaaaaactt    5340 gtgcgagtta ttataaaatg gcagcttatt atgcaaaact tgcaaaaaat tataaagccc    5400
tttataaatg tttgttttaaa agcctaagta taaaaatcaa cgctcctgct ttgatattac    5460
tcattttaag tataattcca aataatatga ttgaaaaaatt atcaaaaatt cgggtggctt    5520
tatgcaaaaa ttaggcattt ttatttattc tttaggaagt ggtggtgctg aaagagttgt    5580 ggcgactta ttgcctattt taagtttgaa atttgaagtg catttgatct tgatgaatga    5640
taaaatttct tatgaaattc cagagtgtca aattcatttt ttagaatgtt caaaacctag    5700
tgaaaatcct attttgaaat ttttaaaact acctttttg gctttaaaat acaaaaaact    5760
ttgcagaaat ttaggtattg atacagaatt tgtttttttta aatcgaccta attatatagc    5820
tttaatggca agaatgtttg gaaacaaaac tcgccttgtg atcaatgaat gcactacgcc    5880
aagtgtgatg tatatgaaaa ataatttaa ttctttggta aataaatttt taatttcttt    5940
gctttaccca aaagctgatt taatcttgcc taattctaag ggaaatttag aagatttagt    6000
gcaaaatttt agtataagtc caaaaaatg tgaaattta tacaatgcca tcgatttaga    6060
aaacataggg caaaaagccc ttgaagacat agctttaaaa gataaattta ttttaagtgt    6120
aggcaggctt gataaaggta aaatcatgc tttattaatt cgtgcttatg cgagattgaa    6180
aacagattta aagcttgtga ttttaggtga aggtgtgctt aaggatgagc ttttagctttt    6240 gattaaagaa ttaaatttgg aagaaaaggt tttgctttta ggatttgata ataatccttta    6300 taaatacatg gctaaatgcg aattttttgc ttttgcttct gtgtttgaag gttttttcaaa    6360 tgttttaatc gaaagtttgg cttgttcttg tgcggtggtt tgcactgatc ataaaagtgg    6420
tgcaagagag cttttttggcg atgatgaatt tggactttta gtagaagtag ataatgaaaa    6480
ctctatgttt cagggtttaa aaactatgct tgaagacgat aaattaagaa agcgtataa    6540 aaacaaagct aaaactaggg ctaaagcctt tgataaagta aaaattgcac gcgatgcttt    6600
```

```
gaaatatttta ttaggataaa agatgttgaa aaaagagtat ttaaaaaacc cttatttagt   6660
tttgtttgcg atgattgtat tagcttatgt ttttagtgta ttttgcaggt tttattgggt   6720
ttggtgggca agtgagttta acgagtattt tttcaataat caattaatga tcatttcaaa   6780
cgatggctat gcttttgctg agggcgcaag agatatgata gcaggttttc atcagcctaa   6840
tgatttgagt tattatggat cttctttatc tacgcttact tattggcttt ataaaatcac   6900
acctttttct tttgaaagta tcattttata tatgagtact ttttatctt ctttggtggt   6960 gattcctatt attttactag ctaatgaata caaacgccct taatgggct tgtagctgc   7020 tcttttagca agtgtagcaa acagttatta taatcgcact atgagtgggt attatgatac   7080
ggatatgctg gtaattgttt tacctatgtt tattttattt tttatggtaa gaatgatttt   7140
aaaaaaagac ttttttttcat tgattgcctt gccattattt ataggaattt atctttggtg   7200
gtatccttca agttatactt taaatgtagc tttaattgga cttttttttaa tttatacact   7260 tattttttcat agaaaagaaa agatttttta tatagctgtg attttgtctt ctcttactct   7320
ttcaaatata gcatggtttt atcaaagtgc cattatagta atacttttttg ctttatttgc   7380 tttagagcaa aaacgcttaa attttatgat tataggaatt ttaggtagtg caactttgat   7440 attttttgatt ttaagtggtg gggttgatcc catactttat cagcttaaat tttatatttt   7500
tagaagcgat gaaagtgcga atttaacaca gggctttatg tattttaatg ttaatcaaac   7560
catacaagaa gttgaaaatg tagattttag cgaatttatg cgaagaatta gtggtagtga   7620
aattgttttc ttgttttctt tgtttggttt tgtatggctt ttgagaaaac ataaaagtat   7680
gattatggct ttacctatat tggtgcttgg gttttttagcc ttaaaaggag gacttagatt   7740
taccatttat tctgtacctg taatggcttt aggatttggt tttttttattga gcgagtttaa   7800 ggctatattg gttaaaaaat atagccaatt aacttcaatg tttgtattgt ttttgcaact   7860
attttgactt tggctccagt atttatccat atttacaact ataaagcgcc aacagttttt   7920
tctcaaaatg aagcatcatt attaaatcaa ttaaaaaata tagccaatag agaagattat   7980
gtggtaactt ggtgggatta tggttatcct gtgcgttatt atagcgatgt gaaaacttta   8040
gtagatggtg gaaagcattt aggtaaggat aatttttttcc cttctttttc tttaagtaaa   8100
gatgaacaag ctgcagctaa tatggcaaga cttagtgtag aatatacaga aaaaagcttt   8160
tatgctccgc aaaatgatat tttaaaatca gacatttac aagccatgat gaaagattat   8220
aatcaaagca atgtggattt atttctagct tcattatcaa aacctgattt taaaatcgat   8280
acaccaaaaa ctcgtgatat ttatctttat atgcccgcta gaatgtcttt gatttttct   8340 acggtggcta gttttttcttt tattaattta gatacaggag ttttggataa accttttacc   8400
tttagcacag cttatccact tgatgttaaa aatggagaaa tttatcttag caacggagtg   8460
gttttaagcg atgattttag aagttttaaa ataggtgata atgtggtttc tgtaaatagt   8520
atcgtagaga ttaattctat taaacaaggt gaatacaaaa tcactccaat cgatgataag   8580
gctcagtttt atatttttta tttaaaggat agtgctattc cttacgcaca atttattta   8640 atggataaaa ccatgtttaa tagtgcttat gtgcaaatgt ttttttttggg aaattatgat   8700 aagaatttat ttgacttggt gattaattct agagatgcta agttttttaa acttaaaatt   8760
taagggttga aaatgagaat aggattttta tcacatgcag gagcgagtat ttatcatttt   8820
agaatgccta ttataaaagc gttaaaagat agaaaagacg aagttttttgt tatagtgccg   8880 caagatgaat acacgcaaaa acttagagat cttggcttaa aagtaattgt ttatgagttt   8940
tcaagagcta gtttaaatcc ttttgtggtt ttaaagaatt tttttttatct tgctaaggtt   9000
```

```
ttgaaaaatt taaatcttga ttttattcaa agtgcggcac acaaaagcaa tacttttgga   9060
attttagcag caaaatgggc aaaaattcct tatcgttttg ccttagtaga aggcttggga   9120
tcttttata  tagatcaagg ttttaaggca aatttagtgc gttttgttat taatagtctt   9180
tataaattaa gttttaaatt tgcacaccaa tttattttg  tcaatgaaag taatgctgag   9240
tttatgcgga atttaggact taaagaaaat aaaatttgcg tgataaaatc tgtagggatc   9300
aatttaaaaa aattttttcc tatttatgta gaatcggaaa aaaagagct  ttttggaaa    9360
aatttaaaca tagataaaaa acccattgtg cttatgatag caagagcttt atggcataag   9420
ggtgtaaaag aattttatga aagtgctact atgctaaaag acaaagcaaa ttttgtttta   9480
gttggtggaa gagatgaaaa tccttcttgt gcaagtttgg agttttaaa  ctctggcgcg   9540
gtgcattatt tgggtgctag aagtgatata gtcgagcttt tgcaaaattg tgatattttt   9600
gttttgccaa gctataaaga aggctttcct gtaagtgttt tggaggcaaa agcttgcggt   9660
aaggctatag tggtgagtga ttgtgaaggt tgtgtggagg ctatttctaa tgcttatgat   9720
ggactttggg caaaaacaaa aaatgctaaa gatttaagcg aaaaaatttc acttttatta   9780
gaagatgaaa aattaagatt aaatttagct aaaaatgccg cccaagatgc tttacaatac   9840
gatgaaaata taatcgcaca gcgttattta aaactttatg atagggtaat taagaatgta   9900
tgaaaaagtt tttaaaagaa tttttgattt tattttagct ttagtgcttt tagtgctttt   9960
ttctccggtg attttaatca ctgctttact tttaaaaatc actcaaggaa gtgtgatttt  10020
tacccaaaat cgtcccgggt tagatgaaaa aattttaaa  atttataaat ttaaaaccat  10080
gagcgatgaa agagatgaaa agggtgagtt attaagcgat gaattgcgtt tgaaagcttt  10140
tggaaaaatc gttagaagct taagtttgga tgagcttttg caacttttta atgttttaaa  10200
aggggatatg agttttgttg gacctagacc tcttttggtt gagtatttgc ctctttacaa  10260
taaagagcaa aaattgcgtc ataaagtgcg tccaggtata acaggatggg cgcaggtaaa  10320
tggtagaaat gctattcttt ggcagaaaaa attcgaactt gatgtgtatt atgtgaaaaa  10380
tatttctttt ttgcttgatt taaaaatcat gttttaaca  gctttaaagg ttttaaaacg  10440
aagtgggta  agcaaagaag gccatgttac aacagagaaa tttaatggca agaactgaaa  10500
aaatttatat ttatggtgct agtggtcatg ggcttgtttg tgaagatgtg gctaaaaata  10560
tgggttataa agaatgtatt ttttagatg  attttaaagg aatgaaattt gaaagtacct  10620
tacctaaata tgatttttt  atagccatag gaaacaatga aattcgaaaa aagatttatc  10680
aaaaaatttc agaaatggc  tttaaaattg tcaatcttat ccataaaagc gcgcttataa  10740
gtcctagcgc aatcgtggaa gaaaatgcag gaatttaat  catgccttat gtagtgatta  10800
acgctaaagc taaaatagaa aaaggtgtga ttttaaatac ttcaagcgta attgagcatg  10860
aatgtgtgat aggggaattt tctcatgtga gtgtgggagc taaatgtgcg ggtaatgtaa  10920
aaattggtaa aaattgtttt tagggatta  attcttgtgt tttgcctaat ttaagtttgg  10980
cagatgatag tattttaggt ggtggagcaa ctttagttaa aaatcaagat gaaaaaggtg  11040
tttttgtggg agtacctgca aaaaggatgt aaattgcatt ttaataacaa tcttgttgtt  11100
cactatatag taaatccttc gcctttgggg tggattgtca ttaatttact aaccatatgt  11160
ctaatatgct acatatttcc tttgaaaaat tctttaaaac acaaaaaact tttagtctt   11220
aaagcaaatg taaattctaa aaatagtagg attataaaat atacaggtat tgctgctttt  11280
ttgggtggat taataggaat ttggtataat tttgaaggtt tttatcaact tctttttttc  11340
```

```
tttgaattag aaaatgaaaa tttaaaaaca ctttggagtt tgcaagtatc agtttcttct   11400
gtgataacag gtatgttatt attgttgata tatgttataa atttagcaat ggtttgtgaa   11460
aatggaattt atatagttag taaatttaat cttttttata tgtattttat aaaacgagaa   11520
gatttggaaa ttgttaaaat agaaaaaatg aaattttaa atcaagttga agtttgtttt    11580
gttatcaaaa caaaaaataa aatactcctt aaatgctttg aaagtattta taaaaaagaa   11640
gacttagaaa agcttaaaaa ttggtatgaa aacaagcttt gactataaaa agaatttaaa   11700
tatttgaatc tttgtaaatt tttttaggta aaatagagtc aatttataaa aattttgttt   11760
tacacaaagg ataaatcatg agattttttc tttctcctcc gcatatgggt ggtaatgaat   11820
taaaatacat agaagaagtt ttcaaaagca attatatagc acctttgggt gaatttgtaa   11880
atcgctttga acaaagtgtc aaggcttaca gtaaaagtga aaatgcctta gctttaaatt   11940
cagccacagc ggctttgcat ttagctttaa gggtggcagg ggtaaaacaa gatgatattg   12000
ttttggcttc ttcttttact tttatcgctt cagtagcacc tatttgttat cttaaagcaa   12060
aacctgtatt tatagattgt gatgaaactt ataatatcga tgtagattta ttaaagcttg   12120
ctattaaaga atgtgaaaaa aaaccaaaag cattgatttt aactcatctt tatggcaatg   12180
cggctaaaat ggatgaaatt gttgaaattt gcaaagaaaa tgaaattgtt ttaatcgaag   12240
atgctgctga agcttaggaa gttttttata agaataaagc tttaggaact tttggagaat   12300
ttggagctta ttcttataat ggcaataaaa ttatcaccac ttcaggtgga ggtatgctta   12360
taggaaaaaa taagaaaaag attgaaaaag caagattta tagcactcaa gctagggaaa    12420
attgtttgca ttatgaacat ttagattatg gttataatta ccgcttaagc aatgttttag   12480
gagctattgg cgtagcgcaa atggaggttt tagaacaaag agtgcttaaa aaaagagaaa   12540
tttatgagtg gtataaagaa tttttaggag agtgttttag cttttttagat gaattagaaa   12600 attcaagaag caatcgctgg ttaagtacag ctttgattga ttttgataaa aatgaactta   12660
attcttgtca aaaagatata aatatcagtc aaaaaaatat tactttgcat ccaaaaattt   12720
caaaactcat agaagatttg aaaaatgaac aaatagaaac aagaccatta tggaaagcta   12780
tgcacgctca agaagtattt aaaggagcta aggcttatct taatggcaat agtgagttat   12840
ttttccaaaa aggaatttgt ttgccaagtg gcacggcgat gagtaaagat gatgtttatg   12900
aaatttcaaa actgatctta aagagcataa aggcttaaaa tgattttta taaaagcaaa    12960 agattagcat ttttttaac ttcagatatt gttttaattt tacttagcgt ttatctggct    13020
ttttctttga gatttagtgg agatattccg agtattttt atcatggtat gatggtttct    13080
gctattattt tgcttgtttt aaaactttca ttttttgtttg ttttagaat ttataaagta    13140 gcttggagat ttttttctct caatgaagca agaaagattt ttatcgcttt gcttttagct   13200
gagttttgtt ttttcttat ttttattttt tttagtgatt ttttaatcc ttttccaaga     13260 agtgctattg tgatagattt tgttctttct tatatgttta taggtacttt aagaattagc   13320
aaaagaatgc ttgtggattt taaaccttct agaatgaaag aagaagaaac tccttgtatt   13380
gtagtagggg caacttctaa ggctttgcat ttgttaaaag gtgcaaaaga aggttcttta   13440
gggctttttc ctgtaggcgt agttgatgcg agaaaagagc ttatagggac ttattgtgat   13500
aaatttattg tagaagaaaa agaaaaaata aaatcttatg tagaacaagg ggtaaaaact   13560
gccattattg ctttaagact tgaacaagaa gagcttaaaa aacttttga agaacttgta    13620 gcttatggta tttgcgatgt aaaaatattt tcttttacaa gaaacgaagc aagagatatc   13680
agtatagaag acttgcttgc tagaaaacca aaagatttag atgatagtgc tgtggcggct   13740
```

-continued

```
tttttaaaag ataaggtagt tttggtaagt ggagcaggtg gaactatagg cagtgaactt    13800
tgtaagcaat gtattaaatt tggtgctaag catcttatca tggttgatca tagtgagtat    13860
aatctttata agatcaatga tgatttaaat ttatataaag aaaaaattac tcctatttta    13920
ctgagtattt tagataagca aagtttagat gaggtattaa aaactataaa acccgagctt    13980
attttacatg cagccgctta taaacatgtg cctctttgcg aacaaaatcc acattcagca    14040
gtaatcaata atattttagg aactaaaatt ttatgcgaca gtgctaaaga aaacaaagta    14100
gctaaatttg tgatgataag tacagataaa gcagtacgac caacaaatat tatgggttgc    14160
actaagagag tttgcgagct ttatacttta agtatgagtg atgaaaattt tgaagttgct    14220
tgtgtgcgtt ttggtaatgt tttaggttct agtggtagtg tgataccgaa atttaaagca    14280
caaattgcca ataatgagcc tttaacttta acgcaccctg atatagtgcg ttattttatg    14340
cttgtggctg aggcagtgca acttgttttta caagctggag ctatcgcaaa agggggagaa    14400 cttttttgttt tggatatggg taagcctgtg aaaatcatag atttagctaa aaaaatgctt    14460
ttactttcta atcgcaatga tttagaaatt aaaatcacag gcttaagaaa aggtgagaag    14520
ctttatgaag agcttttgat tgatgaaaat gatgctaaaa cacaatatga gagtattttt    14580
gtagcaaaga atgagaaggt tgaccttgat tggcttaata aagagataga aaatttacaa    14640
atatgtgaag atatttcaga ggctttatta aagattgtac ctgaatttaa acacaataaa    14700
gaaggtgtat aatgtatata aagatatac aaagatttga agataatcgc tatcgtgcta    14760
gagcttatat gagttatatt ttaacaagaa atctgcccaa taaacttcct gacattcacc    14820
ttgaaacgat taaaacagct ttggataaaa tagctcatga agttgttgtt tttgatgctt    14880
tgtatatttt agatatttca ggcatgcaaa tagaaaatgc gatttcctta aataaagctc    14940
atgaaatagg gcagggtgag gatagaagta ctcgttctta ttttttataga gctgtaaaat    15000 taagacgatg tgttttgagc gatccttatc cttcggtttt aaataatgag ctttgcgtga    15060
cagcttctat gccaatttac gatgataaaa ataacttgct ttttgttgtt tgtattgata    15120
tcaagcttga agatatttta aagattattc aagcaggaaa atttgaattt gtttttactc    15180
agtttagtcg tttggtatat ttttgcttcg cactggtttt atttgtgatt acttgttttt    15240
tatttcaaaa aggtttttttt agtcttttttg ataatcaagc tataggtata gaacatatgt    15300
ttgaaagtac catcgctata actttggctt tagctatttt tgatttggca aaacttttga    15360
tcgaacaaga agtattagga aggacgaaaa aagaagaagg tggaattcaa aaaactatgg    15420
tgagattttt gggttctatt atcattgctt tagctataga agcttgatg ttggtattta    15480 aacttgctat tggtgatctt tctcagatga tttatgcgat ttatcttatc ggtggagtga    15540
gcttgcttct tttaggttta agtgtatatt tatttacggt taagtataaa ataataata    15600 tttgaactta gt                                                         15612
```

<210> SEQ ID NO 43
<211> LENGTH: 795
<212> TYPE: DNA
<213> ORGANISM: Campylobacter jejuni

<400> SEQUENCE: 43

```
atggcaaaaa atgaaggtta tatttgtgtt tttgattgtg agagtgtgcc agatgttgag      60
cttatccgca aaactttggg ttttgaagga agtgatttag aggtaagttt aaaagcactt     120
cagtggcaaa aagaacaaag tgggagtgag ttttttgcctt tgccttatca taaaattatc     180
```

```
agtatttgtg cggttttaag tgataatttt ggaaaattta tcaaagtgaa taaaattgat    240
ggacaaaatg aaaagaaat gattgagaat tttttcaatt ttatagaaaa ttatgagcca     300
aaattagtca gttttaatgg taaaaatttc gatatgcctg ttcttgtttt aagggcttta    360
aaatacaatt taaaagcagc aacttatttg gatactcaaa gtgataaatg gaataattat    420
aaaacaagat tttcagaatt aaaacattgt gatttattag aatccttagg atctaacggg    480
cgtggaataa agcttgatac actttgttct atggtgggtt tgccaggaaa atatgatgtg    540
catggcgatg aggtaatgaa acttttttat gaaaataaac ttgaaaaaat ccacgaatat    600
tgtgaaagtg atgttttaaa cacctatatg ctttttttaa aatatgaact tattaaagct    660
aatgttgatg aagaagatta tgttggtttt cttctttata tgagagattt cttgtgtgca    720
aaaaaatcag atcgttctta tacagaagtt tttgcaaaag cttgtgagag tgaaatttca    780
aaagttcgat cttaa                                                    795
```

<210> SEQ ID NO 44
<211> LENGTH: 264
<212> TYPE: PRT
<213> ORGANISM: Campylobacter jejuni

<400> SEQUENCE: 44

```
Met Ala Lys Asn Glu Gly Tyr Ile Cys Val Phe Asp Cys Glu Ser Val
1               5                   10                  15

Pro Asp Val Glu Leu Ile Arg Lys Thr Leu Gly Phe Glu Gly Ser Asp
            20                  25                  30

Leu Glu Val Ser Leu Lys Ala Leu Gln Trp Gln Lys Glu Gln Ser Gly
        35                  40                  45

Ser Glu Phe Leu Pro Leu Pro Tyr His Lys Ile Ile Ser Ile Cys Ala
    50                  55                  60

Val Leu Ser Asp Asn Phe Gly Lys Phe Ile Lys Val Asn Lys Ile Asp
65                  70                  75                  80

Gly Gln Asn Glu Lys Glu Met Ile Glu Asn Phe Phe Asn Phe Ile Glu
                85                  90                  95

Asn Tyr Glu Pro Lys Leu Val Ser Phe Asn Gly Lys Asn Phe Asp Met
            100                 105                 110

Pro Val Leu Val Leu Arg Ala Leu Lys Tyr Asn Leu Lys Ala Ala Thr
        115                 120                 125

Tyr Leu Asp Thr Gln Ser Asp Lys Trp Asn Asn Tyr Lys Thr Arg Phe
    130                 135                 140

Ser Glu Leu Lys His Cys Asp Leu Leu Glu Ser Leu Gly Ser Asn Gly
145                 150                 155                 160

Arg Gly Ile Lys Leu Asp Thr Leu Cys Ser Met Val Gly Leu Pro Gly
                165                 170                 175

Lys Tyr Asp Val His Gly Asp Glu Val Met Lys Leu Phe Tyr Glu Asn
            180                 185                 190

Lys Leu Glu Lys Ile His Glu Tyr Cys Glu Ser Asp Val Leu Asn Thr
        195                 200                 205

Tyr Met Leu Phe Leu Lys Tyr Glu Leu Ile Lys Ala Asn Val Asp Glu
    210                 215                 220

Glu Asp Tyr Val Gly Phe Leu Ser Tyr Met Arg Asp Phe Leu Cys Ala
225                 230                 235                 240

Lys Lys Ser Asp Arg Ser Tyr Thr Glu Val Phe Ala Lys Ala Cys Glu
                245                 250                 255

Ser Glu Ile Ser Lys Val Arg Ser
            260
```

<210> SEQ ID NO 45
<211> LENGTH: 654
<212> TYPE: DNA
<213> ORGANISM: Campylobacter jejuni

<400> SEQUENCE: 45

```
atgaaaaagg tgttttgtg ggagtacctg caaaaaggat gtaaattgca ttttaataac      60
aatcttgttg ttcactatat agtaaatcct tcgcctttgg ggtggattgt cattaattta     120
ctaaccatat gtctaatatg ctacatattt cctttgaaaa attctttaaa acacaaaaaa     180
cttttagtc ttaaagcaaa tgtaaattct aaaaatagta ggattataaa atatacaggt      240
attgctgctt ttttgggtgg attaatagga atttggtata attttgaagg tttttatcaa     300
cttctttttt tctttgaatt agaaaatgaa atttaaaaa cactttggag tttgcaagta      360
tcagtttctt ctgtgataac aggtatgtta ttattgttga tatatgttat aaatttagca     420
atggtttgtg aaaatggaat ttatatagtt agtaaattta atcttttta tatgtatttt      480
ataaaacgag aagatttgga aattgttaaa atagaaaaaa tgaattttt aaatcaagtt      540
gaagtttgtt ttgttatcaa aacaaaaaat aaaatactcc ttaaatgctt tgaaagtatt     600
tataaaaaag aagacttaga aaagcttaaa aattggtatg aaaacaagct ttga           654
```

<210> SEQ ID NO 46
<211> LENGTH: 217
<212> TYPE: PRT
<213> ORGANISM: Campylobacter jejuni

<400> SEQUENCE: 46

```
Met Lys Lys Val Phe Leu Trp Glu Tyr Leu Gln Lys Gly Cys Lys Leu
1               5                   10                  15

His Phe Asn Asn Asn Leu Val Val His Tyr Ile Val Asn Pro Ser Pro
                20                  25                  30

Leu Gly Trp Ile Val Ile Asn Leu Leu Thr Ile Cys Leu Ile Cys Tyr
            35                  40                  45

Ile Phe Pro Leu Lys Asn Ser Leu Lys His Lys Lys Leu Phe Ser Leu
        50                  55                  60

Lys Ala Asn Val Asn Ser Lys Asn Ser Arg Ile Ile Lys Tyr Thr Gly
65                  70                  75                  80

Ile Ala Ala Phe Leu Gly Gly Leu Ile Gly Ile Trp Tyr Asn Phe Glu
                85                  90                  95

Gly Phe Tyr Gln Leu Leu Phe Phe Phe Glu Leu Glu Asn Glu Asn Leu
            100                 105                 110

Lys Thr Leu Trp Ser Leu Gln Val Ser Val Ser Ser Val Ile Thr Gly
        115                 120                 125

Met Leu Leu Leu Ile Tyr Val Ile Asn Leu Ala Met Val Cys Glu
130                 135                 140

Asn Gly Ile Tyr Ile Val Ser Lys Phe Asn Leu Phe Tyr Met Tyr Phe
145                 150                 155                 160

Ile Lys Arg Glu Asp Leu Glu Ile Val Lys Ile Glu Lys Met Lys Phe
                165                 170                 175

Leu Asn Gln Val Glu Val Cys Phe Val Ile Lys Thr Lys Asn Lys Ile
            180                 185                 190

Leu Leu Lys Cys Phe Glu Ser Ile Tyr Lys Lys Glu Asp Leu Glu Lys
        195                 200                 205
```

<210> SEQ ID NO 47
<211> LENGTH: 993
<212> TYPE: DNA
<213> ORGANISM: Campylobacter jejuni

<400> SEQUENCE: 47

```
atgatgatga aaattcttat tagcggtggt gcaggttata taggttctca tactttaaga      60
caattttta aaacagatca tgaaatttgt gttttagata atctttctaa gggttctaaa     120
atcgcaatag aagatttgca aaaaacaaga gcttttaaat ttttcgaaca agatttaagt     180
gattttcaag gcgtaaaagc attgtttgag agagaaaaat ttgacgctat tgtgcatttt     240
gcagcaagca ttgaagtttt tgaaagtatg caaaatcctt aaaatatta tatgaacaac     300
actgttaata cgacaaatct catcgaaact tgtttgcaaa ctggagtgaa taaatttata     360
tttcttcaa cggcggccac ttatggcgaa ccacaaactc ccgttgtgag cgaaacaagt     420
cctttagcac ctattaatcc ttatgggcgt agtaagctta tgagtgaaga agttttgcgt     480
gatgcaagta tggcaaatcc tgaatttaag cattgtattt taagatattt taatgttgca     540
ggtgcttgta tggattatac tttaggacaa cgctatccaa aagcgacttt gcttataaaa     600
gttgcagctg aatgtgccgc aggaaaacgt gataaacttt tcatatttgg cgatgattat     660
gatacaaaag atggtacttg cataagagat tttatccatg tagatgatat ttcaagtgca     720
catttagcgg ctttggatta tttaaaagag aatgaaagca atgttttta tgtaggttat     780
ggacatggtt ttagcgtaaa agaagtgatt gaagcgatga aaaaagttag cggagtggat     840
tttaaagtag aacttgcccc acgccgtgcg ggtgatccta gtgtattgat ttctgatgca     900
agtaaaatca gaaatcttac ttcttggcag cctaaatatg atgatttaga gcttatttgt     960
aaatctgctt ttgattggga aaaacagtgt taa                                  993
```

<210> SEQ ID NO 48
<211> LENGTH: 330
<212> TYPE: PRT
<213> ORGANISM: Campylobacter jejuni

<400> SEQUENCE: 48

Met Met Met Lys Ile Leu Ile Ser Gly Gly Ala Gly Tyr Ile Gly Ser
1               5                   10                  15

His Thr Leu Arg Gln Phe Leu Lys Thr Asp His Glu Ile Cys Val Leu
            20                  25                  30

Asp Asn Leu Ser Lys Gly Ser Lys Ile Ala Ile Glu Asp Leu Gln Lys
        35                  40                  45

Thr Arg Ala Phe Lys Phe Phe Glu Gln Asp Leu Ser Asp Phe Gln Gly
    50                  55                  60

Val Lys Ala Leu Phe Glu Arg Glu Lys Phe Asp Ala Ile Val His Phe
65                  70                  75                  80

Ala Ala Ser Ile Glu Val Phe Glu Ser Met Gln Asn Pro Leu Lys Tyr
                85                  90                  95

Tyr Met Asn Asn Thr Val Asn Thr Thr Asn Leu Ile Glu Thr Cys Leu
            100                 105                 110

Gln Thr Gly Val Asn Lys Phe Ile Phe Ser Ser Thr Ala Ala Thr Tyr
        115                 120                 125

Gly Glu Pro Gln Thr Pro Val Val Ser Glu Thr Ser Pro Leu Ala Pro
    130                 135                 140

Ile Asn Pro Tyr Gly Arg Ser Lys Leu Met Ser Glu Glu Val Leu Arg
145                 150                 155                 160

Asp Ala Ser Met Ala Asn Pro Glu Phe Lys His Cys Ile Leu Arg Tyr
                165                 170                 175

Phe Asn Val Ala Gly Ala Cys Met Asp Tyr Thr Leu Gly Gln Arg Tyr
            180                 185                 190

Pro Lys Ala Thr Leu Leu Ile Lys Val Ala Ala Glu Cys Ala Ala Gly
        195                 200                 205

Lys Arg Asp Lys Leu Phe Ile Phe Gly Asp Asp Tyr Asp Thr Lys Asp
    210                 215                 220

Gly Thr Cys Ile Arg Asp Phe Ile His Val Asp Asp Ile Ser Ser Ala
225                 230                 235                 240

His Leu Ala Ala Leu Asp Tyr Leu Lys Glu Asn Glu Ser Asn Val Phe
                245                 250                 255

Asn Val Gly Tyr Gly His Gly Phe Ser Val Lys Glu Val Ile Glu Ala
            260                 265                 270

Met Lys Lys Val Ser Gly Val Asp Phe Lys Val Glu Leu Ala Pro Arg
        275                 280                 285

Arg Ala Gly Asp Pro Ser Val Leu Ile Ser Asp Ala Ser Lys Ile Arg
    290                 295                 300

Asn Leu Thr Ser Trp Gln Pro Lys Tyr Asp Asp Leu Glu Leu Ile Cys
305                 310                 315                 320

Lys Ser Ala Phe Asp Trp Glu Lys Gln Cys
                325                 330

<210> SEQ ID NO 49
<211> LENGTH: 1594
<212> TYPE: DNA
<213> ORGANISM: Campylobacter jejuni
<220> FEATURE:
<221> NAME/KEY: modified_base
<222> LOCATION: (61)..(61)
<223> OTHER INFORMATION: a, c, t, g, unknown or other
<220> FEATURE:
<221> NAME/KEY: modified_base
<222> LOCATION: (182)..(182)
<223> OTHER INFORMATION: a, c, t, g, unknown or other
<220> FEATURE:
<221> NAME/KEY: modified_base
<222> LOCATION: (303)..(303)
<223> OTHER INFORMATION: a, c, t, g, unknown or other
<220> FEATURE:
<221> NAME/KEY: modified_base
<222> LOCATION: (424)..(424)
<223> OTHER INFORMATION: a, c, t, g, unknown or other
<220> FEATURE:
<221> NAME/KEY: modified_base
<222> LOCATION: (545)..(545)
<223> OTHER INFORMATION: a, c, t, g, unknown or other
<220> FEATURE:
<221> NAME/KEY: modified_base
<222> LOCATION: (666)..(666)
<223> OTHER INFORMATION: a, c, t, g, unknown or other
<220> FEATURE:
<221> NAME/KEY: modified_base
<222> LOCATION: (787)..(787)
<223> OTHER INFORMATION: a, c, t, g, unknown or other
<220> FEATURE:
<221> NAME/KEY: modified_base
<222> LOCATION: (908)..(908)
<223> OTHER INFORMATION: a, c, t, g, unknown or other
<220> FEATURE:
<221> NAME/KEY: modified_base
<222> LOCATION: (1029)..(1029)
<223> OTHER INFORMATION: a, c, t, g, unknown or other
<220> FEATURE:

```
<221> NAME/KEY: modified_base
<222> LOCATION: (1150)..(1150)
<223> OTHER INFORMATION: a, c, t, g, unknown or other
<220> FEATURE:
<221> NAME/KEY: modified_base
<222> LOCATION: (1271)..(1271)
<223> OTHER INFORMATION: a, c, t, g, unknown or other
<220> FEATURE:
<221> NAME/KEY: modified_base
<222> LOCATION: (1392)..(1392)
<223> OTHER INFORMATION: a, c, t, g, unknown or other
<220> FEATURE:
<221> NAME/KEY: modified_base
<222> LOCATION: (1513)..(1513)
<223> OTHER INFORMATION: a, c, t, g, unknown or other

<400> SEQUENCE: 49
```

| | | | | | |
|---|---|---|---|---|---|
| atgccttta | tcactttggc | tagtgatttt | tcttattttg | atcgtaataa | atatttaatc | 60 |
| nagcctaaaa | gaatatctta | atatccctgt | ttttgaaatc | attgtttatt | ttggagtggg | 120 |
| gcttattgtt | ttttatgtgt | ttagagcttt | gttaaatgcg | tattattttc | atcttttggc | 180 |
| anagattttc | taaagggcgt | tatcatgcga | tcgcttataa | ggttttttct | aaattttaa | 240 |
| atattaatta | tgaaaaattt | actcaaaaaa | atcaatctga | aattttaaag | tccattacag | 300 |
| ggngaagttt | ataatctaag | cactatgatt | tcatcatttt | tacttttgat | gagtgaaatt | 360 |
| tttgtagtac | ttttgcttta | tgctttaatg | cttttgatta | attataaaat | cactttgttt | 420 |
| ttanagtatt | tttatggtgt | taaatgcctt | tattttagtg | aaaattttaa | gccctatcat | 480 |
| taaaaagca | ggagtaagac | gcgaagaagc | gatgaaaaat | ttctttgaaa | ttttaaatac | 540 |
| aaatnttaaa | taatttcaaa | tttattaagc | ttaaaaccaa | agaagatgga | gtattaagtc | 600 |
| tttttaaagc | gcaaagtgaa | gcttttttcta | aagcaaatat | taccaacgaa | agcgtagctg | 660 |
| cggtgnccta | gaatttatct | tgaaggaata | ggcttttgcg | tacttgtttt | tatcgtggta | 720 |
| tttttggttt | tgaaaaatga | aagtgatatt | tcaggtattt | tatccacgat | ttctattttt | 780 |
| gttttangcg | ctttatcgct | taatgccaag | tgcaaatcgt | attattacaa | gttatcatga | 840 |
| tttgctttat | tatcattctt | ctttggatat | tatttatcaa | aatttaagac | aagaagaaga | 900 |
| aaatttgngg | cgaggaaaaa | ttaagcttta | atcaagagct | taaaatttgc | aatcttagct | 960 |
| ttggttatga | gggaaaaaaa | tatttattta | aaaatcttaa | cttaaatatt | aaaaaaggcg | 1020 |
| aaaaaatcng | cttttatagg | ggagagtggt | tgtggaaaaa | gtaccttagt | agatcttatc | 1080 |
| ataggacttt | taaaccaaa | agaagggcaa | attttaattg | atgagcaaga | attaaatgca | 1140 |
| aataatacan | aaaaattatc | gccaaaaaat | aggctatatc | ccgcaaaata | tctatctttt | 1200 |
| taatgacagt | atagctaaaa | atatcacttt | tggagatgcg | gttgatgaag | aaaaacttaa | 1260 |
| tagggttatc | naaacaagca | aatttagagc | attttataaa | aaatttaccct | caaggagtgc | 1320 |
| aaacaaaagt | gggcgatggg | gggagtaatt | taagcggggg | acaaaaacaa | cgcatagcta | 1380 |
| tagcaagagc | tnttatattt | agagcctgaa | atgttagtgc | ttgatgaagc | aacttctgcg | 1440 |
| cttgatactc | aaagtgaagc | aaaaattatg | gatgaaattt | ataaaatttc | taaagataaa | 1500 |
| accatgatta | ttnatcgcac | atcgcctttc | tacgataaca | caatgtgata | aggtttatcg | 1560 |
| tttagaacac | ggtaagctta | agaggagaa | atga | | | 1594 |

```
<210> SEQ ID NO 50
<211> LENGTH: 526
<212> TYPE: PRT
<213> ORGANISM: Campylobacter jejuni

<400> SEQUENCE: 50
```

```
Met Pro Phe Ile Thr Leu Ala Ser Asp Phe Ser Tyr Phe Asp Arg Asn
1               5                   10                  15

Lys Tyr Leu Ile Ser Leu Lys Glu Tyr Leu Asn Ile Pro Val Phe Glu
                20                  25                  30

Ile Ile Val Tyr Phe Gly Val Gly Leu Ile Val Phe Tyr Val Phe Arg
                35                  40                  45

Ala Leu Leu Asn Ala Tyr Tyr Phe His Leu Leu Ala Arg Phe Ser Lys
    50                  55                  60

Gly Arg Tyr His Ala Ile Ala Tyr Lys Val Phe Ser Lys Phe Leu Asn
65                  70                  75                  80

Ile Asn Tyr Glu Lys Phe Thr Gln Lys Asn Gln Ser Glu Ile Leu Lys
                85                  90                  95

Ser Ile Thr Gly Glu Val Tyr Asn Leu Ser Thr Met Ile Ser Ser Phe
                100                 105                 110

Leu Leu Leu Met Ser Glu Ile Phe Val Val Leu Leu Tyr Ala Leu
            115                 120                 125

Met Leu Leu Ile Asn Tyr Lys Ile Thr Leu Phe Leu Ser Ile Phe Met
    130                 135                 140

Val Leu Asn Ala Phe Ile Leu Val Lys Ile Leu Ser Pro Ile Ile Lys
145                 150                 155                 160

Lys Ala Gly Val Arg Arg Glu Ala Met Lys Asn Phe Phe Glu Ile
                165                 170                 175

Leu Asn Thr Asn Leu Asn Asn Phe Lys Phe Ile Lys Leu Lys Thr Lys
                180                 185                 190

Glu Asp Gly Val Leu Ser Leu Phe Lys Ala Gln Ser Glu Ala Phe Ser
                195                 200                 205

Lys Ala Asn Ile Thr Asn Glu Ser Val Ala Ala Val Pro Arg Ile Tyr
    210                 215                 220

Leu Glu Gly Ile Gly Phe Cys Val Leu Val Phe Ile Val Val Phe Leu
225                 230                 235                 240

Val Leu Lys Asn Glu Ser Asp Ile Ser Gly Ile Leu Ser Thr Ile Ser
                245                 250                 255

Ile Phe Val Leu Ala Leu Tyr Arg Leu Met Pro Ser Ala Asn Arg Ile
                260                 265                 270

Ile Thr Ser Tyr His Asp Leu Leu Tyr His Ser Ser Leu Asp Ile
                275                 280                 285

Ile Tyr Gln Asn Leu Arg Gln Glu Glu Asn Leu Gly Glu Glu Lys
    290                 295                 300

Leu Ser Phe Asn Gln Glu Leu Lys Ile Cys Asn Leu Ser Phe Gly Tyr
305                 310                 315                 320

Glu Gly Lys Lys Tyr Leu Phe Lys Asn Leu Asn Leu Asn Ile Lys Lys
                325                 330                 335

Gly Glu Lys Ile Ala Phe Ile Gly Glu Ser Gly Cys Gly Lys Ser Thr
                340                 345                 350

Leu Val Asp Leu Ile Ile Gly Leu Leu Lys Pro Lys Glu Gly Gln Ile
                355                 360                 365

Leu Ile Asp Glu Gln Glu Leu Asn Ala Asn Asn Thr Lys Asn Tyr Arg
    370                 375                 380

Gln Lys Ile Gly Tyr Ile Pro Gln Asn Ile Tyr Leu Phe Asn Asp Ser
385                 390                 395                 400

Ile Ala Lys Asn Ile Thr Phe Gly Asp Ala Val Asp Glu Glu Lys Leu
                405                 410                 415
```

```
Asn Arg Val Ile Lys Gln Ala Asn Leu Glu His Phe Ile Lys Asn Leu
            420                 425                 430
Pro Gln Gly Val Gln Thr Lys Val Gly Asp Gly Gly Ser Asn Leu Ser
        435                 440                 445
Gly Gly Gln Lys Gln Arg Ile Ala Ile Ala Arg Ala Leu Tyr Leu Glu
    450                 455                 460
Pro Glu Met Leu Val Leu Asp Glu Ala Thr Ser Ala Leu Asp Thr Gln
465                 470                 475                 480
Ser Glu Ala Lys Ile Met Asp Glu Ile Tyr Lys Ile Ser Lys Asp Lys
                485                 490                 495
Thr Met Ile Ile Ile Ala His Arg Leu Ser Thr Ile Thr Gln Cys Asp
            500                 505                 510
Lys Val Tyr Arg Leu Glu His Gly Lys Leu Lys Glu Glu Lys
        515                 520                 525
```

<210> SEQ ID NO 51
<211> LENGTH: 1062
<212> TYPE: DNA
<213> ORGANISM: Campylobacter jejuni

<400> SEQUENCE: 51

```
aaaataagct ttattatcgc aactttaaat tcaggaggtg ctgagcgtgc tttagtaacc      60
ttagctaatg cactttgcaa agagcatgaa gtaagtatta ttaaatttca tgcaggagaa     120
tcttttttata agcttgaaaa tgaagttaaa gttacaagtt tggaacaatt tagatttgac    180
acgctttatc ataaaatcgc aagtcgtttt aagaaatttt ttgctttaag aaaggctttg    240
aaagaaagta agtctgatgt ttttatttct ttttttggata cgactaatat tgcttgtatt   300
gctgcgaaaa tagggcttaa aactccactc attataagtg agcatagcaa tgaagcgtat    360
ttaaaaccta aaatttggcg ttttttaaga agggtaagct atcctttttg tgatgcttta    420
agtgtgcttg aagcagtgaa taaggtgtat tatgaaagat tgtaaaaag gttaagctt      480
ttattaaacc cttgtcattt tagcgatgaa atttctttttg attctagttt tgaaaaggaa   540
aatttggttc tttttatagg gcgtttagat cacaacaaaa accctgtaat gttttttaaaa   600
gctatagcgc atttggataa aaatttacaa gaaaattata aatttgttat agcaggagat    660
ggacagttaa dcaagaact tgaatataag gtaaaatctt taggaataaa agttgatttt     720
ttaggacgcg ttgaaaatgt caaggctctt tatgaaaaag caaagtgct tgcctttgt     780
tcttttgtag agggtttgcc aacggttta attgaaagtt tgtattttga ggttgtaga    840
atttcaagtt cttattataa tggtgctaag gatttaatca agataatca tgatgggctt   900
ttggtaggtt gtgatgatga aatagcactt gctaaaaaac ttgaacttgt tttaaatgat   960
gaaaatttta aaagaact tgtaaataat gccaacaaa ggtgtaaga ctttgaaatt     1020
tctcatatca aagaagaatg gcttaagctt atagccgagg tt                      1062
```

<210> SEQ ID NO 52
<211> LENGTH: 354
<212> TYPE: PRT
<213> ORGANISM: Campylobacter jejuni

<400> SEQUENCE: 52

```
Lys Ile Ser Phe Ile Ile Ala Thr Leu Asn Ser Gly Gly Ala Glu Arg
1               5                   10                  15
Ala Leu Val Thr Leu Ala Asn Ala Leu Cys Lys Glu His Glu Val Ser
            20                  25                  30
```

| | | | | | | | | | | | |
|---|---|---|---|---|---|---|---|---|---|---|---|
|Ile|Ile|Lys|Phe|His|Ala|Gly|Glu|Ser|Phe|Tyr|Lys|Leu|Glu|Asn|Glu|
| | |35| | | |40| | | |45| | | | | |

Ile Ile Lys Phe His Ala Gly Glu Ser Phe Tyr Lys Leu Glu Asn Glu
            35                  40                  45

Val Lys Val Thr Ser Leu Glu Gln Phe Arg Phe Asp Thr Leu Tyr His
 50                  55                  60

Lys Ile Ala Ser Arg Phe Lys Lys Phe Phe Ala Leu Arg Lys Ala Leu
 65                  70                  75                  80

Lys Glu Ser Lys Ser Asp Val Phe Ile Ser Phe Leu Asp Thr Thr Asn
                 85                  90                  95

Ile Ala Cys Ile Ala Ala Lys Ile Gly Leu Lys Thr Pro Leu Ile Ile
            100                 105                 110

Ser Glu His Ser Asn Glu Ala Tyr Leu Lys Pro Lys Ile Trp Arg Phe
            115                 120                 125

Leu Arg Arg Val Ser Tyr Pro Phe Cys Asp Ala Leu Ser Val Leu Gly
130                 135                 140

Ser Ser Asp Lys Val Tyr Tyr Glu Arg Phe Val Lys Arg Val Lys Leu
145                 150                 155                 160

Leu Leu Asn Pro Cys His Phe Ser Asp Glu Ile Ser Phe Asp Ser Ser
                165                 170                 175

Phe Glu Lys Glu Asn Leu Val Leu Phe Ile Gly Arg Leu Asp His Asn
            180                 185                 190

Lys Asn Pro Val Met Phe Leu Lys Ala Ile Ala His Leu Asp Lys Asn
            195                 200                 205

Leu Gln Glu Asn Tyr Lys Phe Val Ile Ala Gly Asp Gly Gln Leu Arg
210                 215                 220

Gln Glu Leu Glu Tyr Lys Val Lys Ser Leu Gly Ile Lys Val Asp Phe
225                 230                 235                 240

Leu Gly Arg Val Glu Asn Val Lys Ala Leu Tyr Glu Lys Ala Lys Val
                245                 250                 255

Leu Cys Leu Cys Ser Phe Val Glu Gly Leu Pro Thr Val Leu Ile Glu
            260                 265                 270

Ser Leu Tyr Phe Glu Val Cys Arg Ile Ser Ser Tyr Tyr Asn Gly
            275                 280                 285

Ala Lys Asp Leu Ile Lys Asp Asn His Asp Gly Leu Leu Val Gly Cys
290                 295                 300

Asp Asp Glu Ile Ala Leu Ala Lys Lys Leu Glu Leu Val Leu Asn Asp
305                 310                 315                 320

Glu Asn Phe Arg Lys Glu Leu Val Asn Asn Ala Lys Gln Arg Cys Lys
                325                 330                 335

Asp Phe Gly Ile Ser His Ile Lys Glu Glu Trp Leu Lys Leu Ile Ala
            340                 345                 350

Glu Val

<210> SEQ ID NO 53
<211> LENGTH: 911
<212> TYPE: DNA
<213> ORGANISM: Campylobacter jejuni

<400> SEQUENCE: 53
atgcctaaac tttctgttat agtaccaact tttaatcgtc aagttttgtt agaaaggct      60 attaaaagca tacaaaatca agattttaaa gatttagaaa ttattgtaag cgatgataat     120
tctagcgatg atactaaaag tgtggtgcaa aatttacaaa agatgatga tcgcattaag     180 tatttttaa atcaaaatta caacaaggt ccaaatggca ataaaaacaa tggcttagat       240
caagcaagtg gcgagtttgt aacttttta gatgatgatg atgagctttt atccggggct      300

```
ttaagtacct tgatgcaaaa agcaaatgag ggttatgctc atgttttggg aaattgtttg    360
atagaaaaag aaggaaattt aagcaaggaa tttagcggca agggcttgga aaaagatagt    420
gaaatttcta aaaagatttt tttaatggct aaatttagcg gagagttttt ttctgttttt    480
aaaaaatccc tacttgaaaa taagcgtttt aatgaagaat tttatggcaa tgaagccacg    540
ctttgggtaa atttatacaa agaaaaaagt ttttatatcc ataaggcttt taggatttat    600
agaattttta ggcaagatag cgtgacttta ggggcgagta aaaatgctta tagggtgtat    660
ttggatattt agagcttgct aaaattttag aaaatgaact tagaatgagt aaggataaag    720
attataaaaa aacttgtgcg agttattata aatggcagc ttattatgca aaacttgcaa     780
aaaattataa agcccttat aaatgtttgt ttaaaagcct aagtataaaa atcaacgctc     840
ctgctttgat attactcatt ttaagtataa ttccaaataa tatgattgaa aaattatcaa    900
aaattcgggt g                                                        911
```

<210> SEQ ID NO 54
<211> LENGTH: 304
<212> TYPE: PRT
<213> ORGANISM: Campylobacter jejuni

<400> SEQUENCE: 54

```
Met Pro Lys Leu Ser Val Ile Val Pro Thr Phe Asn Arg Gln Val Leu
1               5                   10                  15

Leu Glu Lys Ala Ile Lys Ser Ile Gln Asn Gln Asp Phe Lys Asp Leu
            20                  25                  30

Glu Ile Ile Val Ser Asp Asp Asn Ser Ser Asp Thr Lys Ser Val
        35                  40                  45

Val Gln Asn Leu Gln Lys Asp Asp Arg Ile Lys Tyr Phe Leu Asn
    50                  55                  60

Gln Asn Tyr Lys Gln Gly Pro Asn Gly Asn Lys Asn Asn Gly Leu Asp
65                  70                  75                  80

Gln Ala Ser Gly Glu Phe Val Thr Phe Leu Asp Asp Asp Glu Leu
            85                  90                  95

Leu Ser Gly Ala Leu Ser Thr Leu Met Gln Lys Ala Asn Glu Gly Tyr
            100                 105                 110

Ala His Val Phe Gly Asn Cys Leu Ile Glu Lys Glu Gly Asn Leu Ser
            115                 120                 125

Lys Glu Phe Ser Gly Lys Gly Leu Glu Lys Asp Ser Glu Ile Ser Lys
            130                 135                 140

Lys Asp Phe Leu Met Ala Lys Phe Ser Gly Glu Phe Phe Ser Val Phe
145                 150                 155                 160

Lys Lys Ser Leu Leu Glu Asn Lys Arg Phe Asn Glu Glu Phe Tyr Gly
                165                 170                 175

Asn Glu Ala Thr Leu Trp Val Asn Leu Tyr Lys Glu Lys Ser Phe Tyr
            180                 185                 190

Ile His Lys Ala Phe Arg Ile Tyr Arg Ile Phe Arg Gln Asp Ser Val
            195                 200                 205

Thr Leu Gly Ala Ser Lys Asn Ala Tyr Arg Val Tyr Leu Gly Tyr Leu
            210                 215                 220

Glu Leu Ala Lys Ile Leu Glu Asn Glu Leu Arg Met Ser Lys Asp Lys
225                 230                 235                 240

Asp Tyr Lys Lys Thr Cys Ala Ser Tyr Tyr Lys Met Ala Ala Tyr Tyr
                245                 250                 255
```

```
Ala Lys Leu Ala Lys Asn Tyr Lys Ala Leu Tyr Lys Cys Leu Phe Lys
            260                 265                 270

Ser Leu Ser Ile Lys Ile Asn Ala Pro Ala Leu Ile Leu Leu Ile Leu
        275                 280                 285

Ser Ile Ile Pro Asn Asn Met Ile Glu Lys Leu Ser Lys Ile Arg Val
        290                 295                 300

<210> SEQ ID NO 55
<211> LENGTH: 1089
<212> TYPE: DNA
<213> ORGANISM: Campylobacter jejuni

<400> SEQUENCE: 55
ttaggcattt ttatttattc tttaggaagt ggtggtgctg aaagagttgt ggcgacttta      60
ttgcctattt taagtttgaa atttgaagtg catttgatct tgatgaatga taaaatttct     120
tatgaaattc cagagtgtca aattcatttt ttagaatgtt caaaacctag tgaaaatcct     180
attttgaaat tttaaaaact accttttttg gctttaaaat acaaaaaact ttgcagaaat     240
ttaggtattg atacagaatt tgttttttta aatcgaccta attatatagc tttaatggca     300
agaatgtttg gaaacaaaac tcgccttgtg atcaatgaat gcactacgcc aagtgtgatg     360
tatatgaaaa ataattttaa ttcttggta ataaattt taatttcttt gctttaccca       420
aaagctgatt taatccttgcc taattctaag ggaaatttag aagatttagt gcaaaatttt     480
agtataagtc caaaaaaatg tgaaatttta tacaatgcca tcgatttaga aaacataggg     540
caaaaagccc ttgaagacat agctttaaaa gataaattta ttttaagtgt aggcaggctt     600
gataaaggta aaaatcatgc tttattaatt cgtgcttatg cgagattgaa acagattta     660 aagcttgtga ttttaggtga aggtgtgctt aaggatgagc ttttagcttt gattaaagaa     720
ttaaatttgg aagaaaaggt tttgctttta ggatttgata taatcccta taaatacatg     780 gctaaatgcg aattttttgc ttttgcttct gtgtttgaag gttttcaaa tgttttaatc     840 gaaagtttgg cttgttcttg tgcggtggtt tgcactgatc ataaaagtgg tgcaagagag     900 cttttttggcg atgatgaatt tggacttta gtagaagtag ataatgaaaa ctctatgttt     960
cagggtttaa aaactatgct tgaagacgat aaattaagaa aagcgtataa aaacaaagct    1020
aaaactaggg ctaaagcctt tgataaagta aaaattgcac gcgatgcttt gaatatttta    1080
ttaggataa                                                            1089

<210> SEQ ID NO 56
<211> LENGTH: 362
<212> TYPE: PRT
<213> ORGANISM: Campylobacter jejuni

<400> SEQUENCE: 56

Leu Gly Ile Phe Ile Tyr Ser Leu Gly Ser Gly Gly Ala Glu Arg Val
1               5                   10                  15

Val Ala Thr Leu Leu Pro Ile Leu Ser Leu Lys Phe Glu Val His Leu
            20                  25                  30

Ile Leu Met Asn Asp Lys Ile Ser Tyr Glu Ile Pro Glu Cys Gln Ile
        35                  40                  45

His Phe Leu Glu Cys Ser Lys Pro Ser Glu Asn Pro Ile Leu Lys Phe
    50                  55                  60

Leu Lys Leu Pro Phe Leu Ala Leu Lys Tyr Lys Lys Leu Cys Arg Asn
65                  70                  75                  80

Leu Gly Ile Asp Thr Glu Phe Val Phe Leu Asn Arg Pro Asn Tyr Ile
```

```
                           85                  90                  95
Ala Leu Met Ala Arg Met Phe Gly Asn Lys Thr Arg Leu Val Ile Asn
                          100                 105                 110

Glu Cys Thr Thr Pro Ser Val Met Tyr Met Lys Asn Phe Asn Ser
                          115                 120                 125

Leu Val Asn Lys Phe Leu Ile Ser Leu Leu Tyr Pro Lys Ala Asp Leu
                          130                 135                 140

Ile Leu Pro Asn Ser Lys Gly Asn Leu Glu Asp Leu Val Gln Asn Phe
145                       150                 155                 160

Ser Ile Ser Pro Lys Lys Cys Glu Ile Leu Tyr Asn Ala Ile Asp Leu
                          165                 170                 175

Glu Asn Ile Gly Gln Lys Ala Leu Glu Asp Ile Ala Leu Lys Asp Lys
                          180                 185                 190

Phe Ile Leu Ser Val Gly Arg Leu Asp Lys Gly Lys Asn His Ala Leu
                          195                 200                 205

Leu Ile Arg Ala Tyr Ala Arg Leu Lys Thr Asp Leu Lys Leu Val Ile
                          210                 215                 220

Leu Gly Glu Gly Val Leu Lys Asp Glu Leu Leu Ala Leu Ile Lys Glu
225                       230                 235                 240

Leu Asn Leu Glu Glu Lys Val Leu Leu Leu Gly Phe Asp Asn Asn Pro
                          245                 250                 255

Tyr Lys Tyr Met Ala Lys Cys Glu Phe Phe Ala Phe Ala Ser Val Phe
                          260                 265                 270

Glu Gly Phe Ser Asn Val Leu Ile Glu Ser Leu Ala Cys Ser Cys Ala
                          275                 280                 285

Val Val Cys Thr Asp His Lys Ser Gly Ala Arg Glu Leu Phe Gly Asp
                          290                 295                 300

Asp Glu Phe Gly Leu Leu Val Glu Val Asp Asn Glu Asn Ser Met Phe
305                       310                 315                 320

Gln Gly Leu Lys Thr Met Leu Glu Asp Asp Lys Leu Arg Lys Ala Tyr
                          325                 330                 335

Lys Asn Lys Ala Lys Thr Arg Ala Lys Ala Phe Asp Lys Val Lys Ile
                          340                 345                 350

Ala Arg Asp Ala Leu Lys Tyr Leu Leu Gly
                          355                 360

<210> SEQ ID NO 57
<211> LENGTH: 2142
<212> TYPE: DNA
<213> ORGANISM: Campylobacter jejuni

<400> SEQUENCE: 57
atgttgaaaa aagagtattt aaaaaaccct tatttagttt tgtttgcgat gattgtatta      60
gcttatgttt ttagtgtatt ttgcaggttt tattgggttt ggtgggcaag tgagtttaac     120
gagtattttt tcaataatca attaatgatc atttcaaacg atggctatgc ttttgctgag     180
ggcgcaagag atatgatagc aggttttcat cagcctaatg atttgagtta ttatggatct     240
tctttatcta cgcttactta ttggctttat aaaatcacac cttttttcttt tgaaagtatc    300 atttatata tgagtacttt tttatcttct ttggtggtga ttcctattat tttactagct     360
aatgaataca aacgcccttt aatgggcttt gtagctgctc ttttagcaag tgtagcaaac    420
agttattata atcgcactat gagtgggtat tatgatacgg atatgctggt aattgtttta    480
cctatgttta ttttatttttt tatggtaaga atgatttttaa aaaaagactt ttttttcattg   540
```

-continued

```
attgccttgc cattatttat aggaatttat ctttggtggt atccttcaag ttatacttta    600
aatgtagctt taattggact ttttttaatt tatacactta ttttcatag aaaagaaaag     660 attttttata tagctgtgat tttgtcttct cttactcttt caaatatagc atggttttat    720
caaagtgcca ttatagtaat acttttgct ttatttgctt tagagcaaaa acgcttaaat    780
tttatgatta taggaatttt aggtagtgca actttgatat ttttgatttt aagtggtggg    840
gttgatccca tactttatca gcttaaattt tatattttta gaagcgatga agtgcgaat     900 ttaacacagg gctttatgta ttttaatgtt aatcaaacca tacaagaagt tgaaaatgta    960
gattttagcg aatttatgcg aagaattagt ggtagtgaaa ttgttttctt gttttctttg    1020
tttggttttg tatggctttt gagaaaacat aaaagtatga ttatggcttt acctatattg    1080
gtgcttgggt ttttagcctt aaaaggagga cttagattta ccatttattc tgtacctgta    1140
atggctttag gatttggttt tttattgagc gagtttaagg ctatattggt taaaaaatat    1200
agccaattaa cttcaaatgt ttgtattgtt tttgcaacta ttttgacttt ggctccagta    1260
tttatccata tttacaacta taaagcgcca acagttttt ctcaaaatga agcatcatta    1320
ttaaatcaat taaaaaatat agccaataga gaagattatg tggtaacttg gtgggattat    1380
ggttatcctg tgcgttatta tagcgatgtg aaaactttag tagatggtgg aaagcattta    1440
ggtaaggata attttttccc ttcttttct ttaagtaaag atgaacaagc tgcagctaat    1500
atggcaagac ttagtgtaga atatacagaa aaaagcttt atgctccgca aaatgatatt    1560
ttaaaatcag acattttaca agccatgatg aaagattata atcaaagcaa tgtggattta    1620
tttctagctt cattatcaaa acctgatttt aaaatcgata caccaaaaac tcgtgatatt    1680
tatctttata tgcccgctag aatgtctttg attttttcta cggtggctag ttttctttt    1740 attaatttag atacaggagt tttggataaa cctttacct ttagcacagc ttatccactt    1800
gatgttaaaa atggagaaat ttatcttagc aacggagtgg ttttaagcga tgatttaga    1860 agttttaaaa taggtgataa tgtggttct gtaaatagta tcgtagagat taattctatt    1920
aaacaaggtg aatacaaaat cactccaatc gatgataagg ctcagttta tatttttat    1980 ttaaaggata gtgctattcc ttacgcacaa tttattttaa tggataaaac catgtttaat    2040
agtgcttatg tgcaaatgtt ttttttggga aattatgata agaatttatt tgacttggtg    2100
attaattcta gagatgctaa agttttaaaa cttaaaattt aa                      2142
```

<210> SEQ ID NO 58
<211> LENGTH: 712
<212> TYPE: PRT
<213> ORGANISM: Campylobacter jejuni

<400> SEQUENCE: 58

```
Met Leu Lys Lys Glu Tyr Leu Lys Asn Pro Tyr Leu Val Leu Phe Ala
1               5                   10                  15

Met Ile Val Leu Ala Tyr Val Phe Ser Val Phe Cys Arg Phe Tyr Trp
            20                  25                  30

Val Trp Trp Ala Ser Glu Phe Asn Glu Tyr Phe Phe Asn Asn Gln Leu
        35                  40                  45

Met Ile Ile Ser Asn Asp Gly Tyr Ala Phe Ala Glu Gly Ala Arg Asp
    50                  55                  60

Met Ile Ala Gly Phe His Gln Pro Asn Asp Leu Ser Tyr Tyr Gly Ser
65                  70                  75                  80

Ser Leu Ser Thr Leu Thr Tyr Trp Leu Tyr Lys Ile Thr Pro Phe Ser
                85                  90                  95
```

```
Phe Glu Ser Ile Ile Leu Tyr Met Ser Thr Phe Leu Ser Ser Leu Val
            100                 105                 110

Val Ile Pro Ile Ile Leu Leu Ala Asn Glu Tyr Lys Arg Pro Leu Met
            115                 120                 125

Gly Phe Val Ala Ala Leu Leu Ala Ser Val Ala Asn Ser Tyr Tyr Asn
        130                 135                 140

Arg Thr Met Ser Gly Tyr Tyr Asp Thr Asp Met Leu Val Ile Val Leu
145                 150                 155                 160

Pro Met Phe Ile Leu Phe Phe Met Val Arg Met Ile Leu Lys Lys Asp
                165                 170                 175

Phe Phe Ser Leu Ile Ala Leu Pro Leu Phe Ile Gly Ile Tyr Leu Trp
            180                 185                 190

Trp Tyr Pro Ser Ser Tyr Thr Leu Asn Val Ala Leu Ile Gly Leu Phe
            195                 200                 205

Leu Ile Tyr Thr Leu Ile Phe His Arg Lys Glu Lys Ile Phe Tyr Ile
        210                 215                 220

Ala Val Ile Leu Ser Ser Leu Thr Leu Ser Asn Ile Ala Trp Phe Tyr
225                 230                 235                 240

Gln Ser Ala Ile Ile Val Ile Leu Phe Ala Leu Phe Ala Leu Glu Gln
                245                 250                 255

Lys Arg Leu Asn Phe Met Ile Ile Gly Ile Leu Gly Ser Ala Thr Leu
            260                 265                 270

Ile Phe Leu Ile Leu Ser Gly Gly Val Asp Pro Ile Leu Tyr Gln Leu
        275                 280                 285

Lys Phe Tyr Ile Phe Arg Ser Asp Glu Ser Ala Asn Leu Thr Gln Gly
        290                 295                 300

Phe Met Tyr Phe Asn Val Asn Gln Thr Ile Gln Glu Val Glu Asn Val
305                 310                 315                 320

Asp Phe Ser Glu Phe Met Arg Arg Ile Ser Gly Ser Glu Ile Val Phe
                325                 330                 335

Leu Phe Ser Leu Phe Gly Phe Val Trp Leu Leu Arg Lys His Lys Ser
            340                 345                 350

Met Ile Met Ala Leu Pro Ile Leu Val Leu Gly Phe Leu Ala Leu Lys
            355                 360                 365

Gly Gly Leu Arg Phe Thr Ile Tyr Ser Val Pro Val Met Ala Leu Gly
        370                 375                 380

Phe Gly Phe Leu Leu Ser Glu Phe Lys Ala Ile Leu Val Lys Lys Tyr
385                 390                 395                 400

Ser Gln Leu Thr Ser Asn Val Cys Ile Val Phe Ala Thr Ile Leu Thr
                405                 410                 415

Leu Ala Pro Val Phe Ile His Ile Tyr Asn Tyr Lys Ala Pro Thr Val
            420                 425                 430

Phe Ser Gln Asn Glu Ala Ser Leu Leu Asn Gln Leu Lys Asn Ile Ala
            435                 440                 445

Asn Arg Glu Asp Tyr Val Val Thr Trp Trp Asp Tyr Gly Tyr Pro Val
        450                 455                 460

Arg Tyr Tyr Ser Asp Val Lys Thr Leu Val Asp Gly Gly Lys His Leu
465                 470                 475                 480

Gly Lys Asp Asn Phe Phe Pro Ser Phe Ser Leu Ser Lys Asp Glu Gln
                485                 490                 495

Ala Ala Asn Met Ala Arg Leu Ser Val Glu Tyr Thr Glu Lys Ser Phe
            500                 505                 510
```

Tyr Ala Pro Gln Asn Asp Ile Leu Lys Ser Asp Ile Leu Gln Ala Met
            515                 520                 525
Met Lys Asp Tyr Asn Gln Ser Asn Val Asp Leu Phe Leu Ala Ser Leu
    530                 535                 540
Ser Lys Pro Asp Phe Lys Ile Asp Thr Pro Lys Thr Arg Asp Ile Tyr
545                 550                 555                 560
Leu Tyr Met Pro Ala Arg Met Ser Leu Ile Phe Ser Thr Val Ala Ser
                565                 570                 575
Phe Ser Phe Ile Asn Leu Asp Thr Gly Val Leu Asp Lys Pro Phe Thr
            580                 585                 590
Phe Ser Thr Ala Tyr Pro Leu Asp Val Lys Asn Gly Glu Ile Tyr Leu
        595                 600                 605
Ser Asn Gly Val Val Leu Ser Asp Asp Phe Arg Ser Phe Lys Ile Gly
    610                 615                 620
Asp Asn Val Val Ser Val Asn Ser Ile Val Glu Ile Asn Ser Ile Lys
625                 630                 635                 640
Gln Gly Glu Tyr Lys Ile Thr Pro Ile Asp Asp Lys Ala Gln Phe Tyr
                645                 650                 655
Ile Phe Tyr Leu Lys Asp Ser Ala Ile Pro Tyr Ala Gln Phe Ile Leu
            660                 665                 670
Met Asp Lys Thr Met Phe Asn Ser Ala Tyr Val Gln Met Phe Phe Leu
        675                 680                 685
Gly Asn Tyr Asp Lys Asn Leu Phe Asp Leu Val Ile Asn Ser Arg Asp
    690                 695                 700
Ala Lys Val Phe Lys Leu Lys Ile
705                 710

<210> SEQ ID NO 59
<211> LENGTH: 1128
<212> TYPE: DNA
<213> ORGANISM: Campylobacter jejuni

<400> SEQUENCE: 59
atgagaatag gattttatc acatgcagga gcgagtattt atcattttag aatgcctatt        60
ataaaagcgt taaagatag aaaagacgaa gttttttgtta tagtgccgca agatgaatac      120
acgcaaaaac ttagagatct tggcttaaaa gtaattgttt atgagttttc aagagctagt     180
ttaaatcctt ttgtggtttt aaagaatttt ttttatcttg ctaaggtttt gaaaaattta     240
aatcttgatt ttattcaaag tgcggcacac aaaagcaata cttttggaat tttagcagca     300
aaatgggcaa aaattcctta tcgttttgcc ttagtagaag gcttgggatc ttttttatata    360 gatcaaggtt ttaaggcaaa tttagtgcgt tttgttatta atagtcttta taaattaagt     420
tttaaatttg cacaccaatt tatttttgtc aatgaaagta atgctgagtt tatgcggaat     480
ttaggactta agaaaataa aatttgcgtg ataaaatctg tagggatcaa tttaaaaaaa     540
ttttttccta tttatgtaga atcggaaaaa aaagagcttt tttggaaaaa tttaaacata     600 gataaaaac ccattgtgct tatgatagca agagcttat ggcataaggg tgtaaaagaa       660 tttttatgaaa gtgctactat gctaaaagac aaagcaaatt ttgttttagt tggtggaaga    720
gatgaaaatc cttcttgtgc aagtttggag ttttaaaact ctggcgcggt gcattatttg    780
ggtgctagaa gtgatatagt cgagcttttg caaaattgtg atattttgt tttgccaagc     840 tataaagaag ctttcctgt aagtgttttg gaggcaaaag cttgcggtaa ggctatagtg     900
gtgagtgatt gtgaaggttg tgtggaggct atttctaatg cttatgatgg acttgggca    960

-continued

```
aaaacaaaaa atgctaaaga tttaagcgaa aaaatttcac ttttattaga agatgaaaaa    1020
ttaagattaa atttagctaa aaatgccgcc caagatgctt tacaatacga tgaaaatata    1080
atcgcacagc gttatttaaa actttatgat agggtaatta agaatgta                1128
```

<210> SEQ ID NO 60
<211> LENGTH: 376
<212> TYPE: PRT
<213> ORGANISM: Campylobacter jejuni

<400> SEQUENCE: 60

```
Met Arg Ile Gly Phe Leu Ser His Ala Gly Ala Ser Ile Tyr His Phe
1               5                   10                  15

Arg Met Pro Ile Ile Lys Ala Leu Lys Asp Arg Lys Asp Glu Val Phe
            20                  25                  30

Val Ile Val Pro Gln Asp Glu Tyr Thr Gln Lys Leu Arg Asp Leu Gly
        35                  40                  45

Leu Lys Val Ile Val Tyr Glu Phe Ser Arg Ala Ser Leu Asn Pro Phe
    50                  55                  60

Val Val Leu Lys Asn Phe Phe Tyr Leu Ala Lys Val Leu Lys Asn Leu
65                  70                  75                  80

Asn Leu Asp Phe Ile Gln Ser Ala Ala His Lys Ser Asn Thr Phe Gly
                85                  90                  95

Ile Leu Ala Ala Lys Trp Ala Lys Ile Pro Tyr Arg Phe Ala Leu Val
            100                 105                 110

Glu Gly Leu Gly Ser Phe Tyr Ile Asp Gln Gly Phe Lys Ala Asn Leu
        115                 120                 125

Val Arg Phe Val Ile Asn Ser Leu Tyr Lys Leu Ser Phe Lys Phe Ala
    130                 135                 140

His Gln Phe Ile Phe Val Asn Glu Ser Asn Ala Glu Phe Met Arg Asn
145                 150                 155                 160

Leu Gly Leu Lys Glu Asn Lys Ile Cys Val Ile Lys Ser Val Gly Ile
                165                 170                 175

Asn Leu Lys Lys Phe Phe Pro Ile Tyr Val Glu Ser Glu Lys Lys Glu
            180                 185                 190

Leu Phe Trp Lys Asn Leu Asn Ile Asp Lys Lys Pro Ile Val Leu Met
        195                 200                 205

Ile Ala Arg Ala Leu Trp His Lys Gly Val Lys Glu Phe Tyr Glu Ser
    210                 215                 220

Ala Thr Met Leu Lys Asp Lys Ala Asn Phe Val Leu Val Gly Gly Arg
225                 230                 235                 240

Asp Glu Asn Pro Ser Cys Ala Ser Leu Glu Phe Leu Asn Ser Gly Ala
                245                 250                 255

Val His Tyr Leu Gly Ala Arg Ser Asp Ile Val Glu Leu Leu Gln Asn
            260                 265                 270

Cys Asp Ile Phe Val Leu Pro Ser Tyr Lys Glu Gly Phe Pro Val Ser
        275                 280                 285

Val Leu Glu Ala Lys Ala Cys Gly Lys Ala Ile Val Val Ser Asp Cys
    290                 295                 300

Glu Gly Cys Val Glu Ala Ile Ser Asn Ala Tyr Asp Gly Leu Trp Ala
305                 310                 315                 320

Lys Thr Lys Asn Ala Lys Asp Leu Ser Glu Ile Ser Leu Leu Leu
                325                 330                 335

Glu Asp Glu Lys Leu Arg Leu Asn Leu Ala Lys Asn Ala Ala Gln Asp
            340                 345                 350
```

Ala Leu Gln Tyr Asp Glu Asn Ile Ile Ala Gln Arg Tyr Leu Lys Leu
        355                          360                       365

Tyr Asp Arg Val Ile Lys Asn Val
        370                          375

<210> SEQ ID NO 61
<211> LENGTH: 597
<212> TYPE: DNA
<213> ORGANISM: Campylobacter jejuni

<400> SEQUENCE: 61

| | | | | | |
|---|---|---|---|---|---|
| gaaaaagttt | ttaaaagaat | ttttgatttt | attttatctt | tagtgctttt | agtgctttt | 60 |
| tctccggtga | ttttaatcac | tgctttactt | ttaaaaatca | ctcaaggaag | tgtgatttt | 120 |
| acccaaaatc | gtcccgggtt | agatgaaaaa | attttaaaa | tttataaatt | taaaaccatg | 180 |
| agcgatgaaa | gagatgaaaa | gggtgagtta | ttaagcgatg | aattgcgttt | gaaagctttt | 240 |
| ggaaaaatcg | ttagaagctt | aagtttggat | gagcttttgc | aactttttaa | tgttttaaaa | 300 |
| ggggatatga | gttttgttgg | acctagacct | cttttggttg | agtatttgcc | tctttacaat | 360 |
| aaagagcaaa | aattgcgtca | taaagtgcgt | ccaggtataa | caggatgggc | gcaggtaaat | 420 |
| ggtagaaatg | ctatttcttg | gcagaaaaaa | ttcgaacttg | atgtgtatta | tgtgaaaaat | 480 |
| atttctttt | tgcttgattt | aaaaatcatg | tttttaacag | ctttaaaggt | tttaaaacga | 540 |
| agtggggtaa | gcaaagaagg | ccatgttaca | acagagaaat | ttaatggcaa | gaactga | 597 |

<210> SEQ ID NO 62
<211> LENGTH: 198
<212> TYPE: PRT
<213> ORGANISM: Campylobacter jejuni

<400> SEQUENCE: 62

Glu Lys Val Phe Lys Arg Ile Phe Asp Phe Ile Leu Ser Leu Val Leu
1               5                    10                  15

Leu Val Leu Phe Ser Pro Val Ile Leu Ile Thr Ala Leu Leu Leu Lys
         20                       25                  30

Ile Thr Gln Gly Ser Val Ile Phe Thr Gln Asn Arg Pro Gly Leu Asp
        35                       40                   45

Glu Lys Ile Phe Lys Ile Tyr Lys Phe Lys Thr Met Ser Asp Glu Arg
 50                   55                  60

Asp Glu Lys Gly Glu Leu Leu Ser Asp Glu Leu Arg Leu Lys Ala Phe
65                   70                  75                  80

Gly Lys Ile Val Arg Ser Leu Ser Leu Asp Glu Leu Leu Gln Leu Phe
                 85                    90                  95

Asn Val Leu Lys Gly Asp Met Ser Phe Val Gly Pro Arg Pro Leu Leu
          100                   105               110

Val Glu Tyr Leu Pro Leu Tyr Asn Lys Glu Gln Lys Leu Arg His Lys
        115                   120               125

Val Arg Pro Gly Ile Thr Gly Trp Ala Gln Val Asn Gly Arg Asn Ala
        130                   135               140

Ile Ser Trp Gln Lys Lys Phe Glu Leu Asp Val Tyr Tyr Val Lys Asn
145                150                155              160

Ile Ser Phe Leu Leu Asp Leu Lys Ile Met Phe Leu Thr Ala Leu Lys
                 165                170              175

Val Leu Lys Arg Ser Gly Val Ser Lys Glu Gly His Val Thr Thr Glu
        180                   185               190

Lys Phe Asn Gly Lys Asn
        195

<210> SEQ ID NO 63
<211> LENGTH: 588
<212> TYPE: DNA
<213> ORGANISM: Campylobacter jejuni

<400> SEQUENCE: 63

```
atggcaagaa ctgaaaaaat ttatatttat ggtgctagtg gtcatgggct tgtttgtgaa      60
gatgtggcta aaatatggg ttataaagaa tgtattttt tagatgattt taaaggaatg      120
aaatttgaaa gtaccttacc taaatatgat ttttttatag ccataggaaa caatgaaatt      180
cgaaaaaaga tttatcaaaa aatttcagaa aatggcttta aaattgtcaa tcttatccat      240
aaaagcgcgc ttataagtcc tagcgcaatc gtggaagaaa atgcaggaat tttaatcatg      300
ccttatgtag tgattaacgc taaagctaaa atagaaaaag gtgtgatttt aaatacttca      360
agcgtaattg agcatgaatg tgtgataggg gaattttctc atgtgagtgt gggagctaaa      420
tgtgcgggta atgtaaaaat tggtaaaaat tgttttttag ggattaattc ttgtgttttg      480
cctaatttaa gtttggcaga tgatagtatt ttaggtggtg gagcaacttt agttaaaaat      540
caagatgaaa aggtgttttt tgtgggagta cctgcaaaaa ggatgtaa                   588
```

<210> SEQ ID NO 64
<211> LENGTH: 195
<212> TYPE: PRT
<213> ORGANISM: Campylobacter jejuni

<400> SEQUENCE: 64

Met Ala Arg Thr Glu Lys Ile Tyr Ile Tyr Gly Ala Ser Gly His Gly
1               5                   10                  15

Leu Val Cys Glu Asp Val Ala Lys Asn Met Gly Tyr Lys Glu Cys Ile
            20                  25                  30

Phe Leu Asp Asp Phe Lys Gly Met Lys Phe Glu Ser Thr Leu Pro Lys
        35                  40                  45

Tyr Asp Phe Phe Ile Ala Ile Gly Asn Asn Glu Ile Arg Lys Lys Ile
    50                  55                  60

Tyr Gln Lys Ile Ser Glu Asn Gly Phe Lys Ile Val Asn Leu Ile His
65                  70                  75                  80

Lys Ser Ala Leu Ile Ser Pro Ser Ala Ile Val Glu Glu Asn Ala Gly
                85                  90                  95

Ile Leu Ile Met Pro Tyr Val Val Ile Asn Ala Lys Ala Lys Ile Glu
            100                 105                 110

Lys Gly Val Ile Leu Asn Thr Ser Ser Val Ile Glu His Glu Cys Val
        115                 120                 125

Ile Gly Glu Phe Ser His Val Ser Val Gly Ala Lys Cys Ala Gly Asn
    130                 135                 140

Val Lys Ile Gly Lys Asn Cys Phe Leu Gly Ile Asn Ser Cys Val Leu
145                 150                 155                 160

Pro Asn Leu Ser Leu Ala Asp Asp Ser Ile Leu Gly Gly Ala Thr
                165                 170                 175

Leu Val Lys Asn Gln Asp Glu Lys Gly Val Phe Val Gly Val Pro Ala
            180                 185                 190

Lys Arg Met
        195

<210> SEQ ID NO 65
<211> LENGTH: 1161
<212> TYPE: DNA
<213> ORGANISM: Campylobacter jejuni

<400> SEQUENCE: 65

```
atgagatttt ttctttctcc tccgcatatg ggtggtaatg aattaaaata catagaagaa      60
gttttcaaaa gcaattatat agcacctttg ggtgaatttg taaatcgctt tgaacaaagt     120
gtcaaggctt acagtaaaag tgaaaatgcc ttagctttaa attcagccac agcggctttg     180
catttagctt taagggtggc aggggtaaaa caagatgata ttgttttggc ttcttctttt     240
acttttatcg cttcagtagc acctatttgt tatcttaaag caaaacctgt atttatagat     300
tgtgatgaaa cttataatat cgatgtagat ttattaaagc ttgctattaa agaatgtgaa     360
aaaaaaccaa aagcattgat tttaactcat ctttatggca atgcggctaa aatggatgaa     420
attgttgaaa tttgcaaaga aaatgaaatt gttttaatcg aagatgctgc tgaagcttta     480
ggaagttttt ataagaataa agctttagga acttttggag aatttggagc ttattcttat     540
aatggcaata aaattatcac cacttcaggt ggaggtatgc ttataggaaa aaataaagaa     600
aagattgaaa aagcaagatt ttatagcact caagctaggg aaaattgttt gcattatgaa     660
catttagatt atggttataa ttaccgctta agcaatgttt taggagctat ggcgtagcg      720
caaatggagg ttttagaaca aagagtgctt aaaaaaagag aaatttatga gtggtataaa     780
gaatttttag gagagtgttt tagctttta gatgaattag aaaattcaag aagcaatcgc     840
tggttaagta cagcttttgat tgattttgat aaaaatgaac ttaattcttg tcaaaaagat     900
ataaatatca gtcaaaaaaa tattactttg catccaaaaa tttcaaaact catagaagat     960
ttgaaaaatg aacaaataga aacaagacca ttatggaaag ctatgcacgc tcaagaagta    1020
tttaaaggag ctaaggctta tcttaatggc aatagtgagt tattttttcca aaaaggaatt    1080
tgtttgccaa gtggcacggc gatgagtaaa gatgatgttt atgaaatttc aaaactgatc    1140
ttaaagagca taaaggctta a                                              1161
```

<210> SEQ ID NO 66
<211> LENGTH: 386
<212> TYPE: PRT
<213> ORGANISM: Campylobacter jejuni

<400> SEQUENCE: 66

Met Arg Phe Phe Leu Ser Pro Pro His Met Gly Gly Asn Glu Leu Lys
1               5                   10                  15

Tyr Ile Glu Glu Val Phe Lys Ser Asn Tyr Ile Ala Pro Leu Gly Glu
            20                  25                  30

Phe Val Asn Arg Phe Glu Gln Ser Val Lys Ala Tyr Ser Lys Ser Glu
        35                  40                  45

Asn Ala Leu Ala Leu Asn Ser Ala Thr Ala Ala Leu His Leu Ala Leu
    50                  55                  60

Arg Val Ala Gly Val Lys Gln Asp Asp Ile Val Leu Ala Ser Ser Phe
65                  70                  75                  80

Thr Phe Ile Ala Ser Val Ala Pro Ile Cys Tyr Leu Lys Ala Lys Pro
                85                  90                  95

Val Phe Ile Asp Cys Asp Glu Thr Tyr Asn Ile Asp Val Asp Leu Leu
            100                 105                 110

Lys Leu Ala Ile Lys Glu Cys Glu Lys Lys Pro Lys Ala Leu Ile Leu
        115                 120                 125

Thr His Leu Tyr Gly Asn Ala Ala Lys Met Asp Glu Ile Val Glu Ile
            130                 135                 140
Cys Lys Glu Asn Glu Ile Val Leu Ile Glu Asp Ala Ala Glu Ala Leu
145                 150                 155                 160
Gly Ser Phe Tyr Lys Asn Lys Ala Leu Gly Thr Phe Gly Glu Phe Gly
                165                 170                 175
Ala Tyr Ser Tyr Asn Gly Asn Lys Ile Ile Thr Ser Gly Gly Gly
            180                 185                 190
Met Leu Ile Gly Lys Asn Lys Glu Ile Glu Lys Ala Arg Phe Tyr
            195                 200                 205
Ser Thr Gln Ala Arg Glu Asn Cys Leu His Tyr Glu His Leu Asp Tyr
210                 215                 220
Gly Tyr Asn Tyr Arg Leu Ser Asn Val Leu Gly Ala Ile Gly Val Ala
225                 230                 235                 240
Gln Met Glu Val Leu Glu Gln Arg Val Leu Lys Lys Arg Glu Ile Tyr
                245                 250                 255
Glu Trp Tyr Lys Glu Phe Leu Gly Glu Cys Phe Ser Phe Leu Asp Glu
            260                 265                 270
Leu Glu Asn Ser Arg Ser Asn Arg Trp Leu Ser Thr Ala Leu Ile Asp
            275                 280                 285
Phe Asp Lys Asn Glu Leu Asn Ser Cys Gln Lys Asp Ile Asn Ile Ser
            290                 295                 300
Gln Lys Asn Ile Thr Leu His Pro Lys Ile Ser Lys Leu Ile Glu Asp
305                 310                 315                 320
Leu Lys Asn Glu Gln Ile Glu Thr Arg Pro Leu Trp Lys Ala Met His
                325                 330                 335
Ala Gln Glu Val Phe Lys Gly Ala Lys Ala Tyr Leu Asn Gly Asn Ser
            340                 345                 350
Glu Leu Phe Phe Gln Lys Gly Ile Cys Leu Pro Ser Gly Thr Ala Met
            355                 360                 365
Ser Lys Asp Asp Val Tyr Glu Ile Ser Lys Leu Ile Leu Lys Ser Ile
    370                 375                 380
Lys Ala
385

<210> SEQ ID NO 67
<211> LENGTH: 1770
<212> TYPE: DNA
<213> ORGANISM: Campylobacter jejuni

<400> SEQUENCE: 67
atgatttttt ataaaagcaa aagattagca tttttttta cttcagatat tgttttaatt      60
ttacttagcg tttatctggc tttttctttg agatttagtg gagatattcc gagtattttt    120
tatcatggta tgatggtttc tgctattatt ttgcttgttt taaaactttc atttttgttt    180 gttttttagaa tttataaagt agcttggaga ttttttttctc tcaatgaagc aagaaagatt    240
tttatcgctt tgcttttagc tgagttttgt tttttttctta tttttttattt tttagtgat    300 tttttttaatc ttttttccaag aagtgctatt gtgatagatt tgttctttc ttatatgttt    360 ataggtactt taagaattag caaaagaatg cttgtggatt ttaaaccttc tagaatgaaa    420
gaagaagaaa ctccttgtat tgtagtaggg gcaacttcta aggctttgca tttgttaaaa    480
ggtgcaaaag aaggttcttt agggcttttt cctgtaggcg tagttgatgc gagaaaagag    540
cttataggga cttattgtga taatttatt gtagaagaaa agaaaaaaat aaaatcttat    600

-continued

```
gtagaacaag gggtaaaaac tgccattatt gctttaagac ttgaacaaga agagcttaaa    660 aaacttttg aagaacttgt agcttatggt atttgcgatg taaaaatatt ttcttttaca    720
agaaacgaag caagagatat cagtatagaa gacttgcttg ctagaaaacc aaaagattta    780
gatgatagtg ctgtggcggc ttttttaaaa gataaggtag ttttggtaag tggagcaggt    840
ggaactatag gcagtgaact ttgtaagcaa tgtattaaat ttggtgctaa gcatcttatc    900
atggttgatc atagtgagta taatctttat aagatcaatg atgatttaaa tttatataaa    960
gaaaaaatta ctcctatttt actgagtatt ttagataagc aaagtttaga tgaggtatta   1020
aaaacttata aacccgagct tattttacat gcagccgctt ataaacatgt gcctctttgc   1080
gaacaaaatc cacattcagc agtaatcaat aatatttag gaactaaaat tttatgcgac   1140
agtgctaaag aaaacaaagt agctaaattt gtgatgataa gtacagataa agcagtacga   1200
ccaacaaata ttatgggttg cactaagaga gtttgcgagc tttatacttt aagtatgagt   1260
gatgaaaatt ttgaagttgc ttgtgtgcgt tttggtaatg ttttaggttc tagtggtagt   1320
gtgataccga aatttaaagc acaaattgcc aataatgagc ctttaacttt aacgcacct   1380 gatatagtgc gttatttat gcttgtggct gaggcagtgc aacttgtttt acaagctgga   1440
gctatcgcaa aagggggaga acttttgtt ttggatatgg gtaagcctgt gaaaatcata   1500
gatttagcta aaaaaatgct tttactttct aatcgcaatg atttagaaat taaaatcaca   1560
ggcttaagaa aaggtgagaa gctttatgaa gagcttttga ttgatgaaaa tgatgctaaa   1620
acacaatatg agagtatttt tgtagcaaag aatgagaagg ttgatcttga ttggcttaat   1680
aaagagatag aaaatttaca aatatgtgaa gatatttcag aggctttatt aaagattgta   1740
cctgaattta aacacaataa agaaggtgta                                     1770
```

<210> SEQ ID NO 68
<211> LENGTH: 590
<212> TYPE: PRT
<213> ORGANISM: Campylobacter jejuni

<400> SEQUENCE: 68

```
Met Ile Phe Tyr Lys Ser Lys Arg Leu Ala Phe Phe Leu Thr Ser Asp
1               5                   10                  15

Ile Val Leu Ile Leu Leu Ser Val Tyr Leu Ala Phe Ser Leu Arg Phe
            20                  25                  30

Ser Gly Asp Ile Pro Ser Ile Phe Tyr His Gly Met Met Val Ser Ala
        35                  40                  45

Ile Ile Leu Leu Val Leu Lys Leu Ser Phe Leu Phe Val Phe Arg Ile
    50                  55                  60

Tyr Lys Val Ala Trp Arg Phe Phe Ser Leu Asn Glu Ala Arg Lys Ile
65                  70                  75                  80

Phe Ile Ala Leu Leu Leu Ala Glu Phe Cys Phe Phe Leu Ile Phe Tyr
                85                  90                  95

Phe Phe Ser Asp Phe Phe Asn Pro Phe Pro Arg Ser Ala Ile Val Ile
            100                 105                 110

Asp Phe Val Leu Ser Tyr Met Phe Ile Gly Thr Leu Arg Ile Ser Lys
        115                 120                 125

Arg Met Leu Val Asp Phe Lys Pro Ser Arg Met Lys Glu Glu Glu Thr
    130                 135                 140

Pro Cys Ile Val Val Gly Ala Thr Ser Lys Ala Leu His Leu Leu Lys
145                 150                 155                 160

Gly Ala Lys Glu Gly Ser Leu Gly Leu Phe Pro Val Gly Val Val Asp
```

```
                165                 170                 175
Ala Arg Lys Glu Leu Ile Gly Thr Tyr Cys Asp Lys Phe Ile Val Glu
            180                 185                 190

Glu Lys Glu Lys Ile Lys Ser Tyr Val Glu Gln Gly Val Lys Thr Ala
            195                 200                 205

Ile Ile Ala Leu Arg Leu Glu Gln Glu Leu Lys Lys Leu Phe Glu
210                 215                 220

Glu Leu Val Ala Tyr Gly Ile Cys Asp Val Lys Ile Phe Ser Phe Thr
225                 230                 235                 240

Arg Asn Glu Ala Arg Asp Ile Ser Ile Glu Asp Leu Leu Ala Arg Lys
            245                 250                 255

Pro Lys Asp Leu Asp Asp Ser Ala Val Ala Ala Phe Leu Lys Asp Lys
            260                 265                 270

Val Val Leu Val Ser Gly Ala Gly Gly Thr Ile Gly Ser Glu Leu Cys
            275                 280                 285

Lys Gln Cys Ile Lys Phe Gly Ala Lys His Leu Ile Met Val Asp His
            290                 295                 300

Ser Glu Tyr Asn Leu Tyr Lys Ile Asn Asp Asp Leu Asn Leu Tyr Lys
305                 310                 315                 320

Glu Lys Ile Thr Pro Ile Leu Leu Ser Ile Leu Asp Lys Gln Ser Leu
            325                 330                 335

Asp Glu Val Leu Lys Thr Tyr Lys Pro Glu Leu Ile Leu His Ala Ala
            340                 345                 350

Ala Tyr Lys His Val Pro Leu Cys Glu Gln Asn Pro His Ser Ala Val
            355                 360                 365

Ile Asn Asn Ile Leu Gly Thr Lys Ile Leu Cys Asp Ser Ala Lys Glu
370                 375                 380

Asn Lys Val Ala Lys Phe Val Met Ile Ser Thr Asp Lys Ala Val Arg
385                 390                 395                 400

Pro Thr Asn Ile Met Gly Cys Thr Lys Arg Val Cys Glu Leu Tyr Thr
            405                 410                 415

Leu Ser Met Ser Asp Glu Asn Phe Glu Val Ala Cys Val Arg Phe Gly
            420                 425                 430

Asn Val Leu Gly Ser Ser Gly Ser Val Ile Pro Lys Phe Lys Ala Gln
            435                 440                 445

Ile Ala Asn Asn Glu Pro Leu Thr Leu Thr His Pro Asp Ile Val Arg
450                 455                 460

Tyr Phe Met Leu Val Ala Glu Ala Val Gln Leu Val Leu Gln Ala Gly
465                 470                 475                 480

Ala Ile Ala Lys Gly Gly Glu Leu Phe Val Leu Asp Met Gly Lys Pro
            485                 490                 495

Val Lys Ile Ile Asp Leu Ala Lys Lys Met Leu Leu Leu Ser Asn Arg
            500                 505                 510

Asn Asp Leu Glu Ile Lys Ile Thr Gly Leu Arg Lys Gly Glu Lys Leu
            515                 520                 525

Tyr Glu Glu Leu Leu Ile Asp Glu Asn Asp Ala Lys Thr Gln Tyr Glu
530                 535                 540

Ser Ile Phe Val Ala Lys Asn Glu Lys Val Asp Leu Asp Trp Leu Asn
545                 550                 555                 560

Lys Glu Ile Glu Asn Leu Gln Ile Cys Glu Asp Ile Ser Glu Ala Leu
            565                 570                 575

Leu Lys Ile Val Pro Glu Phe Lys His Asn Lys Glu Gly Val
            580                 585                 590
```

<210> SEQ ID NO 69
<211> LENGTH: 894
<212> TYPE: DNA
<213> ORGANISM: Campylobacter jejuni

<400> SEQUENCE: 69

```
atgtatataa aagatataca aagatttgaa gataatcgct atcgtgctag agcttatatg      60
agttatattt taacaagaaa tctgcccaat aaacttcctg atattcacct tgaaacgatt     120
aaaacagctt tggataaaat agctcatgaa gttgttgttt ttgatgcttt gtatatttta     180
gatatttcag gcatgcaaat agaaaatgcg atttccttaa ataaagctca tgaaataggg     240
cagggtgagg atagaagtac tcgttcttat ttttatagag ctgtaaaatt aagacgatgt     300
gttttgagcg atccttatcc ttcggtttta aataatgagc tttgcgtgac agcttctatg     360
ccaatttacg atgataaaaa taacttgctt tttgttgttt gtattgatat caagcttgaa     420
gatattttaa agattattca agcaggaaaa tttgaatttg tttttactca gtttagtcgt     480
ttggtatatt tttgcttcgc actggtttta tttgtgatta cttgttttt atttcaaaaa      540
ggttttttta gtcttttga taatcaagct ataggtatag aacatatgtt tgaaagtacc     600
atcgctataa ctttggcttt agctattttt gatttggcaa aactttgat cgaacaagaa     660
gtattaggaa ggacgaaaaa agaagaaggt ggaattcaaa aaactatggt gagattttg      720
ggttctatta tcattgcttt agctatagaa gctttgatgt tggtatttaa acttgctatt     780
ggtgatcttt ctcagatgat ttatgcgatt tatcttatcg gtggagtgag cttgcttctt     840
ttaggtttaa gtgtatattt atttacggtt aagtataaaa ataataatat ttga           894
```

<210> SEQ ID NO 70
<211> LENGTH: 297
<212> TYPE: PRT
<213> ORGANISM: Campylobacter jejuni

<400> SEQUENCE: 70

```
Met Tyr Ile Lys Asp Ile Gln Arg Phe Glu Asp Asn Arg Tyr Arg Ala
1               5                   10                  15

Arg Ala Tyr Met Ser Tyr Ile Leu Thr Arg Asn Leu Pro Asn Lys Leu
            20                  25                  30

Pro Asp Ile His Leu Glu Thr Ile Lys Thr Ala Leu Asp Lys Ile Ala
        35                  40                  45

His Glu Val Val Val Phe Asp Ala Leu Tyr Ile Leu Asp Ile Ser Gly
    50                  55                  60

Met Gln Ile Glu Asn Ala Ile Ser Leu Asn Lys Ala His Glu Ile Gly
65                  70                  75                  80

Gln Gly Glu Asp Arg Ser Thr Arg Ser Tyr Phe Tyr Arg Ala Val Lys
                85                  90                  95

Leu Arg Arg Cys Val Leu Ser Asp Pro Tyr Pro Ser Val Leu Asn Asn
            100                 105                 110

Glu Leu Cys Val Thr Ala Ser Met Pro Ile Tyr Asp Asp Lys Asn Asn
        115                 120                 125

Leu Leu Phe Val Val Cys Ile Asp Ile Lys Leu Glu Asp Ile Leu Lys
    130                 135                 140

Ile Ile Gln Ala Gly Lys Phe Glu Phe Val Phe Thr Gln Phe Ser Arg
145                 150                 155                 160

Leu Val Tyr Phe Cys Phe Ala Leu Val Leu Phe Val Ile Thr Cys Phe
                165                 170                 175
```

```
Leu Phe Gln Lys Gly Phe Phe Ser Leu Phe Asp Asn Gln Ala Ile Gly
                180                 185                 190

Ile Glu His Met Phe Glu Ser Thr Ile Ala Ile Thr Leu Ala Leu Ala
            195                 200                 205

Ile Phe Asp Leu Ala Lys Thr Leu Ile Glu Gln Glu Val Leu Gly Arg
        210                 215                 220

Thr Lys Lys Glu Glu Gly Gly Ile Gln Lys Thr Met Val Arg Phe Leu
225                 230                 235                 240

Gly Ser Ile Ile Ile Ala Leu Ala Ile Glu Ala Leu Met Leu Val Phe
                245                 250                 255

Lys Leu Ala Ile Gly Asp Leu Ser Gln Met Ile Tyr Ala Ile Tyr Leu
            260                 265                 270

Ile Gly Gly Val Ser Leu Leu Leu Leu Gly Leu Ser Val Tyr Leu Phe
        275                 280                 285

Thr Val Lys Tyr Lys Asn Asn Asn Ile
    290                 295

<210> SEQ ID NO 71
<211> LENGTH: 1107
<212> TYPE: DNA
<213> ORGANISM: Campylobacter jejuni

<400> SEQUENCE: 71
atgcagcgat ttaaaaaatg gttttgtct atcataaaaa atttcaagca acatgaaaaa      60
attaagatag atcttaataa tacaaagata gatcttaata atacaaagat agatcttaat    120
aatacaaaga tagatcttaa taatacaaag atagatctta ataatacaaa gatagatctt    180
aataatacaa agatagatct taataataca agatagatc ttaataatac aaagatagat    240
cttaataata caaagataga attatcgcaa ttaaaaaaag agcactataa agtattagat    300
tttcatttaa gaaaaattac acctcaagct tttttagaga ttgttgaaat tcatttagcc    360
gaatcatgta atttaaattg ttttggttgt aatcattttt cacaaatagc tgaaaaagaa    420
tttccagata tagaaatttt taaaaaagat atgcaaagac tttcagaaat atctaaaggt    480
attgtcggaa cttttagatt gatgggtggc gaacctcttt taaatcccaa ttgtatacag    540
ttttttgaca ttcaagata tttttttcca aaaagtgcca tttggttggt aactaatggt    600
attttacttg ataagcaaaa tgaggatttt tggaattcat gccaaggaa taaaatgcaa    660 attcgtccaa caaagtatcc tataaaaatt aattgggatt tgattaaaga taagtgtgat    720
caatatgata tccccttgat atttttaac aatggagagt tggaaaaaac ttcttggaaa    780
ttttctctag atccttctgg aaattgtgat aattaccata gttttacaaa ttgtagtatg    840
gcaaatcact gtgttcagtt taagatgga aagctattta cttgtacctt tcctgcacat    900
gtacagcatt ttaataaaaa gtatggaaat cattttgaag tttgcgaatt tgactttatt    960
gatatttata agccaaggaa ttatcaagaa atttttattt ttctttctaa gcctattcct   1020
ttttgtagat attgcaaggt atcacaatgg gcagaaattg aaaatggcg ttctagcaat   1080 aaaacaaaac atgaatattt aatttga                                      1107

<210> SEQ ID NO 72
<211> LENGTH: 1107
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 72

```
atgcagcgtt tcaaaaaatg gttcctgtct atcatcaaaa acttcaaaca gcacgaaaaa      60
atcaaaatcg acctgaacaa caccaaaatc gacctgaaca caccaaaat cgacctgaac      120
aacaccaaaa tcgacctgaa caacaccaaa atcgacctga caacaccaa aatcgacctg      180
aacaacacca aaatcgacct gaacaacacc aaaatcgacc tgaacaacac caaaatcgac      240
ctgaacaaca ccaaaatcga actgtctcag ctgaaaaaag aacactacaa agttctggac      300
ttccacctgc gtaaaatcac cccgcaggcg ttcctggaaa tcgttgaaat ccacctggcg      360
gaatcttgca acctgaactg cttcggttgc aaccacttct ctcagatcgc ggaaaaagaa      420
ttcccggaca tcgaaatctt caaaaaagac atgcagcgtc tgtctgaaat ctctaaaggt      480
atcgttggta ccttccgtct gatgggtggt gaaccgctgc tgaacccgaa ctgcatccag      540
ttcttcgaca tcacccgtta cttcttcccg aaatctgcga tctggctggt taccaacggt      600
atcctgctgg acaaacagaa cgaagacttc tggaactctt gccagcgtaa caaaatgcag      660
atccgtccga ccaaataccc gatcaaaatc aactgggacc tgatcaaaga caaatgcgac      720
cagtacgaca tcccgctgat cttcttcaac aacggtgaac tggaaaaaac ctcttggaaa      780
ttctctctgg acccgtctgg taactgcgac aactaccact ctttcaccaa ctgctctatg      840
gcgaaccact gcgttcagtt caaagacggt aaactgttca cctgcacctt cccggcgcac      900
gttcagcact tcaacaaaaa atacggtaac cacttcgaag tttgcgaatt cgacttcatc      960
gacatctaca agcgaaaga ctaccaggaa atcctgttct tcctgtctaa accgatcccg      1020
ttctgccgat actgcaaagt ttctcagtgg gcggaaatcg gtaaatggcg ttcttctaac      1080
aaaaccaaac acgaatacct gatctga                                          1107
```

<210> SEQ ID NO 73
<211> LENGTH: 1107
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 73

```
atgcagcgtt tcaaaaaatg gttcctgtcc atcatcaaaa acttcaaaca gcacgaaaaa      60
atcaaaatcg acctgaacaa caccaaaatc gacctgaaca caccaaaat cgacctgaac      120
aacaccaaaa tcgacctgaa caacaccaaa atcgacctga caacaccaa aatcgacctg      180
aacaacacca aaatcgacct gaacaacacc aaaatcgacc tgaacaacac caaaatcgac      240
ctgaacaaca ccaaaatcga actgtcccag ctgaaaaaag aacactacaa agtgctggac      300
ttccacctgc gtaaaatcac cccgcaggcg ttcctggaaa tcgtggaaat ccacctggcg      360
gaatcctgca acctgaactg cttcggctgc aaccacttct cccagatcgc ggaaaaagaa      420
ttcccggaca tcgaaatctt caaaaaagac atgcagcgtc tgtccgaaat ctctaaaggc      480
atcgtgggca ccttccgtct gatgggcggc gaaccgctgc tgaacccgaa ctgcatccag      540
ttcttcgaca tcacccgtta cttcttcccg aaatccgcga tctggctggt gaccaacggc      600
atcctgctgg acaaacagaa cgaagacttc tggaactcct gccagcgtaa caaaatgcag      660
atccgtccga ccaaataccc gatcaaaatc aactgggacc tgatcaaaga caaatgcgac      720
cagtacgaca tcccgctgat cttcttcaac aacggcgaac tggaaaaaac ctcctggaaa      780
ttctccctgg acccgtccgg caactgcgac aactaccact ccttcaccaa ctgctccatg      840
```

-continued

```
gcgaaccact gcgtgcagtt caaagacggc aaactgttca cctgcacctt cccggcgcac    900
gtgcagcact tcaacaaaaa atacggcaac cacttcgaag tgtgcgaatt cgacttcatc    960
gacatctaca aagcgaaaga ctaccaggaa atcctgttct tcctgtccaa accgatcccg   1020
ttctgccgat actgcaaagt gtcccagtgg gcggaaatcg gcaaatggcg ttcctccaac   1080
aaaaccaaac acgaatacct gatctga                                       1107
```

<210> SEQ ID NO 74
<211> LENGTH: 368
<212> TYPE: PRT
<213> ORGANISM: Campylobacter jejuni

<400> SEQUENCE: 74

```
Met Gln Arg Phe Lys Lys Trp Phe Leu Ser Ile Ile Lys Asn Phe Lys
1               5                   10                  15

Gln His Glu Lys Ile Lys Ile Asp Leu Asn Asn Thr Lys Ile Asp Leu
            20                  25                  30

Asn Asn Thr Lys Ile Asp Leu Asn Asn Thr Lys Ile Asp Leu Asn Asn
        35                  40                  45

Thr Lys Ile Asp Leu Asn Asn Thr Lys Ile Asp Leu Asn Asn Thr Lys
    50                  55                  60

Ile Asp Leu Asn Asn Thr Lys Ile Asp Leu Asn Asn Thr Lys Ile Asp
65                  70                  75                  80

Leu Asn Asn Thr Lys Ile Glu Leu Ser Gln Leu Lys Lys Glu His Tyr
                85                  90                  95

Lys Val Leu Asp Phe His Leu Arg Lys Ile Thr Pro Gln Ala Phe Leu
            100                 105                 110

Glu Ile Val Glu Ile His Leu Ala Glu Ser Cys Asn Leu Asn Cys Phe
        115                 120                 125

Gly Cys Asn His Phe Ser Gln Ile Ala Glu Lys Glu Phe Pro Asp Ile
    130                 135                 140

Glu Ile Phe Lys Lys Asp Met Gln Arg Leu Ser Glu Ile Ser Lys Gly
145                 150                 155                 160

Ile Val Gly Thr Phe Arg Leu Met Gly Gly Glu Pro Leu Leu Asn Pro
                165                 170                 175

Asn Cys Ile Gln Phe Phe Asp Ile Thr Arg Tyr Phe Phe Pro Lys Ser
            180                 185                 190

Ala Ile Trp Leu Val Thr Asn Gly Ile Leu Leu Asp Lys Gln Asn Glu
        195                 200                 205

Asp Phe Trp Asn Ser Cys Gln Arg Asn Lys Met Gln Ile Arg Pro Thr
    210                 215                 220

Lys Tyr Pro Ile Lys Ile Asn Trp Asp Leu Ile Lys Asp Lys Cys Asp
225                 230                 235                 240

Gln Tyr Asp Ile Pro Leu Ile Phe Phe Asn Asn Gly Glu Leu Glu Lys
                245                 250                 255

Thr Ser Trp Lys Phe Ser Leu Asp Pro Ser Gly Asn Cys Asp Asn Tyr
            260                 265                 270

His Ser Phe Thr Asn Cys Ser Met Ala Asn His Cys Val Gln Phe Lys
        275                 280                 285

Asp Gly Lys Leu Phe Thr Cys Thr Phe Pro Ala His Val Gln His Phe
    290                 295                 300

Asn Lys Lys Tyr Gly Asn His Phe Glu Val Cys Glu Phe Asp Phe Ile
305                 310                 315                 320
```

Asp Ile Tyr Lys Ala Lys Asp Tyr Gln Glu Ile Leu Phe Phe Leu Ser
             325                 330                 335

Lys Pro Ile Pro Phe Cys Arg Tyr Cys Lys Val Ser Gln Trp Ala Glu
         340                 345                 350

Ile Gly Lys Trp Arg Ser Ser Asn Lys Thr Lys His Glu Tyr Leu Ile
     355                 360                 365

<210> SEQ ID NO 75
<211> LENGTH: 1149
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75
atgaaaaaga cagctatcgc gattgcagtg gcactggctg gtttcgctac cgtagcgcag      60
gccgctccga agataacac ctggtacgct ggtgctaaac tgggctggtc tcagtaccat     120
gacaccggct tcattcacaa tgatggcccg actcatgaaa accaactggg cgcaggtgct     180
tttggtggtt accaggttaa cccgtatgtc gacatcaaaa tcgacctgaa caacaccaaa     240
atcgacctga caacaccaa atcgacctg aacaacacca aatcgacct gaacaacacc      300 aaaatcgacc tgaacaacac caaaatcgac tgaacaaca ccaaaatcga cctgaacaac     360
accaaaatcg acctgaacaa caccaaaatc gacctgaaca caccaaaat cctgcagatc     420 actgacgatc tggacgttta cccgtctctg gtggtatgg tatggcgtgc agacaccaag     480
tctaacgtcc ctggcggccc gtctactaaa gaccacgaca ccggcgtttc cccggtattc     540
gcgggcggta tcgagtatgc tatcaccct gaaatcgcaa cccgtctgga ataccagtgg     600
actaacaaca tcggtgatgc caacaccatc ggcacccgtc cggacaacgg cctgctgagc     660
gtaggtgttt cctaccgttt cggccagcaa gaagctgctc cggtagtagc tccggcacca     720
gctccggctc cggaagtaca gaccaagcac ttcactctga gtctgacgt actgttcaac     780 ttcaacaaat ctaccctgaa gccggaaggc cagcaggctc tggatcagct gtacagccag     840
ctgagcaacc tggatccgaa agacggttcc gttgtcgttc tgggcttcac tgaccgtatc     900
ggttctgacg cttacaacca gggtctgtcc gagaaacgtg ctcagtctgt tgttgattac     960
ctgatctcca aggtattcc gtctgacaaa atctccgcac gtggtatggg cgaatctaac    1020
ccggttaccg gcaacacctg tgacaacgtg aaacctcgcg ctgccctgat cgattgcctg    1080
gctccggatc gtcgcgtaga gatcgaagtt aaaggcgtta agacgtggt aactcagccg    1140 caggcttaa                                                         1149

<210> SEQ ID NO 76
<211> LENGTH: 382
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Met Lys Lys Thr Ala Ile Ala Ile Ala Val Ala Leu Ala Gly Phe Ala
1               5                   10                  15

Thr Val Ala Gln Ala Ala Pro Lys Asp Asn Thr Trp Tyr Ala Gly Ala
            20                  25                  30

Lys Leu Gly Trp Ser Gln Tyr His Asp Thr Gly Phe Ile His Asn Asp
        35                  40                  45

Gly Pro Thr His Glu Asn Gln Leu Gly Ala Gly Ala Phe Gly Gly Tyr
50                  55                  60

Gln Val Asn Pro Tyr Val Asp Ile Lys Ile Asp Leu Asn Asn Thr Lys
65                  70                  75                  80

Ile Asp Leu Asn Asn Thr Lys Ile Asp Leu Asn Asn Thr Lys Ile Asp
                85                  90                  95

Leu Asn Asn Thr Lys Ile Asp Leu Asn Asn Thr Lys Ile Asp Leu Asn
            100                 105                 110

Asn Thr Lys Ile Asp Leu Asn Asn Thr Lys Ile Asp Leu Asn Asn Thr
        115                 120                 125

Lys Ile Asp Leu Asn Asn Thr Lys Ile Leu Gln Ile Thr Asp Asp Leu
130                 135                 140

Asp Val Tyr Thr Arg Leu Gly Gly Met Val Trp Arg Ala Asp Thr Lys
145                 150                 155                 160

Ser Asn Val Pro Gly Gly Pro Ser Thr Lys Asp His Asp Thr Gly Val
                165                 170                 175

Ser Pro Val Phe Ala Gly Gly Ile Glu Tyr Ala Ile Thr Pro Glu Ile
            180                 185                 190

Ala Thr Arg Leu Glu Tyr Gln Trp Thr Asn Asn Ile Gly Asp Ala Asn
        195                 200                 205

Thr Ile Gly Thr Arg Pro Asp Asn Gly Leu Leu Ser Val Gly Val Ser
210                 215                 220

Tyr Arg Phe Gly Gln Gln Glu Ala Ala Pro Val Ala Pro Ala Pro
225                 230                 235                 240

Ala Pro Ala Pro Glu Val Gln Thr Lys His Phe Thr Leu Lys Ser Asp
                245                 250                 255

Val Leu Phe Asn Phe Asn Lys Ser Thr Leu Lys Pro Glu Gly Gln Gln
            260                 265                 270

Ala Leu Asp Gln Leu Tyr Ser Gln Leu Ser Asn Leu Asp Pro Lys Asp
        275                 280                 285

Gly Ser Val Val Val Leu Gly Phe Thr Asp Arg Ile Gly Ser Asp Ala
290                 295                 300

Tyr Asn Gln Gly Leu Ser Glu Lys Arg Ala Gln Ser Val Val Asp Tyr
305                 310                 315                 320

Leu Ile Ser Lys Gly Ile Pro Ser Asp Lys Ile Ser Ala Arg Gly Met
                325                 330                 335

Gly Glu Ser Asn Pro Val Thr Gly Asn Thr Cys Asp Asn Val Lys Pro
            340                 345                 350

Arg Ala Ala Leu Ile Asp Cys Leu Ala Pro Asp Arg Arg Val Glu Ile
        355                 360                 365

Glu Val Lys Gly Val Lys Asp Val Val Thr Gln Pro Gln Ala
370                 375                 380

<210> SEQ ID NO 77
<211> LENGTH: 1149
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77
atgaaaaaga cagctatcgc gattgcagtg gcactggctg gtttcgctac cgtagcgcag        60
gccgctccga aagataacac ctggtacgct ggtgctaaac tgggctggtc tcagtaccat       120

```
gacaccggct tcattcacaa tgatggcccg actcatgaaa accaactggg cgcaggtgct    180
tttggtggtt accaggttaa cccgtatgtc gacatcaaaa tcgacctgaa caacaccaaa    240
atcgacctga caacaccaa atcgacctg aacaacacca aaatcgacct gaacaacacc      300
aaaatcgacc tgaacaacac caaaatcgac ctgaacaaca ccaaaatcga cctgaacaac    360
accaaaatcg acctgaacaa caccaaaatc gacctgaaca caccaaaat cctgcagatc     420 actgacgatc tggacgttta tcccgtctg ggtggtatgg tatggcgtgc agacaccaag     480
tctaacgtcc ctggcggccc gtctactaaa gaccacgaca ccggcgtttc cccggtattc    540
gcgggcggta tcgagtatgc tatcaccccct gaaatcgcaa cccgtctgga ataccagtgg   600
actaacaaca tcggtgatgc caacaccatc ggcacccgtc cggacaacgg cctgctgagc    660
gtaggtgttt cctaccgttt cggccagcaa gaagctgctc cggtagtagc tccggcacca   720
gctccggctc cggaagtaca gaccaagcac ttcactctga agtctgacgt actgttcaac    780
ttcaacaaat ctaccctgaa gccggaaggc cagcaggctc tggatcagct gtacagccag    840
ctgagcaacc tggatccgaa agacggttcc gttgtcgttc tgggcttcac tgaccgtatc    900
ggttctgacg cttacaacca gggtctgtcc gagaaacgtg ctcagtctgt tgttgattac    960
ctgatctcca aaggtattcc gtctgacaaa atctccgcac gtggtatggg cgaatctaac   1020
ccggttaccg gcaacacctg tgacaacgtg aaacctcgcg ctgccctgat cgattgcctg   1080
gctccggatc gtcgcgtaga gatcgaagtt aaaggcgtta agacgtggt aactcagccg    1140 caggcttaa                                                            1149

<210> SEQ ID NO 78
<211> LENGTH: 1083
<212> TYPE: DNA
<213> ORGANISM: Escherichia coli

<400> SEQUENCE: 78
gtgaaaccag taacgttata cgatgtcgca gagtatgccg gtgtctctta tcagaccgtt    60
tcccgcgtgg tgaaccaggc cagccacgtt tctgcgaaaa cgcgggaaaa agtggaagcg   120
gcgatggcga agctgaatta cattcccaac cgcgtggcac aacaactggc gggcaaacag   180
tcgttgctga ttggcgttgc cacctccagt ctggccctgc acgcgccgtc gcaaattgtc   240
gcggcgatta aatctcgcgc cgatcaactg ggtgccagcg tggtggtgtc gatggtagaa   300
cgaagcggcg tcgaagcctg taaagcggcg gtgcacaatc ttctcgcgca acgcgtcagt   360
gggctgatca ttaactatcc gctggatgac caggatgcca ttgctgtgga agctgcctgc   420
actaatgttc cggcgttatt tcttgatgtc tctgaccaga cacccatcaa cagtattatt    480
ttctcccatg aagacggtac gcgactgggc gtggagcatc tggtcgcatt gggtcaccag   540
caaatcgcgc tgttagcggg cccattaagt tctgtctcgg cgcgtctgcg tctggctggc   600
tggcataaat atctcactcg caatcaaatt cagccgatag cggaacggga aggcgactgg   660
agtgccatgt ccgttttca acaaaccatg caaatgctga atgagggcat cgttcccact    720
gcgatgctgg ttgccaacga tcagatggcg ctgggcgcaa tgcgcgccat taccgagtcc   780
gggctgcgcg ttggtgcgga tatctcggta gtgggatacg acgataccga agacagctca   840
tgttatatcc cgccgttaac caccatcaaa caggatttc gcctgctggg caaaccagc    900 gtggaccgct gctgcaact ctctcagggc caggcggtga aggcaatca gctgttgccc    960 gtctcactgg tgaaagaaa aaccaccctg gcgcccaata cgcaaaccgc ctctccccgc   1020
gcgttggccg attcattaat gcagctggca cgacaggttt cccgactgga aagcgggcag  1080
``` tga                                                                  1083

<210> SEQ ID NO 79
<211> LENGTH: 360
<212> TYPE: PRT
<213> ORGANISM: Escherichia coli

<400> SEQUENCE: 79

Met Lys Pro Val Thr Leu Tyr Asp Val Ala Glu Tyr Ala Gly Val Ser
1               5                   10                  15

Tyr Gln Thr Val Ser Arg Val Val Asn Gln Ala Ser His Val Ser Ala
            20                  25                  30

Lys Thr Arg Glu Lys Val Glu Ala Ala Met Ala Glu Leu Asn Tyr Ile
        35                  40                  45

Pro Asn Arg Val Ala Gln Gln Leu Ala Gly Lys Gln Ser Leu Leu Ile
    50                  55                  60

Gly Val Ala Thr Ser Ser Leu Ala Leu His Ala Pro Ser Gln Ile Val
65                  70                  75                  80

Ala Ala Ile Lys Ser Arg Ala Asp Gln Leu Gly Ala Ser Val Val Val
                85                  90                  95

Ser Met Val Glu Arg Ser Gly Val Glu Ala Cys Lys Ala Ala Val His
            100                 105                 110

Asn Leu Leu Ala Gln Arg Val Ser Gly Leu Ile Ile Asn Tyr Pro Leu
        115                 120                 125

Asp Asp Gln Asp Ala Ile Ala Val Glu Ala Ala Cys Thr Asn Val Pro
    130                 135                 140

Ala Leu Phe Leu Asp Val Ser Asp Gln Thr Pro Ile Asn Ser Ile Ile
145                 150                 155                 160

Phe Ser His Glu Asp Gly Thr Arg Leu Gly Val Glu His Leu Val Ala
                165                 170                 175

Leu Gly His Gln Gln Ile Ala Leu Leu Ala Gly Pro Leu Ser Ser Val
            180                 185                 190

Ser Ala Arg Leu Arg Leu Ala Gly Trp His Lys Tyr Leu Thr Arg Asn
        195                 200                 205

Gln Ile Gln Pro Ile Ala Glu Arg Glu Gly Asp Trp Ser Ala Met Ser
    210                 215                 220

Gly Phe Gln Gln Thr Met Gln Met Leu Asn Glu Gly Ile Val Pro Thr
225                 230                 235                 240

Ala Met Leu Val Ala Asn Asp Gln Met Ala Leu Gly Ala Met Arg Ala
                245                 250                 255

Ile Thr Glu Ser Gly Leu Arg Val Gly Ala Asp Ile Ser Val Val Gly
            260                 265                 270

Tyr Asp Asp Thr Glu Asp Ser Ser Cys Tyr Ile Pro Pro Leu Thr Thr
        275                 280                 285

Ile Lys Gln Asp Phe Arg Leu Leu Gly Gln Thr Ser Val Asp Arg Leu
    290                 295                 300

Leu Gln Leu Ser Gln Gly Gln Ala Val Lys Gly Asn Gln Leu Leu Pro
305                 310                 315                 320

Val Ser Leu Val Lys Arg Lys Thr Thr Leu Ala Pro Asn Thr Gln Thr
                325                 330                 335

Ala Ser Pro Arg Ala Leu Ala Asp Ser Leu Met Gln Leu Ala Arg Gln
            340                 345                 350

Val Ser Arg Leu Glu Ser Gly Gln
        355                 360

```
<210> SEQ ID NO 80
<211> LENGTH: 6
<212> TYPE: DNA
<213> ORGANISM: Unknown
<220> FEATURE:
<223> OTHER INFORMATION: Description of Unknown:
      Shine-Dalgarno sequence

<400> SEQUENCE: 80 aggagg                                                              6

<210> SEQ ID NO 81
<211> LENGTH: 5
<212> TYPE: PRT
<213> ORGANISM: Campylobacter jejuni

<400> SEQUENCE: 81

Asp Leu Asn Asn Thr
1               5

<210> SEQ ID NO 82
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
tataatattt ttggcagttt gttttaaagg atgtttta                          38
```

FOOD SAFETY VACCINE TO CONTROL *SALMONELLA ENTERICA* AND REDUCE *CAMPYLOBACTER* IN POULTRY

RELATED APPLICATION

This application is a continuation application of U.S. patent application Ser. No. 16/480,904, filed on Jul. 25, 2019, which, in turn, is a 35 U.S.C. § 371 national stage filing of International Application No. PCT/US2018/015438, filed on Jan. 26, 2018, which in turn claims priority to U.S. Provisional Application No. 62/451,146, filed on Jan. 27, 2017. The entire contents of each of the foregoing applications is expressly incorporated herein by reference.

GOVERNMENTAL RIGHTS

This invention was made with government support under Grant No. 12229724 awarded by the National Institute of Food and Agriculture of the United States Department of Agriculture. The government has certain rights in the invention.

REFERENCE TO SEQUENCE LISTING

This application contains a Sequence Listing in computer readable form, which has been submitted electronically via EFS-web in ASCII format. Said ASCII copy, created on Mar. 22, 2021, is named 130667-00203_Seq_Listing and is 170,765 bytes in size. The computer readable form of the sequence listing is part of the specification or is otherwise incorporated herein by reference.

BACKGROUND

Foodborne human pathogens are a major public health problem. In particular, *Campylobacter* and *Salmonella* are leading causes of bacterial foodborne disease worldwide. *Campylobacter* gastroenteritis is associated with poor handling of raw chicken or consumption of undercooked chicken. (1)(2) Domestic poultry supply, including chickens, turkeys, ducks, and geese, is frequently infected with *C. jejuni* and *C. coli*. (3) *Salmonella* human infections are associated, in part, with the ingestion of foods contaminated by animal feces or cross-contaminated by other sources, including poultry. (4)(5) The increasing consumption of poultry and poultry products has rendered foodborne diseases associated with poultry a significant public health concern.

Strategies for controlling *Campylobacter* and *Salmonella* in poultry include the administration of antibiotics. However, the overuse of antibiotics and the risk of developing antibiotic-resistant bacterial strains has decreased interest in the use of antibiotics for these purposes. Thus, poultry vaccination has emerged as an important strategy to mitigate the prevalence of at least these two foodborne pathogens in poultry supplies.

Recombinant attenuated *Salmonella* vaccines (RASVs) have been developed as vaccines and antigen delivery systems to stimulate protective immune responses against a multitude of antigens. Improved RASVs that are engineered to include inducible promoter-regulated pathogenic attributes have been recently developed. Improvements in this technology has included the development of Regulated Delayed Attenuated RASVs (RDA RASVs) which are grown in vitro in the presence of an inducer (e.g., a sugar) to induce the expression of genes associated with pathogenesis. Upon administration to a subject, the RDA RASVs replicate with full virulence and colonize lymphoid tissues to induce potent immune responses. However, as the levels of inducer decreases within the subject and after multiple rounds of replication, the RDA RASVs become attenuated, thereby preventing further proliferation of the bacteria in vivo.

The use of RASVs for the prophylaxis and treatment of foodborne pathogens in poultry is particularly promising. However, new means to enhance the immunogenicity and safety of the vaccines in vivo are necessary. RASVs and pharmaceutical compositions capable of inducing potent immune responses to multiple foodborne pathogens in poultry are particularly desirable.

SUMMARY

The instant disclosure provides strains of recombinant bacteria, including *Salmonella*, with enhanced immunogenic properties and desirable safety features. The recombinant bacteria can be safely used to effectively deliver antigenic compounds to a subject (e.g., poultry) in order to mount potent immunogenic responses against pathogens such as *Campylobacter* and *Salmonella*. These strains deliver multiple conserved protective *Salmonella* surface/secreted antigens and/or *Campylobacter* N-glycan modified surface/secreted antigens to induce protective immunity.

In some embodiments, disclosed herein is a recombinant derivative of a pathogenic bacterium, comprising regulated-delayed attenuation, a regulated-delayed synthesis of an antigen of interest, a regulated-delayed lysis in vivo phenotype, and synthesizing and delivering one or more protein antigens of *C. jejuni*.

In some embodiments, the recombinant bacteria described herein are capable of synthesizing and attaching a *Campylobacter* N-glycan to an antigen of interest in order to enhance the immunogenicity of the antigen in vivo. The recombinant bacteria may depend on two or three sugars to regulate the virulence phenotype of the bacteria by controlling the expression of multiple virulence genes and, optionally, the antigen of interest, as well as a regulated delayed lysis phenotype, allowing for biological containment and the enhancement of immunogenic properties. The dependence on multiple sugars enhances the safety of the recombinant bacteria, given the improbability that the organisms will encounter all sugars in a naturally-occurring environment. See PCT/US18/14860, filed on Jan. 23, 2018, the entire contents of which are expressly incorporated herein by reference.

Specifically, the bacteria disclosed herein are based upon a recombinant attenuated *Salmonella* vaccine (RASV) derived from the highly avian virulent S. *Typhimurium* UK-1 strain and can be used to synthesize and deliver multiple *Campylobacter jejuni* conserved protective protein antigens. Vaccination with these RASVs have been found to induce immunity against multiple *Salmonella* serotypes and *C. jejuni* infecting poultry. The instant disclosure further provides an innovative new RASV design strategy to generate these food safety vaccines that induce superior levels of protective immunity to several poultry pathogens. These RASV vectors were programed to undergo regulated delayed lysis in various cell compartments within the immunized animal to induce superior mucosal and systemic antibody and cellular immunities. In addition, these live RASVs display complete biological containment with no persistence in vivo and no survival if excreted. Widespread use of these RASVs is predicted to substantially reduce Salmonella and C. jejuni infections and ultimately eliminate C. jejuni colonization of chickens to reduce transmission of these pathogens through the food chain to humans. Furthermore, the use of these much improved vector systems will also decrease use of antibiotics during poultry husbandry and thus reduce the selective pressure for drug-resistant bacterial species that can also be transmitted through the food chain to humans.

The instant disclosure further provides a validated and highly immunogenic S. typhimurium UK-1 RASV that displays regulated delayed attenuation, regulated delayed synthesis of recombinant antigens and regulated delayed lysis phenotypes. Derivatives were constructed that are enabled to synthesize and deliver multiple C. jejuni protein antigens. Thus, because of the RASV's inability to synthesize the serotype-specific LPS O-antigen in vivo to expose the LPS core that is the same in all, Salmonella serotypes induce cross protective immunity to most Salmonella serotypes while also delivering multiple C. jejuni protein antigens to induce superior protective immunity against C. jejuni.

The RASVs constructed were designed to display at the time of course spray or oral delivery to poultry the same attributes as the wild-type virulent UK-1 parent strain to contend with host defense strategies, and successfully invade through mucosal surfaces to efficiently colonize internal effector lymphoid tissues before displaying the attenuation phenotype, and thus the inability to induce any disease symptoms or impair or reduce growth. The RASVs reaching these internal tissues were found to gradually commence to serve as factories to synthesize protective C. jejuni antigens to be delivered by secretion and ultimately by lysis of the RASV. Since lysis is enabled to occur in diverse extracellular and intracellular compartments, desired mucosal, systematic antibody and cellular immune responses were induced. These innovative strategies provide a classical means of attenuation used previously that reduced immunogenicity because of impaired colonizing abilities of attenuated strains. In addition, these RASVs with the regulated delayed lysis phenotype display completed biological containment with no persistence of vaccine cells in vivo and no survivors if excreted.

In one aspect, disclosed herein is a recombinant derivative of a pathogenic bacterium comprising a regulated-delayed attenuation phenotype; a regulated-delayed expression of an antigen of interest; a regulated-delayed lysis in vivo phenotype; and which is capable of synthesizing and delivering one or more protein antigens of C. jejuni. In one embodiment, the bacterium further comprises mutations that cause display of the universal LPS core polysaccharide in vivo.

In one aspect, disclosed herein is a recombinant derivative of a pathogenic bacterium comprising a regulated-delayed attenuation phenotype; a regulated-delayed expression of an antigen of interest; a regulated-delayed lysis in vivo phenotype; and which is capable of synthesizing and delivering one or more protein antigens that display the Campylobacter jejuni N-glycan.

In one aspect, disclosed herein is a recombinant derivative of a pathogenic bacterium comprising a regulated-delayed attenuation phenotype; a regulated-delayed expression of an antigen of interest; a regulated-delayed lysis in vivo phenotype; and which is capable of synthesizing and delivering one or more protein antigens of C. jejuni and also displays the Campylobacter jejuni N-glycan.

In one embodiment, the bacterium comprises one or more Campylobacter pgl operon genes. In one embodiment, the one or more Campylobacter pgl operon genes are codon-optimized for expression in the bacterium.

In one embodiment, the bacterium is a Gram-negative bacterium. In one embodiment, the bacterium belongs to the family Enterobacteriaceae.

In one embodiment, the antigen of interest is a Campylobacter antigen. In one embodiment, the Campylobacter antigen is an antigen selected from Table 4, or an antigen having homology or identity thereto, as described herein. In one embodiment, the antigen of interest is selected from the group consisting of PebI, CjaA, Dps, TlyA, Omp18, Cj0998c, Cj0034c, Cj0168c, Cj0248, Peb3, CmeC, Cj0404, Cj0420, Cj0427, Cj0428, PorA, FlaA, CadF, and Cj1656c.

In one embodiment, the C. jejuni N-glycan is attached to the antigen of interest.

In one embodiment, the bacterium comprises insertion of all or part of the cj1433c gene into a deletion of the ompA gene to generate a fusion of the Cj1433c protein.

In one embodiment, the regulated-delayed attenuation is conferred by the gene fur or mntR.

In one embodiment, the regulated-delayed lysis in vivo phenotype is conferred by $\Delta P_{murA}$::TT araC $P_{BAD}$ murA, $\Delta asdA$::TT araC $P_{BAD}$ c2, or $\Delta$(wza-wcAM) deletions or deletion/insertion mutations.

In one embodiment, the bacterium further comprises a mutation in the sifA gene.

In one embodiment, the bacterium further comprises a mutation in the relA gene.

In one aspect, disclosed herein is a pharmaceutical composition comprising the recombinant bacterium, and a pharmaceutically acceptable carrier. In one embodiment, the pharmaceutical composition further comprises a second recombinant derivative of a pathogenic bacterium, wherein said bacterium comprises a nucleic acid encoding a second antigen of interest. In one embodiment, the second antigen of interest is a Salmonella antigen.

In one aspect, disclosed herein is a method for inducing protective immunity in an avian, the method comprising administering to the avian an effective amount of a pharmaceutical composition disclosed herein.

Other aspects and iterations of the invention are described more thoroughly below.

BRIEF DESCRIPTION OF THE FIGURES

In FIG. 1A, representative samples of splenic lymphocytes isolated from chickens immunized with the non-lysis vector control RASV χ11840(pYA3342) (G2), non-lysis RASV χ11442(pYA5301) (G3), non-lysis ΔsifA RASV χ11840(pYA5301) (G4), lysis vector control RASV χ11791(pYA3681) (G5), lysis RASV χ11730(pYA5293) (G6), and lysis ΔsifA RASV χ11791(pYA5293) (G7), were labeled with CSFE and stimulated with the Eimeria SO7 antigen. The proliferative lymphocyte population was defined by CFSE dilution. FIG. 1B presents a graphic analysis of cell proliferation in each group described in FIG. 1A. Bar, mean, and SD are the sum of 3 independent experiments each using three chickens per group. Asterisks represent significant differences between the groups as indicated ($p<0.05$). Also correlated with increased INF-γ and IL-2 production and increased CD4 and CD8 responses.

FIGS. 1C and 1D depict the induction of intestinal immunoglobulin A (IgA) against E. tenella SO7 in immunized chickens, either on day 35 post-immunization (FIG. 1C) or on day 42 post-immunization (FIG. 1D).

FIG. 2A depicts SO7-specific CD4 and CD8 proliferation analysis in non-lysis versus lysis RASVs without and with escape from SCV due to the ΔsifA mutation.

Figure 1B:
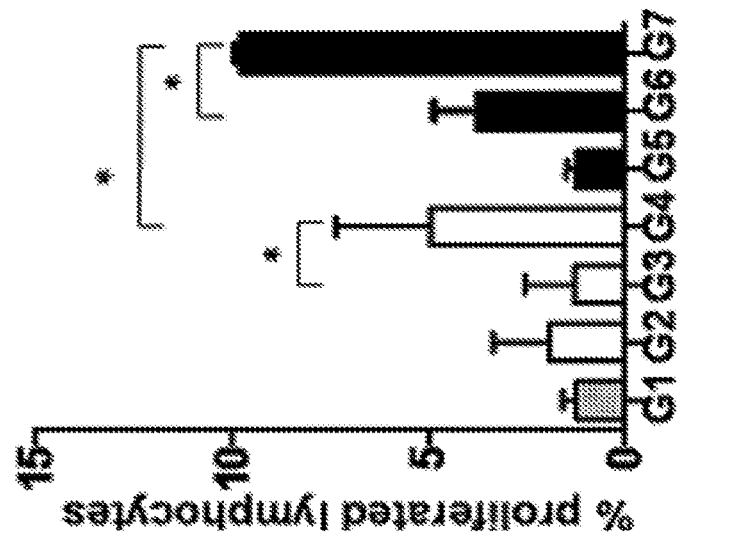
FIGS. 1A and 1B depict proliferation assays of antigen-specific lymphocytes.

In the presence of arabinose, the AraC protein is a positive regulatory element that allows expression from $P_{araBAD}$. In the absence of arabinose, the AraC protein represses expression from $P_{BAD}$. Other enteric bacteria contain arabinose regulatory systems homologous to the araC-araBAD system from *E. coli*, including, for example, *S. typhimurium*. For example, the *E. coli* AraC protein only activates *E. coli* $P_{araBAD}$ (in the presence of arabinose) and not *S. typhimurium* $P_{araBAD}$. Thus, an arabinose-regulated promoter may be used in a recombinant bacterium that possesses a similar arabinose operon, without substantial interference between the two, if the promoter and the operon are derived from two different species of bacteria. Generally speaking, the concentration of arabinose necessary to induce expression is typically less than about 2% (w/w) in a culture media. In some embodiments, the concentration is less than about 1.5%, 1%, 0.5%, 0.2%, 0.1%, or 0.05% (w/w) in a culture media. In other embodiments, the concentration is 0.05% or below, e.g. about 0.04%, 0.03%, 0.02%, or 0.01% (w/w). In an exemplary embodiment, the concentration is about 0.05% (w/w) in a culture media.

In other embodiments, the promoter may be responsive to the level of maltose in the environment, otherwise referred to herein as a "maltose-regulatable promoter". In some embodiments, the recombinant bacteria described herein are cultured in a medium comprising maltose. The malT gene encodes MalT, a positive regulator of four maltose-responsive promoters ($P_{PQ}$, $P_{EFG}$, $P_{KBM}$, and $P_S$). The combination of malT and a mal promoter creates a tightly regulated expression system that has been shown to work as a strong promoter induced in the presence of maltose. Unlike the araC-$P_{araBAD}$ system, malT expression is regulated by a promoter (i.e., $P_T$) that is functionally unrelated to the other mal promoters. $P_T$ is not regulated by MalT. The malEFG-malKBM promoter is a bidirectional promoter that controls expression of the malKBM nucleic acid sequences in one direction, and the malEFG nucleic acid sequences in the other direction. For convenience, the portion of the malEFG-malKBM promoter that mediates expression of the malKBM nucleic acid sequence, and which is controlled by MalT, is referred to herein as $P_{malKBM}$, and the portion of the malEFG-malKBM promoter that mediates expression of the malEFG nucleic acid sequence, and which is controlled by MalT, is referred to herein as $P_{EFG}$. Full induction of $P_{KBM}$ requires the presence of the MalT binding sites of $P_{malEFG}$. For use in the vectors and systems described herein, a gene cassette comprising a nucleic acid sequence encoding MalT and a mal promoter may be used. This gene cassette is referred to herein as malT-$P_{mal}$. In the presence of maltose, the MalT is a positive regulatory element that allows for expression mediated by $P_{mal}$. Generally speaking, the concentration of maltose necessary to induce expression is typically less than about 1% (w/w) in a culture media. In some embodiments, the concentration is less than about 1.0%, 0.9%, 0.8%, 0.7%, 0.6%, 0.5%, 0.4%, 0.3% 0.2%, 0.1%, or 0.05% (w/w) in a culture media. In other embodiments, the concentration is 0.05% or below, e.g. about 0.04%, 0.03%, 0.02%, or 0.01% (w/w). In an exemplary embodiment, the concentration is about 0.2% to about 0.4% (w/w) in a culture media.

In still other embodiments, the promoter used herein is responsive to the level of rhamnose in the environment, otherwise referred to herein as a "rhamnose-regulatable promoter". Analogous to the araC-$P_{araBAD}$ system described above, the rhaRS-$P_{rhaB}$ activator-promoter system is tightly regulated by rhamnose. Expression from the rhamnose promoter ($P_{rha}$) is induced to high levels in the presence of rhamnose. In some embodiments, the bacteria are cultured in the presence of rhamnose. Rhamnose is commonly found in bacteria but rarely found in human subjects. The rhaBAD operon is controlled by the $P_{rhaBAD}$ promoter. This promoter is regulated by two activators, RhaS and RhaR, and the corresponding nucleic acid sequences belong to one transcription unit that is located in the opposite direction of the rhaBAD nucleic acid sequences. In the presence of L-rhamnose, RhaR binds to the $P_{rhaRS}$ promoter and activates the production of RhaR and RhaS. RhaS together with L-rhamnose, in turn, bind to the $P_{rhaBAD}$ and the $P_{rhaT}$ promoters and activates the transcription of the structural nucleic acid sequences. Full induction of the arabinose, maltose and rhamonse regulated promoters described herein requires binding of the Crp-cAMP complex, which is a key regulator of catabolite repression.

Although both L-arabinose and L-rhamnose act directly as inducers of the expression of regulons that mediate their catabolism, important differences exist in regard to the regulatory mechanisms. L-Arabinose acts as an inducer with the activator AraC in the positive control of the arabinose regulon. However, the L-rhamnose regulon is subject to a regulatory cascade, and is therefore subject to even tighter control than the araC-$P_{araBAD}$ system. L-Rhamnose acts as an inducer with the activator RhaR for synthesis of RhaS, which in turn acts as an activator in the positive control of the rhamnose regulon. In the present disclosure, rhamnose may be used to interact with the RhaR protein and then the RhaS protein may activate transcription of a nucleic acid sequence operably-linked to the $P_{rhaBAD}$ promoter.

In still other embodiments, the promoter may be responsive to the level of xylose in the environment, referred to herein as a "xylose-regulatable promoter". Generally, xylose concentrations of between 0.0002% to 0.63% (w/w) in the environment activate the expression of a xylose inducible promoter described herein. (6) The xylR-$P_{xyla}$ system is another well-established inducible activator-promoter system. Xylose induces xylose-specific operons (e.g., xylE, xylFGHR, and xylAB) which are regulated by XylR and the cyclic AMP-Crp system. The XylR protein serves as a positive regulator by binding to two distinct regions of the xyl nucleic acid sequence promoters. As with the araC-$P_{araBAD}$ system described above, the xylR-$P_{xylAB}$ and/or xylR-$P_{xylFGH}$ regulatory systems may be used. In these embodiments, xylR-$P_{xylAB}$ xylose interacting with the XylR protein activates transcription of nucleic acid sequences operably-linked to either of the two $P_{xyl}$ promoters.

As used herein, the term "exogenous" refers to a substance (e.g., a nucleic acid or polypeptide) present in a cell other than its native source. The term exogenous can refer to a nucleic acid or a protein that has been introduced by a process involving the hand of man into a biological system such as a cell or organism in which it is not normally found or in which it is found in undetectable amounts. A substance can be considered exogenous if it is introduced into a cell or an ancestor of the cell that inherits the substance. In contrast, the term "endogenous" refers to a substance that is native to the biological system or cell.

As used herein, the term "invasive" when used in reference to a bacterium refers to a bacterium that is able to be absorbed by an eukaryotic cell, or a bacterium that actively penetrates an eukaryotic cell. In some embodiments, an invasive bacterium penetrates an eukaryotic cell and reaches the eukaryotic cell cytoplasm by lysis of a vacuolar membrane.

As used herein, the term "pathogenic" when used in reference to a bacterium refers to a bacterium capable of infecting and causing disease in a host, as well as producing infection-related symptoms in the infected host. A bacterial species that is a pathogen and is pathogenic can be rendered attenuated or avirulent such that it no longer produces infection-related symptoms in the infected host. Such bacteria are referred to as "attenuated derivatives of pathogenic bacteria."

A "pharmaceutical composition," as used herein, refers to a composition comprising an active ingredient (e.g., a recombinant bacterium described herein) with other components such as a physiologically suitable carrier and/or excipient.

As used herein, the term "pharmaceutically acceptable carrier" or a "pharmaceutically acceptable excipient" refers to a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline (e.g., phosphate-buffered saline (PBS)); (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, disintegrating agents, binders, sweetening agents, flavoring agents, perfuming agents, protease inhibitors, plasticizers, emulsifiers, stabilizing agents, viscosity increasing agents, film forming agents, solubilizing agents, surfactants, preservative and antioxidants can also be present in the formulation. The terms such as "excipient", "carrier", "pharmaceutically acceptable excipient" or the like are used interchangeably herein.

A "plasmid" or "vector" includes a nucleic acid construct designed for delivery to a host cell or transfer between different host cell. The nucleic acid incorporated into the plasmid can be operatively linked to an expression control sequence when the expression control sequence controls and regulates the transcription and translation of that polynucleotide sequence.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. The terms "protein" and "polypeptide" as used herein refer to both large polypeptides and small peptides. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

A "nucleic acid" or "nucleic acid sequence" may be any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA, rRNA, and tRNA.

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations are very well established and include, for example, those disclosed by Walder et al. (7); Bauer et al. (8); Craik (9); Smith et al. (10); and U.S. Pat. No. 4,518,584 (11) and U.S. Pat. No. 4,737,462 (12), which are herein incorporated by reference in their entireties. Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

The term "statistically significant" or "significantly" refers to statistical significance and generally means a two standard deviation (2SD) or greater difference.

As used herein, the term "host cell" refers to a cell in an organism to which the recombinant bacterium is being administered in order to, for example, induce an immune response. In one embodiment, a host is a bird, equine, or human and a host cell refers, respectively, to a bird cell, an equine cell, or a human cell.

Other than in the operating examples, or where otherwise indicated, all numbers expressing quantities of ingredients or reaction conditions used herein should be understood as modified in all instances by the term "about." The term "about" when used in connection with percentages can mean±1%.

The articles "a" and "an," as used herein, should be understood to mean "at least one," unless clearly indicated to the contrary.

The phrase "and/or," when used between elements in a list, is intended to mean either (1) that only a single listed element is present, or (2) that more than one element of the list is present. For example, "A, B, and/or C" indicates that the selection may be A alone; B alone; C alone; A and B; A and C; B and C; or A, B, and C. The phrase "and/or" may be used interchangeably with "at least one of" or "one or more of" the elements in a list.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

I. Recombinant Bacteria

The present disclosure provides, in some embodiments, a recombinant bacterium capable of regulated expression of at least one nucleic acid sequence encoding an antigen of interest (e.g., a *Campylobacter* antigen). The recombinant bacterium described herein is particularly effective in eliciting an immune response (e.g., protective immunity) against the antigen of interest because the bacterium comprise multiple recombinant regulatory systems that permit the bacterium to replicate upon administration and to colonize lymphoid tissues in a subject in order to elicit potent immune responses. However, after multiple replication cycles in vivo, the bacterium ultimately exhibits an attenuated phenotype which allows for safe administration to a subject, for example as a vaccine composition. The recombinant regulatory systems of the bacteria described herein depend, in part, on multiple genetic regulatory elements that are responsive to one or more sugars (e.g., arabinose, rhamnose, mannose, maltose, xylose, and galactose) that not available to the bacterium in vivo. Thus, using the phenotype of the recombinant bacteria described herein can be altered upon administration to a subject. In some embodiments, the phenotype of the recombinant bacteria described herein is regulated-delayed expression of an antigen of interest, and the gene conferring the phenotype encodes an antigen of interest. In some embodiments, the subject is administered one or more sugars before, after or concurrently with the administration of a recombinant bacterium described herein in order to activate and/or repress a sugar-responsive regulatory system of the bacteria. In some embodiments, the recombinant bacterium described herein comprises at least three regulatory systems, each dependent on a different sugar, which facilitates initial invasion of a host cell in the subject, delayed attenuation, and improved immunogenicity.

In some embodiments, the recombinant bacterium described herein can be regulated for delayed attenuation in vivo. In some embodiments, the recombinant bacterium described herein is capable of regulated delayed expression of a nucleic acid encoding an antigen of interest. In some embodiments, the recombinant bacterium described herein exhibits regulated production of Generalized Modules for Membrane Antigens (GMMA) in vivo, which may lead to enhanced production of conserved outer membrane proteins present in the bacterium, and ultimately improved immunogenicity. In some embodiments, the recombinant bacterium described herein is capable of both regulated expression of at least one nucleic acid encoding at least one antigen of interest and regulated attenuation. In some embodiments, the recombinant bacterium described herein is capable of both regulated expression of at least one nucleic acid encoding at least one antigen of interest and regulated production of GMMA in vivo. In some embodiments, the recombinant bacterium described herein is capable of both regulated production of GMMA in vivo, and regulated attenuation. In some embodiments, the recombinant bacterium described herein is capable of regulated expression of at least one nucleic acid encoding at least one antigen of interest, regulated attenuation, and regulated production of GMMA in vivo. In some embodiments, each of these properties is directly or indirectly regulated by the abundance of at least one sugar (e.g., arabinose, rhamnose, mannose, xylose, maltose, and galactose).

In some embodiments, the bacterium described herein is a Gram negative bacterium. In some embodiments, the bacterium is a pathogenic bacterium. In some embodiments, the bacterium is an avirulent bacterium. In some embodiments, the bacterium belongs to the *Enterobaceteriaceae*. In some embodiments, the bacterium belongs to a genus selected from: *Alterococcus, Aquamonas, Aranicola, Arsenophonus, Brenneria, Budvicia, Buttiauxella, Candidatus Phlomobacter, Cedeceae, Citrobacter, Edwardsiella, Enterobacter, Erwinia, Escherichia, Ewingella, Hafnia, Klebsiella, Kluyvera, Leclercia, Leminorella, Moellerella, Morganella, Obesumbacterium, Pantoea, Pectobacterium, Photorhabdus, Plesiomonas, Pragia, Proteus, Providencia, Rahnella, Raoultella, Salmonella, Samsonia, Serratia, Shigella, Sodalis, Tatumella, Trabulsiella, Wigglesworthia, Xenorhbdus, Yersinia, Yokenella*. In some embodiments, the bacterium is a pathogenic species of *Enterobaceteriaceae*. In some embodiments, the bacterium is selected from the group consisting of *Escherichia coli, Shigella, Edwardsiella, Salmonella, Citrobacter, Klebsiella, Enterobacter, Serratia, Proteus, Morganella, Providencia* and *Yersinia*. In some embodiments, the bacterium is of the genus *Salmonella*. In some embodiments, the bacterium is of the genus *Yersinia*. In some embodiments, the bacterium is of the genus *Edwardsiella*. In some embodiments, the bacterium is of a genus, species, or strain commonly used as a live or attenuated vaccine.

Some embodiments of the instant disclosure comprise a species or subspecies of the *Salmonella* genera (e.g., *S. enterica* or *S. bongori*). For instance, the recombinant bacterium may be a *Salmonella enterica* serovar, including, for example, Paratyphi A, *Enteritidis, Typhi*, and *Typhimurium*. In some embodiments, the recombinant bacterium is of the serovar *S. Typhimurium, S. Typhi, S. Paratyphi, S. Gallinarum, S. Enteritidis, S. Choleraesius, S. Arizonae, S. Newport, S. Heidelberg, S. Infantis, S. Cholerasiuis*, or *S. Dublin*.

A recombinant bacterium derived from *Salmonella* may be particularly suited to use as a vaccine. For example, oral infection of a host with a *Salmonella* strain typically leads to colonization of the gut-associated lymphoid tissue (GALT), which leads to the induction of a generalized mucosal immune response to the recombinant bacterium. Further penetration of the bacterium into the mesenteric lymph nodes, liver and spleen may augment the induction of systemic and cellular immune responses directed against the bacterium. Thus, the use of recombinant *Salmonella* for oral immunization stimulates all three branches of the immune system, which is particularly important for immunizing against infectious disease agents that colonize on and/or invade through mucosal surfaces. In some embodiments, the recombinant bacterium described herein is used to induce an immune response in poultry (e.g., as a vaccine). When used in poultry, the recombinant bacterium may be administered by course spray and thereby inoculate the conjunctiva-associated lymphoid tissue (CALT) via eye exposure, the nasal-associated lymphoid tissue (NALT) and bronchus-associated lymphoid tissue (BALT) via respiratory exposure and the GALT via oral exposure. In some embodiments, the recombinant bacterium described herein is administered to newly-hatched chicks.

A. Antigens

As used herein, "antigen" refers to a biomolecule capable of eliciting an immune response in a host. In some embodiments, an antigen may be a protein, or fragment of a protein. In some embodiments, the recombinant bacterium comprises a nucleic acid (e.g., a plasmid) encoding an antigen of interest, wherein the nucleic acid is expressed by the host cell (e.g., a DNA vaccine). In some embodiments, the recombinant bacterium comprises a nucleic acid encoding an antigen of interest. In some embodiments, the recombinant bacterium comprises at least one, at least two, at least three, at least four, at least five, at least six, at least seven, at least eight or more nucleic acids encoding an antigen of interest (e.g., one or more copies of a nucleic acid encoding a specific antigen, one or more nucleic acids encoding different antigens of interest, or combinations thereof). In an exemplary embodiment, the antigen elicits a protective immune response in a subject.

As used herein, "protective" means that the immune response contributes to the lessening of any symptoms associated with infection of a host with the pathogen the antigen was derived from or designed to elicit a response against. For example, a protective antigen from a pathogen, such as Salmonella, may induce an immune response that helps to ameliorate symptoms associated with Salmonella infection or reduce the morbidity and mortality associated with infection with the pathogen or may reduce the ability of Salmonella to infect and colonize the host. The use of the term "protective" in this disclosure does not necessarily require that the host is completely protected from the effects of the pathogen.

C. jejuni is a commensal for poultry and causes no disease symptoms. Thus, when "protective" immunity to C. jejuni is induced in poultry, this refers to the ability of the vaccine to reduce the levels of Cj colonization in the intestine and ceca. This is also true for Salmonella. Thus, although several stains of Salmonella can cause disease and mortality in newly hatched chicks, chicks become totally tolerant of Salmonella by one week of age, after which most strains of Salmonella persist in the GI tract as a commensal.

In some embodiments, the antigen of interest is an antigen derived from an infectious agent. In some embodiments, the antigen of interest is derived from an infectious agent selected from the group consisting of a virus, a bacteria, a protozoan, a prion, a fungi, and a helminth. In some embodiments, the antigen of interest is derived from a bacteria.

Alternatively, antigens may be derived from organisms newly identified or newly associated with a disease or pathogenic condition, or new or emerging pathogens of animals or humans, including those now known or identified in the future, may be expressed by a bacterium detailed herein. Furthermore, antigens are not limited to those from pathogenic organisms.

Immunogenicity of the bacterium may be augmented and/or modulated by constructing strains that also express sequences for cytokines, adjuvants, and other immunomodulators.

Some examples of microorganisms useful as a source for antigen are listed below. These may include microorganisms for the control of plague caused by Yersinia pestis and other Yersinia species such as Y. pseudotuberculosis and Y. enterocolitica, for the control of gonorrhea caused by Neisseria gonorrhoea, for the control of syphilis caused by Treponema pallidum, and for the control of venereal diseases as well as eye infections caused by Chlamydia trachomatis. Species of Streptococcus from both group A and group B, such as those species that cause sore throat or heart diseases, Streptococcus equi, which causes strangles in equines, Streptococcus mutans, which causes cavities, and Streptococcus pneumoniae, Erysipelothrix rhusiopathiae, Neisseria meningitidis, Mycoplasma pneumoniae and other Mycoplasma-species, Hemophilus influenza, Bordetella pertussis, Mycobacterium tuberculosis, Mycobacterium leprae, other Bordetella species, Escherichia coli, Streptococcus equi, Streptococcus pneumoniae, Brucella abortus, Pasteurella hemolytica and P. multocida, Vibrio cholera, Shigella species, Borrellia species, Bartonella species, Heliobacter pylori, Campylobacter species, Pseudomonas species, Moraxella species, Brucella species, Francisella species, Aeromonas species, Actinobacillus species, Clostridium species, Rickettsia species, Bacillus species, Coxiella species, Ehrlichia species, Listeria species, and Legionella pneumophila are additional examples of bacteria within the scope of this disclosure from which antigen nucleic acid sequences could be obtained.

In some embodiments, the antigen is a Campylobacter antigen (e.g., a C. jejuni antigen or a C. coli antigen). In some embodiments, the Campylobacter antigen is selected from the group consisting of Peb1 (encoded by the cj0921c gene), CjaA (encoded by the cj0982c gene), Dps (encoded by the cj1534c gene), TlyA (encoded by the cj0588 gene), Omp18 (encoded by the cj0113 gene), Cj0998c (encoded by the cj0998c gene), Cj0034c (encoded by the cj0034c gene), Cj0168c (encoded by the cj0168c gene), Cj0248 (encoded by the cj0248 gene), Peb3 (encoded by the cj0289 gene), CmeC (encoded by the cj0365 gene), Cj0404 (encoded by the cj0404 gene), Cj0420 (encoded by the cj0420 gene), Cj0427 (encoded by the cj0427 gene), Cj0428 (encoded by the cj0428 gene), PorA (encoded by the cj1259 gene), Fla (encoded by the cj1339c gene), CadF (encoded by the cj1478c gene), and Cj1656c (encoded by the cj1656c gene).

In some embodiments, the Campylobacter antigen comprises a canonical Campylobacter N-glycosylation amino acid sequence. In some embodiments, the canonical Campylobacter N-glycosylation amino acid sequence comprises the amino acid sequence Asp/Glu-Xaa-Asn-Tyr-Ser/Thr (SEQ ID NO: 1). The presence of the canonical Campylobacter N-glycosylation amino acid sequence allows for the glycosylation of the antigen when produced by a recombinant bacterium comprising a pgl operon (e.g., a Campylobacter pgl operon) or one or more pgl operon genes (e.g., wlaA, gne, pglK, pglH, pglI, pglJ, pglB, pglA, pglC, pglD, wlaJ, pglE, pglF, and pglG). In one embodiment, the PglB enzyme can add the N-glycan to a slightly different aa sequence, DGGK (SEQ ID NO: 2), different from the N-glycosylation sequence used in eukaryotes (Barre et al., 2017. Glycobiology 27:978-989).

In some embodiments, the antigen of interest comprises a native canonical Campylobacter N-glycosylation amino acid sequence. In some embodiments, the antigen of interest is engineered to comprise at least one non-native canonical Campylobacter N-glycosylation amino acid sequence Asp/Glu-Xaa-Asn-Tyr-Ser/Thr (SEQ ID NO: 1), such that the antigen is N-glycosylated when produced by a recombinant bacterium comprising a pgl operon (e.g., a Campylobacter pgl operon) or one or more pgl operon genes.

In certain embodiments, an antigen may comprise a B-cell epitope or a T-cell epitope. Alternatively, an antigen to which an immune response is desired may be expressed as a fusion to a carrier protein that contains a strong promiscuous T-cell epitope and/or serves as an adjuvant and/or facilitates presentation of the antigen to enhance, in all cases, the immune response to the antigen or its component part. This can be accomplished by methods known in the art. Fusion to tetanus toxin fragment C, CT-B, LT-B and hepatitis virus B core are particularly useful for these purposes, although other epitope presentation systems are well known in the art.

In further embodiments, a nucleic acid sequence encoding an antigen may comprise a secretion signal.

As stated above, the level of synthesis of an antigen of interest may be optimized by modifying the nucleic acid sequence encoding the repressor and/or promoter. As used herein, "modify" refers to an alteration of the nucleic acid sequence of the repressor and/or promoter that results in a change in the level of transcription of the nucleic acid sequence encoding the repressor, or that results in a change in the level of synthesis of the repressor. For instance, in one embodiment, modify may refer to altering the start codon of the nucleic acid sequence encoding the repressor. Generally speaking, a GTG or TTG start codon, as opposed to an ATG start codon, may decrease translation efficiency ten-fold. In another embodiment, modify may refer to altering the Shine-Dalgarno (SD) sequence of the nucleic acid sequence encoding the repressor. The SD sequence is a ribosomal binding site generally located 6-7 nucleotides upstream of the start codon. The SD consensus sequence is AGGAGG (SEQ ID NO:80), and variations of the consensus sequence may alter translation efficiency. In yet another embodiment, modify may refer to altering the distance between the SD sequence and the start codon. In still another embodiment, modify may refer to altering the −35 sequence for RNA polymerase recognition. In a similar embodiment, modify may refer to altering the −10 sequence for RNA polymerase binding. In an additional embodiment, modify may refer to altering the number of nucleotides between the −35 and −10 sequences. In an alternative embodiment, modify may refer to optimizing the codons of the nucleic acid sequence encoding the repressor to alter the level of translation of the mRNA encoding the repressor. For instance, non-A rich codons initially after the start codon of the nucleic acid sequence encoding the repressor may not maximize translation of the mRNA encoding the repressor. Similarly, the codons of the nucleic acid sequence encoding any of the proteins described herein may be codon-optimized, i.e., altered so as to mimic the codons from highly synthesized proteins of a particular organism. In a further embodiment, modify may refer to altering the GC content of the nucleic acid sequence encoding the repressor to change the level of translation of the mRNA encoding the repressor. Methods of modifying a nucleic acid sequence are known in the art.

In some embodiments, more than one modification or type of modification may be performed to optimize the expression level of a nucleic acid described herein (e.g., a nucleic acid encoding a repressor or antigen of interest). For instance, at least one, two, three, four, five, six, seven, eight, or nine modifications, or types of modifications, may be performed to optimize the expression level of a nucleic acid described herein. By way of non-limiting example, when the repressor is LacI, then the nucleic acid sequence of LacI and the promoter may be altered so as to increase the level of LacI synthesis. In one embodiment, the start codon of the LacI repressor may be altered from GTG to ATG. In another embodiment, the SD sequence may be altered from AGGG to AGGA. In yet another embodiment, the codons of lacI may be optimized according to the codon usage for highly synthesized proteins of *Salmonella*. In a further embodiment, the start codon of lac' may be altered, the SD sequence may be altered, and the codons of lacI may be optimized.

In some embodiments, the recombinant bacterium comprises a nucleic acid that is located in a plasmid or vector. As used herein, "vector" refers to an autonomously replicating nucleic acid unit. The present disclosure can be practiced with any known type of vector, including viral, cosmid, phasmid, and plasmid vectors. The most preferred type of vector is a plasmid vector. In some embodiments, the plasmid or vector is a high copy plasmid. In some embodiments, the plasmid or vector is a low copy plasmid or vector.

As is well known in the art, plasmids and other vectors may possess a wide array of promoters, multiple cloning sequences, transcription terminators, etc., and vectors may be selected so as to control the level of expression of the nucleic acid sequence encoding an antigen by controlling the relative copy number of the vector. In some instances in which the vector might encode a surface localized adhesin as the antigen, or an antigen capable of stimulating T-cell immunity, it may be preferable to use a vector with a low copy number such as at least two, three, four, five, six, seven, eight, nine, or ten copies per bacterial cell. A non-limiting example of a low copy number vector may be a vector comprising the pSC101 ori.

In some embodiments, the plasmid comprises a nucleic acid sequence encoding an aspartate-semialdehyde dehydrogenase gene (e.g., asdA). These plasmids may be advantageously used to complement a bacterium that comprises an aspartate-semialdehyde dehydrogenase gene (e.g., asdA). In some embodiments, the plasmid is selected from the group consisting of pYA3342, pYA3337, and pYA3332.

In other cases, an intermediate copy number vector might be optimal for inducing desired immune responses. For instance, an intermediate copy number vector may have at least 10, 11, 12, 13, 14, 15, 16, 17, 18, 19, 20, 21, 22, 23, 24, 25, 26, 27, 28, 29, or 30 copies per bacterial cell. A non-limiting example of an intermediate copy number vector may be a vector comprising the p15A ori.

In still other cases, a high copy number vector might be optimal for the induction of maximal antibody responses. A high copy number vector may have at least 31, 35, 40, 45, 50, 55, 60, 65, 70, 75, 80, 85, 90, 95, or 100 copies per bacterial cell. In some embodiments, a high copy number vector may have at least 100, 125, 150, 175, 200, 225, 250, 275, 300, 325, 350, 375, or 400 copies per bacterial cell. Non-limiting examples of high copy number vectors may include a vector comprising the pBR ori or the pUC ori.

Additionally, vector copy number may be increased by selecting for mutations that increase plasmid copy number. These mutations may occur in the bacterial chromosome but are more likely to occur in the plasmid vector.

Preferably, vectors used herein do not comprise antibiotic resistance markers to select for maintenance of the vector.

In some embodiments, the nucleic acid sequences described herein are operably-linked to a promoter. Promoters for use in the embodiments described herein are known in the art. One of skill in the art would recognize that the selection of a repressor dictates, in part, the selection of the promoter to be used to regulate the expression of a nucleic acid described herein. For instance, if the repressor is LacI, then the promoter may be selected from the group consisting of LacI responsive promoters, such as $P_{trc}$, $P_{lac}$, $P_{T7lac}$ and $P_{tac}$. If the repressor is C2, then the promoter may be selected from the group consisting of C2 responsive promoters, such as P22 promoters $P_L$ and $P_R$. If the repressor is C1, then the promoter may be selected from the group consisting of C1 responsive promoters, such as λ promoters $P_L$ and $P_R$.

In each embodiment herein, the promoter regulates expression of a nucleic acid sequence. In some embodiments, the promoter comprises a regulatory sequence controlled by a repressor, such that expression of the nucleic acid sequence is repressed when the repressor is synthesized (e.g., during in vitro growth of the bacterium), but expression of the nucleic acid sequence encoding an antigen is high when the repressor is not synthesized (e.g., in vivo). Generally speaking, the concentration of the repressor will decrease with every cell division after expression of the gene encoding the repressor ceases. In some embodiments, the concentration of the repressor decreases such that high levels of expression of the nucleic acid sequence that is being regulated is achieved after about 2, 3, 4, 5, 6, 7, 8, 9, 10, 11, or 12 divisions of the bacterium. In an exemplary embodiment, the concentration of the repressor decreases enough to allow high-level expression of the nucleic acid sequence encoding an antigen after about 5 divisions of the bacterium in vivo.

In certain embodiments, the promoter may comprise other regulatory elements. For instance, the promoter may comprise lacO if the repressor is LacI. This is the case with the lipoprotein promoter $P_{lpplacO}$ that is regulated by LacI since it possesses the LacI binding domain lacO. In one embodiment, the repressor is a LacI repressor and the promoter is $P_{trc}$.

In some embodiments, the expression of the nucleic acid sequence regulated by a repressor is repressed in vivo. Expression may be "repressed" or "partially repressed" when it is about 50%, 45%, 40%, 35%, 30%, 25%, 20%, 15%, 10%, 5%, 1%, or even less than 1% of the expression under non-repressed conditions. Thus although the level of expression under conditions of "complete repression" might be exceeding low, it is likely to be detectable using very sensitive methods since repression can never by absolute.

Conversely, the expression of the nucleic acid sequence encoding the antigen should be high when the expression of the repressor is repressed. For instance, if the repressor is not expressed during growth of the recombinant bacterium in a host, the expression of the nucleic acid under the control of the repressor will be high. As used herein, "high level" expression refers to expression that is strong enough to elicit an immune response to the antigen. Consequently, the copy number correlating with high level expression can and will vary depending on the antigen and the type of immune response desired. Methods of determining whether an antigen elicits an immune response such as by measuring antibody levels or antigen-dependent T cell populations or antigen-dependent cytokine levels are known in the art, and methods of measuring levels of expression of antigen encoding sequences by measuring levels of mRNA transcribed or by quantitating the expression level of a protein are also known in the art.

In each of the above embodiments, a recombinant bacterium capable of regulated expression may also be attenuated. "Attenuated" refers to the state of the bacterium wherein the bacterium has been weakened from its wild-type fitness by some form of recombinant or physical manipulation. This includes altering the genotype of the bacterium to reduce its ability to cause disease. However, the bacterium's ability to colonize the gut (in the case of *Salmonella*) and induce immune responses is, preferably, not substantially compromised.

In an exemplary embodiment, a recombinant bacterium may be attenuated as described above. In which case, both regulated attenuation and regulated expression of an antigen encoding sequence may be dependent upon a sugar regulatable system. Consequently, the concentration of sugar (e.g., arabinose) needed for optimal expression of the regulated antigen encoding sequence may not be the same as the concentration for optimal expression of attenuation. In an exemplary embodiment, the concentration of arabinose for the optimization of both regulated attenuation and regulated expression of sequences encoding antigen will be substantially the same.

Accordingly, the promoter and/or the nucleic acid sequence encoding an attenuation protein may be modified to optimize the system. Methods of modification are detailed above. Briefly, for example, the SD ribosome binding sequence may be altered, and/or the start codon may be altered from ATG to GTG for the nucleic acid sequences fur and phoPQ, so that the production levels of Fur and PhoPQ are optimal for both the regulated attenuation phenotype and the regulated expression when growing strains with a given concentration of arabinose. One of skill in the art will appreciate that other nucleic acid sequences, in addition to fur and phoPQ, may also be altered as described herein in combination with other well-known protocols. In addition, these attenuating nucleic acid sequences may be regulated by other systems using well-established protocols known to one of skill in the art. For example, they may be regulated using with promoters dependent on addition of maltose, rhamnose, or xylose rather than arabinose.

cj0034c—In some embodiments, the recombinant bacterium comprises a nucleic acid comprising a cj0034c gene (e.g., a *C. jejuni* cj0034c gene).

In some embodiments, the nucleic acid comprising a cj0034c gene is located on a plasmid in the bacterium. In some embodiments, the nucleic acid comprising a cj0034c gene is located on a chromosome of the bacterium.

The nucleic acid sequence of an exemplary *C. jejuni* cj0034c gene is provided below:

```
                                             (SEQ ID NO: 3)
ATGAAAACAAATAATATCTTTATGGCTTTAGCCATAGTTTTGGCAAGTTT

GATTCTAGCTTTTGGATTTAACAAGGCTTTAAGTGATTTTAAAACACTTG

AAAGAAGTGTAAGTGTAAAGGGTTTAAGTCAAAAAGAAGTCGAAGCGGAT

ACTTTGATACTTCCTATAAAATTCACAAGATCAAACAACAATCTTACAAA

TTTATACGAAGAACTAGAACAAGATAAAGAAAATATCATCAAATTTTTAG

AAAAACAAGGCATAAAAGAAGATGAGATCAGCTACAACTCGCCAAATATC

ATAGATCGTTTAAGCGATCCTTATAGCAACGACACTCAAGCTGCATACCG

ATACATAGGCACTGCGAATTTACTCATCTATACTCAAAATGTAAAGCTTG

GAAAAAGCATACTAGAAAACATTTCAAGTCTTGCAAAATTTGGTATAGTA

ACAAAAATCGATGATTATGATATAGAATACCTTTACACCAAGCTAAATGA

TATAAAACCACAAATGATAGAAGAAGCAACGCTCAATGCTAGAAATGCAG

CGATAAAATTCGCACAAGACTCAAACAGCCATCTAGGCAAGATAAAAAAG

GCTTCTCAAGGACAATTTAGCATTAGCAACAGAGATAAAAACACCCCTTA

TATCAAAACCATAAGAGTGGTTTCTACTATAGAATACTACTTAAAAGACT

GA
```

The amino acid sequence of the Cj0034c protein encoded by the nucleic acid of SEQ ID NO: 3 is provided below:

```
                                            (SEQ ID NO: 4)
MKTNNIFMALAIVLASLILAFGFNKALSDFKTLERSVSVKGLSQKEVEAD

TLILPIKFTRSNNNLTNLYEELEQDKENIIKFLEKQGIKEDEISYNSPNI

IDRLSDPYSNDTQAAYRYIGTANLLIYTQNVKLGKSILENISSLAKFGIV

TKIDDYDIEYLYTKLNDIKPQMIEEATLNARNAAIKFAQDSNSHLGKIKK

ASQGQFSISNRDKNTPYIKTIRVVSTIEYYLKD
```

In some embodiments, the nucleic acid comprises a *C. jejuni* cj0034c gene (provided as SEQ ID NO: 3). In some embodiments, the nucleic acid comprises a cj0034c gene, wherein the cj0034c gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 3. In some embodiments, the nucleic acid comprises a cj0034c gene, wherein the cj0034c gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 3.

In some embodiments, the nucleic acid comprises a nucleic acid sequence encoding a Cj0034c protein, wherein said Cj0034c protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 4. In some embodiments, the nucleic acid comprises a nucleic acid sequence encoding a Cj0034c protein, wherein said Cj0034c protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 4.

cj0113—In some embodiments, the recombinant bacterium comprises a nucleic acid comprising a cj0113 gene (e.g., a *C. jejuni* cj0113 gene).

In some embodiments, the nucleic acid comprising a cj0113 gene is located on a plasmid in the bacterium. In some embodiments, the nucleic acid comprising a cj0113 gene is located on a chromosome of the bacterium.

The nucleic acid sequence of an exemplary *C. jejuni* cj0113 gene is provided below:

```
                                            (SEQ ID NO: 5)
ATGAAAAAAGTTTTATTGAGTTCATTGGTTGCGGTGTCTTTGTTAAGCAC

AGGTTTGTTTGCTAAAGAATATACTTTAGATAAAGCACATACAGATGTAG

GTTTTAAAATCAAACATTTACAAATTAGCAATGTAAAAGGAAATTTCAAA

GATTATTCTGCGGTGATTGATTTTGATCCTGCGAGTGCTGAATTTAAAAA

GCTTGATGTAACTATAAAAATCGCATCTGTAAATACAGAAAATCAAACAA

GAGATAATCACTTACAACAAGATGATTTTTTCAAAGCAAAAAAATATCCT

GATATGACTTTTACAATGAAAAAATATGAAAAAATCGATAATGAAAAAGG

CAAAATGACAGGAACTTTAACTATAGCTGGAGTTTCTAAAGATATCGTTT

TAGATGCTGAAATCGGCGGTGTAGCTAAAGGCAAAGATGGAAAAGAAAAA

ATAGGATTTTCTTTAAATGGAAAAATCAAACGCTCTGATTTTAAATTTGC

AACAAGTACTTCAACTATTACTTTAAGTGATGATATTAATTTAAATATCG

AAGTTGAAGCGAACGAAAAATAA
```

The amino acid sequence of the Omp18 protein encoded by the nucleic acid of SEQ ID NO: 5 is provided below:

```
                                            (SEQ ID NO: 6)
MKKVLLSSLVAVSLLSTGLFAKEYTLDKAHTDVGFKIKHLQISNVKGNFK

DYSAVIDFDPASAEFKKLDVTIKIASVNTENQTRDNHLQQDDFFKAKKYP

DMTFTMKKYEKIDNEKGKMTGTLTIAGVSKDIVLDAEIGGVAKGKDGKEK

IGFSLNGKIKRSDFKFATSTSTITLSDDINLNIEVEANEK
```

In some embodiments, the nucleic acid comprises a *C. jejuni* cj0113 gene (provided as SEQ ID NO: 5). In some embodiments, the nucleic acid comprises a cj0113 gene, wherein the cj0113 gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 5. In some embodiments, the nucleic acid comprises a cj0113 gene, wherein the cj0113 gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 5.

In some embodiments, the nucleic acid comprises a nucleic acid sequence encoding a Omp18 protein, wherein said Omp18 protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 6. In some embodiments, the nucleic acid comprises a nucleic acid sequence encoding a Omp18 protein, wherein said Omp18 protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 6.

cj0168c—In some embodiments, the recombinant bacterium comprises a nucleic acid comprising a cj0168c gene (e.g., a *C. jejuni* cj0168c gene).

In some embodiments, the nucleic acid comprising a cj0168c gene is located on a plasmid in the bacterium. In some embodiments, the nucleic acid comprising a cj0168c gene is located on a chromosome of the bacterium.

The nucleic acid sequence of an exemplary *C. jejuni* cj0168c gene is provided below:

(SEQ ID NO: 7)
ATGAAAAAAGTTGTACTAATCTCAGCATTACTAGGTGCTTTCGCAGCTAA

TGTTTTTGCAGCTAATACTCCAAGCGATGTAAATCAAACACATACAAAAG

CTAAAGCTGATAAAAAACATGAAGCTAAAACTCACAAAAAAACAAAAGAG

CAAACACCAGCTCAATAA

The amino acid sequence of the Cj0168c protein encoded by the nucleic acid of SEQ ID NO: 7 is provided below:

(SEQ ID NO: 8)
MKKVVLISALLGAFAANVFAANTPSDVNQTHTKAKADKKHEAKTHKKTKE

QTPAQ

In some embodiments, the nucleic acid comprises a *C. jejuni* cj0168c gene (provided as SEQ ID NO: 7). In some embodiments, the nucleic acid comprises a cj0168c gene, wherein the cj0168c gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 7. In some embodiments, the nucleic acid comprises a cj0168c gene, wherein the cj0168c gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 7.

In some embodiments, the nucleic acid comprises a nucleic acid sequence encoding a Cj0168c protein, wherein said Cj0168c protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 8. In some embodiments, the nucleic acid comprises a nucleic acid sequence encoding a Cj0168c protein, wherein said Cj0168c protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 8.

cj0248—In some embodiments, the recombinant bacterium comprises a nucleic acid comprising a cj0248 gene (e.g., a *C. jejuni* cj0248 gene).

In some embodiments, the nucleic acid comprising a cj0248 gene is located on a plasmid in the bacterium. In some embodiments, the nucleic acid comprising a cj0248 gene is located on a chromosome of the bacterium.

The nucleic acid sequence of an exemplary *C. jejuni* cj0248 gene is provided below:

(SEQ ID NO: 9)
ATGATTGGAGATATGAATGAGCTTTTATTAAAAAGCGTTGAAGTATTGCC

ACCTTTACCTGATACTGTAAGTAAGTTAAGAAAATATGTGAGCGAGGCTA

ATTCAAATATAGAAACTATGAAAGTTGCTGAAATCATTTCAAGCGATCCG

TTGATGACGGCTAAGCTTTTGCAATTAGCAAATTCTCCTTATTATGGTTT

TACAAGAGAAATTACAACCATAAATCAAGTGATTACTTTATTAGGCGTTG

GTAATATCATCAATATAGTTATGGCTGACTCCATTAGAGATAATTTTAAA

ATAGACGTTTCACCTTATGGTTTAAATACTCAAAATTTTTTAAAAACGTG

CAATGAAGAGGCAACTTTTATCGCAAATTGGCTTAATGATGAAGATAAAA

AACTTTCTCATCTTTTAGTTCCTTGTGCAATGCTTTTAAGGCTTGGTATT

GTTATTTTTTCAAATTTTCTTATACAAAATCATAAGGATAAGGATTTTTT

AGCTTTTTTAAATAAAAATGAAAATCTTGCTTTAGCGGAGAATGAATTTT

TAGGCGTAGATCATATTTCTTTCTTGGGATTTTTGTTACATCGTTGGAAT

TTTGATGATGTTTTGATTGAAAGTATATGTTTTGTTCGCACTCCTCATGC

TGCTCGCGAAAAAGTGAAAAAATCCGCTTATGCTTTAGCAATAACAGATC

ATCTTTTTGCTCCGCATGATGGTTCTTCTCCATTTAACGCAAAAGCTGCA

GTTGCTTTACTTAAAGAGGCAAAAACTCAAGGAATTAATTTTGATTTAAA

CAATCTTTTATCTAAGCTTCCTAACAAAGCTAAGGAAAATTTAAACAAAG

AAGATTAA

The amino acid sequence of the Cj0248 protein encoded by the nucleic acid of SEQ ID NO: 9 is provided below:

(SEQ ID NO: 10)
MIGDMNELLLKSVEVLPPLPDTVSKLRKYVSEANSNIETMKVAEIISSDP

LMTAKLLQLANSPYYGFTREITTINQVITLLGVGNIINIVMADSIRDNFK

IDVSPYGLNTQNFLKTCNEEATFIANWLNDEDKKLSHLLVPCAMLLRLGI

VIFSNFLIQNHKDKDFLAFLNKNENLALAENEFLGVDHISFLGFLLHRWN

FDDVLIESICFVRTPHAAREKVKKSAYALAITDHLFAPHDGSSPFNAKAA

VALLKEAKTQGINFDLNNLLSKLPNKAKENLNKED

In some embodiments, the nucleic acid comprises a *C. jejuni* cj0248 gene (provided as SEQ ID NO: 9). In some embodiments, the nucleic acid comprises a cj0248 gene, wherein the cj0248 gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 9. In some embodiments, the nucleic acid comprises a cj0248 gene, wherein the cj0248 gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 9.

In some embodiments, the nucleic acid comprises a nucleic acid sequence encoding a Cj0248 protein, wherein said Cj0248 protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 10. In some embodiments, the nucleic acid comprises a nucleic acid sequence encoding a Cj0248 protein, wherein said Cj0248 protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 10.

cj0289c—In some embodiments, the recombinant bacterium comprises a nucleic acid comprising a cj0289c gene (e.g., a *C. jejuni* cj0289c gene).

In some embodiments, the nucleic acid comprising a cj0289c gene is located on a plasmid in the bacterium. In some embodiments, the nucleic acid comprising a cj0289c gene is located on a chromosome of the bacterium.

The nucleic acid sequence of an exemplary *C. jejuni* cj0289c gene is provided below:

In some embodiments, the nucleic acid comprising a cj0289c gene is located on a plasmid in the bacterium. In some embodiments, the nucleic acid comprising a cj0289c gene is located on a chromosome of the bacterium.

The nucleic acid sequence of an exemplary *C. jejuni* cj0289c gene is provided below:

```
                                        (SEQ ID NO: 11)
ATGAAAAAAATTATTACTTTATTTGGTGCATGTGCCTTAGCTTTTAGTAT

GGCAAATGCAGACGTGAACCTGTACGGCCCGGGCGGCCCGCACACGGCCC

TGAAAGACATCGCAAACAAATATAGCGAAAAAACCGGCGTGAAAGTGAAC

GTGAACTTTGGCCCGCAGGCGACCTGGTTTGAAAAAGCGAAAAAAGACGC

GGACATCCTGTTTGGCGCGTCAGACCAGTCCGCTCTGGCTATCGCGAGCG

ACTTTGGCAAAGACTTTAACGTGAGCAAAATCAAACCGCTGTATTTTCGT

GAAGCCATCATCCTGACCCAGAAAGGCAACCCGCTGAAAATCAAAGGCCT

GAAAGACCTGGCGAACAAAAAAGTGCGTATCGTGGTGCCGGAAGGCGCGG

GCAAAAGCAACACCTCTGGCACCGGCGTGTGGGAAGACATGATCGGCCGT

ACCCAGGACATCAAAACCATCCAGAACTTTCGTAACAACATCGTGGCCTT

TGTGCCGAACAGCGGTAGCGCGCGTAAACTGTTCGCGCAGGACCAGGCCG

ACGCTTGGATCACTTGGATCGACTGGTCAAAAAGCAACCCGGACATCGGC

ACTGCCGTGGCTATCGAAAAAGACCTGGTGGTGTATCGTACTTTTAACGT

GATCGCGAAAGAAGGCGCGAGCAAAGAAACACAGGACTTTATCGCTTATC

TGAGTTCTAAAGAAGCGAAAGAAATCTTTAAAAAATACGGCTGGCGTGAA

TAA
```

The amino acid sequence of the Peb3 protein encoded by the nucleic acid of SEQ ID NO: 11 is provided below:

```
                                        (SEQ ID NO: 12)
MKKIITLFGACALAFSMANADVNLYGPGGPHTALKDIANKYSEKTGVKVN

VNFGPQATWFEKAKKDADILFGASDQSALAIASDFGKDFNVSKIKPLYFR

EAIILTQKGNPLKIKGLKDLANKKVRIVVPEGAGKSNTSGTGVWEDMIGR

TQDIKTIQNFRNNIVAFVPNSGSARKLFAQDQADAWITWIDWSKSNPDIG

TAVAIEKDLVVYRTFNVIAKEGASKETQDFIAYLSSKEAKEIFKKYGWRE
```

In some embodiments, the nucleic acid comprises a *C. jejuni* cj0289c gene (provided as SEQ ID NO: 11). In some embodiments, the nucleic acid comprises a cj0289c gene, wherein the cj0289c gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 11. In some embodiments, the nucleic acid comprises a cj0289c gene, wherein the cj0289c gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 11.

In some embodiments, the nucleic acid comprises a nucleic acid sequence encoding a Peb3 protein, wherein said Peb3 protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 12. In some embodiments, the nucleic acid comprises a nucleic acid sequence encoding a Peb3 protein, wherein said Peb3 protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 12.

cj0365c—In some embodiments, the recombinant bacterium comprises a nucleic acid comprising a cj0365c gene (e.g., a *C. jejuni* cj0365c gene).

In some embodiments, the nucleic acid comprising a cj0365c gene is located on a plasmid in the bacterium. In some embodiments, the nucleic acid comprising a cj0365c gene is located on a chromosome of the bacterium.

The nucleic acid sequence of an exemplary *C. jejuni* cj0365c gene is provided below:

```
                                        (SEQ ID NO: 13)
ATGAATAAAATAATTTCAATTAGTGCTATAGCAAGTTTTACTCTTTTGAT

TTCAGCTTGCTCTTTAAGTCCAAATTTAAATATTCCCGAAGCAAACTATA

GCATTGATAATAAGCTTGGAGCCTTATCTTGGGAAAAAGAAAACAATAGC
```

-continued

```
TCTATCACAAAAAATTGGTGGAAAGACTTTGATGATGAAAATTTAAATAA

AGTGGTTGATTTAGCACTTAAAAATAATAATGATTTAAAACTTGCTTTCA

TACACATGGAACAAGCTGCTGCTCAATTAGGTATAGATTTTAGCAGTTTG

TTGCCAAAATTTGATGGTAGCGCAAGCGGAAGTCGTGCAAAAACAGCTAT

AAATGCTCCAAGCAATCGAACTGGGGAAGTAAGTTACGGTAATGATTTTA

AAATGGGACTTAATTTAAGCTATGAAATCGATCTTTGGGGAAAATATCGC

GATACATATCGCGCCTCAAAATCAGGCTTTAAAGCAAGTGAGTATGATTA

TGAAGCTGCAAGACTTTCTGTTATTTCAAATACAGTTCAAACTTATTTTA

ATCTTGTAAATGCTTATGAAAATGAAAATGCTCTTAAAGAAGCCTATAAA

TCTGCAAAAGAAATTTATAGGATTAATGATGAAAAATTTCAAGTTGGTGC

TGTAGGTGAATATGAACTTGCTCAAGCAAGAGCCAACTTAGAAAGTATGG

CTTTGCAATATAATGAAGCAAAGTTAAATAAAGAAAATTACCTTAAAGCT

TTAAAAATTTTAACTTCAAATGATTTAAATGACATACTTTACAAAAATCA

AAGCTATCAAGTTTTTAATCTTAAAGAATTTGACATTCCAACTGGAATTT

CAAGTACCATCTTGCTTCAACGTCCAGATATTGGCTCTTCTTTAGAAAAA

TTAACTCAGCAAAATTATCTTGTTGGAGTAGCTCGCACGGCTTTCTTACC

TAGCCTTTCTTTAACAGGATTATTGGGATTTGAAAGCGGGGATTTAGATA

CCTTGGTTAAAGGAGGTTCTAAGACTTGGAATATAGGTGGAAACTTTACT

CTGCCTATTTTTCATTGGGGTGAAATTTACCAAAATGTAAATTTAGCCAA

GCTTAATAAAGATGAAGCTTTTGTAAATTATCAAAATACTTTGATTACTG

CTTTTGGAGAAATTCGCTATGCTTTAGTAGCTAGAAAAACTATACGCTTA

CAATACGATAATGCACAAGCAAGCGAACAATCTTACAAAAGAATCTATGA

AATTGCTAAAGAACGCTATGATATAGGAGAAATGTCTTTGCAAGATTATT

TAGAGGCACGTCAAAATTGGCTTAATGCTGCGGTTGCTTTTAATAATATT

AAATATTCTTATGCCAATTCCATAGTAGATGTAATCAAAGCATTTGGTGG

AGGATTTGAGCAAAGTGAAGATACGAGTAAAAATATAAAAGAAGAATCAA

AAAAATTTAGATATGTCTTTTAGAGAATAG
```

The amino acid sequence of the CmeC protein encoded by the nucleic acid of SEQ ID NO: 13 is provided below:

(SEQ ID NO: 14)
```
MNKIISISAIASFTLLISACSLSPNLNIPEANYSIDNKLGALSWEKENNS

SITKNWWKDFDDENLNKVVDLALKNNNDLKLAFIHMEQAAAQLGIDFSSL

LPKFDGSASGSRAKTAINAPSNRTGEVSYGNDFKMGLNLSYEIDLWGKYR

DTYRASKSGFKASEYDYEAARLSVISNTVQTYFNLVNAYENENALKEAYK

SAKEIYRINDEKFQVGAVGEYELAQARANLESMALQYNEAKLKNENYLKA

LKILTSNDLNDILYKNQSYQVFNLKEFDIPTGISSTILLQRPDIGSSLEK

LTQQNYLVGVARTAFLPSLSLTGLLGFESGDLDTLVKGGSKTWNIGGNFT

LPIFHWGEIYQNVNLAKLNKDEAFVNYQNTLITAFGEIRYALVARKTIRL

QYDNAQASEQSYKRIYEIAKERYDIGEMSLQDYLEARQNWLNAAVAFNNI

KYSYANSIVDVIKAFGGGFEQSEDTSKNIKEESKNLDMSFRE
```

In some embodiments, the nucleic acid comprises a *C. jejuni* cj0365c gene (provided as SEQ ID NO: 13). In some embodiments, the nucleic acid comprises a cj0365c gene, wherein the cj0365c gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 13. In some embodiments, the nucleic acid comprises a cj0365c gene, wherein the cj0365c gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 13.

In some embodiments, the nucleic acid comprises a nucleic acid sequence encoding a CmeC protein, wherein said CmeC protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 14. In some embodiments, the nucleic acid comprises a nucleic acid sequence encoding a CmeC protein, wherein said CmeC protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 14.

cj0404—In some embodiments, the recombinant bacterium comprises a nucleic acid comprising a cj0404 gene (e.g., a *C. jejuni* cj0404 gene).

In some embodiments, the nucleic acid comprising a cj0404 gene is located on a plasmid in the bacterium. In some embodiments, the nucleic acid comprising a cj0404 gene is located on a chromosome of the bacterium.

The nucleic acid sequence of an exemplary *C. jejuni* cj0404 gene is provided below:

(SEQ ID NO: 15)
```
ATGGAAAATCAAAAAAATGAATTTGATGATATTATTTTAGAAAAAAGTAA

TAAAAGTGAAAAAGTAAAAAAAATTCTTTTACGAGTTATTGCTTTAGTTA

TTTTGTTTTTAGCTATCATGATAGTTATGAAGCTTATTAATGGTAGTGGT

GATGAAAATACGCAAAATCAAAGTGTATTGCCAAGTGAACCTATAGCAAC

TCAAGACAATAACAATGATACTTCTTTTGAAAGTATGCCAATTACAGATA

ATACTTCAGCAGAAGATCAATTTGAGGCATTAAGAAAACAATTTCAAGAT

GAACAAAATACAACTCAAAATACAACAACCTCTAGTTCAAATAACAATGA

TACTACAAATTTTGCTATGCCTGATCAAGAAGTTCCAGCAGAACCAACAG

CAACTACTTCAGCAAATACCACTCCACAAGCAAGTACTCCTAAACAAGAA

GTAACACAAACTGCAAAATCTAAAGAAGAAGCAAAAAAACAAACAGCTGT

AAAAAAAGAAAAAGAAAGTGCAAAACAAACCCCTAAAAAAGAACAAAATG
```

-continued

CAAATGATTTATTTAAAAATGTTGATGCTAAACCTGTACATCCAAGTGGT

TTAGCATCGGGTATTTATGTGCAAATTTTCTCAGTAAGTAATTTGGATCA

AAAATCAAAAGAACTTGCTTCTGTAAAGCAAAAAGGTTATGATTATAAAC

TTTATAAAACTACAGTTGGAAGTAAAGAAATTACCAAGGTTTTAATAGGA

CCATTTGAAAAGGCAGATATTGCAGCAGAACTTGCTAAAATCCGTAAGGA

TATTGCAAAAGATGCTTTTTCTTTTACTTTAAAATGA

The amino acid sequence of the Cj0404 protein encoded by the nucleic acid of SEQ ID NO: 15 is provided below:

(SEQ ID NO: 16)
MENQKNEFDDIILEKSNKSEKVKKILLRVIALVILFLAIMIVMKLINGSG

DENTQNQSVLPSEPIATQDNNNDTSFESMPITDNTSAEDQFEALRKQFQD

EQNTTQNTTTSSSNNNDTTNFAMPDQEVPAEPTATTSANTTPQASTPKQE

VTQTAKSKEEAKKQTAVKKEKESAKQTPKKEQNANDLFKNVDAKPVHPSG

LASGIYVQIFSVSNLDQKSKELASVKQKGYDYKLYKTTVGSKEITKVLIG

PFEKADIAAELAKIRKDIAKDAFSFTLK

In some embodiments, the nucleic acid comprises a *C. jejuni* cj0404 gene (provided as SEQ ID NO: 15). In some embodiments, the nucleic acid comprises a cj0404 gene, wherein the cj0404 gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 15. In some embodiments, the nucleic acid comprises a cj0404 gene, wherein the cj0404 gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 15.

In some embodiments, the nucleic acid comprises a nucleic acid sequence encoding a Cj0404 protein, wherein said Cj0404 protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 16. In some embodiments, the nucleic acid comprises a nucleic acid sequence encoding a Cj0404 protein, wherein said Cj0404 protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 16.

cj0420—In some embodiments, the recombinant bacterium comprises a nucleic acid comprising a cj0420 gene (e.g., a *C. jejuni* cj0420 gene).

In some embodiments, the nucleic acid comprising a cj0420 gene is located on a plasmid in the bacterium. In some embodiments, the nucleic acid comprising a cj0420 gene is located on a chromosome of the bacterium.

The nucleic acid sequence of an exemplary *C. jejuni* cj0420 gene is provided below:

(SEQ ID NO: 17)
ATGAAAAAAGTTTTATTGAGTTCATTGGTTGCGGTGTCTTTGTTAAGCAC

AGGTTTGTTTGCTAAAGAATATACTTTAGATAAAGCACATACAGATGTAG

GTTTTAAAATCAAACATTTACAAATTAGCAATGTAAAAGGAAATTTCAAA

GATTATTCTGCGGTGATTGATTTTGATCCTGCGAGTGCTGAATTTAAAAA

GCTTGATGTAACTATAAAAATCGCATCTGTAAATACAGAAAATCAAACAA

GAGATAATCACTTACAACAAGATGATTTTTTCAAAGCAAAAAAATATCCT

GATATGACTTTTACAATGAAAAAATATGAAAAAATCGATAATGAAAAAGG

CAAAATGACAGGAACTTTAACTATAGCTGGAGTTTCTAAAGATATCGTTT

TAGATGCTGAAATCGGCGGTGTAGCTAAAGGCAAAGATGGAAAAGAAAAA

ATAGGATTTTCTTTAAATGGAAAAATCAAACGCTCTGATTTTAAATTTGC

AACAAGTACTTCAACTATTACTTTAAGTGATGATATTAATTTAAATATCG

AAGTTGAAGCGAACGAAAAATAA

The amino acid sequence of the Cj0420 protein encoded by the nucleic acid of SEQ ID NO: 17 is provided below:

(SEQ ID NO: 18)
MKKVLLSSLVAVSLLSTGLFAKEYTLDKAHTDVGFKIKHLQISNVKGNFK

DYSAVIDFDPASAEFKKLDVTIKIASVNTENQTRDNHLQQDDFFKAKKYP

DMTFTMKKYEKIDNEKGKMTGTLTIAGVSKDIVLDAEIGGVAKGKDGKEK

IGFSLNGKIKRSDFKFATSTSTITLSDDINLNIEVEANEK

In some embodiments, the nucleic acid comprises a *C. jejuni* cj0420 gene (provided as SEQ ID NO: 17). In some embodiments, the nucleic acid comprises a cj0420 gene, wherein the cj0420 gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 17. In some embodiments, the nucleic acid comprises a cj0420 gene, wherein the cj0420 gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 17.

In some embodiments, the nucleic acid comprises a nucleic acid sequence encoding a Cj0420 protein, wherein said Cj0420 protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 18. In some embodiments, the nucleic acid comprises a nucleic acid sequence encoding a Cj0420 protein, wherein said Cj0420 protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 18.

cj0427—In some embodiments, the recombinant bacterium comprises a nucleic acid comprising a cj0427 gene (e.g., a *C. jejuni* cj0427 gene).

In some embodiments, the nucleic acid comprising a cj0427 gene is located on a plasmid in the bacterium. In some embodiments, the nucleic acid comprising a cj0427 gene is located on a chromosome of the bacterium.

The nucleic acid sequence of an exemplary *C. jejuni* cj0427 gene is provided below:

(SEQ ID NO: 19)
ATGATGGCTAAATTTAGAATTCAATACAGCGCAGGTTTTGGGCACTATAC

GCAAAATCACAAGGGTTTTGGACCTACGATTTATATAGAAGAGGTCGTAG

AGTTTGATAATGGCAAGGATTATTTTGACTATATAGATTTTTATAAAACT

TATTCAAAGAGCGATGATACTTATTTTCATATCAGTTTTTTAGAAGATAG

ACCTCTAAGCGATAAAGAAATCACCATTCGCAATGAATACCGCAAAATGC

GTGATGAAAACTGTAAAAAAGCCAAGGAGGAATTTATAGCCAACAATGAG

CTTGATGTGGAGCATTTGCCTACTCACCATGATTAA

The amino acid sequence of the Cj0427 protein encoded by the nucleic acid of SEQ ID NO: 19 is provided below:

(SEQ ID NO: 20)
MMAKFRIQYSAGFGHYTQNHKGFGPTIYIEEVVEFDNGKDYFDYIDFYKT

YSKSDDTYFHISFLEDRPLSDKEITIRNEYRKMRDENCKKAKEEFIANNE

LDVEHLPTHHD

In some embodiments, the nucleic acid comprises a *C. jejuni* cj0427 gene (provided as SEQ ID NO: 19). In some embodiments, the nucleic acid comprises a cj0427 gene, wherein the cj0427 gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 19. In some embodiments, the nucleic acid comprises a cj0427 gene, wherein the cj0427 gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 19.

In some embodiments, the nucleic acid comprises a nucleic acid sequence encoding a Cj0427 protein, wherein said Cj0427 protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 20. In some embodiments, the nucleic acid comprises a nucleic acid sequence encoding a Cj0427 protein, wherein said Cj0427 protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 20.

cj0428—In some embodiments, the recombinant bacterium comprises a nucleic acid comprising a cj0428 gene (e.g., a *C. jejuni* cj0428 gene).

In some embodiments, the nucleic acid comprising a cj0428 gene is located on a plasmid in the bacterium. In some embodiments, the nucleic acid comprising a cj0428 gene is located on a chromosome of the bacterium.

The nucleic acid sequence of an exemplary *C. jejuni* cj0428 gene is provided below:

(SEQ ID NO: 21)
ATGCAGGTAAATTATAGAACGATTAGCTCGTATGAATACGATGCTATTAG

TGGTCAGTATAAACAGGTGGATAAACAGATTGAAGATTATTCTTCATCTG

GAGATTCTGATTTTATGGATATGTTAAATAAGGCGGATGAGAAGTCAAGC

GGAGATGCTTTAAATTCTAGCAGTAGTTTTCAAAGCAATGCGCAAAACTC

AAATTCAAATTTAAGTAATTATGCTCAAATGTCAAATGTTTACGCTTATC

GTTTTAGACAAAATGAAGGCGAGCTGTCTATGAGAGCTCAAAGTGCTAGC

GTTCATAATGATCTTACACAACAAGGTGCAAATGAACAAAGTAAGAATAA

TACTTTGTTAAATGATTTATTGAACGCAATTTAA

The amino acid sequence of the Cj0428 protein encoded by the nucleic acid of SEQ ID NO: 21 is provided below:

(SEQ ID NO: 22)
MQVNYRTISSYEYDAISGQYKQVDKQIEDYSSSGDSDFMDMLNKADEKSS

GDALNSSSSFQSNAQNSNSNLSNYAQMSNVYAYRFRQNEGELSMRAQSAS

VHNDLTQQGANEQSKNNTLLNDLLNAI

In some embodiments, the nucleic acid comprises a *C. jejuni* cj0428 gene (provided as SEQ ID NO: 21). In some embodiments, the nucleic acid comprises a cj0428 gene, wherein the cj0428 gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 21. In some embodiments, the nucleic acid comprises a cj0428 gene, wherein the cj0428 gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 21.

In some embodiments, the nucleic acid comprises a nucleic acid sequence encoding a Cj0428 protein, wherein said Cj0428 protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 22. In some embodiments, the nucleic acid comprises a nucleic acid sequence encoding a Cj0428 protein, wherein said Cj0428 protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 22.

cj0588— In some embodiments, the recombinant bacterium comprises a nucleic acid comprising a cj0588 gene (e.g., a *C. jejuni* cj0588 gene).

In some embodiments, the nucleic acid comprising a cj0588 gene is located on a plasmid in the bacterium. In some embodiments, the nucleic acid comprising a cj0588 gene is located on a chromosome of the bacterium.

The nucleic acid sequence of an exemplary *C. jejuni* cj0588 gene is provided below:

```
                                               (SEQ ID NO: 23)
ATGCGTTTCGACTTCTTCGTGTCCAAACGTCTGAACATCAGCCGTAACAA

AGCGCTGGAGCTGATCGAAAACGAAGAGATCCTGCTGAACGGCAAAAGCT

TCAAAGCGTCCTTCGACGTGAAAAACTTCCTGGAAAACCTGAAAAAAACC

CAGGACCTGAACCCGGAAGACATCCTGCTGGCGAACGAGCTGAAACTGGA

CCTGCTGAGCGAAATCTACGTGTCCCGTGCGGCGCTGAAACTGAAAAAAT

TCCTGGAAGAAAACGACATCGAAATCAAACACAAAAACTGTCTGGACATC

GGCTCCAGCACCGGCGGCTTCGTGCAGATCCTGCTGGAAAACCAGGCGCT

GAAAATCACCGCGCTGGACGTGGGCAGCAACCAGCTGCACCCGAGCCTGC

GTGTGAACGAAAAAATCATCCTGCACGAAAACACCGACCTGCGTGCGTTC

AAAAGCGAAGAAAAATTCGAACTGGTGACCTGCGACGTGAGCTTCATCTC

CCTGATCAACCTGCTGTACTACATCGACAACCTGGCGCTGAAAGAAATCA

TCCTGCTGTTCAAACCGCAGTTCGAAGTGGGCAAAAACATCAAACGTGAC

AAAAAAGGCGTGCTGAAAGACGACAAAGCGATCCTGAAAGCGCGTATGGA

CTTCGAAAAAGCGTGCGCGAAACT
```

The amino acid sequence of the TlyA protein encoded by the nucleic acid of SEQ ID NO: 23 is provided below:

```
                                               (SEQ ID NO: 24)
MRFDFFVSKRLNISRNKALELIENEEILLNGKSFKASFDVKNFLENLKKT

QDLNPEDILLANELKLDLLSEIYVSRAALKLKKFLEENDIEIKHKNCLDI

GSSTGGFVQILLENQALKITALDVGSNQLHPSLRVNEKIILHENTDLRAF

KSEEKFELVTCDVSFISLINLLYYIDNLALKEIILLFKPQFEVGKNIKRD

KKGVLKDDKAILKARMDFEKACAKLGWLLKNTQKSSIKGKEGNVEYFYYY

IKN
```

In some embodiments, the nucleic acid comprises a *C. jejuni* cj0588 gene (provided as SEQ ID NO: 23). In some embodiments, the nucleic acid comprises a cj0588 gene, wherein the cj0588 gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 23. In some embodiments, the nucleic acid comprises a cj0588 gene, wherein the cj0588 gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 23.

In some embodiments, the nucleic acid comprises a nucleic acid sequence encoding a TlyA protein, wherein said TlyA protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO:24. In some embodiments, the nucleic acid comprises a nucleic acid sequence encoding a TlyA protein, wherein said TlyA protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 24.

cj0921c—In some embodiments, the recombinant bacterium comprises a nucleic acid comprising a cj0921c gene (e.g., a *C. jejuni* cj0921c gene).

In some embodiments, the nucleic acid comprising a cj0921c gene is located on a plasmid in the bacterium. In some embodiments, the nucleic acid comprising a cj0921c gene is located on a chromosome of the bacterium.

The nucleic acid sequence of an exemplary *C. jejuni* cj0921c gene is provided below:

```
                                               (SEQ ID NO: 25)
ATGGTTTTTAGAAAATCTTTGTTAAAGTTGGCAGTTTTTGCTCTAGGTGC

TTGTGTTGCATTTAGCAATGCTAATGCAGCAGAAGGCAAACTGGAGTCCA

TCAAATCCAAAGGCCAGCTGATCGTGGGCGTGAAAAACGACGTGCCGCAC

TACGCTCTGCTGGACCAGGCAACCGGCGAAATCAAAGGCTTCGAAGTGGA

CGTGGCCAAACTGCTGGCTAAAAGCATCCTGGGGGACGACAAAAAAATCA

AACTGGTGGCAGTGAACGCCAAAACCCGTGGCCCGCTGCTGGACAACGGC

AGCGTGGACGCGGTGATCGCAACCTTCACCATCACCCCGGAGCGCAAACG

TATCTATAACTTCTCCGAGCCGTATTATCAGGACGCTATCGGCCTGCTGG

TTCTGAAAGAAAAAAAATATAAATCTCTGGCTGACATGAAAGGTGCAAAC

ATCGGCGTGGCTCAAGCTGCAACTACAAAAAAAGCTATCGGCGAAGCTGC

TAAAAAAATCGGCATCGACGTGAAATTCAGCGAATTCCCGGACTATCCGA

GCATCAAAGCTGCTCTGGACGCTAAACGTGTGGACGCGTTCTCTGTGGAC
```

-continued
```
AAATCCATCCTGCTGGGCTATGTGGACGACAAAAGCGAAATCCTGCCGGA

CAGCTTCGAACCGCAGAGCTATGGCATCGTGACCAAAAAAGACGACCCGG

CTTTCGCAAAATATGTGGACGACTTCGTGAAAGAACACAAAAACGAAATC

GACGCTCTGGCGAAAAAATGGGGCCTGTAA
```

The amino acid sequence of the Peb1 protein encoded by the nucleic acid of SEQ ID NO: 25 is provided below:

```
                                              (SEQ ID NO: 26)
MVFRKSLLKLAVFALGACVAFSNANAAEGKLESIKSKGQLIVGVKNDVPH

YALLDQATGEIKGFEVDVAKLLAKSILGDDKKIKLVAVNAKTRGPLLDNG

SVDAVIATFTITPERKRIYNFSEPYYQDAIGLLVLKEKKYKSLADMKGAN

IGVAQAATTKKAIGEAAKKIGIDVKFSEFPDYPSIKAALDAKRVDAFSVD

KSILLGYVDDKSEILPDSFEPQSYGIVTKKDDPAFAKYVDDFVKEHKNEI

DALAKKWGL
```

In some embodiments, the nucleic acid comprises a *C. jejuni* cj0921c gene (provided as SEQ ID NO: 25). In some embodiments, the nucleic acid comprises a cj0921c gene, wherein the cj0921c gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 25. In some embodiments, the nucleic acid comprises a cj0921c gene, wherein the cj0921c gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 25.

In some embodiments, the nucleic acid comprises a nucleic acid sequence encoding a Peb 1 protein, wherein said Peb 1 protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 26. In some embodiments, the nucleic acid comprises a nucleic acid sequence encoding a Peb1 protein, wherein said Peb 1 protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 26.

cj0982c—In some embodiments, the recombinant bacterium comprises a nucleic acid comprising a cj0982c gene (e.g., a *C. jejuni* cj0982c gene).

In some embodiments, the nucleic acid comprising a cj0982c gene is located on a plasmid in the bacterium. In some embodiments, the nucleic acid comprising a cj0982c gene is located on a chromosome of the bacterium.

The nucleic acid sequence of an exemplary *C. jejuni* cj0982c gene is provided below:

```
                                              (SEQ ID NO: 27)
ATGAAAAAAATACTTCTAAGTGTTTTAACGGCCTTTGTTGCAGTAGTATT

GGCTGCGGCGGCAACTCCGACTCCAAAACCCTGAACTCCCTGGACAAAAT

CAAACAGAACGGCGTGGTGCGTATCGGCGTGTTTGGCGACAAACCGCCGT

TTGGCTATGTGGACGAAAAAGGCAACAACCAGGGCTATGACATCGCTCTG

GCTAAACGTATCGCGAAAGAACTGTTTGGCGACGAAAACAAAGTGCAGTT

TGTGCTGGTGGAAGCTGCGAACCGTGTGGAGTTTCTGAAATCCAACAAAG

TGGACATCATCCTGGCTAACTTTACCCAGACCCCGCAGCGTGCGGAGCAG

GTGGACTTTTGCTCCCCGTATATGAAAGTGGCTCTGGGCGTGGCTGTGCC

GAAAGACAGCAACATCACCAGCGTGGAAGACCTGAAAGACAAAACCCTGC

TGCTGAACAAAGGCACCACCGCGGACGCTTATTTTACCCAGAACTATCCG

AACATCAAAACCCTGAAATATGACCAGAACACCGAAACCTTTGCGGCTCT

GATGGACAAACGTGGCGACGCTCTGAGCCACGACAACACCCTGCTGTTTG

CTTGGGTGAAAGACCACCCGGACTTTAAAATGGGCATCAAAGAGCTGGGC

AACAAAGACGTGATCGCGCCGGCGGTGAAAAAAGGCGACAAAGAACTGAA

AGAATTTATCGACAACCTGATCATCAAACTGGGCCAGGAGCAGTTTTTTC

ACAAAGCTTATGACGAAACCCTGAAAGCTCACTTTGGCGACGACGTGAAA

GCGGACGACGTGGTGATCGAAGGCGGCAAAATCTAA
```

The amino acid sequence of the CjaA protein encoded by the nucleic acid of SEQ ID NO: 27 is provided below:

```
                                              (SEQ ID NO: 28)
MKKILLSVLTAFVAVVLAACGGNSDSKTLNSLDKIKQNGVVRIGVFGDKP

PFGYVDEKGNNQGYDIALAKRIAKELFGDENKVQFVLVEAANRVEFLKSN

KVDIILANFTQTPQRAEQVDFCSPYMKVALGVAVPKDSNITSVEDLKDKT

LLLNKGTTADAYFTQNYPNIKTLKYDQNTETFAALMDKRGDALSHDNTLL

FAWVKDHPDFKMGIKELGNKDVIAPAVKKGDKELKEFIDNLIIKLGQEQF

FHKAYDETLKAHFGDDVKADDVVIEGGKI
```

In some embodiments, the nucleic acid comprises a *C. jejuni* cj0982c gene (provided as SEQ ID NO: 27). In some embodiments, the nucleic acid comprises a cj0982c gene, wherein the cj0982c gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 27. In some embodiments, the nucleic acid comprises a cj0982c gene, wherein the cj0982c gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 27.

In some embodiments, the nucleic acid comprises a nucleic acid sequence encoding a CjaA protein, wherein said CjaA protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 28. In some embodiments, the nucleic acid comprises a nucleic acid sequence encoding a CjaA protein, wherein said CjaA protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 28.

cj0998c— In some embodiments, the recombinant bacterium comprises a nucleic acid comprising a cj0998c gene (e.g., a *C. jejuni* cj0998c gene).

In some embodiments, the nucleic acid comprising a cj0998c gene is located on a plasmid in the bacterium. In some embodiments, the nucleic acid comprising a cj0998c gene is located on a chromosome of the bacterium.

The nucleic acid sequence of an exemplary *C. jejuni* cj0998c gene is provided below:

(SEQ ID NO: 29)
ATGAAAAAAATTCTTGTAAGTGTTTTAAGTTCTTGCTTGTTAGCTTCGGC

TTTAAGTGCGGTGTCCTTCAAAGAAGACAGCCTGAAAATCTCCTTCGAAG

GCTACAAAACCAAAGACATGATCGGCACCAAAGGCGAATTCAAAAACGTG

GAATACAAATTCTCCAAAAACATCAAAGACCTGGCGAGCTACCTGAAAGG

CGCGAAAGCGACCATCAAACCGAGCAACGCGTTCATGGGCGAAGGCAACG

ACATCATCACCAACAACATCACCAAAGTGTTCTTCCCGGCGCTGCTGGGC

GACACGGACATCAAAGTGGTGTTTCAGGACGTGATCGCGGGCGAAAACAA

AGGCGTGATCTCCGCGAAAATCACCATGGACAAAAAAAGCACCATCGTGC

CGCTGACCTATACCATCAAAGACAACAAATTTGAAGCGAAAGGCCAGCTG

GACCTGCACACCTTTAAAAACGGCTCCAAAGCGCTGAAAGCGCTGAGCGA

CGTGGCTGCAGGCCACGGCGGCATCTCCTGGCCGCTGGTGGACATCAGCT

TTAACGCGGACCTGGCGGAATAA

The amino acid sequence of the Cj0998c protein encoded by the nucleic acid of SEQ ID NO: 29 is provided below:

(SEQ ID NO: 30)
MKKILVSVLSSCLLASALSAVSFKEDSLKISFEGYKTKDMIGTKGEFKNV

EYKFSKNIKD

LASYLKGAKATIKPSNAFMGEGNDIITNNITKVFFPALLGDTDIKVVFQD

VIAGENKGVI

SAKITMDKKSTIVPLTYTIKDNKFEAKGQLDLHTFKNGSKALKALSDVAA

GHGGISWPLVDISFNADLAE

In some embodiments, the nucleic acid comprises a *C. jejuni* cj0998c gene (provided as SEQ ID NO: 29). In some embodiments, the nucleic acid comprises a cj0998c gene, wherein the cj0998c gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 29. In some embodiments, the nucleic acid comprises a cj0998c gene, wherein the cj0998c gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 29.

In some embodiments, the nucleic acid comprises a nucleic acid sequence encoding a Cj0998c protein, wherein said Cj0998c protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 30. In some embodiments, the nucleic acid comprises a nucleic acid sequence encoding a Cj0998c protein, wherein said Cj0998c protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 30.

cj1259—In some embodiments, the recombinant bacterium comprises a nucleic acid comprising a cj1259 gene (e.g., a *C. jejuni* cj1259 gene).

In some embodiments, the nucleic acid comprising a cj1259 gene is located on a plasmid in the bacterium. In some embodiments, the nucleic acid comprising a cj1259 gene is located on a chromosome of the bacterium.

The nucleic acid sequence of an exemplary *C. jejuni* cj1259 gene is provided below:

(SEQ ID NO: 31)
ATGAAACTAGTTAAACTTAGTTTAGTTGCAGCTCTTGCTGCAGGTGCTTT

TTCAGCAGCTAACGCTACCCCGCTGGAAGAAGCGATCAAAGACGTGGACG

TGTCCGGCGTGCTGCGTTACCGTTACGACACCGGCAACTTTGACAAAAAC

TTCGTGAACAACTCCAACCTGAACAACAGCAAACAGGACCACAAATATCG

TGCACAGGTGAACTTCAGTGCTGCTATCGCTGACAACTTCAAAGCTTTTG

TGCAGTTTGACTATAACGCTGCTGACGGTGGCTATGGCGCTAACGGCATC

AAAAACGACCAGAAAGGCCTGTTTGTGCGTCAGCTGTACCTGACTTATAC

CAACGAAGACGTGGCTACCAGTGTGATCGCTGGTAAACAGCAGCTGAACC

TGATCTGGACGGACAACGCTATCGACGGTCTGGTGGGCACCGGTGTGAAA

GTGGTGAACAACAGCATCGACGGTCTGACTCTGGCTGCTTTTGCTGTGGA

CAGCTTCATGGCTGCGGAGCAGGGTGCGGACCTGCTGGAACACAGTAACA

TCTCCACCACCTCCAACCAGGCTCCGTTTAAAGTGGACTCCGTGGGCAAC

CTGTACGGTGCTGCTGCTGTGGGTTCTTATGACCTGGCTGGTGGCCAGTT

CAACCCGCAGCTGTGGCTGGCTTATTGGGACCAGGTGGCATTCTTCTATG

CTGTGGACGCAGCTTATAGCACAACTATCTTTGACGGCATCAACTGGACA

-continued

```
CTGGAAGGCGCTTACCTGGGAAACAGCCTGGACAGCGAACTGGACGACAA

AACACACGCTAACGGCAACCTGTTTGCTCTGAAAGGCAGCATCGAAGTGA

ACGGCTGGGACGCTAGCCTGGGTGGTCTGTACTACGGCGACAAAGAAAAA

GCTTCTACAGTGGTGATCGAAGACCAGGGTAACCTGGGTTCTCTGCTGGC

AGGTGAGGAAATCTTCTATACTACTGGCTCACGCCTGAACGGTGACACTG

GTCGTAACATCTTCGGTTATGTGACTGGTGGATATACTTTCAACGAAACA

GTGCGCGTGGGTGCTGACTTCGTGTATGGTGGAACAAAAACAGAAGCTGC

TAACCACCTGGGTGGTGGTAAAAAACTGGAAGCTGTGGCACGCGTGGACT

ACAAATACTCTCCGAAACTGAACTTCTCAGCATTCTATTCTTATGTGAAC

CTGGACCAGGGTGTGAACACTAACGAAAGTGCTGACCACAGCACTGTGCG

TCTGCAGGCTCTGTACAAATTCTAA
```

The amino acid sequence of the PorA protein encoded by the nucleic acid of SEQ ID NO: 31 is provided below:

```
                                          (SEQ ID NO: 32)
MKLVKLSLVAALAAGAFSAANATPLEEAIKDVDVSGVLRYRYDTGNFDKN

FVNNSNLNNSKQDHKYRAQVNFSAAIADNFKAFVQFDYNAADGGYGANGI

KNDQKGLFVRQLYLTYTNEDVATSVIAGKQQLNLIWTDNAIDGLVGTGVK

VVNNSIDGLTLAAFAVDSFMAAEQGADLLEHSNISTTSNQAPFKVDSVGN

LYGAAAVGSYDLAGGQFNPQLWLAYWDQVAFFYAVDAAYSTTIFDGINWT

LEGAYLGNSLDSELDDKTHANGNLFALKGSIEVNGWDASLGGLYYGDKEK

ASTVVIEDQGNLGSLLAGEEIFYTTGSRLNGDTGRNIFGYVTGGYTFNET

VRVGADFVYGGTKTEAANHLGGGKKLEAVARVDYKYSPKLNFSAFYSYVN

LDQGVNTNESADHSTVRLQALYKF
```

In some embodiments, the nucleic acid comprises a *C. jejuni* cj1259 gene (provided as SEQ ID NO: 31). In some embodiments, the nucleic acid comprises a cj1259 gene, wherein the cj1259 gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 31. In some embodiments, the nucleic acid comprises a cj1259 gene, wherein the cj1259 gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 31.

In some embodiments, the nucleic acid comprises a nucleic acid sequence encoding a PorA protein, wherein said PorA protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 32. In some embodiments, the nucleic acid comprises a nucleic acid sequence encoding a PorA protein, wherein said PorA protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 32.

cj1339c—In some embodiments, the recombinant bacterium comprises a nucleic acid comprising a cj1339c gene (e.g., a *C. jejuni* cj1339c gene).

In some embodiments, the nucleic acid comprising a cj1339c gene is located on a plasmid in the bacterium. In some embodiments, the nucleic acid comprising a cj1339c gene is located on a chromosome of the bacterium.

The nucleic acid sequence of an exemplary *C. jejuni* cj1339c gene is provided below:

```
                                          (SEQ ID NO: 33)
ATGGGTTTTCGTATCAACACCAACGTGGCGGCTCTGAACGCAAAAGCAAA

CGCGGATCTGAACAGCAAAAGCCTGGATGCTTCTCTGAGCCGTCTGAGCT

CCGGCCTGCGTATCAACTCCGCAGCAGATGATGCTTCCGGGATGGCGATC

GCAGATAGCCTGCGTTCTCAGGCTAACACTCTGGGCCAGGCTATCTCTAA

CGGCAACGATGCTCTGGGCATCCTGCAGACTGCTGATAAAGCTATGGACG

AGCAGCTGAAAATCCTGGATACCATCAAAACTAAAGCAACCCAGGCGGCT

CAGGATGGCCAGAGCCTGAAAACCCGTACCATGCTGCAGGCAGATATCAA

CCGTCTGATGGAAGAACTGGACAACATCGCAAACACTACTTCCTTTAACG

GTAAACAGCTGCTGAGCGGCAACTTTATCAACCAGGAATTTCAGATCGGC

GCAAGCTCCAACCAGACTGTGAAAGCTACTATCGGCGCAACTCAGTCTTC

TAAAATCGGTCTGACCCGCTTTGAAACCGGCGGCCGTATCTCCACTAGCG

GCGAAGTGCAGTTTACTCTGAAAAAACTACAACGGTATCGATGATTTTCAG

TTTCAGAAAGTGGTGATCTCCACTTCCGTGGGCACCGGCCTGGGCGCTCT

GGCAGATGAGATCAACAAAAACGCTGATAAAACCGGTGTGCGTGCTACTT

TTACAGTGGAAACTCGTGGTATCGCTGCAGTGCGTGCAGGCGCTACTTCA

GATACTTTTGCTATCAACGGGGTGAAAATCGGCAAAGTGGATTACAAAGA

TGGCGATGCTAACGGCGCCCTGGTGGCTGCAATCAACTCGGTGAAAGATA

CCACCGGCGTGGAAGCTTCGATCGATGCTAACGGCCAGCTGCTGCTGACT

TCCCGTGAAGGCCGTGGCATCAAAATCGATGGTAACATCGGTGGCGGTGC

CTTTATCAACGCTGATATGAAAGAAACTATGGCCGCCTGTCTCTGGTGA

AAAACGATGGTAAAGATATCCTGATCAGCGGTAGCAACCTGTCTTCTGCA

GGTTTTGGTGCAACCCAGTTTATCTCTCAGGCTTCTGTGTCTCTGCGTGA

GTCCAAAGGCCAGATCGATGCTAACATCGCTGATGCTATGGGCTTTGGCT

CTGCAAACAAAGGCGTGGTGCTGGGTGGTTATTCTTCTGTGAGCGCCTAT

ATGAGCAGCGCAGGCAGCGGCTTTTCTTCCGGTTCCGGTTATTCTGTGGG

TAGCGGCAAAAACTATTCCACCGGTTTTGCAAACGCTATCGCTATCTCCG

CTGCTTCGCAGCTGTCTACGGTGTATAACGTGTCTGCAGGCTCAGGTTTT

TCAAGCGGTTCCACCCTGTCTCAGTTTGCCACTATGAAAACCACTGCTTT
```

-continued
```
TGGCGTGAAAGATGAAACCGCAGGTGTGACCACCCTGAAAGGCGCTATGG

CTGTGATGGATATCGCTGAAACCGCTATCACCAACCTGGATCAGATCCGT

GCCGACATCGGCTCGGTGCAGAACCAGGTGACATCCACTATCAACAACAT

CACCGTGACTCAGGTGAACGTGAAAGCAGCAGAATCGCAGATCCGTGATG

TGGACTTTGCAGCCGAGAGCGCAAACTACTCTAAAGCAAACATCCTGGCT

CAGAGCGGCTCTTATGCCATGGCACAGGCTAACTCTGTGCAGCAGAACGT

GCTGCGTCTGCTGCAGTA
```

The amino acid sequence of the FlaA protein encoded by the nucleic acid of SEQ ID NO: 33 is provided below:

```
                                        (SEQ ID NO: 34)
MGFRINTNVAALNAKANADLNSKSLDASLSRLSSGLRINSAADDASGMAI

ADSLRSQANTLGQAISNGNDALGILQTADKAMDEQLKILDTIKTKATQAA

QDGQSLKTRTMLQADINRLMEELDNIANTTSFNGKQLLSGNFINQEFQIG

ASSNQTVKATIGATQSSKIGLTRFETGGRISTSGEVQFTLKNYNGIDDFQ

FQKVVISTSVGTGLGALADEINKNADKTGVRATFTVETRGIAAVRAGATS

DTFAINGVKIGKVDYKDGDANGALVAAINSVKDTTGVEASIDANGQLLLT

SREGRGIKIDGNIGGGAFINADMKENYGRLSLVKNDGKDILISGSNLSSA

GFGATQFISQASVSLRESKGQIDANIADAMGFGSANKGVVLGGYSSVSAY

MSSAGSGFSSGSGYSVGSGKNYSTGFANAIAISAASQLSTVYNVSAGSGF

SSGSTLSQFATMKTTAFGVKDETAGVTTLKGAMAVMDIAETAITNLDQIR

ADIGSVQNQVTSTINNITVTQVNVKAAESQIRDVDFAAESANYSKANILA

QSGSYAMAQASVQQNVLRLLQ
```

In some embodiments, the nucleic acid comprises a *C. jejuni* cj1339c gene (provided as SEQ ID NO: 33). In some embodiments, the nucleic acid comprises a cj1339c gene, wherein the cj1339c gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 33. In some embodiments, the nucleic acid comprises a cj1339c gene, wherein the cj1339c gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 33.

In some embodiments, the nucleic acid comprises a nucleic acid sequence encoding a FlaA protein, wherein said FlaA protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 34. In some embodiments, the nucleic acid comprises a nucleic acid sequence encoding a FlaA protein, wherein said FlaA protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 34.

cj1478c—In some embodiments, the recombinant bacterium comprises a nucleic acid comprising a cj1478c gene (e.g., a *C. jejuni* cj1478c gene).

In some embodiments, the nucleic acid comprising a cj1478c gene is located on a plasmid in the bacterium. In some embodiments, the nucleic acid comprising a cj1478c gene is located on a chromosome of the bacterium.

The nucleic acid sequence of an exemplary *C. jejuni* cj1478c gene is provided below:

```
                                        (SEQ ID NO: 35)
ATGAAAAAAATCTTCCTGTGTCTGGGCCTGGCGAGCGTGCTGTTTGGCGC

TGACAACAACGTGAAATTTGAAATCACCCCGACCCTGAACTATAACTACT

TTGAAGGCAACCTGGACATGGACAACCGTTATGCGCCGGGGATCCGTCTG

GGCTATCACTTTGACGACTTTTGGCTGGACCAGCTGGAATTTGGGCTGGA

GCACTATTCTGACGTGAAATATACCAACACCAACAAAACCACCGACATCA

CCCGTACCTATCTGAGCGCTATCAAAGGCATCGACGTGGGTGAGAAATTT

TATTTCTATGGCCTGGCAGGCGGCGGCTATGAGGACTTTTCCAACGCTGC

GTATGACAACAAAAGCGGCGGCTTTGGCCACTATGGCGCGGGCGTGAAAT

TCCGTCTGAGCGACTCTCTGGCTCTGCGTCTGGAAACCCGTGACCAGATC

AACTTCAACCACGCAAACCACAACTGGGTGTCCACTCTGGGCATCAGCTT

TGGCTTTGGCGGCAAAAAAGAAAAAGCTGTGGAAGAAGTGGCTGACACCC

GTGCAACTCCGCAGGCCAAATGTCCGGTGGAACCGCGTGAAGGCGCTCTG

CTGGACGAAAACGGCTGCGAAAAAACCATCTCTCTGGAAGGCCACTTTGG

CTTTGACAAAACCACCATCAACCCGACTTTTCAGGAAAAAATCAAAGAAA

TCGCAAAAGTGCTGGACGAAAACGAACGTTATGACACTATCCTGGAAGGC

CACACCGACAACATCGGCTCCCGTGCTTATAACCAGAAACTGTCCGAACG

TCGTGCTAAAAGCGTGGCTAACGAACTGGAAAAATATGGCGTGGAAAAAA

GCCGCATCAAAACAGTGGGCTATGGCCAGGACAACCCGCGCTCCAGCAAC

GACACCAAAGAAGGCCGCGCGGACAACCGTCGCGTGGACGCTAAATTTAT

CCTGCGCTAA
```

The amino acid sequence of the CadF protein encoded by the nucleic acid of SEQ ID NO: 35 is provided below:

```
                                        (SEQ ID NO: 36)
MKKIFLCLGLASVLFGADNNVKFEITPTLNYNYFEGNLDMDNRYAPGIRL

GYHFDDFWLDQLEFGLEHYSDVKYTNTNKTTDITRTYLSAIKGIDVGEKF

YFYGLAGGGYEDFSNAAYDNKSGGFGHYGAGVKFRLSDSLALRLETRDQI

NFNHANHNWVSTLGISFGFGGKKEKAVEEVADTRATPQAKCPVEPREGAL

LDENGCEKTISLEGHFGFDKTTINPTFQEKIKEIAKVLDENERYDTILEG

HTDNIGSRAYNQKLSERRAKSVANELEKYGVEKSRIKTVGYGQDNPRSSN

DTKEGRADNRRVDAKFILR
```

In some embodiments, the nucleic acid comprises a *C. jejuni* cj1478c gene (provided as SEQ ID NO: 35). In some embodiments, the nucleic acid comprises a cj1478c gene, wherein the cj1478c gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 35. In some embodiments, the nucleic acid comprises a cj1478c gene, wherein the cj1478c gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 35.

In some embodiments, the nucleic acid comprises a nucleic acid sequence encoding a CadF protein, wherein said CadF protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 36. In some embodiments, the nucleic acid comprises a nucleic acid sequence encoding a CadF protein, wherein said CadF protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 36.

cj1534c—In some embodiments, the recombinant bacterium comprises a nucleic acid comprising a cj1534c gene (e.g., a *C. jejuni* cj1534c gene).

In some embodiments, the nucleic acid comprising a cj1534c gene is located on a plasmid in the bacterium. In some embodiments, the nucleic acid comprising a cj1534c gene is located on a chromosome of the bacterium.

The nucleic acid sequence of an exemplary *C. jejuni* cj1534c gene is provided below:

```
                                            (SEQ ID NO: 37)
ATGTCCGTGACCAAACAGCTGCTGCAGATGCAGGCGGACGCGCACCACCT

GTGGGTGAAATTCCACAACTACCACTGGAACGTGAAAGGCCTGCAGTTCT

TCTCCATCCACGAGTACACCGAAAAAGCGTACGAAGAAATGGCAGAACTG

TTCGACAGCTGTGCGGAACGTGTGCTGCAGCTGGGCGAAAAAGCGATCAC

CTGCCAGAAAGTGCTGATGGAAAACGCGAAAAGCCCGAAAGTGGCGAAAG

ACTGCTTCACCCCGCTGGAAGTGATCGAACTGATCAAACAGGACTACGAA

TACCTGCTGGCGGAATTCAAAAAACTGAACGAAGCGGCAGAAAAAGAAAG

CGACACCACCACCGCTGCTTTCGCGCAGGAAAACATCGCGAAATATGAAA

AAAGTCTGTGGATGATCGGCGCTACCCTGCAGGGCGCTTGCAAAATGTAA
```

The amino acid sequence of the Dps protein encoded by the nucleic acid of SEQ ID NO: 37 is provided below:

```
                                            (SEQ ID NO: 38)
MSVTKQLLQMQADAHHLWVKFHNYHWNVKGLQFFSIHEYTEKAYEEMAEL

FDSCAERVLQLGEKAITCQKVLMENAKSPKVAKDCFTPLEVIELIKQDYE

YLLAEFKKLNEAAEKESDTTTAAFAQENIAKYEKSLWMIGATLQGACKM
```

In some embodiments, the nucleic acid comprises a *C. jejuni* cj1534c gene (provided as SEQ ID NO: 37). In some embodiments, the nucleic acid comprises a cj1534c gene, wherein the cj1534c gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 37. In some embodiments, the nucleic acid comprises a cj1534c gene, wherein the cj1534c gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 37.

In some embodiments, the nucleic acid comprises a nucleic acid sequence encoding a Dps protein, wherein said Dps protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 38. In some embodiments, the nucleic acid comprises a nucleic acid sequence encoding a Dps protein, wherein said Dps protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 38.

cj1656c—In some embodiments, the recombinant bacterium comprises a nucleic acid comprising a cj1656c gene (e.g., a *C. jejuni* cj1656c gene).

In some embodiments, the nucleic acid comprising a cj1534c gene is located on a plasmid in the bacterium. In some embodiments, the nucleic acid comprising a cj1534c gene is located on a chromosome of the bacterium.

The nucleic acid sequence of an exemplary *C. jejuni* cj1656c gene is provided below:

```
                                            (SEQ ID NO: 39)
ATGGTTTCAGATGTTTCTATGGGTAATGTTAATTTAATGACTGCTGTTAA

TACTTCAGTTTTGAAAAAATCTATGGACACAAACGAGGCATTGATGAATG

AACTCATCGAAGGTATGGAAGGTGTCTCTCAAGCCTCCGCTCCACAAGCT

TCTAGCTCTAGTGGTTTGGATATTTACGCTTAA
```

The amino acid sequence of the Cj1656c protein encoded by the nucleic acid of SEQ ID NO: 39 is provided below:

(SEQ ID NO: 40)
MVSDVSMGNVNLMTAVNTSVLKKSMDTNEALMNELIEGMEGVSQASAPQA

SSSSGLDIYA

In some embodiments, the nucleic acid comprises a *C. jejuni* cj1656c gene (provided as SEQ ID NO: 39). In some embodiments, the nucleic acid comprises a cj1656c gene, wherein the cj1656c gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 39. In some embodiments, the nucleic acid comprises a cj1656c gene, wherein the cj1656c gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO:39.

In some embodiments, the nucleic acid comprises a nucleic acid sequence encoding a Cj1656c protein, wherein said Cj1656cs protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 40. In some embodiments, the nucleic acid comprises a nucleic acid sequence encoding a Cj1656c protein, wherein said Cj1656c protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 40.

B. *Campylobacter* Glycosylation Proteins

In some embodiments, the recombinant bacterium has been genetically engineered to produce the *Campylobacter jejuni* N-glycan in its surface. The *C. jejuni* N-glycan is a heptasaccharide ((GalNAc-α1,4-GalNAc-α1,4-[Glc-β-1,3] GalNAc-α1,4-GalNAc-α1,4-GalNAc-α1,3-diNAcBac; diNAcBac is 2,4-diacetamido-2,4,6-trideoxy-D-glucopyranose, GalNAc is N-acetylgalactosamine and Glc is glucose), and is commonly found in all *C. jejuni* and *Campylobacter coli* isolates. In *Campylobacter*, the N-glycan is added to multiple periplasmic and membrane proteins, and is immunogenic in rabbits and humans (see, e.g., Nothaft et al. (2012) *Mol. Cell. Proteomics* 11: 1203-19 (13); and Szymanski et al. (2003) *J Biol Chem.* 278: 24509-20 (14)).

Figure 6:
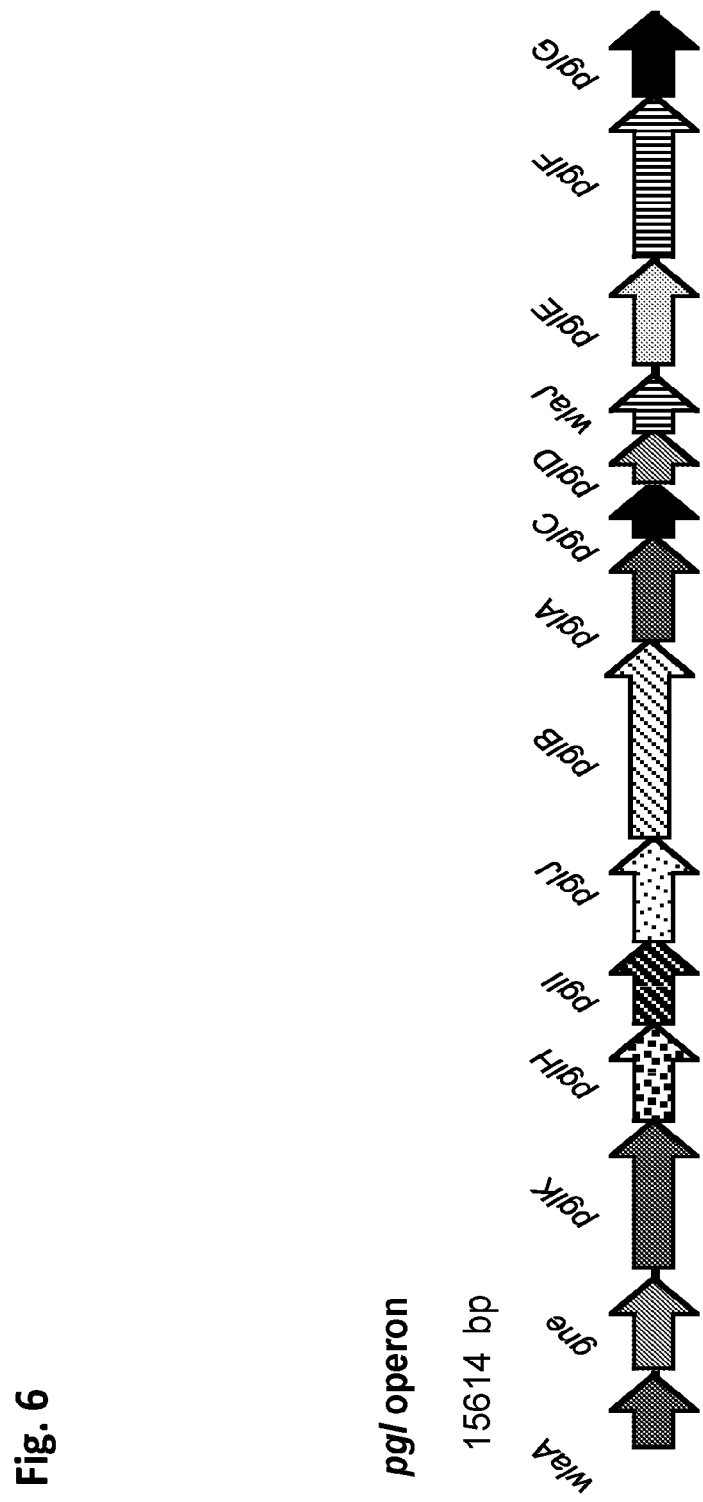

The *C. jejuni* N-glycan is conjugated onto the asparagine within the Glu/Asp Xaa1 Asn-Xaa2-Ser/Thr (SEQ ID NO: 41) glycosylation consensus motif. In *C. jejuni*, the genes encoding proteins that mediate N-linked glycosylation are present in a 17-kb locus named the pgl operon which contains 14 open reading frames (ORFs) (see Wacker et al. (2002) *Science* 298: 1790-3(15)). The 14 ORFs encode several glycotransferases and sugar biosynthetic enzymes which in concert generate a lipid-linked heptasaccharide precursor. The heptasaccharide is transferred onto the target asparagine by PglB in the bacterial periplasm. The *C. jejuni* pgl operon comprises the following genes: wlaA, gne, pglK, pglH, pglI, pglJ, pglB, pglA, pglC, pglD, wlaJ, pglE, pglF, and pglG (FIG. 6).

TABLE A pgl operon gene size and GC contents

| gene | aa | bp | GC % |
|---|---|---|---|
| wlaA | 264 | 795 | 29.6 |
| gne | 330 | 993 | 34.0 |
| pglK | 526 | 1581 | 29.0 |
| pglH | 354 | 1062 | 30.7 |
| pglI | 304 | 912 | 29.3 |
| pglJ | 362 | 1089 | 29.6 |
| pglB | 713 | 2142 | 29.2 |
| pglA | 376 | 1128 | 30.8 |
| pglC | 198 | 597 | 31.7 |
| pglD | 195 | 588 | 31.1 |
| wlaJ | 217 | 654 | 24.3 |
| pglE | 386 | 1161 | 31.0 |
| pglF | 590 | 1770 | 30.7 |
| pglG | 297 | 894 | 30.1 |

In some embodiments, the recombinant bacterium comprises a nucleic acid comprising a pgl operon (e.g., a *C. jejuni* pgl operon or a *C. coli* pgl operon). In some embodiments, the recombinant bacterium comprises at least one pgl operon gene selected from the group consisting of walA, gne, pglK, pglH, pglI, pglJ, pglB, pglA, pglC, pglD, pglE, pglF, and pglG. Expression of the nucleic acid comprising the pgl operon or of one or more of the pgl operon genes may confer the bacterium (e.g., a non-*Campylobacter* bacterium) the ability to synthesize and N-glycan and conjugate the N-glycan to proteins comprising the Glu/Asp Xaa1 Asn-Xaa2-Ser/Thr (SEQ ID NO: 41) glycosylation consensus motif.

In some embodiments, the nucleic acid comprising a pgl operon is located on a plasmid in the bacterium. In some embodiments, the nucleic acid comprising a pgl operon is located on a chromosome of the bacterium. In some embodiments, the nucleic acid comprising a pgl operon is located at the chromosomal locus corresponding to the locus of an endogenous cysG gene that has been deleted or altered in the bacterial chromosome. In some embodiments, the nucleic acid comprising a pgl operon is operably linked to a regulatable promoter (e.g., a LacI-regulatable promoter such as $P_{trc}$).

The nucleic acid sequence of an exemplary *C. jejuni* pgl operon is provided below:

(SEQ ID NO: 42)
GGATTACAAATGGCAAAAAATGAAGGTTATATTTGTGTTTTTGATTGTGA

GAGTGTGCCAGATGTTGAGCTTATCCGCAAAACTTTGGGTTTTGAAGGAA

GTGATTTAGAGGTAAGTTTAAAAGCACTTCAGTGGCAAAAAGAACAAAGT

GGGAGTGAGTTTTTGCCTTTGCCTTATCATAAAATTATCAGTATTTGTGC

GGTTTTAAGTGATAATTTTGGAAAATTTATCAAAGTGAATAAAATTGATG

GACAAAATGAAAAAGAAATGATTGAGAATTTTTTCAATTTTATAGAAAAT

TATGAGCCAAAATTAGTCAGTTTTAATGGTAAAAATTTCGATATGCCTGT

TCTTGTTTTAAGGGCTTTAAAATACAATTTAAAAGCAGCAACTTATTTGG

```
ATACTCAAAGTGATAAATGGAATAATTATAAAACAAGATTTTCAGAATTA
AAACATTGTGATTTATTAGAATCCTTAGGATCTAACGGGCGTGGAATAAA
GCTTGATACACTTTGTTCTATGGTGGGTTTGCCAGGAAAATATGATGTGC
ATGGCGATGAGGTAATGAAACTTTTTTATGAAAATAAACTTGAAAAAATC
CACGAATATTGTGAAAGTGATGTTTTAAACACCTATATGCTTTTTTTAAA
ATATGAACTTATTAAAGCTAATGTTGATGAAGAAGATTATGTTGGTTTTC
TTTCTTATATGAGAGATTTCTTGTGTGCAAAAAAATCAGATCGTTCTTAT
ACAGAAGTTTTTGCAAAAGCTTGTGAGAGTGAAATTTCAAAAGTTCGATC
TTAAGTATTTAAGAAAATATATTAAAATTTATTTTTGACATTTTTAAAAA
AAGGAATGATGATGAAAATTCTTATTAGCGGTGGTGCAGGTTATATAGGT
TCTCATACTTTAAGACAATTTTTAAAAACAGATCATGAAATTTGTGTTTT
AGATAATCTTTCTAAGGGTTCTAAAATCGCAATAGAAGATTTGCAAAAAA
CAAGAGCTTTTAAATTTTTCGAACAAGATTTAAGTGATTTTCAAGGCGTA
AAAGCATTGTTTGAGAGAGAAAATTTGACGCTATTGTGCATTTTGCAGC
AAGCATTGAAGTTTTTGAAAGTATGCAAAATCCTTTAAAATATTATATGA
ACAACACTGTTAATACGACAAATCTCATCGAAACTTGTTTGCAAACTGGA
GTGAATAAATTTATATTTCTTCAACGGCGGCCACTTATGGCGAACCACA
AACTCCCGTTGTGAGCGAAACAAGTCCTTTAGCACCTATTAATCCTTATG
GGCGTAGTAAGCTTATGAGTGAAGAAGTTTTGCGTGATGCAAGTATGGCA
AATCCTGAATTTAAGCATTGTATTTTAAGATATTTTAATGTTGCAGGTGC
TTGTATGGATTATACTTTAGGACAACGCTATCCAAAAGCGACTTTGCTTA
TAAAAGTTGCAGCTGAATGTGCCGCAGGAAAACGTGATAAACTTTTCATA
TTTGGCGATGATTATGATACAAAAGATGGTACTTGCATAAGAGATTTTAT
CCATGTAGATGATATTTCAAGTGCACATTTAGCGGCTTTGGATTATTTAA
AAGAGAATGAAAGCAATGTTTTTAATGTAGGTTATGGACATGGTTTTAGC
GTAAAAGAAGTGATTGAAGCGATGAAAAAAGTTAGCGGAGTGGATTTTAA
AGTAGAACTTGCCCCACGCCGTGCGGGTGATCCTAGTGTATTGATTTCTG
ATGCAAGTAAAATCAGAAATCTTACTTCTTGGCAGCCTAAATATGATGAT
TTAGAGCTTATTTGTAAATCTGCTTTTGATTGGGAAAAACAGTGTTAAAA
AAACTTTTTTTATTTAAGTAAGGAAGATAAAAATTTTTTATTTTTCTT
GCTTGTTTTTCAGTATTTATTTCTTTTATAGAAACTTTTGCAATTTCTT
TGGTAATGCCTTTTATCACTTTGGCTAGTGATTTTTCTTATTTTGATCGT
AATAAATATTTAATCAGCCTAAAAGAATATCTTAATATCCCTGTTTTTGA
AATCATTGTTTATTTTGGAGTGGGCTTATTGTTTTTATGTGTTTAGAG
CTTTGTTAAATGCGTATTATTTTCATCTTTTGGCAAGATTTTCTAAAGGG
CGTTATCATGCGATCGCTTATAAGGTTTTTTCTAAATTTTTAAATATTAA
TTATGAAAAATTTACTCAAAAAAATCAATCTGAAATTTTAAAGTCCATTA
CAGGGGAAGTTTATAATCTAAGCACTATGATTTCATCATTTTTACTTTTG
ATGAGTGAAATTTTTGTAGTACTTTTGCTTTATGCTTTAATGCTTTTGAT
TAATTATAAAATCACTTTGTTTTTAAGTATTTTTATGGTGTTAAATGCCT
TTATTTTAGTGAAAATTTTAAGCCCTATCATTAAAAAAGCAGGAGTAAGA
CGCGAAGAAGCGATGAAAAATTTCTTTGAAATTTTAAATACAAATTTAAA
TAATTTCAAATTTATTAAGCTTAAAACCAAAGAAGATGGAGTATTAAGTC
TTTTTAAAGCGCAAAGTGAAGCTTTTTCTAAAGCAAATATTACCAACGAA
AGCGTAGCTGCGGTGCCTAGAATTTATCTTGAAGGAATAGGCTTTTGCGT
ACTTGTTTTTATCGTGGTATTTTTGGTTTTGAAAAATGAAAGTGATATTT
CAGGTATTTTATCCACGATTTCTATTTTTGTTTTAGCGCTTTATCGCTTA
ATGCCAAGTGCAAATCGTATTATTACAAGTTATCATGATTTGCTTTATTA
TCATTCTTCTTTGGATATTATTTATCAAAATTTAAGACAAGAAGAAGAAA
ATTTGGGCGAGGAAAAATTAAGCTTTAATCAAGAGCTTAAAATTTGCAAT
CTTAGCTTTGGTTATGAGGGAAAAAAATATTTATTTAAAAATCTTAACTT
AAATATTAAAAAAGGCGAAAAAATCGCTTTTATAGGGGAGAGTGGTTGTG
GAAAAAGTACCTTAGTAGATCTTATCATAGGACTTTTAAAACCAAAAGAA
GGGCAAATTTTAATTGATGAGCAAGAATTAAATGCAAATAATACAAAAAA
TTATCGCCAAAAAATAGGCTATATCCCGCAAAATATCTATCTTTTTAATG
ACAGTATAGCTAAAAATATCACTTTTGGAGATGCGGTTGATGAAGAAAAA
CTTAATAGGGTTATCAAACAAGCAAATTTAGAGCATTTTATAAAAAATTT
ACCTCAAGGAGTGCAAACAAAAGTGGGCGATGGGGGAGTAATTTAAGCG
GGGGACAAAAACAACGCATAGCTATAGCAAGAGCTTTATATTTAGAGCCT
GAAATGTTAGTGCTTGATGAAGCAACTTCTGCGCTTGATACTCAAAGTGA
AGCAAAAATTATGGATGAAATTTATAAAATTTCTAAAGATAAAACCATGA
TTATTATCGCACATCGCCTTTCTACGATAACACAATGTGATAAGGTTTAT
CGTTTAGAACACGGTAAGCTTAAAGAGGAGAAATGATGAAAATAAGCTTT
ATTATCGCAACTTTAAATTCAGGAGGTGCTGAGCGTGCTTTAGTAACCTT
AGCTAATGCACTTTGCAAAGAGCATGAAGTAAGTATTATTAAATTTCATG
CAGGAGAATCTTTTTATAAGCTTGAAAATGAAGTTAAAGTTACAAGTTTG
GAACAATTTAGATTTGACACGCTTTATCATAAAATCGCAAGTCGTTTTAA
GAAATTTTTTGCTTTAAGAAAGGCTTTGAAAGAAAGTAAGTCTGATGTTT
TTATTTCTTTTTTGGATACGACTAATATTGCTTGTATTGCTGCGAAAATA
GGGCTTAAAACTCCACTCATTATAAGTGAGCATAGCAATGAAGCGTATTT
AAAACCTAAAATTTGGCGTTTTTTAAGAAGGGTAAGCTATCCTTTTTGTG
ATGCTTTAAGTGTGCTTGGAAGCAGTGATAAGGTGTATTATGAAAGATTT
GTAAAAAGGGTTAAGCTTTTATTAAACCCTTGTCATTTAGCGATGAAAT
TTCTTTTGATTCTAGTTTTGAAAAGGAAAATTTGGTTCTTTTTATAGGGC
GTTTAGATCACAACAAAAACCCTGTAATGTTTTAAAAGCTATAGCGCAT
TTGGATAAAAATTTACAAGAAAATTATAAATTTGTTATAGCAGGAGATGG
ACAGTTAAGACAAGAACTTGAATATAAGGTAAAATCTTTAGGAATAAAAG
TTGATTTTTTAGGACGCGTTGAAAATGTCAAGGCTCTTTATGAAAAAGCA
AAAGTGCTTTGCCTTTGTTCTTTTGTAGAGGGTTTGCCAACGGTTTTAAT
TGAAAGTTTGTATTTTGAGGTTTGTAGAATTTCAAGTTCTTATTATAATG
GTGCTAAGGATTTAATCAAAGATAATCATGATGGGCTTTTGGTAGGTTGT
```

```
GATGATGAAATAGCACTTGCTAAAAAACTTGAACTTGTTTTAAATGATGA
AAATTTTAGAAAAGAACTTGTAAATAATGCCAAACAAAGGTGTAAAGACT
TTGAAATTTCTCATATCAAAGAAGAATGGCTTAAGCTTATAGCCGAGGTT
AAAAATGCCTAAACTTTCTGTTATAGTACCAACTTTTAATCGTCAAGTTT
TGTTAGAAAAGGCTATTAAAAGCATACAAAATCAAGATTTTAAAGATTTA
GAAATTATTGTAAGCGATGATAATTCTAGCGATGATACTAAAAGTGTGGT
GCAAAATTTACAAAAAGATGATGATCGCATTAAGTATTTTTAAATCAAA
ATTACAAACAAGGTCCAAATGGCAATAAAAACAATGGCTTAGATCAAGCA
AGTGGCGAGTTTGTAACTTTTTTAGATGATGATGATGAGCTTTTATCCGG
GGCTTTAAGTACCTTGATGCAAAAAGCAAATGAGGGTTATGCTCATGTTT
TTGGAAATTGTTTGATAGAAAAGAAGGAAATTTAAGCAAGGAATTTAGC
GGCAAGGGCTTGGAAAAAGATAGTGAAATTTCTAAAAAAGATTTTTTAAT
GGCTAAATTTAGCGGAGAGTTTTTTTCTGTTTTAAAAAATCCCTACTTG
AAAATAAGCGTTTTAATGAAGAATTTTATGGCAATGAAGCCACGCTTTGG
GTAAATTTATACAAAGAAAAAGTTTTTATATCCATAAGGCTTTTAGGAT
TTATAGAATTTTTAGGCAAGATAGCGTGACTTTAGGGGCGAGTAAAAATG
CTTATAGGGTGTATTTGGGATATTTAGAGCTTGCTAAAATTTTAGAAAAT
GAACTTAGAATGAGTAAGGATAAAGATTATAAAAAAACTTGTGCGAGTTA
TTATAAAATGGCAGCTTATTATGCAAAACTTGCAAAAAATTATAAAGCCC
TTTATAAATGTTTGTTTAAAAGCCTAAGTATAAAAATCAACGCTCCTGCT
TTGATATTACTCATTTTAAGTATAATTCCAAATAATATGATTGAAAAATT
ATCAAAAATTCGGGTGGCTTTATGCAAAAATTAGGCATTTTTATTTATTC
TTTAGGAAGTGGTGGTGCTGAAAGAGTTGTGGCGACTTTATTGCCTATTT
TAAGTTTGAAATTTGAAGTGCATTTGATCTTGATGAATGATAAAATTTCT
TATGAAATTCCAGAGTGTCAAATTCATTTTTTAGAATGTTCAAAACCTAG
TGAAAATCCTATTTTGAAATTTTTAAAACTACCTTTTTTGGCTTTAAAAT
ACAAAAAACTTTGCAGAAATTTAGGTATTGATACAGAATTGTTTTTTTA
AATCGACCTAATTATATAGCTTTAATGGCAAGAATGTTTGGAAACAAAAC
TCGCCTTGTGATCAATGAATGCACTACGCCAAGTGTGATGTATATGAAAA
ATAATTTTAATTCTTTGGTAAATAAATTTTTAATTTCTTTGCTTTACCCA
AAAGCTGATTTAATCTTGCCTAATTCTAAGGGAAATTTAGAAGATTTAGT
GCAAAATTTTAGTATAAGTCCAAAAAAATGTGAAATTTTATACAATGCCA
TCGATTTAGAAAACATAGGGCAAAAAGCCCTTGAAGACATAGCTTTAAAA
GATAAATTTATTTTAAGTGTAGGCAGGCTTGATAAAGGTAAAAATCATGC
TTTATTAATTCGTGCTTATGCGAGATTGAAAACAGATTTAAAGCTTGTGA
TTTTAGGTGAAGGTGTGCTTAAGGATGAGCTTTTAGCTTTGATTAAAGAA
TTAAAATTTGGAAGAAAAGGTTTTGCTTTTAGGATTTGATAATAATCCTTA
TAAATACATGGCTAAATGCGAATTTTTTGCTTTTGCTTCTGTGTTTGAAG
GTTTTTCAAATGTTTTAATCGAAAGTTTGGCTTGTTCTTGTGCGGTGGTT
TGCACTGATCATAAAAGTGGTGCAAGAGAGCTTTTTGGCGATGATGAATT
```
```
TGGACTTTTAGTAGAAGTAGATAATGAAAACTCTATGTTTCAGGGTTTAA
AAACTATGCTTGAAGACGATAAATTAAGAAAAGCGTATAAAAACAAAGCT
AAAACTAGGGCTAAAGCCTTTGATAAAGTAAAAATTGCACGCGATGCTTT
GAAATATTTATTAGGATAAAAGATGTTGAAAAAAGAGTATTTAAAAAACC
CTTATTTAGTTTTGTTTGCGATGATTGTATTAGCTTATGTTTTTAGTGTA
TTTTGCAGGTTTTATTGGGTTTGGTGGGCAAGTGAGTTTAACGAGTATTT
TTTCAATAATCAATTAATGATCATTTCAAACGATGGCTATGCTTTTGCTG
AGGGCGCAAGAGATATGATAGCAGGTTTTCATCAGCCTAATGATTTGAGT
TATTATGGATCTTCTTTATCTACGCTTACTTATTGGCTTTATAAAATCAC
ACCTTTTTCTTTTGAAAGTATCATTTTATATATGAGTACTTTTTTATCTT
CTTTGGTGGTGATTCCTATTATTTTACTAGCTAATGAATACAAACGCCCT
TTAATGGGCTTTGTAGCTGCTCTTTTAGCAAGTGTAGCAAACAGTTATTA
TAATCGCACTATGAGTGGGTATTATGATACGGATATGCTGGTAATTGTTT
TACCTATGTTTATTTATTTTTTATGGTAAGAATGATTTTAAAAAAAGAC
TTTTTTTCATTGATTGCCTTGCCATTATTTATAGGAATTTATCTTTGGTG
GTATCCTTCAAGTTATACTTTAAATGTAGCTTTAATTGGACTTTTTTTAA
TTTATACACTTATTTTTCATAGAAAAGAAAAGATTTTTTATATAGCTGTG
ATTTTGTCTTCTCTTACTCTTTCAAATATAGCATGGTTTTATCAAAGTGC
CATTATAGTAATACTTTTTGCTTTATTTGCTTTAGAGCAAAAACGCTTAA
ATTTTATGATTATAGGAATTTTAGGTAGTGCAACTTTGATATTTTTGATT
TTAAGTGGTGGGGTTGATCCCATACTTTATCAGCTTAAATTTTATATTTT
TAGAAGCGATGAAAGTGCGAATTTAACACAGGGCTTTATGTATTTTAATG
TTAATCAAACCATACAAGAAGTTGAAAATGTAGATTTTAGCGAATTTATG
CGAAGAATTAGTGGTAGTGAAATTGTTTTCTTGTTTTCTTTGTTTGGTTT
TGTATGGCTTTTGAGAAAACATAAAAGTATGATTATGGCTTTACCTATAT
TGGTGCTTGGGTTTTAGCCTTAAAAGGAGGACTTAGATTTACCATTTAT
TCTGTACCTGTAATGGCTTTAGGATTTGGTTTTTTATTGAGCGAGTTTAA
GGCTATATTGGTTAAAAAATATAGCCAATTAACTTCAATGTTTGTATTGT
TTTTTGCAACTATTTTGACTTTGGCTCCAGTATTTATCCATATTTACAACT
ATAAAGCGCCAACAGTTTTTTCTCAAAATGAAGCATCATTATTAAATCAA
TTAAAAAATATAGCCAATAGAGAAGATTATGTGGTAACTTGGTGGGATTA
TGGTTATCCTGTGCGTTATTATAGCGATGTGAAAACTTTAGTAGATGGTG
GAAAGCATTTAGGTAAGGATAATTTTTTCCCTTCTTTTTCTTTAAGTAAA
GATGAACAAGCTGCAGCTAATATGGCAAGACTTAGTGTAGAATATACAGA
AAAAAGCTTTTATGCTCCGCAAAATGATATTTTAAAATCAGACATTTTAC
AAGCCATGATGAAAGATTATAATCAAAGCAATGTGGATTTATTTCTAGCT
TCATTATCAAAACCTGATTTTAAAATCGATACACCAAAAACTCGTGATAT
TTATCTTTATATGCCCGCTAGAATGTCTTTGATTTTTTCTACGGTGGCTA
GTTTTTCTTTTATTAATTTAGATACAGGAGTTTTGGATAAACCTTTTACC
TTTAGCACAGCTTATCCACTTGATGTTAAAAATGGAGAAATTTATCTTAG
CAACGGAGTGGTTTTAAGCGATGATTTTAGAAGTTTTAAAATAGGTGATA
```

-continued

```
ATGTGGTTTCTGTAAATAGTATCGTAGAGATTAATTCTATTAAACAAGGT
GAATACAAAATCACTCCAATCGATGATAAGGCTCAGTTTTATATTTTTA
TTTAAAGGATAGTGCTATTCCTTACGCACAATTTATTTTAATGGATAAAA
CCATGTTTAATAGTGCTTATGTGCAAATGTTTTTTTGGGAAATTATGAT
AAGAATTTATTTGACTTGGTGATTAATTCTAGAGATGCTAAAGTTTTTAA
ACTTAAAATTTAAGGGTTGAAAATGAGAATAGGATTTTTATCACATGCAG
GAGCGAGTATTTATCATTTTAGAATGCCTATTATAAAAGCGTTAAAAGAT
AGAAAAGACGAAGTTTTTGTTATAGTGCCGCAAGATGAATACACGCAAAA
ACTTAGAGATCTTGGCTTAAAAGTAATTGTTTATGAGTTTTCAAGAGCTA
GTTTAAATCCTTTTGTGGTTTTAAAGAATTTTTTTTATCTTGCTAAGGTT
TTGAAAAATTTAAATCTTGATTTTATTCAAAGTGCGGCACACAAAAGCAA
TACTTTTGGAATTTTAGCAGCAAAATGGGCAAAAATTCCTTATCGTTTTG
CCTTAGTAGAAGGCTTGGGATCTTTTTATATAGATCAAGGTTTTAAGGCA
AATTTAGTGCGTTTTGTTATTAATAGTCTTTATAAATTAAGTTTTAAATT
TGCACACCAATTTATTTTTGTCAATGAAAGTAATGCTGAGTTTATGCGGA
ATTTAGGACTTAAAGAAAATAAAATTTGCGTGATAAAATCTGTAGGGATC
AATTTAAAAAAATTTTTCCTATTTATGTAGAATCGGAAAAAAAGAGCT
TTTTTGGAAAAATTTAAACATAGATAAAAAACCCATTGTGCTTATGATAG
CAAGAGCTTTATGGCATAAGGGTGTAAAAGAATTTTATGAAAGTGCTACT
ATGCTAAAAGACAAAGCAAATTTTGTTTTAGTTGGTGGAAGAGATGAAAA
TCCTTCTTGTGCAAGTTTGGAGTTTTTAAACTCTGGCGCGGTGCATTATT
TGGGTGCTAGAAGTGATATAGTCGAGCTTTTGCAAAATTGTGATATTTTT
GTTTTGCCAAGCTATAAAGAAGGCTTTCCTGTAAGTGTTTTGGAGGCAAA
AGCTTGCGGTAAGGCTATAGTGGTGAGTGATTGTGAAGGTTGTGTGGAGG
CTATTTCTAATGCTTATGATGGACTTTGGGCAAAAACAAAAAATGCTAAA
GATTTAAGCGAAAAAATTTCACTTTTATTAGAAGATGAAAAATTAAGATT
AAATTTAGCTAAAAATGCCGCCCAAGATGCTTTACAATACGATGAAAATA
TAATCGCACAGCGTTATTTAAAACTTTATGATAGGGTAATTAAGAATGTA
TGAAAAGTTTTTAAAAGAATTTTTGATTTTATTTTAGCTTTAGTGCTTT
TAGTGCTTTTTTCTCCGGTGATTTTAATCACTGCTTTACTTTTAAAAATC
ACTCAAGGAAGTGTGATTTTTACCCAAAATCGTCCCGGGTTAGATGAAAA
AATTTTTAAAATTTATAAATTTAAAACCATGAGCGATGAAAGAGATGAAA
AGGGTGAGTTATTAAGCGATGAATTGCGTTTGAAAGCTTTTGGAAAAATC
GTTAGAAGCTTAAGTTTGGATGAGCTTTTGCAACTTTTTAATGTTTTAAA
AGGGGATATGAGTTTTGTTGGACCTAGACCTCTTTTGGTTGAGTATTTGC
CTCTTTACAATAAAGAGCAAAAATTGCGTCATAAAGTGCGTCCAGGTATA
ACAGGATGGGCGCAGGTAAATGGTAGAAATGCTATTTCTTGGCAGAAAAA
ATTCGAACTTGATGTGTATTATGTGAAAAATATTTCTTTTTTGCTTGATT
TAAAAATCATGTTTTTAACAGCTTTAAAGGTTTTAAAACGAAGTGGGGTA
AGCAAAGAAGGCCATGTTACAACAGAGAAATTTAATGGCAAGAACTGAAA
AAATTTATATTTATGGTGCTAGTGGTCATGGGCTTGTTTGTGAAGATGTG
GCTAAAAATATGGGTTATAAAGAATGTATTTTTTTAGATGATTTTAAAGG
AATGAAATTTGAAAGTACCTTACCTAAATATGATTTTTTTATAGCCATAG
GAAACAATGAAATTCGAAAAAAGATTTATCAAAAAATTTCAGAAAATGGC
TTTAAAATTGTCAATCTTATCCATAAAAGCGCGCTTATAAGTCCTAGCGC
AATCGTGGAAGAAAATGCAGGAATTTAATCATGCCTTATGTAGTGATTA
ACGCTAAAGCTAAAATAGAAAAGGTGTGATTTTAAATACTTCAAGCGTA
ATTGAGCATGAATGTGTGATAGGGGAATTTTCTCATGTGAGTGTGGGAGC
TAAATGTGCGGGTAATGTAAAAATTGGTAAAAATTGTTTTTTAGGGATTA
ATTCTTGTGTTTTGCCTAATTTAAGTTTGGCAGATGATAGTATTTTAGGT
GGTGGAGCAACTTTAGTTAAAAATCAAGATGAAAAGGTGTTTTTGTGGG
AGTACCTGCAAAAAGGATGTAAATTGCATTTTAATAACAATCTTGTTGTT
CACTATATAGTAAATCCTTCGCCTTTGGGGTGGATTGTCATTAATTTACT
AACCATATGTCTAATATGCTACATATTTCCTTTGAAAAATTCTTTAAAAC
ACAAAAAACTTTTTAGTCTTAAAGCAAATGTAAATTCTAAAAATAGTAGG
ATTATAAAATATACAGGTATTGCTGCTTTTTTGGGTGGATTAATAGGAAT
TTGGTATAATTTTGAAGGTTTTTATCAACTTCTTTTTTTCTTTGAATTAG
AAAATGAAAATTTAAAAACACTTTGGAGTTTGCAAGTATCAGTTTCTTCT
GTGATAACAGGTATGTTATTATTGTTGATATATGTTATAAATTTAGCAAT
GGTTTGTGAAAATGGAATTTATATAGTTAGTAAATTTAATCTTTTTATA
TGTATTTTATAAAACGAGAAGATTTGGAAATTGTTAAAATAGAAAAAATG
AAATTTTTAAATCAAGTTGAAGTTTGTTTTGTTATCAAAACAAAAAATAA
AATACTCCTTAAATGCTTTGAAAGTATTTATAAAAAAGAAGACTTAGAAA
AGCTTAAAAATTGGTATGAAAACAAGCTTTGACTATAAAAGAATTTAAA
TATTTGAATCTTTGTAAATTTTTTAGGTAAAATAGAGTCAATTTATAAA
AATTTTGTTTTACACAAAGGATAAATCATGAGATTTTTTCTTTCTCCTCC
GCATATGGGTGGTAATGAATTAAAATACATAGAAGAAGTTTTCAAAAGCA
ATTATATAGCACCTTTGGGTGAATTTGTAAATCGCTTTGAACAAAGTGTC
AAGGCTTACAGTAAAAGTGAAAATGCCTTAGCTTTAAATTCAGCCACAGC
GGCTTTGCATTTAGCTTTAAGGGTGGCAGGGGTAAAACAAGATGATATTG
TTTTGGCTTCTTCTTTTACTTTTATCGCTTCAGTAGCACCTATTTGTTAT
CTTAAAGCAAACCTGTATTTATAGATTGTGATGAAACTTATAATATCGA
TGTAGATTATTAAAGCTTGCTATTAAAGAATGTGAAAAAAAACCAAAAG
CATTGATTTTAACTCATCTTTATGGCAATGCGGCTAAAATGGATGAAATT
GTTGAAATTTGCAAAGAAATGAAATTGTTTTAATCGAAGATGCTGCTGA
AGCTTTAGGAAGTTTTTATAAGAATAAAGCTTTAGGAACTTTTGGAGAAT
TTGGAGCTTATTCTTATAATGGCAATAAAATTATCACCACTTCAGGTGGA
GGTATGCTTATAGGAAAAATAAAGAAAGATTGAAAAAGCAAGATTTTA
TAGCACTCAAGCTAGGGAAAATTGTTTGCATTATGAACATTTAGATTATG
GTTATAATTACCGCTTAAGCAATGTTTTAGGAGCTATTGGCGTAGCGCAA
ATGGAGGTTTTAGAACAAAGAGTGCTTAAAAAAAGAGAAATTTATGAGTG
```

-continued

GTATAAAGAATTTTTAGGAGAGTGTTTTAGCTTTTTAGATGAATTAGAAA

ATTCAAGAAGCAATCGCTGGTTAAGTACAGCTTTGATTGATTTTGATAAA

AATGAACTTAATTCTTGTCAAAAAGATATAAATATCAGTCAAAAAAATAT

TACTTTGCATCCAAAAATTTCAAAACTCATAGAAGATTTGAAAAATGAAC

AAATAGAAACAAGACCATTATGGAAAGCTATGCACGCTCAAGAAGTATTT

AAAGGAGCTAAGGCTTATCTTAATGGCAATAGTGAGTTATTTTTCCAAAA

AGGAATTTGTTTGCCAAGTGGCACGGCGATGAGTAAAGATGATGTTTATG

AAATTTCAAAACTGATCTTAAAGAGCATAAAGGCTTAAAATGATTTTTTA

TAAAAGCAAAAGATTAGCATTTTTTTTAACTTCAGATATTGTTTTAATTT

TACTTAGCGTTTATCTGGCTTTTTCTTTGAGATTTAGTGGAGATATTCCG

AGTATTTTTATCATGGTATGATGGTTTCTGCTATTATTTTGCTTGTTTT

AAAACTTTCATTTTTGTTTGTTTTTAGAATTTATAAAGTAGCTTGGAGAT

TTTTTTCTCTCAATGAAGCAAGAAAGATTTTTATCGCTTTGCTTTTAGCT

GAGTTTTGTTTTTTTCTTATTTTTTATTTTTTAGTGATTTTTTTAATCC

TTTTCCAAGAAGTGCTATTGTGATAGATTTTGTTCTTTCTTATATGTTTA

TAGGTACTTTAAGAATTAGCAAAAGAATGCTTGTGGATTTTAAACCTTCT

AGAATGAAAGAAGAAGAAACTCCTTGTATTGTAGTAGGGGCAACTTCTAA

GGCTTTGCATTTGTTAAAAGGTGCAAAAGAAGGTTCTTTAGGGCTTTTTC

CTGTAGGCGTAGTTGATGCGAGAAAAGAGCTTATAGGGACTTATTGTGAT

AAATTTATTGTAGAAGAAAAAGAAAAAATAAAATCTTATGTAGAACAAGG

GGTAAAAACTGCCATTATTGCTTTAAGACTTGAACAAGAAGAGCTTAAAA

AACTTTTTGAAGAACTTGTAGCTTATGGTATTTGCGATGTAAAAATATTT

TCTTTTACAAGAAACGAAGCAAGAGATATCAGTATAGAAGACTTGCTTGC

TAGAAAACCAAAAGATTTAGATGATAGTGCTGTGGCGGCTTTTTTAAAAG

ATAAGGTAGTTTTGGTAAGTGGAGCAGGTGGAACTATAGGCAGTGAACTT

TGTAAGCAATGTATTAAATTTGGTGCTAAGCATCTTATCATGGTTGATCA

TAGTGAGTATAATCTTTATAAGATCAATGATGATTTAATTTATATAAAG

AAAAAATTACTCCTATTTTACTGAGTATTTTAGATAAGCAAAGTTTAGAT

GAGGTATTAAAAACTTATAAACCCGAGCTTATTTTACATGCAGCCGCTTA

TAAACATGTGCCTCTTTGCGAACAAAATCCACATTCAGCAGTAATCAATA

ATATTTTAGGAACTAAAATTTTATGCGACAGTGCTAAAGAAAACAAAGTA

GCTAAATTTGTGATGATAAGTACAGATAAAGCAGTACGACCAACAAATAT

TATGGGTTGCACTAAGAGAGTTTGCGAGCTTTATACTTTAAGTATGAGTG

ATGAAAATTTTGAAGTTGCTTGTGTGCGTTTTGGTAATGTTTTAGGTTCT

AGTGGTAGTGTGATACCGAAATTTAAAGCACAAATTGCCAATAATGAGCC

TTTAACTTTAACGCACCCTGATATAGTGCGTTATTTTATGCTTGTGGCTG

AGGCAGTGCAACTTGTTTTACAAGCTGGAGCTATCGCAAAAGGGGGAGAA

CTTTTTGTTTTGGATATGGGTAAGCCTGTGAAAATCATAGATTTAGCTAA

AAAAATGCTTTTACTTTCTAATCGCAATGATTTAGAAATTAAAATCACAG

GCTTAAGAAAAGGTGAGAAGCTTTATGAAGAGCTTTTGATTGATGAAAT

GATGCTAAAACACAATATGAGAGTATTTTTGTAGCAAAGAATGAGAAGGT

TGACCTTGATTGGCTTAATAAAGAGATAGAAAATTTACAAATATGTGAAG

ATATTTCAGAGGCTTTATTAAAGATTGTACCTGAATTTAAACACAATAAA

GAAGGTGTATAATGTATATAAAAGATATACAAAGATTTGAAGATAATCGC

TATCGTGCTAGAGCTTATATGAGTTATATTTTAACAAGAAATCTGCCCAA

TAAACTTCCTGACATTCACCTTGAAACGATTAAAACAGCTTTGGATAAAA

TAGCTCATGAAGTTGTTGTTTTTGATGCTTTGTATATTTTAGATATTTCA

GGCATGCAAATAGAAAATGCGATTTCCTTAAATAAAGCTCATGAAATAGG

GCAGGGTGAGGATAGAAGTACTCGTTCTTATTTTTATAGAGCTGTAAAAT

TAAGACGATGTGTTTTGAGCGATCCTTATCCTTCGGTTTTAAATAATGAG

CTTTGCGTGACAGCTTCTATGCCAATTTACGATGATAAAAATAACTTGCT

TTTTGTTGTTTGTATTGATATCAAGCTTGAAGATATTTTAAAGATTATTC

AAGCAGGAAAATTTGAATTTGTTTTTACTCAGTTTAGTCGTTTGGTATAT

TTTTGCTTCGCACTGGTTTTATTTGTGATTACTTGTTTTTTATTTCAAAA

AGGTTTTTTTAGTCTTTTTGATAATCAAGCTATAGGTATAGAACATATGT

TTGAAAGTACCATCGCTATAACTTTGGCTTTAGCTATTTTTGATTTGGCA

AAAACTTTGATCGAACAAGAAGTATTAGGAAGGACGAAAAAAGAAGAAGG

TGGAATTCAAAAAACTATGGTGAGATTTTTGGGTTCTATTATCATTGCTT

TAGCTATAGAAGCTTTGATGTTGGTATTTAAACTTGCTATTGGTGATCTT

TCTCAGATGATTTATGCGATTTATCTTATCGGTGGAGTGAGCTTGCTTCT

TTTAGGTTTAAGTGTATATTTATTTACGGTTAAGTATAAAAATAATAATA

TTTGAACTTAGT.

In some embodiments, the nucleic acid comprises a C. jejuni pgl operon (provided as SEQ ID NO: 42). In some embodiments, the nucleic acid comprises a C. jejuni pgl operon, wherein the C. jejuni pgl operon comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 42. In some embodiments, the nucleic acid comprises C. jejuni pgl operon, wherein C. jejuni pgl operon comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 42.

wlaA—In some embodiments, the recombinant bacterium comprises a nucleic acid comprising a wlaA gene (e.g., a C. jejuni wlaA gene).

In some embodiments, the nucleic acid comprising a wlaA gene is located on a plasmid in the bacterium. In some embodiments, the nucleic acid comprising a wlaA gene is located on a chromosome of the bacterium.

The nucleic acid sequence of an exemplary C. jejuni wlaA gene is provided below:

(SEQ ID NO: 43)
ATGGCAAAAAATGAAGGTTATATTTGTGTTTTTGATTGTGAGAGTGTGCC

AGATGTTGAGCTTATCCGCAAAACTTTGGGTTTTGAAGGAAGTGATTTAG

AGGTAAGTTTAAAAGCACTTCAGTGGCAAAAAGAACAAAGTGGGAGTGAG

TTTTTGCCTTTGCCTTATCATAAAATTATCAGTATTTGTGCGGTTTTAAG

TGATAATTTTGGAAAATTTATCAAAGTGAATAAAATTGATGGACAAAATG

AAAAAGAAATGATTGAGAATTTTTTCAATTTTATAGAAAATTATGAGCCA

AAATTAGTCAGTTTTAATGGTAAAAATTTCGATATGCCTGTTCTTGTTTT

AAGGGCTTTAAAATACAATTTAAAAGCAGCAACTTATTTGGATACTCAAA

GTGATAAATGGAATAATTATAAAACAAGATTTTCAGAATTAAAACATTGT

GATTTATTAGAATCCTTAGGATCTAACGGGCGTGGAATAAAGCTTGATAC

ACTTTGTTCTATGGTGGGTTTGCCAGGAAAATATGATGTGCATGGCGATG

AGGTAATGAAACTTTTTTATGAAAATAAACTTGAAAAAATCCACGAATAT

TGTGAAAGTGATGTTTTAAACACCTATATGCTTTTTTTAAAATATGAACT

TATTAAAGCTAATGTTGATGAAGAAGATTATGTTGGTTTTCTTTCTTATA

TGAGAGATTTCTTGTGTGCAAAAAAATCAGATCGTTCTTATACAGAAGTT

TTTGCAAAAGCTTGTGAGAGTGAAATTTCAAAAGTTCGATCTTAA

The amino acid sequence of the WlaA protein encoded by the nucleic acid of SEQ ID NO: 43 is provided below:

MAKNEGYICVFDCESVPDVELIRKTLGFEGSDLEVSLKALQWQKEQSGSE

FLPLPYHKIISICAVLSDNFGKFIKVNKIDGQNEKEMIENFFNFIENYEP

KLVSFNGKNFDMPVLVLRALKYNLKAATYLDTQSDKWNNYKTRFSELKHC

DLLESLGSNGRGIKLDTLCSMVGLPGKYDVHGDEVMKLFYENKLEKIHEY

CESDVLNTYMLFLKYELIKANVDEEDYVGFLSYMRDFLCAKKSDRSYTEV

FAKACESEISKVRS

In some embodiments, the nucleic acid comprises a C. jejuni wlaA gene (provided as SEQ ID NO: 43). In some embodiments, the nucleic acid comprises a wlaA gene, wherein the wlaA gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO:43. In some embodiments, the nucleic acid comprises a wlaA gene, wherein the wlaA gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 43.

In some embodiments, the nucleic acid comprises a nucleic acid sequence encoding a WlaA protein, wherein said WlaA protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 44. In some embodiments, the nucleic acid comprises a nucleic acid sequence encoding a WlaA protein, wherein said WlaA protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 44.

wlaJ—In some embodiments, the recombinant bacterium comprises a nucleic acid comprising a wlaJ gene (e.g., a C. jejuni wlaA gene).

In some embodiments, the nucleic acid comprising a wlaJ gene is located on a plasmid in the bacterium. In some embodiments, the nucleic acid comprising a wlaJ gene is located on a chromosome of the bacterium.

The nucleic acid sequence of an exemplary C. jejuni wlaJ gene is provided below:

(SEQ ID NO: 45)
ATGAAAAAGGTGTTTTTGTGGGAGTACCTGCAAAAAGGATGTAAATTGCA

TTTTAATAACAATCTTGTTGTTCACTATATAGTAAATCCTTCGCCTTTGG

GGTGGATTGTCATTAATTTACTAACCATATGTCTAATATGCTACATATTT

CCTTTGAAAAATTCTTTAAAACACAAAAAACTTTTTAGTCTTAAAGCAAA

TGTAAATTCTAAAAATAGTAGGATTATAAAATATACAGGTATTGCTGCTT

TTTTGGGTGGATTAATAGGAATTTGGTATAATTTTGAAGGTTTTTATCAA

CTTCTTTTTTTCTTTGAATTAGAAAATGAAAATTTAAAAACACTTTGGAG

TTTGCAAGTATCAGTTTCTTCTGTGATAACAGGTATGTTATTATTGTTGA

TATATGTTATAAATTTAGCAATGGTTTGTGAAAATGGAATTTATATAGTT

AGTAAATTTAATCTTTTTTATATGTATTTTATAAAACGAGAAGATTTGGA

AATTGTTAAAATAGAAAAAATGAAATTTTTAAATCAAGTTGAAGTTTGTT

TTGTTATCAAAACAAAAAATAAAATACTCCTTAAATGCTTTGAAAGTATT

TATAAAAAAGAAGACTTAGAAAAGCTTAAAAATTGGTATGAAAACAAGCT

TTGA.

The amino acid sequence of the WlaJ protein encoded by the nucleic acid of SEQ ID NO: 45 is provided below:

MKKVFLWEYLQKGCKLHFNNNLVVHYIVNPSPLGWIVINLLTICLICYIF

PLKNSLKHKKLFSLKANVNSKNSRIIKYTGIAAFLGGLIGIWYNFEGFYQ

LLFFFELENENLKTLWSLQVSVSSVITGMLLLLIYVINLAMVCENGIYIV

SKFNLFYMYFIKREDLEIVKIEKMKFLNQVEVCFVIKTKNKILLKCFESI

YKKEDLEKLKNWYENKL.

In some embodiments, the nucleic acid comprises a C. jejuni wlaJ gene (provided as SEQ ID NO: 45). In some embodiments, the nucleic acid comprises a wlaJ gene, wherein the wlaJ gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 45. In some embodiments, the nucleic acid comprises a wlaJ gene, wherein the wlaJ gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 45.

In some embodiments, the nucleic acid comprises a nucleic acid sequence encoding a WlaJ protein, wherein said WlaJ protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 46. In some embodiments, the nucleic acid comprises a nucleic acid sequence encoding a WlaJ protein, wherein said WlaJ protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 46.

gne—In some embodiments, the recombinant bacterium comprises a nucleic acid comprising a gne gene (e.g., a *C. jejuni* gne gene).

In some embodiments, the nucleic acid comprising a gne gene is located on a plasmid in the bacterium. In some embodiments, the nucleic acid comprising a gne gene is located on a chromosome of the bacterium.

The nucleic acid sequence of an exemplary *C. jejuni* gne gene is provided below:

```
                                        (SEQ ID NO: 47)
ATGATGATGAAAATTCTTATTAGCGGTGGTGCAGGTTATATAGGTTCTCA

TACTTTAAGACAATTTTTAAAAACAGATCATGAAATTTGTGTTTTAGATA

ATCTTTCTAAGGGTTCTAAAATCGCAATAGAAGATTTGCAAAAAACAAGA

GCTTTTAAATTTTTCGAACAAGATTTAAGTGATTTTCAAGGCGTAAAAGC

ATTGTTTGAGAGAGAAAATTTGACGCTATTGTGCATTTTGCAGCAAGCA

TTGAAGTTTTTGAAAGTATGCAAAATCCTTTAAAATATTATATGAACAAC

ACTGTTAATACGACAAATCTCATCGAAACTTGTTTGCAAACTGGAGTGAA

TAAATTTATATTTTCTTCAACGGCGGCCACTTATGGCGAACCACAAACTC

CCGTTGTGAGCGAAACAAGTCCTTTAGCACCTATTAATCCTTATGGGCGT

AGTAAGCTTATGAGTGAAGAAGTTTTGCGTGATGCAAGTATGGCAAATCC

TGAATTTAAGCATTGTATTTTAAGATATTTTAATGTTGCAGGTGCTTGTA

TGGATTATACTTTAGGACAACGCTATCCAAAAGCGACTTTGCTTATAAAA

GTTGCAGCTGAATGTGCCGCAGGAAAACGTGATAAACTTTTCATATTTGG

CGATGATTATGATACAAAAGATGGTACTTGCATAAGAGATTTTATCCATG

TAGATGATATTTCAAGTGCACATTTAGCGGCTTTGGATTATTTAAAAGAG

AATGAAAGCAATGTTTTTAATGTAGGTTATGGACATGGTTTTAGCGTAAA
```

AGAAGTGATTGAAGCGATGAAAAAAGTTAGCGGAGTGGATTTTAAAGTAG

AACTTGCCCCACGCCGTGCGGGTGATCCTAGTGTATTGATTTCTGATGCA

AGTAAAATCAGAAATCTTACTTCTTGGCAGCCTAAATATGATGATTTAGA

GCTTATTTGTAAATCTGCTTTTGATTGGGAAAAACAGTGTTAA

The amino acid sequence of the Gne protein encoded by the nucleic acid of SEQ ID NO: 47 is provided below:

```
                                        (SEQ ID NO: 48)
MMMKILISGGAGYIGSHTLRQFLKTDHEICVLDNLSKGSKIAIEDLQKTR

AFKFFEQDLSDFQGVKALFEREKFDAIVHFAASIEVFESMQNPLKYYMNN

TVNTTNLIETCLQTGVNKFIFSSTAATYGEPQTPVVSETSPLAPINPYGR

SKLMSEEVLRDASMANPEFKHCILRYFNVAGACMDYTLGQRYPKATLLIK

VAAECAAGKRDKLFIFGDDYDTKDGTCIRDFIHVDDISSAHLAALDYLKE

NESNVFNVGYGHGFSVKEVIEAMKKVSGVDFKVELAPRRAGDPSVLISDA

SKIRNLTSWQPKYDDLELICKSAFDWEKQC.
```

In some embodiments, the nucleic acid comprises a *C. jejuni* gne gene (provided as SEQ ID NO: 47). In some embodiments, the nucleic acid comprises a gne gene, wherein the gne gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 47. In some embodiments, the nucleic acid comprises a gne gene, wherein the gne gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 47.

In some embodiments, the nucleic acid comprises a nucleic acid sequence encoding a Gne protein, wherein said Gne protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 48. In some embodiments, the nucleic acid comprises a nucleic acid sequence encoding a Gne protein, wherein said Gne protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 48.

pglK—In some embodiments, the recombinant bacterium comprises a nucleic acid comprising a pglK gene (e.g., a *C. jejuni* pglK gene).

In some embodiments, the nucleic acid comprising a pglK gene is located on a plasmid in the bacterium. In some embodiments, the nucleic acid comprising a pglK gene is located on a chromosome of the bacterium.

The nucleic acid sequence of an exemplary *C. jejuni* pglK gene is provided below:

(SEQ ID NO: 49)
ATGCCTTTTATCACTTTGGCTAGTGATTTTTCTTATTTTGATCGTAATAA

ATATTTAATCMAGCCTAAAAGAATATCTTAATATCCCTGTTTTTGAAATC

ATTGTTTATTTTGGAGTGGGGCTTATTGTTTTTTATGTGTTTAGAGCTTT

GTTAAATGCGTATTATTTTCATCTTTTGGCALAGATTTTCTAAAGGGCGT

TATCATGCGATCGCTTATAAGGTTTTTTCTAAATTTTTAAATATTAATTA

TGAAAAATTTACTCAAAAAAATCAATCTGAAATTTTAAAGTCCATTACAG

GGIGAAGTTTATAATCTAAGCACTATGATTTCATCATTTTTACTTTTGAT

GAGTGAAATTTTTGTAGTACTTTTGCTTTATGCTTTAATGCTTTTGATTA

ATTATAAAATCACTTTGTTTTTAVAGTATTTTTATGGTGTTAAATGCCTT

TATTTTAGTGAAAATTTTAAGCCCTATCATTAAAAAAGCAGGAGTAAGAC

GCGAAGAAGCGATGAAAAATTTCTTTGAAATTTTAAATACAAATKTTAAA

TAATTTCAAATTTATTAAGCTTAAAACCAAAGAAGATGGAGTATTAAGTC

TTTTTAAAGCGCAAAGTGAAGCTTTTTCTAAAGCAAATATTACCAACGAA

AGCGTAGCTGCGGTGKCCTAGAATTTATCTTGAAGGAATAGGCTTTTGCG

TACTTGTTTTTATCGTGGTATTTTTGGTTTTGAAAAATGAAAGTGATATT

TCAGGTATTTTATCCACGATTTCTATTTTTGTTTTAVGCGCTTTATCGCT

TAATGCCAAGTGCAAATCGTATTATTACAAGTTATCATGATTTGCTTTAT

TATCATTCTTCTTTGGATATTATTTATCAAAATTTAAGACAAGAAGAAGA

AAATTTGYGGCGAGGAAAAATTAAGCTTTAATCAAGAGCTTAAAATTTGC

AATCTTAGCTTTGGTTATGAGGGAAAAAAATATTTATTTAAAAATCTTAA

CTTAAATATTAAAAAAGGCGAAAAAATCEGCTTTTATAGGGGAGAGTGGT

TGTGGAAAAAGTACCTTAGTAGATCTTATCATAGGACTTTTAAAACCAAA

AGAAGGGCAAATTTTAATTGATGAGCAAGAATTAAATGCAAATAATACAL

AAAAATTATCGCCAAAAAATAGGCTATATCCCGCAAAATATCTATCTTTT

TAATGACAGTATAGCTAAAAATATCACTTTTGGAGATGCGGTTGATGAAG

AAAAACTTAATAGGGTTATCIAAACAAGCAAATTTAGAGCATTTTATAAA

AAATTTACCTCAAGGAGTGCAAACAAAAGTGGGCGATGGGGGAGTAATT

TAAGCGGGGACAAAAACAACGCATAGCTATAGCAAGAGCTGTTATATTT

AGAGCCTGAAATGTTAGTGCTTGATGAAGCAACTTCTGCGCTTGATACTC

AAAGTGAAGCAAAAATTATGGATGAAATTTATAAAATTTCTAAAGATAAA

ACCATGATTATTSATCGCACATCGCCTTTCTACGATAACACAATGTGATA

AGGTTTATCGTTTAGAACACGGTAAGCTTAAAGAGGAGAAATGA

The amino acid sequence of the PglK protein encoded by the nucleic acid of SEQ ID NO: 49 is provided below:

(SEQ ID NO: 50)
MPFITLASDFSYFDRNKYLISLKEYLNIPVFEIIVYFGVGLIVFYVFRAL

LNAYYFHLLARFSKGRYHAIAYKVFSKFLNINYEKFTQKNQSEILKSITG

EVYNLSTMISSFLLLMSEIFVVLLLYALMLLINYKITLFLSIFMVLNAFI

-continued
LVKILSPIIKKAGVRREEAMKNFFEILNTNLNNFKFIKLKTKEDGVLSLF

KAQSEAFSKANITNESVAAVPRIYLEGIGFCVLVFIVVFLVLKNESDISG

ILSTISIFVLALYRLMPSANRIITSYHDLLYYHSSLDIIYQNLRQEEENL

GEEKLSFNQELKICNLSFGYEGKKYLFKNLNLNIKKGEKIAFIGESGCGK

STLVDLIIGLLKPKEGQILIDEQELNANNTKNYRQKIGYIPQNIYLFNDS

IAKNITFGDAVDEEKLNRVIKQANLEHFIKNLPQGVQTKVGDGGSNLSGG

QKQRIAIARALYLEPEMLVLDEATSALDTQSEAKIMDEIYKISKDKTMII

IAHRLSTITQCDKVYRLEHGKLKEEK.

In some embodiments, the nucleic acid comprises a *C. jejuni* pglK gene (provided as SEQ ID NO: 49). In some embodiments, the nucleic acid comprises a pglK gene, wherein the pglK gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 49. In some embodiments, the nucleic acid comprises a pglK gene, wherein the pglK gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 49.

In some embodiments, the nucleic acid comprises a nucleic acid sequence encoding a PglK protein, wherein said PglK protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 50. In some embodiments, the nucleic acid comprises a nucleic acid sequence encoding a PglK protein, wherein said PglK protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 50.

pglH—In some embodiments, the recombinant bacterium comprises a nucleic acid comprising a pglH gene (e.g., a *C. jejuni* pglH gene).

In some embodiments, the nucleic acid comprising a pglH gene is located on a plasmid in the bacterium. In some embodiments, the nucleic acid comprising a pglH gene is located on a chromosome of the bacterium.

The nucleic acid sequence of an exemplary *C. jejuni* pglH gene is provided below:

(SEQ ID NO: 51)
AAAATAAGCTTTATTATCGCAACTTTAAATTCAGGAGGTGCTGAGCGTGC

TTTAGTAACCTTAGCTAATGCACTTTGCAAAGAGCATGAAGTAAGTATTA

TTAAATTTCATGCAGGAGAATCTTTTTATAAGCTTGAAAATGAAGTTAAA

-continued

```
GTTACAAGTTTGGAACAATTTAGATTTGACACGCTTTATCATAAAATCGC

AAGTCGTTTTAAGAAATTTTTTGCTTTAAGAAAGGCTTTGAAAGAAAGTA

AGTCTGATGTTTTTATTTCTTTTTTGGATACGACTAATATTGCTTGTATT

GCTGCGAAAATAGGGCTTAAAACTCCACTCATTATAAGTGAGCATAGCAA

TGAAGCGTATTTAAAACCTAAAATTTGGCGTTTTTTAAGAAGGGTAAGCT

ATCCTTTTTGTGATGCTTTAAGTGTGCTTGGAAGCAGTGATAAGGTGTAT

TATGAAAGATTTGTAAAAGGGTTAAGCTTTTATTAAACCCTTGTCATTT

TAGCGATGAAATTTCTTTTGATTCTAGTTTTGAAAAGGAAAATTTGGTTC

TTTTTATAGGGCGTTTAGATCACAACAAAAACCCTGTAATGTTTTTAAAA

GCTATAGCGCATTTGGATAAAAATTTACAAGAAAATTATAAATTTGTTAT

AGCAGGAGATGGACAGTTAAGACAAGAACTTGAATATAAGGTAAAATCTT

TAGGAATAAAAGTTGATTTTTTAGGACGCGTTGAAAATGTCAAGGCTCTT

TATGAAAAAGCAAAAGTGCTTTGCCTTTGTTCTTTTGTAGAGGGTTTGCC

AACGGTTTTAATTGAAAGTTTGTATTTTGAGGTTTGTAGAATTTCAAGTT

CTTATTATAATGGTGCTAAGGATTTAATCAAAGATAATCATGATGGGCTT

TTGGTAGGTTGTGATGATGAAATAGCACTTGCTAAAAAACTTGAACTTGT

TTTAAATGATGAAAATTTTAGAAAAGAACTTGTAAATAATGCCAAACAAA

GGTGTAAAGACTTTGAAATTTCTCATATCAAAGAAGAATGGCTTAAGCTT

ATAGCCGAGGTT
```

The amino acid sequence of the PglH protein encoded by the nucleic acid of SEQ ID NO: 51 is provided below:

```
                                        (SEQ ID NO: 52)
KISFIIATLNSGGAERALVTLANALCKEHEVSIIKFHAGESFYKLENEVK

VTSLEQFRFDTLYHKIASRFKKFFALRKALKESKSDVFISFLDTTNIACI

AAKIGLKTPLIISEHSNEAYLKPKIWRFLRRVSYPFCDALSVLGSSDKVY

YERFVKRVKLLLNPCHFSDEISFDSSFEKENLVLFIGRLDHNKNPVMFLK

AIAHLDKNLQENYKFVIAGDGQLRQELEYKVKSLGIKVDF

LGRVENVKALYEKAKVLCLCSFVEGLPTVLIESLYFEVCRISSSYYNGAK

DLIKDNHDGLLVGCDDEIALAKKLELVLNDENFRKELVNNAKQRCKDFEI

SHIKEEWLKLIAEV
```

In some embodiments, the nucleic acid comprises a C. jejuni pglH gene (provided as SEQ ID NO: 51). In some embodiments, the nucleic acid comprises a pglH gene, wherein the pglH gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 51. In some embodiments, the nucleic acid comprises a pglH gene, wherein the pglH gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 51.

In some embodiments, the nucleic acid comprises a nucleic acid sequence encoding a PglH protein, wherein said PglH protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 52. In some embodiments, the nucleic acid comprises a nucleic acid sequence encoding a PglH protein, wherein said PglH protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 52.

pglI—In some embodiments, the recombinant bacterium comprises a nucleic acid comprising a pglI gene (e.g., a C. jejuni pglI gene).

In some embodiments, the nucleic acid comprising a pglI gene is located on a plasmid in the bacterium. In some embodiments, the nucleic acid comprising a pglI gene is located on a chromosome of the bacterium.

The nucleic acid sequence of an exemplary C. jejuni pglI gene is provided below:

```
                                        (SEQ ID NO: 53)
ATGCCTAAACTTTCTGTTATAGTACCAACTTTTAATCGTCAAGTTTTGTT

AGAAAAGGCTATTAAAAGCATACAAAATCAAGATTTTAAAGATTTAGAAA

TTATTGTAAGCGATGATAATTCTAGCGATGATACTAAAAGTGTGGTGCAA

AATTTACAAAAAGATGATGATCGCATTAAGTATTTTTTAAATCAAAATTA

CAAACAAGGTCCAAATGGCAATAAAAACAATGGCTTAGATCAAGCAAGTG

GCGAGTTTGTAACTTTTTTAGATGATGATGATGAGCTTTTATCCGGGGCT

TTAAGTACCTTGATGCAAAAAGCAAATGAGGGTTATGCTCATGTTTTTGG

AAATTGTTTGATAGAAAAAGAAGGAAATTTAAGCAAGGAATTTAGCGGCA

AGGGCTTGGAAAAAGATAGTGAAATTTCTAAAAAAGATTTTTTAATGGCT

AAATTTAGCGGAGAGTTTTTTCTGTTTTTAAAAAATCCCTACTTGAAAA

TAAGCGTTTTAATGAAGAATTTTATGGCAATGAAGCCACGCTTTGGGTAA

ATTTATACAAAGAAAAAGTTTTTATATCCATAAGGCTTTTAGGATTTAT

AGAATTTTTAGGCAAGATAGCGTGACTTTAGGGGCGAGTAAAAATGCTTA

TAGGGTGTATTTGGATATTTAGAGCTTGCTAAAATTTTAGAAAATGAACT

TAGAATGAGTAAGGATAAAGATTATAAAAAAACTTGTGCGAGTTATTATA

AAATGGCAGCTTATTATGCAAAACTTGCAAAAAATTATAAAGCCCTTTAT

AAATGTTTGTTTAAAAGCCTAAGTATAAAAATCAACGCTCCTGCTTTGAT

ATTACTCATTTTAAGTATAATTCCAAATAATATGATTGAAAAATTATCAA

AAATTCGGGTG
```

The amino acid sequence of the PglI protein encoded by the nucleic acid of SEQ ID NO: 53 is provided below:

(SEQ ID NO: 54)
MPKLSVIVPTFNRQVLLEKAIKSIQNQDFKDLEIIVSDDNSSDDTKSVVQ

NLQKDDDRIKYFLNQNYKQGPNGNKNNGLDQASGEFVTFLDDDDELLSGA

LSTLMQKANEGYAHVFGNCLIEKEGNLSKEFSGKGLEKDSEISKKDFLMA

KFSGEFFSVFKKSLLENKRFNEEFYGNEATLWVNLYKEKSFYIHKAFRIY

RIFRQDSVTLGASKNAYRVYLGYLELAKILENELRMSKDKDYKKTCASYY

KMAAYYAKLAKNYKALYKCLFKSLSIKINAPALILLILSIIPNNMIEKLS

KIRV

In some embodiments, the nucleic acid comprises a *C. jejuni* pglI gene (provided as SEQ ID NO: 53). In some embodiments, the nucleic acid comprises a pglI gene, wherein the pglI gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 53. In some embodiments, the nucleic acid comprises a pglI gene, wherein the pglI gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 53.

In some embodiments, the nucleic acid comprises a nucleic acid sequence encoding a PglI protein, wherein said PglI protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 54. In some embodiments, the nucleic acid comprises a nucleic acid sequence encoding a PglI protein, wherein said PglI protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 54.

pglJ—In some embodiments, the recombinant bacterium comprises a nucleic acid comprising a pglJ gene (e.g., a *C. jejuni* pglI gene).

In some embodiments, the nucleic acid comprising a pglJ gene is located on a plasmid in the bacterium. In some embodiments, the nucleic acid comprising a pglJ gene is located on a chromosome of the bacterium.

The nucleic acid sequence of an exemplary *C. jejuni* pglJ gene is provided below:

(SEQ ID NO: 55)
TTAGGCATTTTTATTTATTCTTTAGGAAGTGGTGGTGCTGAAAGAGTTGT

GGCGACTTTATTGCCTATTTTAAGTTTGAAATTTGAAGTGCATTTGATCT

TGATGAATGATAAAATTTCTTATGAAATTCCAGAGTGTCAAATTCATTTT

TTAGAATGTTCAAAACCTAGTGAAAATCCTATTTTGAAATTTTTAAAACT

ACCTTTTTTGGCTTTAAAATACAAAAAACTTTGCAGAAATTTAGGTATTG

ATACAGAATTTGTTTTTTTAAATCGACCTAATTATATAGCTTTAATGGCA

AGAATGTTTGGAAACAAAACTCGCCTTGTGATCAATGAATGCACTACGCC

AAGTGTGATGTATATGAAAAATAATTTTAATTCTTTGGTAAATAAATTTT

TAATTTCTTTGCTTTACCCAAAAGCTGATTTAATCTTGCCTAATTCTAAG

GGAAATTTAGAAGATTTAGTGCAAAATTTTAGTATAAGTCCAAAAAAATG

TGAAATTTTATACAATGCCATCGATTTAGAAAACATAGGGCAAAAAGCCC

TTGAAGACATAGCTTTAAAAGATAAATTTATTTTAAGTGTAGGCAGGCTT

GATAAAGGTAAAAATCATGCTTTATTAATTCGTGCTTATGCGAGATTGAA

AACAGATTTAAAGCTTGTGATTTTAGGTGAAGGTGTGCTTAAGGATGAGC

TTTTAGCTTTGATTAAAGAATTAAATTTGGAAGAAAAGGTTTTGCTTTTA

GGATTTGATAATAATCCTTATAAATACATGGCTAAATGCGAATTTTTTGC

TTTTGCTTCTGTGTTTGAAGGTTTTTCAAATGTTTTAATCGAAAGTTTGG

CTTGTTCTTGTGCGGTGGTTTGCACTGATCATAAAAGTGGTGCAAGAGAG

CTTTTTGGCGATGATGAATTTGGACTTTTAGTAGAAGTAGATAATGAAAA

CTCTATGTTTCAGGGTTTAAAAACTATGCTTGAAGACGATAAATTAAGAA

AAGCGTATAAAAACAAAGCTAAAACTAGGGCTAAAGCCTTTGATAAAGTA

AAAATTGCACGCGATGCTTTGAAATATTTATTAGGATAA

The amino acid sequence of the PglJ protein encoded by the nucleic acid of SEQ ID NO: 55 is provided below:

(SEQ ID NO: 56)
LGIFIYSLGSGGAERVVATLLPILSLKFEVHLILMNDKISYEIPECQIHF

LECSKPSENPILKFLKLPFLALKYKKLCRNLGIDTEFVFLNRPNYIALMA

RMFGNKTRLVINECTTPSVMYMKNNFNSLVNKFLISLLYPKADLILPNSK

GNLEDLVQNFSISPKKCEILYNAIDLENIGQKALEDIALKDKFILSVGRL

DKGKNHALLIRAYARLKTDLKLVILGEGVLKDELLALIKELNLEEKVLLL

GFDNNPYKYMAKCEFFAFASVFEGFSNVLIESLACSCAVVCTDHKSGARE

LFGDDEFGLLVEVDNENSMFQGLKTMLEDDKLRKAYKNKAKTRAKAFDKV

KIARDALKYLLG

In some embodiments, the nucleic acid comprises a *C. jejuni* pglJ gene (provided as SEQ ID NO: 55). In some embodiments, the nucleic acid comprises a pglJ gene, wherein the pglJ gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 55. In some embodiments, the nucleic acid comprises a pglJ gene, wherein the pglJ gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 55.

In some embodiments, the nucleic acid comprises a nucleic acid sequence encoding a PglJ protein, wherein said PglJ protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 56. In some embodiments, the nucleic acid comprises a nucleic acid sequence encoding a PglJ protein, wherein said PglJ protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 56.

pglB—In some embodiments, the recombinant bacterium comprises a nucleic acid comprising a pglB gene (e.g., a *C. jejuni* pglB gene).

In some embodiments, the nucleic acid comprising a pglB gene is located on a plasmid in the bacterium. In some embodiments, the nucleic acid comprising a pglB gene is located on a chromosome of the bacterium.

The nucleic acid sequence of an exemplary *C. jejuni* pglB gene is provided below:

```
                                          (SEQ ID NO: 57)
ATGTTGAAAAAAGAGTATTTAAAAAACCCTTATTTAGTTTTGTTTGCGAT

GATTGTATTAGCTTATGTTTTAGTGTATTTTGCAGGTTTTATTGGGTTT

GGTGGGCAAGTGAGTTTAACGAGTATTTTTTCAATAATCAATTAATGATC

ATTTCAAACGATGGCTATGCTTTTGCTGAGGGCGCAAGAGATATGATAGC

AGGTTTTCATCAGCCTAATGATTTGAGTTATTATGGATCTTCTTTATCTA

CGCTTACTTATTGGCTTTATAAATCACACCTTTTTCTTTTGAAAGTATC

ATTTTATATATGAGTACTTTTTTATCTTCTTTGGTGGTGATTCCTATTAT

TTTACTAGCTAATGAATACAAACGCCCTTTAATGGGCTTTGTAGCTGCTC

TTTTAGCAAGTGTAGCAAACAGTTATTATAATCGCACTATGAGTGGGTAT

TATGATACGGATATGCTGGTAATTGTTTTACCTATGTTTATTTTATTTTT

TATGGTAAGAATGATTTTAAAAAAAGACTTTTTTTCATTGATTGCCTTGC

CATTATTTATAGGAATTTATCTTTGGTGGTATCCTTCAAGTTATACTTTA

AATGTAGCTTTAATTGGACTTTTTTTAATTTATACACTTATTTTTCATAG

AAAAGAAAAGATTTTTTATATAGCTGTGATTTTGTCTTCTCTTACTCTTT

CAAATATAGCATGGTTTTATCAAAGTGCCATTATAGTAATACTTTTTGCT

TTATTTGCTTTAGAGCAAAAACGCTTAAATTTTATGATTATAGGAATTTT

AGGTAGTGCAACTTTGATATTTTTGATTTTAAGTGGTGGGGTTGATCCCA

TACTTTATCAGCTTAAATTTTATATTTTTAGAAGCGATGAAAGTGCGAAT

TTAACACAGGGCTTTATGTATTTTAATGTTAATCAAACCATACAAGAAGT

TGAAAATGTAGATTTTAGCGAATTTATGCGAAGAATTAGTGGTAGTGAAA

TTGTTTTCTTGTTTTCTTTGTTTGGTTTTGTATGGCTTTTGAGAAAACAT
```

AAAAGTATGATTATGGCTTTACCTATATTGGTGCTTGGGTTTTTAGCCTT

AAAAGGAGGACTTAGATTTACCATTTATTCTGTACCTGTAATGGCTTTAG

GATTTGGTTTTTTATTGAGCGAGTTTAAGGCTATATTGGTTAAAAAATAT

AGCCAATTAACTTCAAATGTTTGTATTGTTTTTGCAACTATTTTGACTTT

GGCTCCAGTATTTATCCATATTTACAACTATAAAGCGCCAACAGTTTTTT

CTCAAAATGAAGCATCATTATTAAATCAATTAAAAAATATAGCCAATAGA

GAAGATTATGTGGTAACTTGGTGGGATTATGGTTATCCTGTGCGTTATTA

TAGCGATGTGAAAACTTTAGTAGATGGTGGAAAGCATTTAGGTAAGGATA

ATTTTTTCCCTTCTTTTTCTTTAAGTAAAGATGAACAAGCTGCAGCTAAT

ATGGCAAGACTTAGTGTAGAATATACAGAAAAAAGCTTTTATGCTCCGCA

AAATGATATTTTAAAATCAGACATTTTACAAGCCATGATGAAAGATTATA

ATCAAAGCAATGTGGATTTATTTCTAGCTTCATTATCAAAACCTGATTTT

AAAATCGATACACCAAAAACTCGTGATATTTATCTTTATATGCCCGCTAG

AATGTCTTTGATTTTTCTACGGTGGCTAGTTTTTCTTTTATTAATTTAG

ATACAGGAGTTTTGGATAAACCTTTTACCTTTAGCACAGCTTATCCACTT

GATGTTAAAAATGGAGAAATTTATCTTAGCAACGGAGTGGTTTTAAGCGA

TGATTTTAGAAGTTTTAAAATAGGTGATAATGTGGTTTCTGTAAATAGTA

TCGTAGAGATTAATTCTATTAAACAAGGTGAATACAAAATCACTCCAATC

GATGATAAGGCTCAGTTTTATATTTTTATTTAAAGGATAGTGCTATTCC

TTACGCACAATTTATTTTAATGGATAAAACCATGTTTAATAGTGCTTATG

TGCAAATGTTTTTTTTGGGAAATTATGATAAGAATTTATTTGACTTGGTG

ATTAATTCTAGAGATGCTAAAGTTTTTAAACTTAAAATTTAA

The amino acid sequence of the PglB protein encoded by the nucleic acid of SEQ ID NO: 57 is provided below:

```
                                          (SEQ ID NO: 58)
MLKKEYLKNPYLVLFAMIVLAYVFSVFCRFYWVWWASEFNEYFFNNQLMI

ISNDGYAFAEGARDMIAGFHQPNDLSYYGSSLSTLTYWLYKITPFSFESI

ILYMSTFLSSLVVIPIILLANEYKRPLMGFVAALLASVANSYYNRTMSGY

YDTDMLVIVLPMFILFFMVRMILKKDFFSLIALPLFIGIYLWWYPSSYTL

NVALIGLFLIYTLIFHRKEKIFYIAVILSSLTLSNIAWFYQSAIIVILFA

LFALEQKRLNFMIIGILGSATLIFLILSGGVDPILYQLKFYIFRSDESAN

LTQGFMYFNVNQTIQEVENVDFSEFMRRISGSEIVFLFSLFGFVWLLRKH

KSMIMALPILVLGFLALKGGLRFTIYSVPVMALGFGFLLSEFKAILVKKY

SQLTSNVCIVFATILTLAPVFIHIYNYKAPTVFSQNEASLLNQLKNIANR

EDYVVTWWDYGYPVRYYSDVKTLVDGGKHLGKDNFFPSFSLSKDEQAANM

ARLSVEYTEKSFYAPQNDILKSDILQAMMKDYNQSNVDLFLASLSKPDFK

IDTPKTRDIYLYMPARMSLIFSTVASFSFINLDTGVLDKPFTFSTAYPLD

VKNGEIYLSNGVVLSDDFRSFKIGDNVVSVNSIVEINSIKQGEYKITPID

DKAQFYIFYLKDSAIPYAQFILMDKTMFNSAYVQMFFLGNYDKNLFDLVI

NSRDAKVFKLKI
```

In some embodiments, the nucleic acid comprises a *C. jejuni* pglB gene (provided as SEQ ID NO: 57). In some embodiments, the nucleic acid comprises a pglB gene, wherein the pglB gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 57. In some embodiments, the nucleic acid comprises a pglB gene, wherein the pglB gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 57.

In some embodiments, the nucleic acid comprises a nucleic acid sequence encoding a PglB protein, wherein said PglB protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 58. In some embodiments, the nucleic acid comprises a nucleic acid sequence encoding a PglB protein, wherein said PglB protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 58.

pglA—In some embodiments, the recombinant bacterium comprises a nucleic acid comprising a pglA gene (e.g., a *C. jejuni* pglA gene).

In some embodiments, the nucleic acid comprising a pglA gene is located on a plasmid in the bacterium. In some embodiments, the nucleic acid comprising a pglA gene is located on a chromosome of the bacterium.

The nucleic acid sequence of an exemplary *C. jejuni* pglA gene is provided below:

```
(SEQ ID NO: 59)
ATGAGAATAGGATTTTTATCACATGCAGGAGCGAGTATTTATCATTTTAG

AATGCCTATTATAAAAGCGTTAAAAGATAGAAAAGACGAAGTTTTTGTTA

TAGTGCCGCAAGATGAATACACGCAAAAACTTAGAGATCTTGGCTTAAAA

GTAATTGTTTATGAGTTTTCAAGAGCTAGTTTAAATCCTTTTGTGGTTTT

AAAGAATTTTTTTATCTTGCTAAGGTTTTGAAAAATTTAAATCTTGATT

TTATTCAAAGTGCGGCACACAAAAGCAATACTTTTGGAATTTTAGCAGCA

AAATGGGCAAAAATTCCTTATCGTTTTGCCTTAGTAGAAGGCTTGGGATC

TTTTTATATAGATCAAGGTTTTAAGGCAAATTTAGTGCGTTTTGTTATTA

ATAGTCTTTATAAATTAAGTTTTAAATTTGCACACCAATTTATTTTTGTC

AATGAAAGTAATGCTGAGTTTATGCGGAATTTAGGACTTAAAGAAAATAA

AATTTGCGTGATAAAATCTGTAGGGATCAATTTAAAAAAATTTTTCCTA

TTTATGTAGAATCGGAAAAAAAAGAGCTTTTTTGGAAAAATTTAAACATA

GATAAAAAACCCATTGTGCTTATGATAGCAAGAGCTTTATGGCATAAGGG
```

```
TGTAAAAGAATTTTATGAAAGTGCTACTATGCTAAAAGACAAAGCAAATT

TTGTTTTAGTTGGTGGAAGAGATGAAAATCCTTCTTGTGCAAGTTTGGAG

TTTTTAAACTCTGGCGCGGTGCATTATTTGGGTGCTAGAAGTGATATAGT

CGAGCTTTTGCAAAATTGTGATATTTTTGTTTTGCCAAGCTATAAAGAAG

GCTTTCCTGTAAGTGTTTTGGAGGCAAAAGCTTGCGGTAAGGCTATAGTG

GTGAGTGATTGTGAAGGTTGTGTGGAGGCTATTTCTAATGCTTATGATGG

ACTTTGGGCAAAAACAAAAAATGCTAAAGATTTAAGCGAAAAAATTTCAC

TTTTATTAGAAGATGAAAAATTAAGATTAAATTTAGCTAAAAATGCCGCC

CAAGATGCTTTACAATACGATGAAAATATAATCGCACAGCGTTATTTAAA

ACTTTATGATAGGGTAATTAAGAATGTA
```

The amino acid sequence of the PglA protein encoded by the nucleic acid of SEQ ID NO: 59 is provided below:

```
(SEQ ID NO: 60)
MRIGFLSHAGASIYHFRMPIIKALKDRKDEVFVIVPQDEYTQKLRDLGLK

VIVYEFSRASLNPFVVLKNFFYLAKVLKNLNLDFIQSAAHKSNTFGILAA

KWAKIPYRFALVEGLGSFYIDQGFKANLVRFVINSLYKLSFKFAHQFIFV

NESNAEFMRNLGLKENKICVIKSVGINLKKFFPIYVESEKKELFWKNLNI

DKKPIVLMIARALWHKGVKEFYESATMLKDKANFVLVGGRDENPSCASLE

FLNSGAVHYLGARSDIVELLQNCDIFVLPSYKEGFPVSVLEAKACGKAIV

VSDCEGCVEAISNAYDGLWAKTKNAKDLSEKISLLLEDEKLRLNLAKNAA

QDALQYDENIIAQRYLKLYDRVIKNV
```

In some embodiments, the nucleic acid comprises a *C. jejuni* pglA gene (provided as SEQ ID NO: 59). In some embodiments, the nucleic acid comprises a pglA gene, wherein the pglA gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 59. In some embodiments, the nucleic acid comprises a pglA gene, wherein the pglA gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 59.

In some embodiments, the nucleic acid comprises a nucleic acid sequence encoding a PglA protein, wherein said PglA protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 60. In some embodiments, the nucleic acid comprises a nucleic acid sequence encoding a PglA protein, wherein said PglA protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 60.

pglC—In some embodiments, the recombinant bacterium comprises a nucleic acid comprising a pglC gene (e.g., a *C. jejuni* pglC gene).

In some embodiments, the nucleic acid comprising a pglC gene is located on a plasmid in the bacterium. In some embodiments, the nucleic acid comprising a pglC gene is located on a chromosome of the bacterium.

The nucleic acid sequence of an exemplary *C. jejuni* pglC gene is provided below:

(SEQ ID NO: 61)
GAAAAAGTTTTTAAAAGAATTTTTGATTTTATTTTATCTTTAGTGCTTTT

AGTGCTTTTTTCTCCGGTGATTTTAATCACTGCTTTACTTTTAAAAATCA

CTCAAGGAAGTGTGATTTTTACCCAAAATCGTCCCGGGTTAGATGAAAAA

ATTTTTAAAATTTATAAATTTAAAACCATGAGCGATGAAAGAGATGAAAA

GGGTGAGTTATTAAGCGATGAATTGCGTTTGAAAGCTTTTGGAAAAATCG

TTAGAAGCTTAAGTTTGGATGAGCTTTTGCAACTTTTTAATGTTTTAAAA

GGGGATATGAGTTTTGTTGGACCTAGACCTCTTTTGGTTGAGTATTTGCC

TCTTTACAATAAAGAGCAAAAATTGCGTCATAAAGTGCGTCCAGGTATAA

CAGGATGGGCGCAGGTAAATGGTAGAAATGCTATTTCTTGGCAGAAAAAA

TTCGAACTTGATGTGTATTATGTGAAAAATATTTCTTTTTTGCTTGATTT

AAAAATCATGTTTTTAACAGCTTTAAAGGTTTTAAAACGAAGTGGGGTAA

GCAAAGAAGGCCATGTTACAACAGAGAAATTTAATGGCAAGAACTGA

The amino acid sequence of the PglC protein encoded by the nucleic acid of SEQ ID NO: 61 is provided below:

(SEQ ID NO: 62)
EKVFKRIFDFILSLVLLVLFSPVILITALLLKITQGSVIFTQNRPGLDEK

IFKIYKFKTMSDERDEKGELLSDELRLKAFGKIVRSLSLDELLQLFNVLK

GDMSFVGPRPLLVEYLPLYNKEQKLRHKVRPGITGWAQVNGRNAISWQKK

FELDVYYVKNISFLLDLKIMFLTALKVLKRSGVSKEGHVTTEKFNGKN

In some embodiments, the nucleic acid comprises a *C. jejuni* pglC gene (provided as SEQ ID NO: 61). In some embodiments, the nucleic acid comprises a pglC gene, wherein the pglC gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO:61. In some embodiments, the nucleic acid comprises a pglC gene, wherein the pglC gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 61. In some embodiments, the nucleic acid comprises a nucleic acid sequence encoding a PglC protein, wherein said PglC protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 62. In some embodiments, the nucleic acid comprises a nucleic acid sequence encoding a PglC protein, wherein said PglC protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 62.

pglD—In some embodiments, the recombinant bacterium comprises a nucleic acid comprising a pglD gene (e.g., a *C. jejuni* pglD gene).

In some embodiments, the nucleic acid comprising a pglD gene is located on a plasmid in the bacterium. In some embodiments, the nucleic acid comprising a pglD gene is located on a chromosome of the bacterium.

The nucleic acid sequence of an exemplary *C. jejuni* pglD gene is provided below:

(SEQ ID NO: 63)
ATGGCAAGAACTGAAAAAATTTATATTTATGGTGCTAGTGGTCATGGGCT

TGTTTGTGAAGATGTGGCTAAAAATATGGGTTATAAAGAATGTATTTTTT

TAGATGATTTTAAAGGAATGAAATTTGAAAGTACCTTACCTAAATATGAT

TTTTTTATAGCCATAGGAAACAATGAAATTCGAAAAAAGATTTATCAAAA

AATTTCAGAAAATGGCTTTAAAATTGTCAATCTTATCCATAAAAGCGCGC

TTATAAGTCCTAGCGCAATCGTGGAAGAAAATGCAGGAATTTTAATCATG

CCTTATGTAGTGATTAACGCTAAAGCTAAAATAGAAAAAGGTGTGATTTT

AAATACTTCAAGCGTAATTGAGCATGAATGTGTGATAGGGGAATTTTCTC

ATGTGAGTGTGGGAGCTAAATGTGCGGGTAATGTAAAAATTGGTAAAAAT

TGTTTTTTAGGGATTAATTCTTGTGTTTTGCCTAATTTAAGTTTGGCAGA

TGATAGTATTTTAGGTGGTGGAGCAACTTTAGTTAAAAATCAAGATGAAA

AAGGTGTTTTTGTGGGAGTACCTGCAAAAAGGATGTAA

The amino acid sequence of the PglD protein encoded by the nucleic acid of SEQ ID NO: 63 is provided below:

(SEQ ID NO: 64)
MARTEKIYIYGASGHGLVCEDVAKNMGYKECIFLDDFKGMKFESTLPKYD

FFIAIGNNEIRKKIYQKISENGFKIVNLIHKSALISPSAIVEENAGILIM

PYVVINAKAKIEKGVILNTSSVIEHECVIGEFSHVSVGAKCAGNVKIGKN

CFLGINSCVLPNLSLADDSILGGGATLVKNQDEKGVFVGVPAKRM

In some embodiments, the nucleic acid comprises a *C. jejuni* pglD gene (provided as SEQ ID NO: 63). In some embodiments, the nucleic acid comprises a pglD gene, wherein the pglD gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 63. In some embodiments, the nucleic acid comprises a pglD gene, wherein the pglD gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 63.

In some embodiments, the nucleic acid comprises a nucleic acid sequence encoding a PglD protein, wherein said PglD protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 64. In some embodiments, the nucleic acid comprises a nucleic acid sequence encoding a PglD protein, wherein said PglD protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 64.

pglE—In some embodiments, the recombinant bacterium comprises a nucleic acid comprising a pglE gene (e.g., a *C. jejuni* pglE gene).

In some embodiments, the nucleic acid comprising a pglE gene is located on a plasmid in the bacterium. In some embodiments, the nucleic acid comprising a pglE gene is located on a chromosome of the bacterium.

The nucleic acid sequence of an exemplary *C. jejuni* pglE gene is provided below:

```
                                          (SEQ ID NO: 65)
ATGAGATTTTTTCTTTCTCCTCCGCATATGGGTGGTAATGAATTAAAATA

CATAGAAGAAGTTTTCAAAAGCAATTATATAGCACCTTTGGGTGAATTTG

TAAATCGCTTTGAACAAAGTGTCAAGGCTTACAGTAAAAGTGAAAATGCC

TTAGCTTTAAATTCAGCCACAGCGGCTTTGCATTTAGCTTTAAGGGTGGC

AGGGGTAAAACAAGATGATATTGTTTTGGCTTCTTCTTTTACTTTTATCG

CTTCAGTAGCACCTATTTGTTATCTTAAAGCAAAACCTGTATTTATAGAT

TGTGATGAAACTTATAATATCGATGTAGATTTATTAAAGCTTGCTATTAA

AGAATGTGAAAAAAACCAAAAGCATTGATTTTAACTCATCTTTATGGCA

ATGCGGCTAAAATGGATGAAATTGTTGAAATTTGCAAAGAAAATGAAATT

GTTTTAATCGAAGATGCTGCTGAAGCTTTAGGAAGTTTTTATAAGAATAA

AGCTTTAGGAACTTTTGGAGAATTTGGAGCTTATTCTTATAATGGCAATA

AAATTATCACCACTTCAGGTGGAGGTATGCTTATAGGAAAAAATAAAGAA

AAGATTGAAAAAGCAAGATTTTATAGCACTCAAGCTAGGGAAAATTGTTT

GCATTATGAACATTTAGATTATGGTTATAATTACCGCTTAAGCAATGTTT

TAGGAGCTATTGGCGTAGCGCAAATGGAGGTTTTAGAACAAAGAGTGCTT

AAAAAAAGAGAAATTTATGAGTGGTATAAAGAATTTTTAGGAGAGTGTTT

TAGCTTTTTAGATGAATTAGAAAATTCAAGAAGCAATCGCTGGTTAAGTA
```

```
-continued
CAGCTTTGATTGATTTTGATAAAAATGAACTTAATTCTTGTCAAAAAGAT

ATAAATATCAGTCAAAAAAATATTACTTTGCATCCAAAAATTTCAAAACT

CATAGAAGATTTGAAAAATGAACAAATAGAAACAAGACCATTATGGAAAG

CTATGCACGCTCAAGAAGTATTTAAAGGAGCTAAGGCTTATCTTAATGGC

AATAGTGAGTTATTTTTCCAAAAAGGAATTTGTTTGCCAAGTGGCACGGC

GATGAGTAAAGATGATGTTTATGAAATTTCAAAACTGATCTTAAAGAGCA

TAAAGGCTTAA
```

The amino acid sequence of the PglE protein encoded by the nucleic acid of SEQ ID NO: 65 is provided below:

```
                                          (SEQ ID NO: 66)
MRFFLSPPHMGGNELKYIEEVFKSNYIAPLGEFVNRFEQSVKAYSKSENA

LALNSATAALHLALRVAGVKQDDIVLASSFTFIASVAPICYLKAKPVFID

CDETYNIDVDLLKLAIKECEKKPKALILTHLYGNAAKMDEIVEICKENEI

VLIEDAAEALGSFYKNKALGTFGEFGAYSYNGNKIITTSGGGMLIGKNKE

KIEKARFYSTQARENCLHYEHLDYGYNYRLSNVLGAIGVAQMEVLEQRVL

KKREIYEWYKEFLGECFSFLDELENSRSNRWLSTALIDFDKNELNSCQKD

INISQKNITLHPKISKLIEDLKNEQIETRPLWKAMHAQEVFKGAKAYLNG

NSELFFQKGICLPSGTAMSKDDVYEISKLILKSIKA
```

In some embodiments, the nucleic acid comprises a *C. jejuni* pglE gene (provided as SEQ ID NO: 65). In some embodiments, the nucleic acid comprises a pglE gene, wherein the pglE gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 65. In some embodiments, the nucleic acid comprises a pglE gene, wherein the pglE gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 65.

In some embodiments, the nucleic acid comprises a nucleic acid sequence encoding a PglE protein, wherein said PglE protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 66. In some embodiments, the nucleic acid comprises a nucleic acid sequence encoding a PglE protein, wherein said PglE protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 66.

pglF—In some embodiments, the recombinant bacterium comprises a nucleic acid comprising a pglF gene (e.g., a *C. jejuni* pglF gene).

In some embodiments, the nucleic acid comprising a pglF gene is located on a plasmid in the bacterium. In some embodiments, the nucleic acid comprising a pglF gene is located on a chromosome of the bacterium.

The nucleic acid sequence of an exemplary *C. jejuni* pglF gene is provided below:

(SEQ ID NO: 67)
ATGATTTTTTATAAAAGCAAAAGATTAGCATTTTTTTTAACTTCAGATAT

TGTTTTAATTTTACTTAGCGTTTATCTGGCTTTTTCTTTGAGATTTAGTG

GAGATATTCCGAGTATTTTTTATCATGGTATGATGGTTTCTGCTATTATT

TTGCTTGTTTTAAAACTTTCATTTTTGTTTGTTTTTAGAATTTATAAAGT

AGCTTGGAGATTTTTTCTCTCAATGAAGCAAGAAAGATTTTTATCGCTT

TGCTTTTAGCTGAGTTTTGTTTTTTCTTATTTTTATTTTTTAGTGAT

TTTTTTAATCCTTTTCCAAGAAGTGCTATTGTGATAGATTTTGTTCTTTC

TTATATGTTTATAGGTACTTTAAGAATTAGCAAAAGAATGCTTGTGGATT

TTAAACCTTCTAGAATGAAAGAAGAAGAAACTCCTTGTATTGTAGTAGGG

GCAACTTCTAAGGCTTTGCATTTGTTAAAAGGTGCAAAAGAAGGTTCTTT

AGGGCTTTTTCCTGTAGGCGTAGTTGATGCGAGAAAAGAGCTTATAGGGA

CTTATTGTGATAAATTTATTGTAGAAGAAAAAGAAAAAATAAAATCTTAT

GTAGAACAAGGGGTAAAAACTGCCATTATTGCTTTAAGACTTGAACAAGA

AGAGCTTAAAAAACTTTTTGAAGAACTTGTAGCTTATGGTATTTGCGATG

TAAAAATATTTCTTTTACAAGAAACGAAGCAAGAGATATCAGTATAGAA

GACTTGCTTGCTAGAAAACCAAAAGATTTAGATGATAGTGCTGTGGCGGC

TTTTTTAAAAGATAAGGTAGTTTTGGTAAGTGGAGCAGGTGGAACTATAG

GCAGTGAACTTTGTAAGCAATGTATTAAATTTGGTGCTAAGCATCTTATC

ATGGTTGATCATAGTGAGTATAATCTTTATAAGATCAATGATGATTTAAA

TTTATATAAAGAAAAAATTACTCCTATTTTACTGAGTATTTTAGATAAGC

AAAGTTTAGATGAGGTATTAAAAACTTATAAACCCGAGCTTATTTTACAT

GCAGCCGCTTATAAACATGTGCCTCTTTGCGAACAAAATCCACATTCAGC

AGTAATCAATAATATTTTAGGAACTAAAATTTTATGCGACAGTGCTAAAG

AAAACAAAGTAGCTAAATTTGTGATGATAAGTACAGATAAAGCAGTACGA

CCAACAAATATTATGGGTTGCACTAAGAGAGTTTGCGAGCTTTATACTTT

AAGTATGAGTGATGAAAATTTTGAAGTTGCTTGTGTGCGTTTTGGTAATG

TTTTAGGTTCTAGTGGTAGTGTGATACCGAAATTTAAAGCACAAATTGCC

AATAATGAGCCTTTAACTTTAACGCACCCTGATATAGTGCGTTATTTTAT

GCTTGTGGCTGAGGCAGTGCAACTTGTTTTACAAGCTGGAGCTATCGCAA

AAGGGGAGAACTTTTTGTTTGGATATGGGTAAGCCTGTGAAAATCATA

GATTTAGCTAAAAAAATGCTTTTACTTTCTAATCGCAATGATTTAGAAAT

TAAAATCACAGGCTTAAGAAAAGGTGAGAAGCTTTATGAAGAGCTTTTGA

TTGATGAAAATGATGCTAAAACACAATATGAGAGTATTTTTGTAGCAAAG

AATGAGAAGGTTGATCTTGATTGGCTTAATAAAGAGATAGAAAATTTACA

AATATGTGAAGATATTTCAGAGGCTTTATTAAAGATTGTACCTGAATTTA

AACACAATAAAGAAGGTGTA

The amino acid sequence of the PglF protein encoded by the nucleic acid of SEQ ID NO: 67 is provided below:

(SEQ ID NO: 68)
MIFYKSKRLAFFLTSDIVLILLSVYLAFSLRFSGDIPSIFYHGMMVSAII

LLVLKLSFLFVFRIYKVAWRFFSLNEARKIFIALLLAEFCFFLIFYFFSD

FFNPFPRSAIVIDFVLSYMFIGTLRISKRMLVDFKPSRMKEEETPCIVVG

ATSKALHLLKGAKEGSLGLFPVGVVDARKELIGTYCDKFIVEEKEKIKSY

VEQGVKTAIIALRLEQEELKKLFEELVAYGICDVKIFSFTRNEARDISIE

DLLARKPKDLDDSAVAAFLKDKVVLVSGAGGTIGSELCKQCIKFGAKHLI

MVDHSEYNLYKINDDLNLYKEKITPILLSILDKQSLDEVLKTYKPELILH

AAAYKHVPLCEQNPHSAVINNILGTKILCDSAKENKVAKFVMISTDKAVR

PTNIMGCTKRVCELYTLSMSDENFEVACVRFGNVLGSSGSVIPKFKAQIA

NNEPLTLTHPDIVRYFMLVAEAVQLVLQAGAIAKGGELFVLDMGKPVKII

DLAKKMLLLSNRNDLEIKITGLRKGEKLYEELLIDENDAKTQYESIFVAK

NEKVDLDWLNKEIENLQICEDISEALLKIVPEFKHNKEGV.

In some embodiments, the nucleic acid comprises a *C. jejuni* pglF gene (provided as SEQ ID NO: 67). In some embodiments, the nucleic acid comprises a pglF gene, wherein the pglF gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 67. In some embodiments, the nucleic acid comprises a pglF gene, wherein the pglF gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 67.

In some embodiments, the nucleic acid comprises a nucleic acid sequence encoding a PglF protein, wherein said PglF protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO:68. In some embodiments, the nucleic acid comprises a nucleic acid sequence encoding a PglF protein, wherein said PglF protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 68.

pglG—In some embodiments, the recombinant bacterium comprises a nucleic acid comprising a pglG gene (e.g., a *C. jejuni* pglG gene).

In some embodiments, the nucleic acid comprising a pglG gene is located on a plasmid in the bacterium. In some embodiments, the nucleic acid comprising an pglG gene is located on a chromosome of the bacterium.

The nucleic acid sequence of an exemplary *C. jejuni* pglG gene is provided below:

(SEQ ID NO: 69)
ATGTATATAAAAGATATACAAAGATTTGAAGATAATCGCTATCGTGCTAG

AGCTTATATGAGTTATATTTTAACAAGAAATCTGCCCAATAAACTTCCTG

ATATTCACCTTGAAACGATTAAAACAGCTTTGGATAAAATAGCTCATGAA

GTTGTTGTTTTGATGCTTTGTATATTTTAGATATTTCAGGCATGCAAAT

AGAAAATGCGATTTCCTTAAATAAAGCTCATGAAATAGGGCAGGGTGAGG

ATAGAAGTACTCGTTCTTATTTTTATAGAGCTGTAAAATTAAGACGATGT

GTTTTGAGCGATCCTTATCCTTCGGTTTTAAATAATGAGCTTTGCGTGAC

AGCTTCTATGCCAATTTACGATGATAAAAATAACTTGCTTTTTGTTGTTT

GTATTGATATCAAGCTTGAAGATATTTTAAAGATTATTCAAGCAGGAAAA

TTTGAATTTGTTTTTACTCAGTTTAGTCGTTTGGTATATTTTTGCTTCGC

ACTGGTTTTATTTGTGATTACTTGTTTTTTATTTCAAAAAGGTTTTTTA

GTCTTTTTGATAATCAAGCTATAGGTATAGAACATATGTTTGAAAGTACC

ATCGCTATAACTTTGGCTTTAGCTATTTTTGATTTGGCAAAAACTTTGAT

CGAACAAGAAGTATTAGGAAGGACGAAAAAAGAAGAAGGTGGAATTCAAA

AAACTATGGTGAGATTTTTGGGTTCTATTATCATTGCTTTAGCTATAGAA

GCTTTGATGTTGGTATTTAAACTTGCTATTGGTGATCTTTCTCAGATGAT

TTATGCGATTTATCTTATCGGTGGAGTGAGCTTGCTTCTTTTAGGTTTAA

GTGTATATTTATTTACGGTTAAGTATAAAAATAATAATATTTGA

The amino acid sequence of the PglG protein encoded by the nucleic acid of SEQ ID NO: 69 is provided below:

(SEQ ID NO: 70)
MYIKDIQRFEDNRYRARAYMSYILTRNLPNKLPDIHLETIKTALDKIAHE

VVVFDALYILDISGMQIENAISLNKAHEIGQGEDRSTRSYFYRAVKLRRC

VLSDPYPSVLNNELCVTASMPIYDDKNNLLFVVCIDIKLEDILKIIQAGK

FEFVFTQFSRLVYFCFALVLFVITCFLFQKGFFSLFDNQAIGIEHMFEST

IAITLALAIFDLAKTLIEQEVLGRTKKEEGGIQKTMVRFLGSIIIALAIE

ALMLVFKLAIGDLSQMIYAIYLIGGVSLLLLGLSVYLFTVKYKNNNI

In some embodiments, the nucleic acid comprises a *C. jejuni* pglG gene (provided as SEQ ID NO: 69). In some embodiments, the nucleic acid comprises a pglG gene, wherein the pglG gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 69. In some embodiments, the nucleic acid comprises a pglG gene, wherein the pglG gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 69.

In some embodiments, the nucleic acid comprises a nucleic acid sequence encoding a PglG protein, wherein said PglG protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 70. In some embodiments, the nucleic acid comprises a nucleic acid sequence encoding a PglG protein, wherein said PglG protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 70.

C. Attenuation

In some embodiments, the recombinant bacterium described herein is modified such that the expression of one or more genes can be regulated in a sugar-responsive manner. In some embodiments, one or more endogenous genes, e.g., virulence genes, are deleted from the bacterial chromosome. In some embodiments, the deletion is a partial deletion of the endogenous gene. In some embodiments, the deletion is a full-length deletion of the endogenous gene. In some embodiments, the gene is genetically-altered to prevent transcription and/or translation of the gene encoding the protein. In some embodiments, the endogenous gene is genetically altered to insert a transcriptional terminator in the open reading frame of the gene. In some embodiments, a regulatory region of the gene, e.g., virulence gene, is genetically-modified to alter (e.g., decrease) the expression of the gene. In some embodiments, the promoter of a gene, e.g., virulence gene, is altered to include one or more regulatory elements (e.g., a sugar-responsive promoter).

In some embodiments, the recombinant bacterium described herein is modified to comprise a nucleic acid comprising a gene. In some embodiments, the recombinant bacterium is modified to comprise a nucleic acid comprising a gene, whereby an endogenous copy of the gene in the bacterial chromosome has been altered and/or deleted. In some embodiments, the nucleic acid comprises a gene that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to an endogenous gene in the bacterial chromosome that has been deleted and/or altered. In some embodiments, the nucleic acid comprises a gene that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to an endogenous gene in the bacterial chromosome that has been deleted and/or altered. In some embodiments, the nucleic acid comprises a gene from a bacterial species, subspecies, serovar, or strain that is different than the bacterial species of the recombinant bacterium.

In some embodiments, the nucleic acid comprises a gene from a bacterial species, subspecies, serovar, or strain that is the same as the bacterial species of the recombinant bacterium. In some embodiments, the nucleic acid comprises a gene that is operably-linked to a regulatable promoter (e.g., a sugar-regulatable promoter). In some embodiments, the nucleic acid comprises a gene that is operably-linked to a rhamnose-regulatable promoter, a xylose-regulatable promoter, a galactose-regulatable promoter, an arabinose-regulatable promoter, a rhamnose-regulatable promoter, a mannose-regulatable promoter, or a maltose-regulatable promoter. In some embodiments, the nucleic acid comprising the gene is located in a plasmid in the bacterium. In some embodiments, the nucleic acid comprising the gene is located in the bacterial chromosome. In some embodiments, the nucleic acid comprising the gene is located at the chromosomal locus corresponding to the locus of an endogenous gene that has been deleted or altered in the bacterial chromosome. In some embodiments, the nucleic acid is codon-optimized (e.g., to improve expression of the nucleic acid in the recombinant bacterium).

GTP Pyrophosphokinase Genes

In some embodiments, the recombinant bacterium comprises a deletion in an endogenous relA gene, which encodes the GTP pyrophosphokinase RelA. The inclusion of a relA deletion in the recombinant bacterium uncouples the occurrence of growth-dependent lysis to the need for continued protein synthesis. In some embodiments, the deletion of the endogenous relA gene is a partial deletion. In some embodiments, the deletion of the endogenous relA gene is a full-length deletion.

Other Attenuation Methods

Other methods of attenuation are known in the art. For instance, attenuation may be accomplished by altering (e.g., deleting) native nucleic acid sequences found in the wild type bacterium. For instance, if the bacterium is *Salmonella*, non-limiting examples of nucleic acid sequences which may be used for attenuation include: a pab nucleic acid sequence, a pur nucleic acid sequence, an aro nucleic acid sequence, asd, a dap nucleic acid sequence, nadA, pncB, galE, pmi, fur, rpsL, ompR, htrA, hemA, cdt, cya, crp, dam, phoP, phoQ, rfc, poxA, galU, mviA, sodC, recA, ssrA, sirA, inv, hilA, rpoE, figM, tonB, slyA, and any combination thereof. Exemplary attenuating mutations may be aroA, aroC, aroD, cdt, cya, crp, phoP, phoQ, ompR, galE, and htrA.

In certain embodiments, the above nucleic acid sequences may be placed under the control of a sugar regulated promoter wherein the sugar is present during in vitro growth of the recombinant bacterium, but substantially absent within an animal or human host. The cessation in transcription of the nucleic acid sequences listed above would then result in attenuation and the inability of the recombinant bacterium to induce disease symptoms.

D. Additional Mutations

In some embodiments, the recombinant bacterium comprises a deletion in an endogenous recF gene, which encodes the DNA replication and repair protein RecF. In some embodiments, the deletion of the endogenous recF gene is a partial deletion. In some embodiments, the deletion of the endogenous recF gene is a full-length deletion. In some embodiments, the endogenous recF gene is genetically altered to insert a transcriptional terminator in the open reading frame of the gene.

In some embodiments, the recombinant bacterium comprises a deletion in an endogenous recJ gene, which encodes the exonuclease RecJ. In some embodiments, the deletion of the endogenous recJ gene is a partial deletion. In some embodiments, the deletion of the endogenous recJ gene is a full-length deletion. In some embodiments, the endogenous rea gene is genetically altered to insert a transcriptional terminator in the open reading frame of the gene.

The bacterium may also be modified to create a balanced-lethal host-vector system, although other types of systems may also be used (e.g., creating complementation heterozygotes). For the balanced-lethal host-vector system, the bacterium may be modified by manipulating its ability to synthesize various essential constituents needed for synthesis of the rigid peptidoglycan layer of its cell wall. In one example, the constituent is diaminopimelic acid (DAP) (see, for example, U.S. Pat. Nos. 5,672,345; 5,840,482; and 6,872,547, the entire contents of each of which are expressly incorporated herein by reference). Various enzymes are involved in the eventual synthesis of DAP.

In some embodiments, the recombinant bacterium comprises a deletion in an endogenous asd gene. In some embodiments, the deletion of the endogenous asd gene is a partial deletion. In some embodiments, the deletion of the endogenous asd gene is a full-length deletion. In some embodiments, the endogenous asd gene is genetically altered to insert a transcriptional terminator in the open reading frame of the gene. In some embodiments, the promoter of an endogenous asd gene is altered to include one or more regulatory elements (e.g., a sugar-responsive promoter). In one example, the bacterium is modified by using a ΔasdA mutation to eliminate the bacterium's ability to produce β-aspartate semialdehyde dehydrogenase, an enzyme essential for the synthesis of DAP. Other mutations that result in the abolition of the synthesis of DAP include, but are not limited to, dapA, dapB, dapC, dapD, dapE, dapF, and asd (see, e.g., U.S. Pat. No. 6,872,547, incorporated herein by reference). Other modifications that may be employed include modifications to a bacterium's ability to synthesize D-alanine or to synthesize D-glutamic acid (e.g., ΔmurI mutations), which are both unique constituents of the peptidoglycan layer of the bacterial cell wall.

Similarly, various embodiments may comprise the araC $P_{araBAD}$ c2 gene cassette inserted into the asd nucleic acid sequence that encodes aspartate semialdehyde dehydrogenase. Since the araC nucleic acid sequence is transcribed in a direction that could lead to interference in the expression of adjacent nucleic acid sequences and adversely affect vaccine strain performance, a transcription termination (TT) sequence is generally inserted 3' to the araC nucleic acid sequence. The chromosomal asd nucleic acid sequence is typically inactivated to enable use of plasmid vectors encoding the wild-type asd nucleic acid sequence in the balanced lethal host-vector system. This allows for stable maintenance of plasmids in vivo in the absence of any drug resistance attributes that are not permissible in live bacterial vaccines. In some of these embodiments, the wild-type asd nucleic acid sequence may be encoded by the vector described herein. The vector enables the regulated expression of an antigen encoding sequence through the repressible promoter.

Regulated Delayed Lysis In Vivo

In some embodiments, the recombinant bacterium may comprise deletions and/or deletion-insertion mutations to facilitate regulated delayed lysis in vivo that prevents bacterial persistence in vivo and survival if excreted (Table 3). These chromosomal mutations may include: Δ(wza-wcaM), $\Delta P_{murA}$::TT araC $P_{BAD}$ murA, and ΔasdA::TT araC $P_{BAD}$ c2. Δ(wza-wcaM) eliminates twenty enzymes needed to synthesize several exopolysaccharides that promote biofilm formation and for synthesis of GDP-fucose that is required for colonic acid synthesis 9194), which can protect cells from undergoing cell wall-less death from lysing (195). $\Delta P_{murA}$::

TT araC P$_{BAD}$ murA, makes synthesis of MurA, the first enzyme in the synthesis of muramic acid, dependent on presence of arabinose in growth medium and ceases to be synthesized in vivo due to the absence of arabinose (142) (118). MurA decreases as a consequence of cell division in vivo to ultimately lead to cell lysis and death (166) (191). The murA defect is complemented by MurA$^+$ plasmid vectors (142) (118). With respect to the ΔasdA::TT araC P$_{BAD}$ c2 mutations, the Asd enzyme is essential for the synthesis of diaminopimelic acid required for peptidoglycan synthesis (167) (192). The arabinose-dependent synthesis of the C2 repressor is to enable a regulated delayed expression of DNA sequences under the control of a promoter repressed by C2 (142) (118). The ΔasdA mutation is complemented by Asd$^+$ plasmid vectors (157) (193).

The latter two mutations are typically complemented by a regulated delayed lysis plasmid vector that has an arabinose-dependent expression of asdA and murA genes. A recombinant bacterium comprising such mutations grows normally in the presence of arabinose. In vivo, however, the bacterium ceases to express any nucleic acids encoding the Asd and MurA enzymes, such that synthesis of the peptidoglycan cell wall layer ceases, ultimately resulting in the lysis of the bacterium. This lysis may result in the release of a bolus of antigen specific for an enteric pathogen, thereby serving as a means to enhance induction of immunity against that enteric pathogen while conferring biological containment.

Additional methods of delayed lysis are described in, for example, U.S. Pat. No. 9,481,888, the entire contents of which are expressly incorporated herein by reference.

sopB Mutation

To be safe for use as a vaccine, the bacterial enteric pathogen must be attenuated for virulence by deletion or regulated expression of a virulence gene. In the case of *Salmonella*, for instance, an effector molecule secreted by the type 3 secretion system, such as sopB, may be altered to achieve attenuation. The genes may be deleted or a regulatable promoter may be inserted in front of the gene to achieve regulated delayed attenuation. As used herein, "regulated delayed attenuation" refers to the ability of the microbe to colonize a host and then display an attenuation phenotype to avoid actually causing a symptomatic infection.

E. Repressor Regulatory Systems

In some embodiments, the recombinant bacterium comprises a nucleic acid (e.g., a gene) that is operably linked to a repressor-regulatable promoter to facilitate the regulatable expression of the gene. Thus, in some embodiments, the recombinant bacterium comprises a nucleic acid comprising a gene encoding a repressor. In some embodiments, the gene encoding the repressor is operably-linked to a regulatable promoter. Methods of chromosomally integrating a nucleic acid sequence encoding a repressor operably-linked to a regulatable promoter are known in the art and detailed in the examples. In some embodiments, the nucleic acid sequence encoding a repressor is not integrated into a chromosomal locus such that the ability of the bacterium to colonize a host cell is disrupted. In some embodiments, the recombinant bacterium comprises a nucleic acid encoding a repressor that is integrated into the relA locus of the bacterial chromosome. In some embodiments, the recombinant bacterium comprises a nucleic acid encoding a repressor that is integrated into the endA locus of the bacterial chromosome. In some embodiments, the recombinant bacterium comprises at least one nucleic acid sequence encoding a repressor. In some embodiments, the recombinant bacterium comprises at least two, at least three, at least four, at least five, at least six or more nucleic acids encoding a repressor. In some embodiments, the nucleic acid encoding the repressor is present on a plasmid in the bacterium. In some embodiments, the nucleic acid encoding the repressor is located in the bacterial chromosome. If there is more than one nucleic acid sequence encoding a repressor, each nucleic acid sequence encoding a repressor may be operably linked to a regulatable promoter, such that each promoter is regulated by the same compound or condition. Alternatively, each nucleic acid sequence encoding a repressor may be operably linked to a regulatable promoter, each of which is regulated by a different compound or condition.

As used herein, a "repressor" refers to a biomolecule that represses the transcriptional activity of a promoter. In some embodiments, the repressor is synthesized by the recombinant bacterium in high enough quantities during in vitro culture, such that the transcription of a nucleic acid that is operably linked to a repressor-regulatable promoter is repressed. This may be particularly advantageous if, for example, expression of the product encoded by said nucleic acid impedes the in vitro growth of the bacterium, and/or the ability of the bacterium to infect and/or colonize a subject. In some embodiments, the nucleic acid that is operably-linked to the repressor-regulatable promoter expresses an antigen of interest. In some embodiments, the concentration of the repressor within the cell gradually decreases with each cell division cycle after transcription of the gene encoding the repressor decreases or ceases (e.g., in vivo). The use of a particular repressor, as described herein, may depend, in part, on the species, subspecies, strain or serovar of the recombinant bacterium being used. In some embodiments, the repressor is derived from the same species (e.g., the same bacterial species or the same phage) from which the repressor-regulatable promoter is derived. In some embodiments the repressor is not derived from the same bacterial species as the bacterial species in which the repressor is expressed. For example, in some embodiments, the repressor is derived from *E. coli* if the recombinant bacterium is of the genus *Salmonella*. Other suitable repressors include repressors derived from a bacteriophage.

A nucleic acid sequence encoding a repressor and regulatable promoter detailed above may be modified so as to optimize the expression level of the nucleic acid sequence encoding the repressor. The optimal level of expression of the nucleic acid sequence encoding the repressor may be estimated, or may be determined by experimentation. Such a determination should take into consideration whether the repressor acts as a monomer, dimer, trimer, tetramer, or higher multiple, and should also take into consideration the copy number of the vector encoding the antigen of interest. In an exemplary embodiment, the level of expression is optimized so that the repressor is synthesized while in a permissive environment (i.e., in vitro growth) at a level that substantially inhibits the expression of the nucleic acid encoding an antigen of interest, and is substantially not synthesized in a non-permissive environment, thereby allowing expression of the nucleic acid encoding an antigen of interest.

In some embodiments, the recombinant bacterium described herein is modified to comprise a nucleic acid comprising a lacI gene, which encodes the LacI repressor protein. The expression of the lacI-encoded repressor in the recombinant bacterium described herein may be used to regulate the expression of an antigen of interest expressed by the bacterium. For example, in some embodiments, the expression of the lacI gene is regulated by a sugar-regulatable promoter (e.g., an arabinose-regulatable promoter).

When cultured in the presence of arabinose, the recombinant bacterium will express the LacI repressor protein, which in turn will repress the expression of a gene encoding an antigen of interest that is operably-linked to a LacI-responsive promoter (e.g., $P_{trc}$, $P_{lac}$, $P_{T7lac}$, and $P_{tac}$). Upon administration to the subject and in the absence of a source of arabinose, the synthesis of LacI repressor ceases, leading to de-repression of the LacI-responsive promoter and the subsequence expression of the antigen of interest. The concentration of LacI in the cell decreases by about half at each cell division in vivo, leading to a gradual decreased level of repression and gradual increased synthesis of the antigen of interest.

In some embodiments, the nucleic acid comprising a lacI gene is located on a plasmid in the bacterium. In some embodiments, the nucleic acid comprising a lacI gene is located on a chromosome of the bacterium. In some embodiments, the nucleic acid comprising a lacI gene is located at the chromosomal locus corresponding to the locus of an endogenous a relA gene that has been deleted or altered in the bacterial chromosome. In some embodiments, the recombinant bacterium is modified to comprise a nucleic acid comprising a lacI gene, whereby an endogenous copy of the lacI gene in the bacterial chromosome has been altered and/or deleted.

In some embodiments, the nucleic acid comprises a *Escherichia coli* lacI gene. The nucleic acid sequence of the *E. coli* lacI gene is provided below:

(SEQ ID NO: 78)
gtgaaaccagtaacgttatacgatgtcgcagagtatgccggtgtctcta tcagaccgtttcccgcgtggtgaaccaggccagccacgtttctgcgaaaa cgcgggaaaaagtggaagcggcgatggcggagctgaattacattcccaac cgcgtggcacaacaactggcgggcaaacagtcgttgctgattggcgttgc cacctccagtctggccctgcacgcgccgtcgcaaattgtcgcggcgatta aatctcgcgccgatcaactgggtgccagcgtggtggtgtcgatggtagaa cgaagcggcgtcgaagcctgtaaagcggcggtgcacaatcttctcgcgca acgcgtcagtgggctgatcattaactatccgctggatgaccaggatgcca ttgctgtggaagctgcctgcactaatgttccggcgttatttcttgatgtc tctgaccagacacccatcaacagtattattttctcccatgaagacggtac gcgactgggcgtggagcatctggtcgcattgggtcaccagcaaatcgcgc tgttagcgggcccattaagttctgtctcggcgcgtctgcgtctggctggc tggcataaatatctcactcgcaatcaaattcagccgatagcggaacggga aggcgactggagtgccatgtccggttttcaacaaaccatgcaaatgctga atgagggcatcgttcccactgcgatgctggttgccaacgatcagatggcg ctgggcgcaatgcgcgccattaccgagtccgggctgcgcgttggtgcgga tatctcggtagtgggatacgacgataccgaagacagctcatgttatatcc cgccgttaaccaccatcaaacaggattttcgcctgctggggcaaaccagc gtggaccgcttgctgcaactctctcagggccaggcggtgaagggcaatca gctgttgcccgtctcactggtgaaaagaaaaaccaccctggcgcccaata cgcaaaccgcctctcccgcgcgttggccgattcattaatgcagctggca cgacaggtttcccgactggaaagcgggcagtga The amino acid sequence of the *E. coli* LacI protein encoded by the nucleic acid of SEQ ID NO:78 is provided below:

(SEQ ID NO: 79)
MKPVTLYDVAEYAGVSYQTVSRVVNQASHVSAKTREKVEAAMAELNYIPN

RVAQQLAGKQSLLIGVATSSLALHAPSQIVAAIKSRADQLGASVVVSMVE

RSGVEACKAAVHNLLAQRVSGLIINYPLDDQDAIAVEAACTNVPALFLDV

SDQTPINSIIFSHEDGTRLGVEHLVALGHQQIALLAGPLSSVSARLRLAG

WHKYLTRNQIQPIAEREGDWSAMSGFQQTMQMLNEGIVPTAMLVANDQMA

LGAMRAITESGLRVGADISVVGYDDTEDSSCYIPPLTTIKQDFRLLGQTS

VDRLLQLSQGQAVKGNQLLPVSLVKRKTTLAPNTQTASPRALADSLMQLA

RQVSRLESGQ

In some embodiments, the nucleic acid comprises a lacI gene, wherein the lacI gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the nucleic acid sequence of SEQ ID NO: 78. In some embodiments, the nucleic acid comprises a lacI gene, wherein the lacI gene comprises a nucleic acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the nucleic acid sequence of SEQ ID NO: 78.

In some embodiments, the nucleic acid comprises a nucleic acid sequence encoding a LacI protein, wherein said LacI protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO: 79. In some embodiments, the nucleic acid comprises a nucleic acid sequence encoding a LacI protein, wherein said LacI protein comprises an amino acid sequence that is at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% homologous to the amino acid sequence of SEQ ID NO: 79.

In some embodiments, the nucleic acid comprises a lacI gene that is operably-linked to a regulatable promoter (e.g., a sugar-regulatable promoter). In some embodiments, the nucleic acid comprises a lacI gene that is operably-linked to a sugar-regulatable promoter. In some embodiments, the sugar regulatable promoter exhibits increased activity (e.g., increased transcription) in the presence of a specific sugar and decreased activity in the absence of a sugar. In some embodiments, the nucleic acid comprises a lacI gene that is operably-linked to a rhamnose-regulatable promoter (e.g., a sugar-regulatable promoter). In some embodiments, the nucleic acid comprises a lacI gene that is operably-linked to an arabinose-regulatable promoter. In some embodiments, the arabinose-regulatable promoter is $P_{araBAD}$. In some embodiments, the recombinant bacterium comprises the mutation ΔrelA::araC $P_{araBAD}$ lacI TT.

II. Pharmaceutical Compositions

A recombinant bacterium may be administered to a host as a pharmaceutical composition. In some embodiments, the pharmaceutical composition may be used as a vaccine to elicit an immune response to the recombinant bacterium, including any antigens that may be synthesized and delivered by the bacterium. In an exemplary embodiment, the immune response is protective. Immune responses to antigens are well studied and widely reported.

In some embodiments, the pharmaceutical composition comprises a recombinant bacterium described herein. In some embodiments, the pharmaceutical composition comprises a recombinant bacterium that synthesizes a *Salmonella* antigen of interest. In some embodiments, the pharmaceutical composition comprises a recombinant bacterium that synthesizes a *Campylobacter* antigen of interest. In some embodiments, the pharmaceutical composition comprises a recombinant bacterium that synthesizes a *Salmonella* antigen of interest and a recombinant bacterium that synthesizes a *Campylobacter* antigen of interest. In some embodiments, the pharmaceutical composition comprises a recombinant bacterium that synthesizes an antigen of interest comprising a *Campylobacter* N-glycan. In some embodiments, the pharmaceutical composition comprises at least one, at least two, at least three, at least four, at least five, at least six, at least seven, at least eight, at least nine or more recombinant bacterial strains, as described herein.

Pharmaceutical compositions may be administered to any host capable of mounting an immune response. Such hosts may include all vertebrates, for example, mammals, including domestic animals, agricultural animals, laboratory animals, and humans, and various species of birds, including domestic birds and birds of agricultural importance. Preferably, the host is a warm-blooded animal. In one embodiment, the host is a cow. In some embodiments, the host is an equine. In another embodiment, the host is an avian. In another embodiment, the host is a human.

The pharmaceutical composition can be administered to the subject as a prophylactic or for treatment purposes. In some embodiments, the pharmaceutical composition can be administered for the prophylaxis or treatment of *salmonellosis*. In some embodiments, the pharmaceutical composition can be administered for the prophylaxis or treatment of a *Campylobacter* infection. In some embodiments, the pharmaceutical composition can be administered for the prophylaxis or treatment of *salmonellosis* and/or a *Campylobacter* infection.

In some embodiments, the recombinant bacterium is alive when administered to a host in a pharmaceutical composition described herein. Suitable vaccine composition formulations and methods of administration are detailed below.

A pharmaceutical composition comprising a recombinant bacterium may optionally comprise one or more possible additives, such as carriers, preservatives, stabilizers, adjuvants, and other substances.

In one embodiment, the pharmaceutical composition comprises an adjuvant. Adjuvants are optionally added to increase the ability of the vaccine to trigger, enhance, or prolong an immune response. In exemplary embodiments, the use of a live attenuated recombinant bacterium may act as a natural adjuvant. In some embodiments, the recombinant bacterium synthesizes and secretes an immune modulator. Additional materials, such as cytokines, chemokines, and bacterial nucleic acid sequences naturally found in bacteria, like CpG, are also potential vaccine adjuvants.

In some embodiments, the pharmaceutical composition comprises buffered saline (e.g., phosphate-buffered saline (PBS)).

In some embodiments, the pharmaceutical composition comprises a food product.

In another embodiment, the pharmaceutical may comprise a pharmaceutical carrier (or excipient). Such a carrier may be any solvent or solid material for encapsulation that is non-toxic to the inoculated host and compatible with the recombinant bacterium. A carrier may give form or consistency, or act as a diluent. Suitable pharmaceutical carriers may include liquid carriers, such as normal saline and other non-toxic salts at or near physiological concentrations, and solid carriers not used for humans, such as talc or sucrose, or animal feed. Carriers may also include stabilizing agents, wetting and emulsifying agents, salts for varying osmolarity, encapsulating agents, buffers, and skin penetration enhancers. Carriers and excipients as well as formulations for parenteral and nonparenteral drug delivery are set forth in Remington's Pharmaceutical Sciences 19th Ed. Mack Publishing (1995). When used for administering via the bronchial tubes, the pharmaceutical composition is preferably presented in the form of an aerosol.

In some embodiments, the pharmaceutical composition is delivered to a farm animal (e.g., poultry). In some embodiments, the pharmaceutical composition is delivered as a course spray (e.g., for use in hatcheries for delivery to poultry). In some embodiments, the pharmaceutical composition is delivered in the drinking water.

Care should be taken when using additives so that the live recombinant bacterium is not killed, or have its ability to effectively colonize lymphoid tissues such as the GALT, NALT and BALT compromised by the use of additives. Stabilizers, such as lactose or monosodium glutamate (MSG), may be added to stabilize the pharmaceutical composition against a variety of conditions, such as temperature variations or a freeze-drying process. The recombinant bacterium may also be co-administered with glutamate and/or arginite as described herein.

The dosages of a pharmaceutical composition can and will vary depending on the recombinant bacterium, the regulated antigen, and the intended host, as will be appreciated by one of skill in the art. Generally speaking, the dosage need only be sufficient to elicit a protective immune response in a majority of hosts. Routine experimentation may readily establish the required dosage. Typical initial dosages of vaccine for oral administration could be about $1 \times 10^7$ to $1 \times 10^{10}$ CFU depending upon the age of the host to be immunized. Administering multiple dosages may also be used as needed to provide the desired level of protective immunity.

In order to stimulate a preferred response of the GALT, NALT or BALT cells, administration of the pharmaceutical composition directly into the gut, nasopharynx, or bronchus is preferred, such as by oral administration, intranasal administration, gastric intubation or in the form of aerosols, although other methods of administering the recombinant bacterium, such as intravenous, intramuscular, subcutaneous injection or intramammary, intrapenial, intrarectal, vaginal administration, or other parenteral routes, are possible, e.g., for anti-cancer applications.

In some embodiments, these compositions are formulated for administration by injection (e.g., intraperitoneally, intravenously, subcutaneously, intramuscularly, etc.).

In another embodiment, the disclosure provides a method for eliciting an immune response against an antigen in a host. The method comprises administering to the host an effective amount of a pharmaceutical composition comprising a recombinant bacterium described herein.

In still another embodiment, a recombinant bacterium may be used in a method for eliciting an immune response against a pathogen in an individual in need thereof. The method comprises administrating to the host an effective amount of a pharmaceutical composition comprising a recombinant bacterium as described herein. In a further embodiment, a recombinant bacterium described herein may be used in a method for ameliorating one or more symptoms of an infectious disease in a host in need thereof. The method comprises administering an effective amount of a pharmaceutical composition comprising a recombinant bacterium as described herein.

EXAMPLES

The present invention is further illustrated by the following examples, which should not be construed as limiting in any way. The contents of all cited references, including literature references, issued patents, and published patent applications, as cited throughout this application are hereby expressly incorporated herein by reference. It should further be understood that the contents of all the figures and tables attached hereto are also expressly incorporated herein by reference.

Example 1: Background and Overview

*Campylobacter* is a leading cause of bacterial foodborne gastroenteritis worldwide and is a major public health problem (21-23). A recent estimate by the CDC indicates that *C. jejuni* is not only among the most common causes of foodborne illnesses in humans (over 800,000 cases per year), but also is a leading cause of hospitalization (over 8,000 annually) (24). Patients infected with *C. jejuni* often experience watery/bloody diarrhea, abdominal cramps, nausea, and fever. Severe neurological sequelae, bacteremia and other extraintestinal complications may develop infrequently (25). *C. jejuni* is widespread in food-producing animals, especially in poultry. The majority of human *C. jejuni* infections are predominantly associated with poor handling of raw chicken or consumption of undercooked chicken (1, 2, 26-32). The predominant role of poultry in human campylobacteriosis is supported by high prevalence of *C. jejuni* in both live birds and on carcasses, findings from epidemiological studies, and detection of identical genotypes in both poultry and human infections (28-30, 33, 34).

Domestic poultry including chickens, turkeys, ducks, and geese, are frequently infected with *C. jejuni* and *C. coli* (3, 35-37). Despite extensive colonization in the intestinal tract, *Campylobacter* infection produces little or no clinical diseases in poultry (3, 35, 38, 39). Prevalence studies conducted in Europe and the U.S. have reported *C. jejuni*-positive flocks ranging from 2% to 100% (38, 40-42). Typically, the prevalence of *C. jejuni* increases as the birds grow and reaches highest points at the slaughter age for broilers. Once a broiler flock is infected with *C. jejuni*, the majority of birds within the flock become colonized in (40, 43-46). The high numbers of *C. jejuni* in the intestinal tract results in contamination of poultry products during slaughter such that *C. jejuni* on poultry carcasses at the end of the processing line (post-chill) is usually over 50% varying from 0 to 100% (33, 47-53). In the U.S., several studies reported that a large percentage of processed broiler carcasses were contaminated with high numbers of *C. jejuni* (47, 53-55). Carcass contamination by *C. jejuni* is attributable to the farm of origin as high prevalence on a farm is usually associated with high-level carcass contamination in processing plants (56-60).

*Salmonellosis* develops different syndromes, including gastroenteritis, enteric fever (typhoid fever), and bacteremia, and as asymptomatic carriage in animals and humans (61). It is the leading cause of foodborne illness in the U.S., with 35% of the hospitalizations and 28% of the deaths (24). There are approximately 1.03 million cases of non-typhoidal *Salmonella* each year in the U.S., costing an economic loss of approximately $3.31 billion due to premature mortality, disability, and medical and productivity costs, with an annual loss of 16,782 quality-adjusted life years (62). *Salmonella* has a broad host range and adapts to survive in a wide range of different environments, even up to 16 months in dry feed stored at 25° C. (63, 64). Although a large number of human infections are associated with food animal sources, infections also come from pets, reptiles, fruits, vegetables and other humans (65-67). Transmission of *Salmonella* to humans typically occurs when ingesting foods that are contaminated by animal feces or cross-contaminated by other sources (4). Among these sources, poultry and poultry-associated products are widely recognized as being among the most important vehicles for human *Salmonella* infections according to CDC reports (5, 67-74). With increasing consumption of poultry and poultry products, the number of *salmonellosis* associated with poultry continues to be a significant public health issue in the U.S.

There are over 2000 *Salmonella* serotypes. *S. Enteritidis*, S. Heidelberg, S. Kentucky and *S. typhimurium* are commonly associated with chickens and to various extents with other food animal species and human infections. According to the CDC and USDA, *S. Enteritidis* was the most common serovar implicated in human illness in the U.S. (74) and most commonly associated with chickens and eggs and to a much lesser extent with other food animal species (74-80). S. Heidelberg is also found in most major food animal species, eggs, and retail meat samples and is among the top five most common serotypes associated with human disease (79, 81, 82). Although, S. Kentucky rarely causes human infections in the United States, it is an emerging serovar in Europe and North Africa (83) and is prevalent in poultry (75, 84, 85).

Traditionally, antibiotics have been used to treat bacterial infections and for growth promotion in food animals. However, these uses of antibiotics contributed to increasing rates of antibiotic resistance (86), resulting in contamination of flocks and food products by antibiotic-resistant *Campylobacter, Salmonella, Enterococcus* and *Escherichia coli* and thereby increasing risks of human infections (87). Public concerns over the spread of antibiotic resistance in zoonotic bacterial pathogens, which poses a threat to the effectiveness of existing antibiotic therapy in both clinical medical and veterinary practice (88-97), led the European Union, in 1999, to ban use of most antibiotics for growth promotion to preserve the effectiveness of important human drugs (98). In 2004, the U.S. FDA banned enrofloxacin in food animals on the grounds that its use contributed to fluoroquinolone resistance in human pathogens. More recently, FDA and industry have agreed to cease use of growth promotion antimicrobials. However, there are concerns that reductions in antibiotic use in animal production may lead to an increase in foodborne pathogens on meat and other animal food. Besides management practices, it is necessary to develop other effective ways to mitigate emergence of antibiotic-resistant bacteria and to control foodborne pathogens. One of the best prevention strategies are development and use of vaccines.

Campylobacter control: Poultry houses can be contaminated by Campylobacter in many different ways from various environmental sources, making prevention of flock colonization by Campylobacter a very challenging task. In general, the on-farm control strategies examined for Campylobacter in poultry can be broadly divided into two approaches: 1) prevention of flock colonization by use of biosecurity-based interventions, and 2) prevention and/or reduction of Campylobacter colonization by non-biosecurity based measures such as vaccination, addition of bacteriocins, bacteriophages and feed additives, and competitive exclusion (42, 99-101). Improving biosecurity on farms apparently has a noticeable effect on lowering the overall flock prevalence. However, even the most stringent biosecurity measures do not always have a consistent and predictable effect on controlling Campylobacter and their effectiveness on flock prevalence is difficult to assess under commercial settings (42, 102-105). In addition, stringent biosecurity measures are cost-prohibitive, hard to maintain, and their effectiveness seems to vary with production systems (36, 42). Multiple non-biosecurity measures have been evaluated for control of Campylobacter in live birds. Currently, there are no commercially available competitive exclusion products, vaccines, bacteriocins, bacteriophages or feed/water additives for excluding Campylobacter from chickens under production conditions although some promising results obtained under laboratory conditions have recently been reported (99, 106-108).

Vaccination against C. jejuni is a promising strategy but requires optimization of the vaccination regimen (e.g., induction of mucosal and possibly cellular immunity and practical delivery systems) using protective antigens. C. jejuni is generally considered as a commensal of chickens even though systemic and mucosal humoral responses have been observed (109-111) and anti-Campylobacter antibodies are detectable in progenies as maternally-derived antibodies (112). However, lack of strong activation of innate/adaptive immune responses in chickens, unlike in humans, requires development of vaccine strategies that enhance the immune response to C. jejuni antigens. For C. jejuni vaccine antigens to be immunogenic, it is critical to deliver antigens to the regional lymph tissues and spleen to stimulate effective mucosal immunity and systemic antibody and cellular immune responses. Therefore, S. typhimurium-derived RASVs delivering C. jejuni protective antigens were constructed to control/reduce C. jejuni prevalence in poultry.

Salmonella control. Since contaminated poultry products are the major source of human Salmonella infection, vaccination of chickens is an important strategy to reduce the levels of Salmonella in poultry flocks, which will ultimately lead to lower rates of human Salmonella infection. Considering the whole life span of broilers as only 5-6 weeks, it is a challenge to develop a safe and effective Salmonella vaccine that could be cross-protective against different serovars. Currently, there are 3 types of vaccine, live attenuated, inactivated and subunit; only the former two are licensed for chickens. Live attenuated vaccines can be administered orally, delivering a bolus of antigens to the host and induce both antibody and cell-mediate immune responses. These live vaccines have used diverse attenuation strategies for strains of S. typhimurium (113-115) and S. Enteritidis (115-121). However, variable efficacy and persistence, reversion to virulence, lack of cross protection and/or possible interference with Salmonella testing procedures are concerns (122-125). Killed vaccines are safe, but they must be delivered by costly injection and require adjuvants to increase efficacy (123-125). Thus, the need for a safe and improved live attenuated but highly immunogenic Salmonella vaccine still exists (125). Salmonella serotypes are defined by the immunologically heterogeneous LPS O-antigen side chains and flagellar antigens. Therefore, induction of immune responses to these heterogeneous antigens will not serve well the purpose of inducing cross-protective immunity to the diversity of serotypes. On the other hand, Salmonella and other enteric bacterial pathogens possess a number of immunologically related cross-reactive antigens. These include the LPS core polysaccharide which is the same in most, if not all, S. enterica serotypes except for S. enterica serotype Arizonae (126). In addition, numerous outer membrane proteins (OMPs), although possessing micro-heterogeneity, nevertheless share antigenic determinants (127) as do the iron regulated outer membrane proteins (IROMPs) that are required for iron acquisition (128), an essential important function for pathogen success within an infected animal. Strategies for Salmonella vaccines have been developed to display wild-type surface antigenic determinants in vitro and during the initial phase of infection through mucosal surfaces in the orally immunized host and then cease to synthesize LPS O-antigen side chains and to constitutively synthesize iron-regulated outer membrane proteins (IROMPs) in internal organs (19, 129). Gradual elimination of LPS O-antigen side chains in vivo also better exposes the immunologically related cross-reactive OMPs and IROMPs for surveillance by and stimulation of the immune system. Immune responses to IROMPs are known to be effective in preventing septicemic infection with enteropathogens, especially E. coli causing colisepticemia in chickens and turkeys (130). Also, antibodies induced to IROMPs from one bacterial serotype can recognize IROMPs synthesized by other serotypes (131). The fur gene encodes a repressor that, in the presence of free iron, represses all genes encoding IROMPs (128). When iron concentrations become low, as is the case in animal host tissues beyond the intestinal wall barrier, the Fur ceases to be synthesized at a high level and one observes constitutive expression of IROMPs and other Fur-regulated genes needed to sequester iron away from the infected animal host (128). fur mutants are attenuated when fed orally, giving a two to three log higher $LD_{50}$ when administered either to mice (132) or day-of-hatch chicks (133). To achieve a high constitutive level of synthesis of all components for iron acquisition including IROMPs, the promoter of the fur gene ($P_{fur}$) was deleted and replaced with a tightly regulated araC $P_{BAD}$ activator-promoter so that expression of the fur gene is solely dependent on the presence of arabinose (129) and is blind to the concentration of iron. Growth of S. Typhimurium vaccines with a $\Delta P_{fur}$::TT araC $P_{araBAD}$ fur deletion-insertion mutation in media with a low level of arabinose results in very good colonization of lymphoid tissues, total attenuation at doses of $10^9$ CFU and very high levels of induced protective immunity (129).

Genetically engineered Salmonella serovars Typhimurium (134), Paratyphi A and Typhi (135, 136) have been created as vaccines for regulated delayed attenuation in vivo (129, 134), regulated delayed in vivo synthesis of protective antigens specified by codon-optimized DNA sequences (137-140) and regulated delayed lysis in vivo (140-142) such that vaccines can be grown under conditions that enable them to display after course spray or oral immunization the capabilities of a wild-type strain to survive host defense stresses and efficiently colonize effector lymphoid tissues before manifesting attenuation to preclude disease symptoms and to synthesize protein antigens to induce protective immune responses. Strains have been engineered to eliminate or decrease synthesis of serotype-specific LPS O-antigen (18, 143) and flagellar antigens, to expose conserved LPS core (18, 19, 143) and over-express immunologically cross-reactive surface outer membrane protein antigens (19, 144) needed for the acquisition of essential iron and manganese ions, to diminish induction of gastroenteritis symptoms (145) while retaining abilities to recruit innate immunity, and to exhibit biological containment by cell lysis to preclude persistence in vivo or survival if excreted (140-142). Strains are totally safe at high doses to newborn (136, 146, 147), pregnant, protein malnourished and immunocompromised mice. Also neonatal pups (7 days old) born from mothers immunized with the same RASV strain develop better immune responses and exhibit higher levels of protective immunity to challenge than pups born from unimmunized mothers. A somewhat analogous result was observed years ago when chicks hatched from eggs laid by immunized hens displayed higher levels of protective immunity to the same attenuated S. typhimurium vaccine used to immunize the hens than chicks from eggs laid by unimmunized hens (148). These technologies have been used to develop vaccines to prevent infections of newborns with Streptococcus pneumoniae (147), Mycobacterium tuberculosis (140, 149), a diversity of enteric bacterial pathogens causing diarrheal diseases in humans and influenza virus (141). In a recent human trial of a S. Typhi derived RASV, complete safety and shedding of zero viable vaccine cells in stools collected for 12 days was observed and with vaccine doses of up to $10^{10}$ CFU administered orally (150). Vaccines have also been developed using S. typhimurium RASVs against pathogens of agriculturally important animals, especially to pathogens of chickens such as Eimeria species causing coccidiosis (151, 152) and Clostridium perfringens causing necrotic enteritis (153, 154). In these regards, six studies (140-142, 154-156) have demonstrated that RASVs with the regulated delayed lysis in vivo phenotype gave superior levels of immune responses and protective immunity compared to RASVs that did not have this lysis phenotype.

To eliminate use of plasmid vectors with non-permitted drug resistance genes and to stabilize plasmid vectors in RASVs in vivo, (157) a balanced-lethal vector-host system was developed by deletion of the asd gene to impose an obligate requirement for diaminopimelic acid (DAP), an essential constituent of the rigid layer of the cell wall and a plasmid vector with the wild-type asd gene. It was also demonstrated that better immune responses to synthesized protective antigens could be achieved by having them secreted using T2SSs such as fusion to the N- and C-terminal β-lactamase sequences (158, 159), which has now been further optimized (154). Enhanced immunogenicity is partially due to enhanced formation of immunogenic outer membrane vesicles containing protective antigens (19, 160).

Plasmids were also constructed (118) and used that are required for the display of the regulated delayed lysis in vivo phenotype in conjunction with the derivatives of χ11730, χ11791 and χ12341. These strains have an araC $P_{araBAD}$ regulated expression of the murA gene encoding the first enzyme in muramic acid synthesis and the Δasd mutation blocking DAP synthesis in its chromosome. These lysis plasmids cause synthesis of protective antigens for delivery by cell lysis and have araC $P_{araBAD}$ regulated murA and asd genes with GTG start codons to decrease translation efficiency. The P22 $P_R$ located with opposite orientation to the transcription of the plasmid araC $P_{araBAD}$ GTG-murA GTG-asd genes is repressed by the C2 repressor made during growth of the strain in medium with arabinose (due to the ΔasdA::TT araC $P_{araBAD}$ c2 mutation). However, C2 concentration decreases due to cell division in vivo to cause $P_R$-directed synthesis of anti-sense mRNA to block translation of residual asdA and murA mRNA. Transcription terminators (TT) flank all plasmid domains for controlled lysis, replication and gene expression so that expression in one domain does not affect activities of another domain.

A. Protective Immunity Against *Eimeria* Infection in Chickens.

Figure 1A:
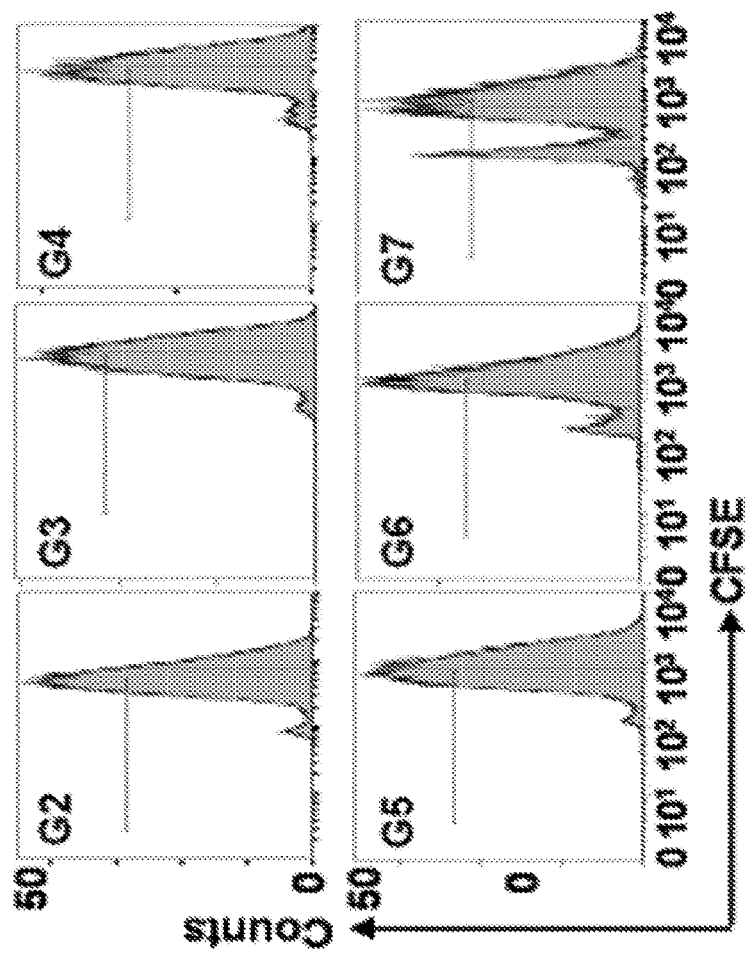
Figure 2B:
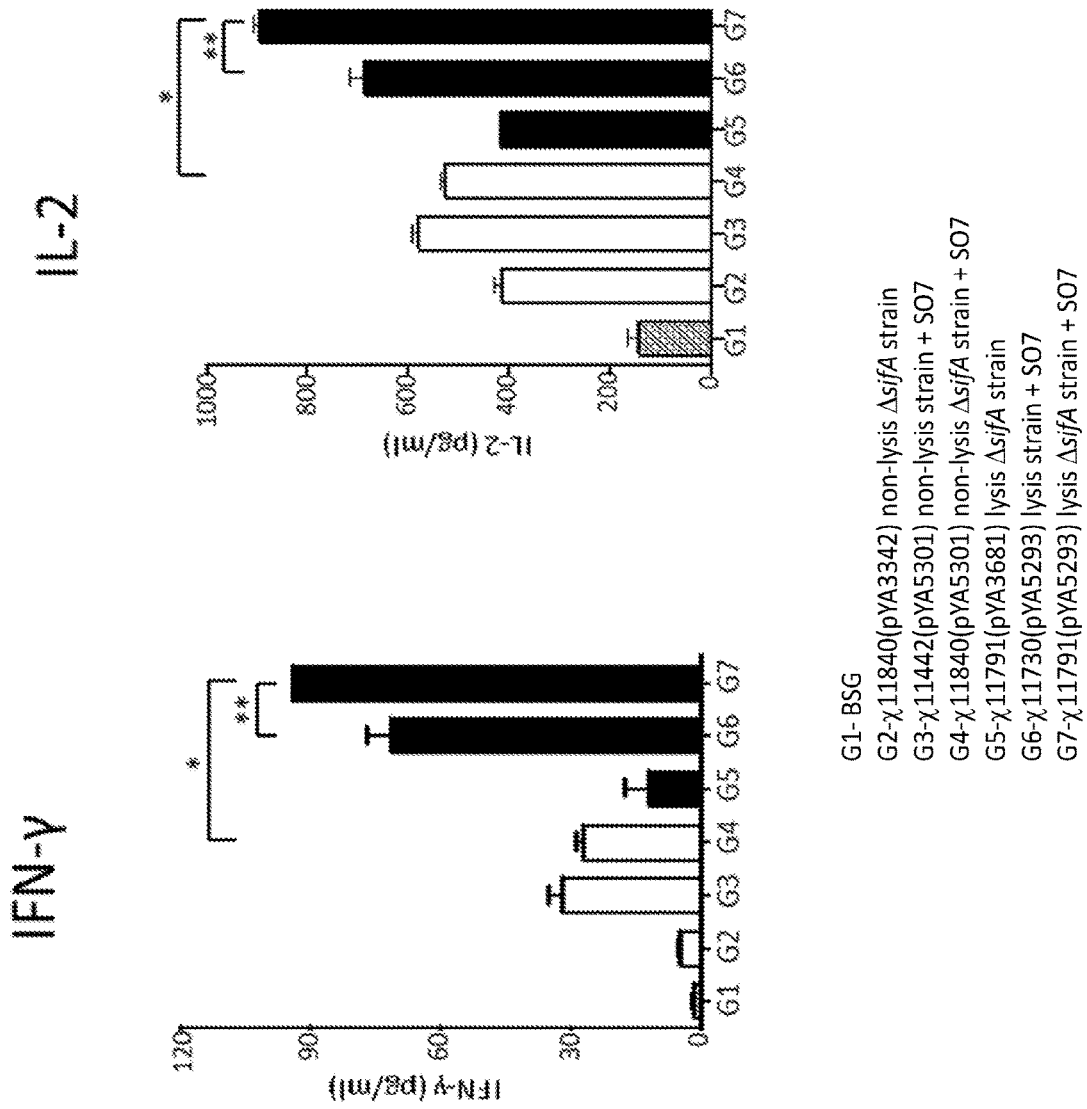
FIG. 2B depicts lymphocyte activation and cytokine secretion after in vitro homologous recall of splenic lymphocytes from chicks vaccinated with RASV vaccine strains.

Protective responses in chickens against *E. acervulina* causing coccidiosis was demonstrated. FIGS. 1A and 1B show comparative data for immunization of chickens with non-lysis and lysis strains without and with the ΔsifA mutation for delivery of the *Eimeria* SO7 antigen. The ΔsifA mutation enables the RASV to escape from the *Salmonella* containing vesicle (SCV) so that lysis occurs in the cytosol to enhance induction of CD8-, CD17- and NKT-dependent cellular immunities. Clearly, the most extensive *Eimeria* SO7-specific lymphocyte proliferation was induced by RASV strains with the lysis phenotype and the ΔsifA mutation (Group 7). This same group gave the highest levels of antigen-specific IgA antibody responses (FIGS. 1C and 1D), CD8 cells (FIG. 2A), cytokine response (FIG. 2B), and weight gain after *Eimeria* oocyst challenge (Table 1). Based on these results, the ΔsifA mutation is included in the RASV vector strains to specify synthesis and delivery of *C. jejuni* protective antigens. These collective results demonstrate the efficacy in using these improved RASVs to develop vaccines that will confer protective immunity to *Salmonella* and *C. jejuni* strains in chickens. The use of RASVs that also exhibit complete biological containment with no persistence in vivo or survival if shed in feces, provides another important benefit.

TABLE 1

Immunization of broiler chickens with RASV strains and challenged with *E. tenella* oocysts

| Group | [a]Primary Immunization | Secondary Immunization | [b]Oocyst challenge | [c]Weight gain (mean ± SEM) | [d]Feed conversion ratio (FCR) |
|---|---|---|---|---|---|
| 1 | BSG | BSG | No | 576 ± 32 | 1.75 ± 0.17 |
| 2 | BSG | BSG | Yes | 510 ± 17 | 1.95 ± 0.06 |
| 3 | χ11791(pYA3681) | Yes | Yes | 491 ± 36 | 2.22 ± 0.47 |
| 4 | χ11442(pYA5301) | Yes | Yes | 502 ± 58 | 2.04 ± 0.17 |
| 5 | χ11840(pYA5301) | Yes | Yes | 433 ± 28 | 2.03 ± 0.19 |
| 6 | χ11730(pYA5293) | Yes | Yes | 558 ± 7 | 1.91 ± 0.08 |
| 7 | χ11791(pYA5293) | Yes | Yes | 598 ± 20 | 1.77 ± 0.00 |

[a]Chickens were orally vaccinated when 1 week old and again 1 week later.
[b]Three weeks later, groups G2 to G7 were inoculated with $10^5$ *E. tenella* oocysts.
Group 3 = Empty Vector Control. Groups 3 & 4 = Non-Lysis RASVs delivering Eimeria S07 antigen. Groups 6 & 7 = Lysis RASVs delivering S07 antigen. Group 7 RASV also escapes from the *Salmonella*-containing vesicle for lysis in the cytosol to induce maximal systemic and cellular immunities.
[c]Weight gain in grams calculated over the infection period (6 days) between *E. tenella* challenge and termination.
[d]FCR, feed conversion ratio calculated as average amount of feed (g) consumed/average weight gain over the infection period (6 days) between *E. tenella* challenge and termination.

B. *S. typhimurium* Vaccine Vector Strains

*E. coli* host strains for construction of recombinant plasmid vectors and for conjugational transfer of suicide vectors for construction of *S. typhimurium* with improved properties with added mutational alterations are listed in Table 2. Strains used for the construction and evaluation of RASV strains synthesizing and delivering the *Eimeria* SO7 antigen and *C. jejuni* antigens are also listed in Table 2. The phenotypic attributes associated with the mutations in these strains are described in Table 3.

TABLE 2

Bacterial Strains

E. coli strains

χ6212(pYA232); φ80d lacZ ΔM15 deoR Δ(lacZYA-argF)U169 supE44 λ⁻ gyrA96 recA1 relA1 endA1 ΔasdA4 Δzhf-2::Tn10 hsdR17 (r⁻ m⁺), lacI$_q$ in pSC101 ori, Tc plasmid 10.2 kb χ7213: thi-1 thr-1 leuB6 glnV44 fhuA21 lacY1 recA1 RP4-2-Tc:Mu [λ pir] ΔasdA4 Δzhf-2::Tn10

S. Typhimurium strains

χ11442: ΔasdA33 ΔrelA198::araC P$_{BAD}$ lacI TT ΔaraBAD23 Δpmi-2426

χ11730: ΔP$_{murA25}$::TT araC P$_{araBAD}$ murA ΔasdA27::TT araC P$_{araBAD}$ c2 Δ(wza-wcaM)-8 Δpmi-2426 ΔrelA198::araC P$_{araBAD}$ lacI TT χ11791: ΔP$_{murA25}$::TT araC P$_{araBAD}$ murA ΔasdA27::TT araC P$_{BAD}$ c2 Δ(wza-wcaM)-8 Δpmi-2426 ΔrelA198::araC P$_{arBAD}$ lacI TT ΔsifA26

χ11840: ΔasdA33 ΔrelA198::araC P$_{araBAD}$ lacI TT ΔaraBAD23 Δpmi-2426 ΔsifA26

χ12341: ΔP$_{murA25}$::TT araC P$_{araBAD}$ murA ΔasdA27::TT araC P$_{araBAD}$ c2 Δ(wza-wcaM)-8 Δpmi-2426 ΔrelA197::araC P$_{araBAD}$ lacI TT ΔrecF126 ΔsifA26 ΔwaaL46 ΔpagL64::TT rhaRS P$_{rhaBAD}$ waaL χ12396: ΔP$_{murA25}$::TT araC P$_{araBAD}$ murA ΔasdA27::TT araC P$_{araBAD}$ c2 Δ(wza-wcaM)-8 Δpmi-2426 ΔrelA197::araC P$_{araBAD}$ lacI TT ΔrecFl26 ΔsifA26 ΔwaaL46 ΔpagL64::TT rhaRS P$_{rhaBAD}$ waaL ΔP$_{fur33}$::TT araC P$_{araBAD}$ fur χ12445: ΔP$_{murA25}$::TT araC P$_{araBAD}$ murA ΔasdA27::TT araC P$_{araBAD}$ c2 Δ(wza-wcaM)-8 Δpmi-2426 ΔrelA197:: araC P$_{araBAD}$ lacI TT ΔrecF126 ΔsifA26 ΔwbaP45 ΔpagL14::TT araC P$_{araBAD}$ wbaP χ12452: ΔP$_{murA25}$::TT araC P$_{araBAD}$ murA ΔasdA27::TT araC P$_{araBAD}$ c2 Δ(wza-wcaM)-8 Δpmi-2426 ΔrelA197::araCP$_{araBAD}$ lacI TT ΔrecF126 ΔsifA26 ΔwaaL46 ΔpagL64::TT rhaRS P$_{rhaBAD}$ waaL ΔompA11 ΔsopB1925

TABLE 3

Mutations and associated phenotypes used in S. Typhimurium vaccine strains[a]

| Genotype | Phenotype |
|---|---|
| A. Deletion and deletion-insertion mutations to confer a regulated delayed attenuation | |
| Δpmi | encodes phosphomannose isomerase needed for synthesis of GDP-mannose for LPS O-antigen and thus necessary for virulence (18). |
| ΔwaaL ΔpagL::TT P$_{rhaBAD}$ waaL | regulates synthesis of enzyme responsible for attaching first subunit of LPS O-antigen to the LPS core (the deletion of the waaL gene is necessary to prevent impairment in expression of other rfb operon genes (161); the regulated expression cassette is therefore inserted into the pagL gene. |
| ΔP$_{fur}$::TT araC P$_{BAD}$ fur | makes synthesis of Fur dependent on presence of arabinose in growth medium and ceases to be synthesized in vivo due to the absence of arabinose (162) (104). Fur decreases as a consequence of cell division in vivo to lead to elevated synthesis of IROMPs and attenuation presumably due to an iron overload. |
| ΔP$_{mntR}$::TT araC P$_{BAD}$ mntR | makes synthesis of MntR dependent on presence of arabinose in growth medium and ceases to be synthesized in vivo due to the absence of arabinose (162) (104). MntR decreases as a consequence of cell division in vivo to cause elevated synthesis of MnROMPs to enhance induction of cross-protective immunity. |
| B. Promoters and deletion-insertion mutations for regulated in vivo synthesis of antigens | |
| P$_{trc}$ | a promoter expressed at high level under both anaerobic and aerobic conditions and repressed by LacI (163). |
| ΔrelA::araC P$_{BAD}$ lacI TT | the relA mutation uncouples growth regulation from a dependence of protein synthesis, an important attribute in strains with regulated delayed lysis (164) (189). The arabinose-dependent synthesis of the LacI repressor is to enable a regulated delayed expression of DNA sequences under the control of P$_{trc}$ (137) (113). |
| Phage P22 P$_L$ and P$_R$ | these promoters are repressible by the arabinose-dependent synthesis of the C2 repressor (Vander Byl and Kropinski) (190) (165). |
| C. Deletion and deletion-insertion mutations to facilitate regulated delayed lysis in vivo | |
| ΔP$_{murA}$::TT araC P$_{BAD}$ murA | makes synthesis of MurA, the first enzyme in the synthesis of muramic acid, dependent on presence of arabinose in growth medium and ceases to be synthesized in vivo due to the absence of arabinose (142) (118). MurA decreases as a consequence of cell division in vivo to ultimately lead to cell lysis and death (166) (191). The murA defect is complemented by MurA⁺ plasmid vectors (142) (118). |

TABLE 3-continued

Mutations and associated phenotypes used in *S. Typhimurium* vaccine strains[a]

| Genotype | Phenotype |
|---|---|
| ΔasdA::TT araC P$_{BAD}$ c2 | the Asd enzyme is essential for the synthesis of diaminopimelic acid required for peptidoglycan synthesis (167) (192). The arabinose-dependent synthesis of the C2 repressor is to enable a regulated delayed expression of DNA sequences under the control of a promoter repressed by C2 (142) (118). The ΔasdA mutation is complemented by Asd$^+$ plasmid vectors (157) (193). |
| Δ(wza-wcaM) | eliminates twenty enzymes needed to synthesize several exopolysaccharides that promote biofilm formation and for synthesis of GDP-fucose that is required for colanic acid synthesis (168) (194), which can protect cells undergoing cell wall-less death from lysing (169) (195). |

| D. Mutations needed to enhance effective delivery of protective T-cell epitope antigens | |
|---|---|
| ΔsifA | enables *Salmonella* to escape endosome = *Salmonella* containing vesicle (SCV) for lysis in cytosol (170) (196). |

| E. Other contributing mutations | |
|---|---|
| ΔrecF | eliminates recombinase that facilitates inter- and intra-plasmidic recombination (171-173) (197-199). |
| ΔsopB | eliminates excessive intestinal inflammation and enhances induction of mucosal immunity (145, 174-176)(122, 123) |
| ΔompA | eliminates a major outer membrane protein that is highly immunogenic (177) but does not contribute to protective immunity (178)with elimination due to mutation leading to enhanced induction of protective immunity to other outer membrane proteins |

[a]Δ = deletion; TT = transcription terminator; P = promoter

C. *Campylobacter jejuni* Putative and Demonstrated Protective Antigens.

Nineteen *C. jejuni* antigens were selected as known or probable protective antigens based on literature review and bioinformatics analyses. They are listed in Table 4 as likely to induce protective immune responses.

TABLE 4

Exemplary *Campylobacter jejuni* antigens

| Gene | Antigen | Function | GC contents | Signal peptide | bp/aa | Identity among *C. jejuni* seq |
|---|---|---|---|---|---|---|
| cj0034c | Cj0034c | putative periplasmic protein | 32.3% | 22/23 for euk | 702/233 | 96-100% |
| cj0113 | Omp18 | peptidoglycan associated lipoprotein | 33.9 | 21/22 for euk | 498/165 | 100% |
| cj0168c | Cj0168c | putative periplasmic protein | 33.3 | Yes 20/21 | 168/55 | 78-100% |
| cj0248 | Cj0248 | virulence factor and play a role in motility | 30.8 | No | 858/285 | 90-100% |
| cj0289c | Peb3 AcfC | major antigenic peptide PEB3 accessory colonization factor | 34.9 | Yes 20/21 | 753/250 | 100% |
| cj0365c | CmeC | outer membrane channel protein CmeC (multidrug efflux system CmeAB | 31.6 | 19/20 euk 23/24 grnN | 1479/492 | 98-100% |
| cj0404 | Cj0404 | putative transmembrane protein | 29.5 | No | 838/278 | 100% |
| cj0420 | Cj0420 | protein yceI precursor, polyisoprenoid-binding protein | 28.8 | 21/22 gmN and euk | 573/191 | 88-100% |
| cj0427 | Cj0427 | conserved hypothetical protein | 34.5 | No | 336/111 | 99-100% |
| cj0428 | Cj0428 | hypothetical protein | 33.1 | No | 384/127 | 82-100% |
| cj0588 | TlyA | putative haemolysin | 25.7 | No | 762/253 | 82-100% |
| cj0921c | Peb1 | bifunctional adhesin/ABC transporter aspartate/glutamate-binding protein | 31.7 | Yes 26/27 | 780/259 | 100% |
| cj0982c | CjaA | surface antigen/glutamine ABC transporter substrate-binding protein | 33.9 | 18/19 gmN/euk | 840/279 | 100% |
| cj0998c | Cj0998c | Hypothetical protein | 29.7 | 19/20 euk 20/21 gmN | 573/190 | 100% |
| cj1259 | Momp (PorA) | major outer membrane protein | 36.1 | Yes 22/23 | 1275/424 | 100% |

TABLE 4-continued

Exemplary *Campylobacter jejuni* antigens

| Gene | Antigen | Function | GC contents | Signal peptide | bp/aa | Identity among C. jejuni seq |
|------|---------|----------|-------------|----------------|-------|------------------------------|
| cj1339c | FlaA | Flagellin A | 37.0 | No | 1719/572 | 100% |
| cj1478c | CadF | outer membrane fibronectin-binding protein | 31.8 | 16/17 euk very weak | 960/319 | 100% |
| cj1534c | Dps | DNA starvation/stationary phase protection protein, putative bacterioferritin | 32.0 | No | 450/149 | 93-100% |
| cj1656c | Cj1656c | putative motility protein | 38.3 | No | 183/60 | 80-100% | cj sequences are from *Campylobacter jejuni* NCTC 11168 (ATCC700819),
* Analyzed using Blast against *C. jejuni* NCTC 11168 (ATCC700819), 327, LMG23211, 84-25, H693-13, CG8486, LMG9872, S3, LMG23269, 414, ATCC33560, 2008-831, 1997-4, 260.94. CF93-6, M1, RM221 & 20 additional sequenced *C. jejuni* genomes
euk: in eukaryotic; gmN: in gram negative These sequences are present in all 39 *C. jejuni* genomes analyzed and have 82% or more amino acid sequence identity in all these strains. These include cj0034c, cj0113 (Omp18), cj0168c, cj0248, cj0289 (Peb3), cj0365 (CmeC), cj0404, cj0420, cj0427, cj0428, cj0588 (TlyA), cj0921c (Pebl), cj0982c (CjaA), cj0998c, cj1259 (PorA), cj1339c (Fla), cj1478c (CadF), cj1534c (Dps) and cj1656c. Each of the 19 antigens were analyzed using a diversity of bioinformatic analyses to determine which antigens are present in all sequenced *C. jejuni* strains, which are highly conserved in amino acid sequence, have signal sequences for export and are cell surface localized. Ten of these were selected, including: Cj0113=Omp18 (Refs needed), Cj0289c=Peb3 (120-123), Cj0982c=CjaA (124-128), Cj1259=PorA (120, 121, 123, 126, 129-134), Cj1339c=FlaA (120, 121, 123, 135-144), Cj1478=CadF (120, 121, 129, 132, 144-147), Cj0588 TlyA (148-150), Cj0921c=Pebl (121-123, 145, 151-157), Cj0998c (U.S. Pat. No. 9,328,148 (150) and Cj1534c=Dps (158, 159) to generate recombinant plasmids using the regulated lysis plasmids pYA4763 and/or pG8R17 depending on whether the antigens did or did not have signal sequences for their secretion from *C. jejuni* strains.

Figure 3A:
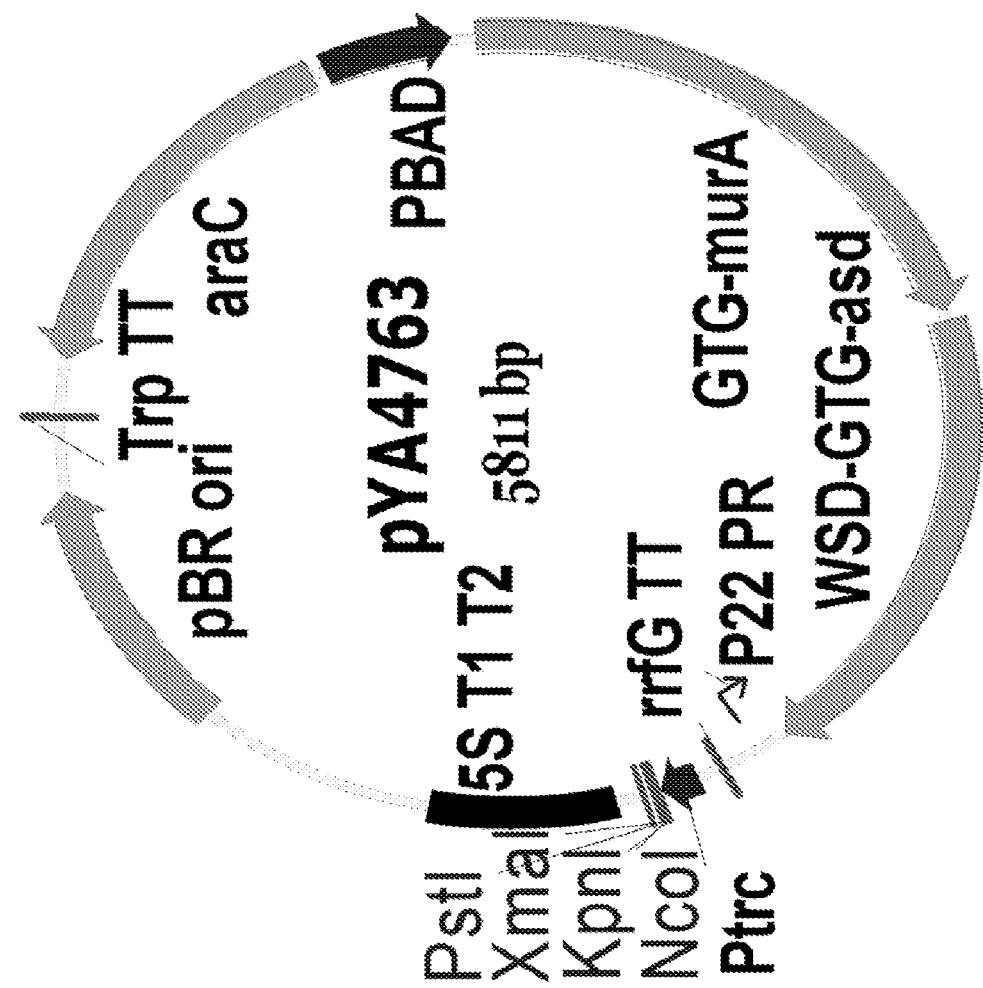
FIGS. 3A and 3B depict
Figure 3B:
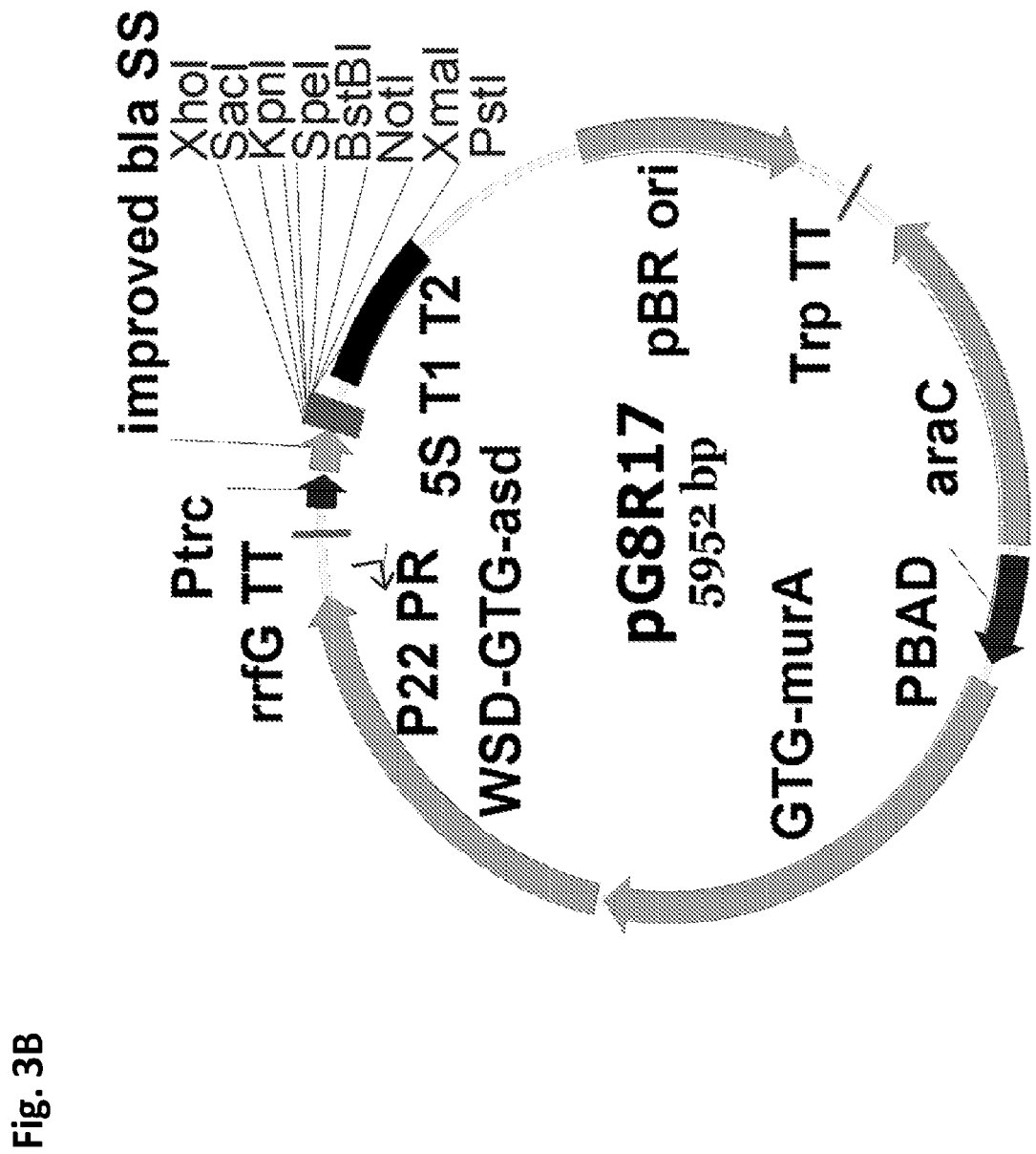

The encoding sequences were codon optimized to adjust GC contents and optimize expression in *Salmonella* and also eliminate potential sites in mRNA subject to cleavage by RNase E so as to prolong half-life of mRNA to also enhance level of antigen synthesis. The codon optimized sequences were modified to delete the native signal peptide encoding sequence (if present), add a sequence encoding a His-tag at the C-terminal end to facilitate protein purification and other sequences on the N- and C-terminal ends to specify the nucleotide sequences to be recognized by restriction enzymes to enable cloning into either pYA4763 (if the antigen was not to be secreted by the RASV) (FIG. 3A) or into pG8R17 (FIG. 3B) with the much improved β-lactamase signal sequence (154)(131) if the antigen was to be secreted. The sequences were also designed to enable excision of the His-tag sequence at a later date, if desired. These sequences were synthesized commercially and returned in promoterless pUC ori vectors. The sequences to be cloned were excised from these plasmids and inserted into either of the lysis plasmids that were then electroporated into the *E. coli* strain χ6212(pYA232) (Table 2). pYA232 encodes the lacI$^q$ gene that overproduces LacI to repress antigen synthesis by the recombinant strains in which the antigen-encoding sequences are under the control of $P_{trc}$ that is repressed by LacI. After selection of the recombinant clones by selection for Asd$^+$ and purification, viability is verified by ability of the *E. coli* recombinants to grow in the presence of IPTG to cause derepression and synthesis of the *C. jejuni* recombinant antigens. Desirably growth is unaltered by antigen synthesis although in some cases growth is slightly retarded due to the high-levels of *C. jejuni* antigen synthesis. The recombinant lysis plasmids were then isolated from the χ6212 host strain and electroporated into the *S. typhimurium* vaccine strain χ12341 (ΔP$_{murA25}$::TT araC P$_{BAD}$ murA ΔasdA27::TT araC P$_{BAD}$ c2 Δpmi-2426 ΔwaaL46 ΔpagL64::TT rhaRS P$_{rhaBAD}$ waaL Δ(wza-wcaM)-8 ΔrelA197::araC P$_{BAD}$ lacI TT ΔrecF126 ΔsifA26)) (Table 2) again selecting for Asd$^+$. After purification, RASVs were tested for rate of growth and synthesis of *C. jejuni* antigens with and without IPTG, for synthesis of LPS O-antigen dependent on growth in the presence of both mannose and rhamnose and for stability of plasmid maintenance and antigen synthesis after 50 generations of growth under permissive growth in media supplemented with DAP.

FIGS. 4A-4B show western blot analyses of recombinant antigen synthesis in χ12341. The selected recombinant pG8R plasmid is indicated at the top of the Figure and also whether the plasmid was derived from pYA4763 or from pG8R17. Protein was detected using horse radish peroxidase tagged anti His-tag monoclonal antibodies. In some cases, such as with pG8R130 encoding the CadF antigen, the level of CadF protein is low indicating poor synthesis or degradation of the antigen. These problems are sometimes encountered and can be evaluated. Antigen synthesis is thus induced by exposure of RASV strains to IPTG for two hours and then adding 50 μg chloramphenicol; ml to block further protein synthesis. Samples are then taken every hour for four hours to measure antigen levels by western blot analyses. Maintenance of constant antigen levels rules out instability. If instability is observed the amino acid sequence is scrutinized with computer programs to indicate potential cleavage sites by proteases and then new constructs are made with nucleotide changes to eliminate such potential protease cleavage sites. If it appears that antigen synthesis is low, the sequence is examined and new constructs are made to fully establish the basis for the problem and ultimately generate recombinant clones with high-level stable synthesis of the recombinant antigens. In some cases this necessitates modification of the SD sequence to enhance ribosome binding or other alterations in the N-terminal coding sequence to enhance translation efficiency. Since the delivery of multiple recombinant *C. jejuni* antigens to poultry is examined to select those that reduce cecal titers of challenge strains by 100-fold or more, it is not likely that more than three or four antigens will be needed in the final vaccine. Thus, problems in getting high-level stable synthesis of all potential antigens might not be necessary.

In evaluating RASV constructs to induce protective immunity against *Salmonella* serotypes prevalent in poultry (Table 5), some of the recombinant plasmids encoding *C. jejuni* antigens were introduced into χ12452 that is a derivative of χ12341 with ΔsopB and ΔompA mutations. pG8R86 encoding CjaA, pG8R88 encoding Omp18, pG8R89 encoding Pebl, pG8R90 encoding Cj0998c, pG8R102 encoding Peb3, pG8R128 encoding Dps and pG8R129 encoding TlyA have thus been introduced. All of these constructs yield good levels of antigen synthesis as shown in FIG. 4. The relative abilities of the χ12341 constructs are compared versus the χ12452 constructs to protect against infection with the selected *Salmonella* serotype strains (Table 5). These constructs are also being evaluated for protection to challenge with the *C. jejuni* strains also listed in Table 5. In order to determine the best combination of *C. jejuni* antigens to result in the largest reductions in *C. jejuni* following challenge infection of non-immunized versus immunized chickens, different combinations of strains each delivering a separate *C. jejuni* antigen are evaluated for additive benefits in reducing cecal titers of challenge strains. In several studies with other RASVs, very similar, if not identical, levels of protective immunity have been found when immunizing with a mixture of two RASVs delivering two different protective antigens, as was observed when a single RASV delivered both antigens.

other *S. typhimurium* strains, and definitely not to the highly virulent UK-1 strain (187). Therefore a strain that displays maximal ability to cause disease is used as the parental strains for all attenuated derivative vaccine strains. LB broth and agar is used as complex media for propagation and plating of *Salmonella* (see 163(188, 189)). Purple broth (Difco), which is devoid of arabinose, mannose and rhamnose, and minimal salts medium and agar are also used (190) (164). Chrome azurol S (CAS) plates is used to evaluate synthesis of Fe acquisition siderophores. MacConkey agar with 0.5% lactose (Lac) and 0.1% arabinose (Ara), when necessary, is used to enumerate bacteria from chickens. Tetrathionate or selenite broth, with or without supplements, is used to enrich for *Salmonella* from cecal and intestinal contents, the bursa of Fabricius, liver and spleen. Bacterial growth is monitored spectrophotometrically and by plating for colony counts. Sequenced and well-characterized *C. jejuni* strains NCTC11168, 81-176, 81116 and R1\4221 and *C. jejuni* isolates from chickens (Table 5) are used in challenge studies. These strains are cultured microaerophilically (85% $N_2$, 10% $CO_2$, 5% $O_2$) on Mueller-Hinton (MH) medium at 42° C. for 24 h. For *C. jejuni* isolation from chicken feces and organs, MH agar plates are supplemented with *Campylobacter* selective supplement (SR117E; Oxoid, Lenexa, Kans.). Bacterial strains for the challenge studies are listed in Table 5.

TABLE 5

Strains used for challenge studies

| Strain | Genotype or Phenotype | Reference |
| --- | --- | --- |
| *Salmonella* | | |
| S. Typhimurium UK-1 χ3761 | Wild Type B, 1, 4, [5], 12: i:1,2 | (179) |
| S. Enteritidis χ3550 | Wild Type D1 1,9,12: g,m | (144) |
| S. Heidelberg χ3749 | Wild Type B 1,4,[5],12:r:1,2:- | (180) |
| S. Montevideo NR35 χ3217 | Wild Type C1 6,7,14,[54]:g,m,[p],s:[1,2,7] | (113) |
| S. Hadar NR14 χ3210 | Wild Type C2 6,8:$Z_{10}$: e,n,x | (113) |
| S. Infantis NR29 χ3213 | WildType C1 6,7,14:r:1,5 | (113) |
| S Newport NR90 χ3240 | Wild Type C2 6,8,20:e,h:1,2 | M. Rosenfeld, Borstel Institute |
| S. Kentucky χ11609 | Wild Type C3 8,20:i:Z6 | John Maurer, U of Georgia |
| *C. jejuni* 81-176 | Human isolate, O:23/36 | (181) |
| *C. jejuni* NCTC11168 | Human isolate, serotype O:2 | (182) |
| *C. jejuni* 81116 (NCTC11828) | Human and Chicken, Lab strain O:6 | (183) |
| *C. jejuni* RM 1221 | Chicken isolate HS:53 | (184, 185) |
| *C. jejuni* Chicken Isolate Mix | Chicken | (186) |

This research enhances food safety by immunization of poultry with multiple *S. typhimurium*-derived RASVs delivering multiple protective *C. jejuni* antigens to reduce colonization and persistence in chickens of *Salmonella* serotypes and *C. jejuni* strains to reduce their transmission through the food chain to humans. It is expected the selected vaccine will also enhance poultry farming productivity and decrease use of antibiotics contributing to improved economics of poultry production. Immunization of breeders as well as broiler chicks with these RASVs should reduce, if not eventually eliminate, transmission of *Salmonella* and *C. jejuni* through the food chain to humans.

D. Materials and Methods a. Bacterial Strains, Media and Bacterial Growth.

Attenuated *S. typhimurium* UK-1 stain induces protective immunity to challenge with all *S. typhimurium* strains whereas other *S. typhimurium* strains attenuated with the same mutations often cannot induce protective immunity to b. Molecular and Genetic Procedures.

Methods for DNA isolation, restriction enzyme digestion, DNA cloning and use of PCR for construction and verification of vectors are standard (see 172 (191)). DNA sequence analyses were performed at the University of Florida Interdisciplinary Center for Biotechnology Research (ICBR). All oligonucleotide and/or gene segment syntheses were performed using codon optimization to enhance translational efficiency in *Salmonella* and stabilize mRNA by eliminating RNase E cleavage sites to prolong mRNA half-life (192-194) (173-175). Since live vaccines cannot display antibiotic resistance, defined unmarked deletion mutations are generated with and without insertions using suicide vector technologies (see 176-181 Edwards et al. (1998) *Gene* 207: 149-57(195); Kaniga et al. (1998) *Infect. Immun.* 66: 5599-606(196); Maloy and Nunn (1981) *J. Bacteriol.* 145: 1110-2(197); Miller and Mekalanos (1988) *J Bacteriol.* 170: 2575-83(198); Ried and Collmer (1987)

Gene 57: 239-46(199); and Roland et al. (1999) Avian Dis. 43: 429-41)(200)). Suicide vectors having flanking sequences derived from the S. typhimurium parent χ3761 for generation of all defined mutations listed in Table 3 have been used. These mutations can be introduced using either phage P22HTint transduction (201, 202) (182, 183) of suicide vectors integrated into the deletion mutation in the parental S. typhimurium strain followed by selection for sucrose resistance or by conjugational transfer of suicide vectors using standard methods (201, 202) (195, 203) (176, 185) with the suicide vector donor strains χ7213 (181). All strains constructed are given Chi numbers and stored at −80° C. Plasmid constructs will be evaluated by DNA sequencing and the ability to specify synthesis of C. jejuni proteins using gel electrophoresis and western blot analyses.

c. RASV Strain Characterization.

Vaccine strains have been fully characterized at each step in their construction and after introducing plasmids encoding C. jejuni antigens. Initially, the C. jejuni antigens Peb1 and Omp18 will be evaluated to enable comparative analyses of the different RASV vector strains χ12341 and χ12452. Then, we will evaluate different combinations of two strains to establish a rank order in giving the largest decrease in cecal titers of the *C. jejuni* challenge strains. Prior to commencing immunization studies, RASVs have been compared with vector control strains for stability of plasmid maintenance, integrity, and antigen synthesis ability when grown in the presence of arabinose and DAP for 50 generations. For constitutive synthesis of the *C. jejuni* antigens, strains are grown in the presence of IPTG to determine whether it results in poor growth and/or genetic instability. Molecular genetic attributes have been confirmed by PCR and/or Southern blot analyses. Measurement of LPS core and O-antigen has been performed after electrophoresis using silver-stained gels (204) (186). This analysis is performed after every step in any strain construction to eliminate rough variants should they arise. Motility tests and use of specific antisera for flagellar antigens are used to determine the presence of flagella. Final RASVs have been assessed for bile sensitivity, acid tolerance, and the ability to survive in sera with and without complement inactivation (104,111). Complete sensitivity of the RASVs to antibiotics will also be evaluated. Metabolic attributes of vaccine strains are evaluated using API-20E tests.

d. Animal Experimentation.

Testing of RASV strains: Studies on RASVs will be conducted in SPAFAS white leghorn chicks and in Cobb and/or Ross broiler chicks obtained from a commercial hatchery. Newly hatched white leghorn chicks will be immunized orally after which food and water will be provided ad libitum. Broiler chicks will be similarly orally immunized one day after receipt from the hatchery to enable them to acclimate but before feeding. Food will be provided after immunization. Vaccine strains to be evaluated (as well as *Salmonella* challenge strains) will be grown in LB broth to an OD600 of ~0.9, sedimented by centrifugation at room temperatures and suspended in PBS at densities of $5\times10^{10}$ CFU/ml to enable oral doses of up to $1\times10^{9}$ CFU to be administered in 20 μl into chicks. Final RASVs will be evaluated for induction of immune responses that diminish tissue (bursa, liver and spleen) and cecal titers of *Salmonella* serotype challenge strains and cecal titers of *C. jejuni* challenge strains. RASVs will be quantitatively enumerated in various tissues as a function of time after oral inoculation.

The NIH RAC and the UF IBC reclassified the RASV strains with the regulated lysis phenotype and complete biological containment for use at level 1 containment, in commercial settings and in outpatients, with initial immunizations in chicks housed in batteries or on litter. However, for challenge with *Salmonella* serotypes, birds are housed in Federal Design Molded Isolators. All experimental work is conducted in compliance with the regulations and policies of the Animal Welfare Act and the Public Health Service Policy on Humane Care and Use of Laboratory Animals and approved by the UF IACUC.

e. Statistical Analysis.

All results are analyzed using the most appropriate statistical test from the SAS program to evaluate the relative significance or lack thereof of results obtained. In specific cases, the staff at the Clinical Translational Science Institute at UF is consulted to provide help with experimental design and statistical analyses services for animal and human studies and trials. Using ten chickens/treatment group will yield a statistical power >0.80. In previous studies it was found that n=10 is an adequate number of birds to obtain statistically significant differences between treatment groups. However, the best RASVs will be evaluated multiple times at two institutions to substantiate conclusions.

Example 2. Construction of RASV Strains

The starting strain for the development of derivative strains was S. *Typhimurium* χ12341 (Δ$P_{murA25}$::TT araC $P_{BAD}$ murA ΔasdA27::TT araC $P_{BAD}$ c2 Δpmi-2426 ΔwaaL46 ΔpagL64::TT rhaRS $P_{araBAD}$ waaL Δ(wza-wcaM)-8 ΔrelA197::araC $P_{BAD}$ lacI TT ΔrecF126 ΔsifA2). This strain was derived in many steps from the *S. typhimurium* UK-1 parent strain χ3761. Since live vaccines cannot display antibiotic resistance, defined unmarked deletion mutations were generated using suicide vector technologies (see Edwards et al. (1998) *Gene* 207: 149-57(195); Kaniga et al. (1998) *Infect. Immun.* 66: 5599-606(196); Maloy and Nunn (1981) *J. Bacteriol.* 145: 1110-2(197); Miller and Mekalanos (1988) *J Bacteriol.* 170: 2575-83(198); Ried and Collmer (1987) *Gene* 57: 239-46(199); and Roland et al. (1999) *Avian Dis.* 43: 429-41)(200). Precise deletion and deletion-insertion mutations without interference on adjacent gene functions and without leaving repetitive scars that can contribute to genetic instability can be generated using a combination of molecular genetics, suicide vectors and phage P22-mediated transduction (Kang et al. (2002) *J. Bacteriol.* 184: 307-12)(205). These procedures were used to introduce the deletion and deletion-insertion mutations listed in Table 3 to construct the strains listed in Table 2 as well as the derivatives described herein into *S. typhimurium* χ12341. Suicide vectors derived from either pRE112 or pMEG-375 have been and are constructed, as necessary. To prevent an adverse effect by an inserted sequence on the expression of any adjacent genes, strong transcription terminator (TT) isolated from a bacteriophage genome can be inserted in appropriate locations to block such undesirable effects. These sequences can be inserted into the suicide vectors as appropriate for the individual constructions. Upon construction of suicide vectors and creating deletion and deletion-insertion mutations, allele numbers and Chi numbers are assigned to enable distinction. Strains are stored at −80° C.

Construction of RASV Displaying the Conserved *C. jejuni* N-Glycan.

In this case, the 14 gene *C. jejuni* pgl operon encoding for synthesis of the highly conserved, cross-protective N-glycan (15, 206) also possessing adjuvant properties that is ligated to and transported by the universal UndPP carrier with attachment to the LPS core will be inserted into a deletion of the cysG gene which is dispensable and a very useful site for insertion of foreign genes. Expression of the pgl operon will be driven by fusion to a LacI-regulatable $P_{trc}$ modified by inclusion of a 35 bp sequence found in promoters of operons encoding many genes involved in polysaccharide synthesis (207, 208), which enables synthesis of long mRNA transcripts. This insertion into ΔcysG will be introduced into the χ12341 derivative χ12445 (Table 2) in which the ΔwaaL46 ΔpagL64::TT rhaRS $P_{rhaBAD}$ waaL mutations have been eliminated since the activity of WaaL is needed to cause ligation and transport of the C. jejuni N-glycan (209, 210). Since regulated cessation of the LPS O-antigen in vivo is desired to better display protective surface antigens, a deletion of the wbaP gene that encodes the enzyme that couples the first sugar galactose of the 0-antigen repeat onto the LPS core and an araC $P_{araBAD}$ wbaP into the pagL gene are present in χ12445. Thus, the waaL gene is expressed continuously and the WaaL enzyme will be able to ligate the C. jejuni N-glycan onto the LPS core, the synthesized Cj1433c protein and any C. jejuni or RASV surface proteins such as OmpC and OmpD with the D/E-$X_1$—N—$X_2$-T/S sequences that serve as the receptor sequence for N-glycosylation.

This χ12445 strain is further modified by insertion of all or part of the cj1433c gene (209) into a deletion of the ompA gene to generate a fusion of the Cj1433c protein, which has nine repeats of a DLNNT sequence for N-glycan binding, with the ompA-encoded signal sequence. It should be noted that the OmpA protein is one of the most abundant Salmonella surface antigens, is totally unnecessary for colonization and virulence and yet is one of the most immunogenic Salmonella proteins but unable to afford any protective immunity.

Example 3: RASV Displaying C. jejuni N-Glycan

One RASV currently being constructed will display the conserved C. jejuni-specific N-glycan antigen and synthesize a C. jejuni outer membrane protein with multiple targets for N-glycosylation. This will be achieved by expression of the 14-gene pgl operon from C. jejuni that encodes the enzymes to synthesize the immuno-protective N-linked glycan attached to many C. jejuni surface proteins on a balanced-lethal plasmid or after insertion into the chromosome and inserting sequences encoding the canonical bacterial N-glycosylation sequence D/E-X—N—Y-T/S in genes encoding RASV surface antigens. This RASV can be further modified to cause in vivo display of conserved cross-reactive antigens for iron and manganese uptake to yield a RASV that will induce cross protective immunity to most Salmonella serotypes while also delivering multiple C. jejuni protein antigens to induce superior protective immunity against C. jejuni.

Construction of RASV Encoding the C. jejuni Pgl Operon.

Figure 5:
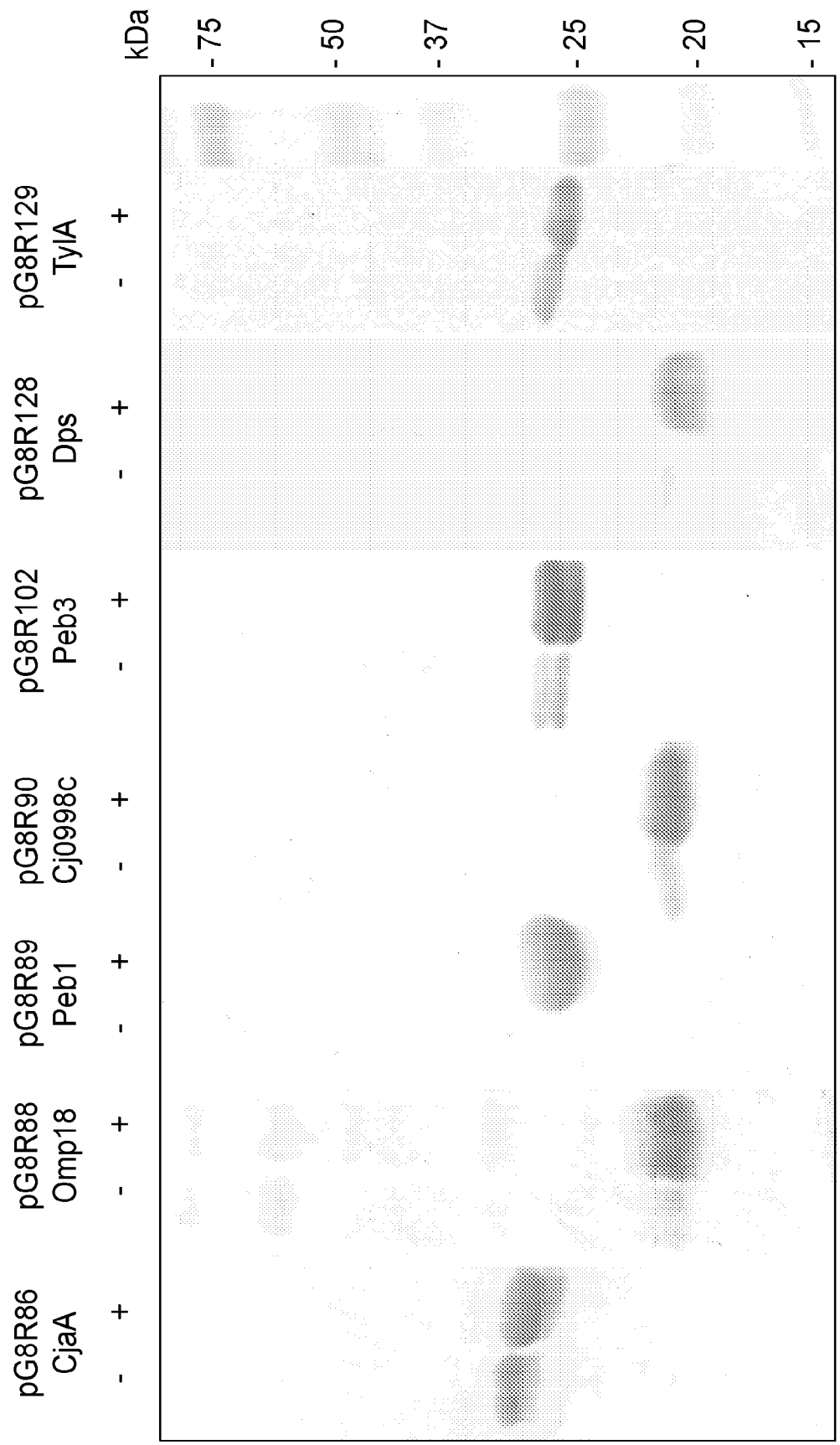
Figure 7:
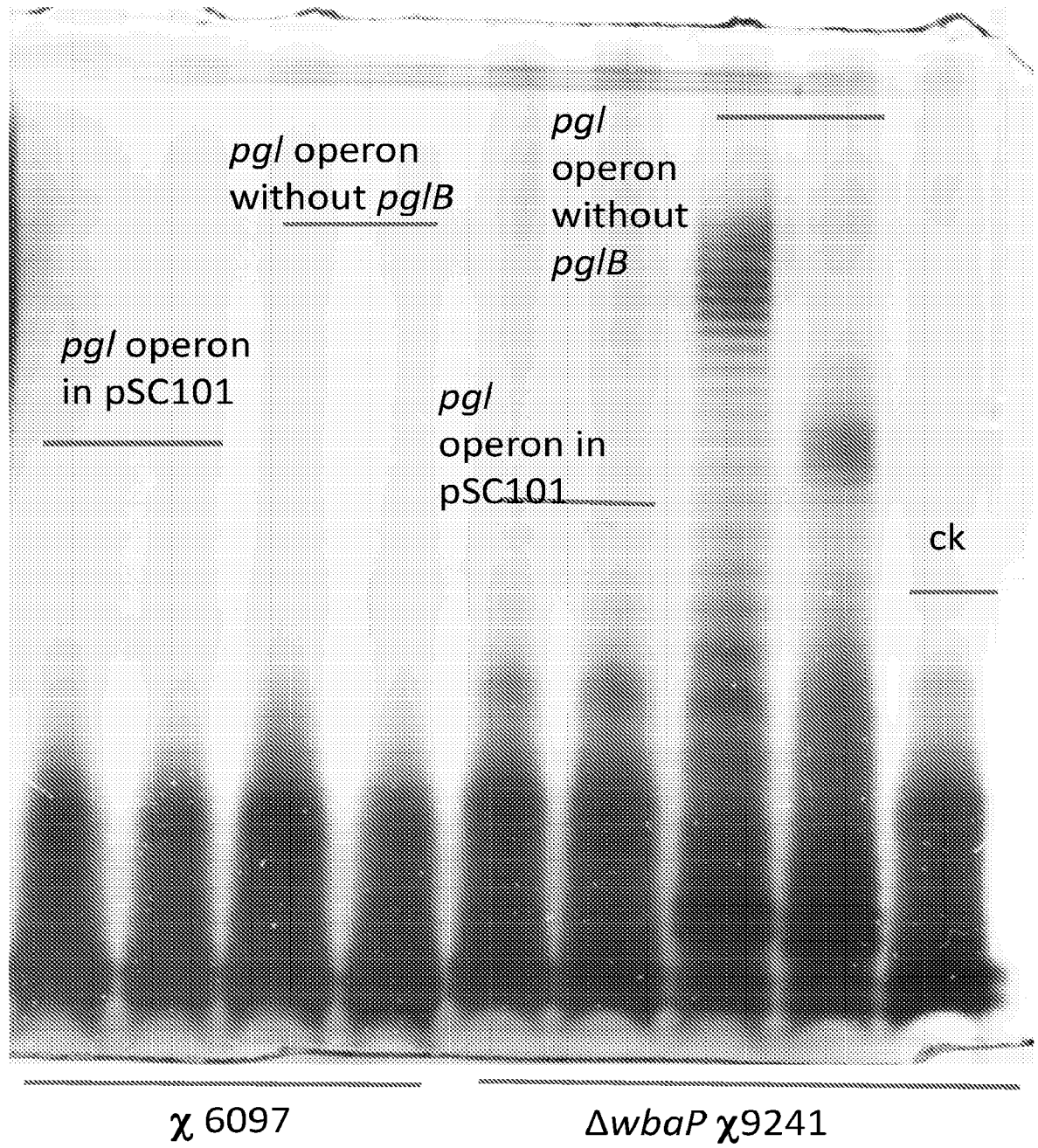

C. jejuni possesses a 14-gene pgl operon encoding enzymes for the synthesis and placement of a highly conserved, cross-protective N-glycan (15, 206). FIG. 7 depicts the pgl operon. The N-glycan possesses adjuvant properties when ligated to and transported by the universal UndPP carrier for attachment to the LPS core. Due to the length of the pgl operon nucleotide sequence, no attempt has yet been made to optimize codons for expression in Salmonella since this would require codon-optimization and synthesis of segments that would then need to be reassembled into a full-length operon. Although this is possible, the native C. jejuni sequence has been initially cloned and inserted into a modified derivative (pG8R160) of the low copy number Asd$^+$ plasmid pYA3337 (pSC101 ori) that possesses the LacI repressible $P_{trc}$ promotor modified by insertion of a 35 bp insertion that enhances complete transcription of long operons (206, 207). Since the pglB gene encodes an oligo polysaccharide transferase, it has a duplicate competing activity to the Salmonella WaaL enzyme and deletion of the pglB gene enabled better addition of the N-glycan to the LPS core (see FIG. 5) to enable its transfer to D/E-X—N—Y-T/S sequences in proteins. The pglB gene in the pG8R160-derived construct pG8R161 was therefore deleted. The inserted pgl operon sequence, which follows, has a ~30% GC content and still contains codons infrequently used in highly-expressed Salmonella genes. However, this may be beneficial for the well-being of the RASV derivative of χ12445 (Δ$P_{murA25}$::TT araC $P_{araBAD}$ murA ΔasdA27::TT araC $P_{araBAD}$ c2 Δpmi-2426 Δ(wza-wcaM)-8 ΔrelA197:: araC $P_{araBAD}$ lacI TT ΔrecF126 ΔsifA26 ΔwbaP45 ΔpagL14::TT araC $P_{araBAD}$ wbaP) since over expression of genes even on a low copy number plasmid can result in decreased growth. Thus lower levels of gene expression are likely beneficial.

Construction of RASV Displaying the Conserved C. jejuni N-Glycan.

The pgl operon has been inserted into the low copy number pYA3337 (pSC101 ori) Asd$^+$ plasmid pG8R161 (see above) and will be inserted into a deletion of the cysG gene, which is dispensable, and a very useful site for insertion of foreign genes. Expression of the pgl operon is driven by fusion to a LacI-regulatable $P_{trc}$ promoter modified by inclusion of a 35 bp sequence found in promoters of operons encoding many genes involved in polysaccharide synthesis (207, 208). This enables synthesis of long mRNA transcripts. The insertion into ΔcysG will be introduced into χ12445 (Table 2) in which the ΔwaaL46 ΔpagL64::TT rhaRS $P_{araBAD}$ waaL mutations have been eliminated since the activity of WaaL is needed to cause ligation and transport of the C. jejuni N-glycan (209, 210). Since regulated cessation of LPS O-antigen synthesis in vivo to better display protective surface antigens, is desired, a deletion of the wbaP gene that encodes the enzyme that couples the first sugar galactose of the 0-antigen repeat onto the LPS core was inserted, and an araC $P_{araBAD}$ wbaP was inserted into the pagL gene. The resulting strain derived in multiple steps from χ12341 is χ12445 (Δ$P_{murA25}$::TT araC$P_{araBAD}$ murA ΔasdA27::TT araC $P_{araBAD}$ c2 Δpmi-2426 Δ(wza-wcaM)-8 ΔrelA197::araC $P_{araBAD}$ lacI TT ΔrecF126 ΔsifA26 ΔwbaP45 ΔpagL14::TT araC $P_{araBAD}$ wbaP). In this strain either with a plasmid or the cysG insertion of the pgl operon, the waaL gene is expressed continuously and the WaaL enzyme will ligate the C. jejuni N-glycan onto the LPS core, the synthesized Cj1433c protein fusion (see below) and any C. jejuni or RASV surface proteins such as OmpC and OmpD with the D/E-$X_1$-N—$X_2$-T/S sequence that serves as the receptor sequence for N-glycosylation. χ12445 is further modified by insertion of the Cj1433c gene (209) into a partial deletion of the ompA gene to generate a fusion of the Cj1433c protein, which has nine repeats of a DLNNT sequence for N-glycan binding, with the ompA-encoded signal sequence. It should be noted that the OmpA protein is one of the most abundant Salmonella surface antigens, is totally unnecessary for colonization and virulence and yet is one of the most immunogenic Salmonella proteins but unable to afford any protective immunity. If desired, the Δ$P_{fur}$::TT araC $P_{BAD}$ fur and Δ$P_{mntR}$::TT araC $P_{BAD}$ mntR deletion-insertion mutations can be added to χ12445 to lead to the up-regulation in vivo of all genes needed for iron and manganese uptake. Since immune responses to IROMPs are cross reactive in the Enterobacteriaceae, this strain, as LPS O-antigen synthesis ceases in vivo (due to the pmi mutation and absence of mannose and the araC $P_{araBAD}$ regulated shutoff of the wbaP gene) to better expose surface protein antigens, will induce enhanced cross-protective immunity to *Salmonella* serotypes and other enteric bacteria.

Construction of Cj1433c-OmpA Fusion and Insertion into the ΔompA11 Mutation in χ12445.

The genome of *C. jejuni* is AT rich, which causes problems in transcription fidelity in *S. typhimurium*. The Cj1433c gene is particularly 'bad' in that it has a GC content of only 26.4%. Two successive codon optimizations to improve faithful expression of this gene or parts of it in RASV strains were performed. The original and improved nucleotide sequences for Cj14433c gene are given below with indication of the sequences specifying N-glycosylation sites in the protein.

Cj1433c 1107 bp (368 aa) No signal peptide, GC of 26.4% Identity among various *C. jejuni*; low (31%-100%) many sequences aligned only with partial sequence 1$^{st}$ line; original (26.4%)
2$^{nd}$ line; best optimized (45.9%)
3$^{rd}$ lime; modified for higher GC (49.1%) serine, valine, glycine (S, V and G) modified
The N-glycan addition sites are underlined

```
                    TATAATATTTTTGGCAGTTTGTTTTAA AGGATGTTTTA

1/1                                           31/11
ATG CAG CGA TTT AAA AAA TGG TTT TTG TCT ATC ATA AAA AAT TTC AAG CAA CAT GAA AAA

ATG CAG CGT TTC AAA AAA TGG TTC CTG TCT ATC ATC AAA AAC TTC AAA CAG CAC GAA AAA

ATG CAG CGT TTC AAA AAA TGG TTC CTG TCC ATC ATC AAA AAC TTC AAG CAG CAC GAA AAA

M   Q   R   F   K   K   W   F   L   S   I   I   K   N   F   K   Q   H   E   K

61/21                                         91/31
ATT AAG ATA GAT CTT AAT AAT ACA AAG ATA GAT CTT AAT AAT ACA AAG ATA GAT CTT AAT

ATC AAA ATC GAC CTG AAC AAC ACC AAC ATC GAC CTG AAC AAC ACC AAG ATC GAC CTG AAC

ATC AAA ATC GAC CTG AAC AAC ACC AAG ATC GAC CTG AAC AAC ACC AAG ATC GAC CTG AAC

I   K   I   D   L   N   N   T   K   I   D   L   N   N   T   K   I   D   L   N

121/41                                        151/51
AAT ACA AAG ATA GAT CTT AAT AAT ACA AAG ATA GAT CTT AAT AAT ACA AAG ATA GAT CTT

AAC ACC AAA ATC GAC CTG AAC AAC ACC AAG ATC GAC CTG AAC AAC ACC AAG ATC GAC CTG

AAC ACC AAA ATC GAC CTG AAC AAC ACC AAG ATC GAC CTG AAC AAC ACC AAG ATC GAC CTG

N   T   K   I   D   L   N   N   T   K   I   D   L   N   N   T   K   I   D   L

181/61                                        211/71
AAT AAT ACA AAG ATA GAT CTT AAT AAT ACA AAG ATA GAT CTT AAT AAT ACA AAG ATA GAT

AAC AAC ACC AAA ATC GAC CTG AAC AAC ACC AAA ATC GAC CTG AAC AAC ACC AAG ATC GAC

AAC AAC ACC AAA ATC GAC CTG AAC AAC ACC AAA ATC GAC CTG AAC AAC ACC AAG ATG GAC

N   N   T   K   I   D   L   N   N   T   K   I   D   L   N   N   T   K   I   D

241/81                                        271/91
CTT AAT AAT ACA AAG ATA GAA TTA TCG CAA TTA AAA AAA GAG CAC TAT AAA GTA TTA GAT

CTG AAC AAC ACC AAA ATC GAA CTC TCT CAG CTG AAA AAA GAG CAC TAC AAA GTT CTG GAC

CTG AAC AAC ACC AAA ATC GAA CTG TCC CAG CTG AAA AAA GAG CAC TAC AAA GTG CTG GAC

L   N   N   T   K   I   E   L   S   Q   L   K   K   E   H   Y   K   V   L   D

301/101                                       331/111
TTT CAT TTA AGA AAA ATT ACA CCT CAA GCT TTT TTA GAG ATT GTT GAA ATT CAT TTA GCC

TTC CAC CTC CGT AAA ATC ACC CCG CAG GCG TTC CTG GAG ATC GTT GAA ATC CAC CTG GCG

TTC CAC CTG CGT AAA ATC ACC CCG CAG GCG TTC CTG GAG ATC GTG GAA ATC CAC CTG GCG

F   H   L   R   K   I   T   P   Q   A   F   L   E   I   V   E   I   H   L   A

361/121                                       391/131
GAA TCA TGT AAT TTA AAT TGT TTT GGT TGT AAT CAT TTT TCA CAA ATA GCT GAA AAA GAA

GAA TCT TGC AAC CTG AAC TGC TTC GGT TGC AAC CAC TTC TCT CAG ATC GCG GAA AAA GAA

GAA TCC TGC AAC CTG AAC TGC TTC GGC TGC AAC CAC TTG TCC CAG ATC GCG GAA AAA GAA

E   S   C   N   L   N   C   F   G   C   N   H   F   S   Q   I   A   E   K   E
```

```
421/141                              451/151
TTT CCA GAT ATA GAA ATT TTT AAA AAA GAT ATG CAA AGA CTT TCA GAA ATA TCT AAA GGT

TTC CCG GAC ATC GAA ATC TTC AAA AAA GAC ATG CAG CGT CTG TCT GAA ATC TCT AAA GGT

TTC CCG GAC ATC GAA ATC TTC AAA AAA GAC ATG CAG CGT CTG TCC GAA ATC TCT AAA GGC

F   P   D   I   E   I   F   K   K   D   M   Q   R   L   S   E   I   S   K   G

481/161                              511/171
ATT GTC GGA ACT TTT AGA TTG ATG GGT GGC GAA CCT CTT TTA AAT CCC AAT TGT ATA CAG

ATC GTT GGT ACC TTC CGT CTG ATG GGT GGT GAA CCG CTG CTG AAC CCG AAC TGC ATC CAG

ATC GTG GGC ACC TTC CGT CTG ATG GGC GGC GAA CCG CTG CTG AAC CCG AAC TGC ACC CAG

I   V   G   T   F   R   L   M   G   G   E   P   L   L   N   P   N   C   I   Q

541/181                              571/191
TTT TTT GAC ATT ACA AGA TAT TTT TTT CCA AAA AGT GCC ATT TGG TTG GTA ACT AAT GGT

TTC TTC GAC ATC ACC CGT TAC TTC TTC CCS AAA TCT GCG ATC TGG CTG GTT ACC AAC GGT

TTC TTC GAC ATC ACC CGT TAC TTC TTC CCS AAA TCC GCG ATC TGG CTG GTG ACC AAC GGC

F   F   D   I   T   R   Y   F   F   P   K   S   A   I   W   L   V   T   N   G

601/201                              631/211
ATT TTA CTT GAT AAG CAA AAT GAG GAT TTT TGG AAT TCA TGC CAA AGG AAT AAA ATG CAA

ATC CTG CTS GAC AAA CAG AAC GAS GAC TTC TGG AAC TCT TGC CAS CGT AAC AAA ATG CAG

ATC CTG CTS GAC AAA CAG AAC GAS GAC TTC TGG AAC TCC TGC CAS CGT AAC AAA ATG CAG

I   L   L   D   K   Q   N   E   D   F   W   N   S   C   Q   R   N   K   M   Q

661/221                              691/231
ATT CGT CCA ACA AAG TAT CCT ATA AAA ATT AAT TGG GAT TTG ATT AAA GAT AAG TGT GAT

ATC CGT CCG ACC AAS TAC CCG ATC AAA ATS AAC TGG GAC CTG ATC AAA GAC AAC TGC GAC

ATC CGT CCC ACC AAS TAC CCS ATC AAA ATC AAC TGG GAC CTG ATC AAA GAC AAS TGC GAC

I   R   P   T   K   Y   P   I   K   I   N   W   D   L   I   K   D   K   C   D

721/241                              751/251
CAA TAT GAT ATC CCC TTG ATA TTT TTT AAC AAT GGA GAG TTG GAA AAA ACT TCT TGG AAA

CAG TAC GAC ATC CCG CTG ATC TTC TTC AAC AAC GGT GAS CTG GAA AAA ACC TCT TGG AAA

CAG TAC GAC ATC CCG CTG ATC TTC TTC AAC AAC GGC GAS CTG GAA AAA ACC TCC TGG AAA

Q   Y   D   I   P   L   I   F   F   N   N   G   E   L   E   K   T   S   W   K

781/261                              811/271
TTT TCT CTA GAT CCT TCT GGA AAT TGT GAT AAT TAC CAT AGT TTT ACA AAT TGT AGT ATG

TTC TCT CTG GAC CCG TCT GGT AAC TGC GAC AAC TAC CAC TCT TTC ACC AAC TGC TCT ATG

TTC TCC CTS GAC CCS TCC GGC AAC TGC GAC AAC TAC CAC TCC TTC ACC AAC TGC TCC ATG

F   S   L   D   P   S   G   N   C   D   N   Y   H   S   F   T   N   C   S   M

841/281                              871/291
GCA AAT CAC TGT GTT CAG TTT AAA GAT GGA AAG CTA TTT ACT TGT ACC TTT CCT GCA CAT

GCG AAC CAC TGC GTT CAG TTC AAA GAC GGT AAS CTS TTC ACS TGC ACC TTG CCS GCG CAC

GCG AAC CAC TGC GTG CAG TTC AAA GAC GGC AAS CTS TTC ACC TGC ACC TTC CCS GCC CAC

A   N   H   C   V   Q   F   K   D   G   K   L   F   T   C   T   F   P   A   H

901/301                              931/311
GTA CAG CAT TTT AAT AAA AAG TAT GGA AAT CAT TTT GAA GTT TGC GAA TTT GAC TTT ATT

GTT CAG CAC TTC AAC AAA AAA TAG GGT AAC CAC TTC GAA GTT TGC GAA TTC GAC TTC ATC

GTG CAG CAC TTC AAC AAA AAA TAC GGC AAG CAC TTG GAA GTG TGC GAA TTC GAC TTC ATC

V   Q   H   F   N   K   K   Y   G   N   H   F   E   V   C   E   F   D   F   I
```

```
961/321                        991/331
GAT ATT TAT AAA GCC AAG GAT TAT CAA GAA ATT TTA TTT TTT CTT TCT AAG CCT ATT CCT

GAC ATC TAC AAA GCG AAA GAC TAC CAG GAA ATC CTG TTC TTC CTG TCT AAC CCS ATC CCS

GAC ATC TAC AAA GCG AAA GAC TAC CAG GAA ATC CTG TTC TTC CTG TCC AAS CCG ATC CCG

D   I   Y   K   A   K   D   Y   Q   E   I   L   F   F   L   S   K   P   I   P

1021/341                             1051/351
TTT TGT AGA TAT GCA AGG TA TCA CAA TGG GCA GAA ATT GGA AAA TGG CGT TCT AGC AAT

TTC TGC CGA TAC TGC AAA GTT TCT CAG TGG GCG GAA ATC GGT AAA TGG CGT TCT TCT AAC

TTC TGC CGA TAC TGC AAA GTG TCC CAG TGG GCG GAA ATC GGC AAA TGG CGT TCC TCC AAC

F   C   R   Y   C   K   V   S   Q   W   A   E   I   G   K   W   R   S   S   N

1081/361
AAA ACA AAA CAT GAA TAT TTA ATT TGA (SEQ ID NO: 71 )

AAA ACC AAA CAC GAA TAC CTC ATC TGA (SEQ ID NO: 72 )

AAA ACC AAA CAC GAA TAC CTC ATC TGA (SEQ ID NO: 73 )

K   T   K   H   E   Y   L   I   *     (SEQ ID NO: 74 )
```

The topology of the OmpA protein indicating all 16 transmembrane sequences was diagramed by Reusch et al., Int. J. Mol. Sci. 2013, 14(6): 10727-10748 (213)(214, 215), the entire contents of which are expressly incorporated herein by reference. Based on bioinformatic analyses, a portion of the *C. jejuni* Cj1433c gene encoding the repeats of the N-glycosylation sites (amino acids 21 to 86) was inserted as a substitute for the loop spanning and including the 3 and 4 transmembrane sequences (amino acids 70 to 107) of OmpA.

Encoding Sequence for Modified OmpA with Insertion of Portion of Cj1433c Sequence Beta loops 3 and 4 of OmpA (aa 70-107) are deleted and 66 aa (aa21 to 86) of Cj1433c are inserted that specify the nine repeats for N-glycosylation.

```
1/1                                  31/11
ATG AAA AAG ACA GCT ATC GCG ATT GCA GTG GCA CTG GCT GGT TTC GCT ACC GTA GCG CAG

M   K   K   T   A   I   A   I   A   V   A   L   A   G   F   A   T   V   A   Q

61/21                                91/31
GCC GCT CCG AAA GAT AAC ACC TGG TAC GCT GGT GCT AAA CTG GGC TGG TCT CAG TAC CAT

A   A   P   K   D   N   T   W   Y   A   G   A   K   L   G   W   S   Q   Y   H

121/41                               151/51
GAC ACC GGC TTC ATT CAC AAT GAT GGC CCG ACT CAT GAA AAC CAA CTG GGC GCA GGT GCT

D   T   G   F   I   H   N   D   G   P   T   H   E   N   Q   L   G   A   G   A

181/61                               211/71
TTT GGT GGT TAC CAG GTT AAC CCG TAT gtc gac ATC AAA ATC GAC CTG AAC AAC ACC AAA F   G   G   Y   Q   V   N   P   Y   V   D   I   K   I   D   L   N   N   T   K
                                 OmpA aa69        Cj1433 aa21-86
241/81                               271/91
ATC GAC CTG AAC AAC ACC AAA ATC GAC CTG AAC AAC ACC AAA ATC GAC CTG AAC AAC ACC

I   D   L   N   N   T   K   I   D   L   N   N   T   K   I   D   L   N   N   T

301/101                              331/111
AAA ATC GAC CTG AAC AAC ACC AAA ATC GAC CTG AAC AAC ACC AAA ATC GAC CTG AAC AAC

K   I   D   L   N   N   T   K   I   D   L   N   N   T   K   I   D   L   N   N

361/121                              391/131
ACC AAA ATC GAC CTG AAC AAC ACC AAA ATC GAC CTG AAC AAC ACC AAA ATC ctg cag ATC T   K   I   D   L   N   N   T   K   I   D   L   N   N   T   K   I   L   Q   I
                                                                     OmpA aa108
421/141                              451/151
ACT GAC GAT CTG GAC GTT TAT ACC CGT CTG GGT GGT ATG GTA TGG CGT GCA GAC ACC AAG T   D   D   L   D   V   Y   T   R   L   G   G   M   V   W   R   A   D   T   K
```

```
481/161                           511/171
TCT AAC GTC CCT GGC GGC CCG TCT ACT AAA GAC CAC GAC ACC GGC GTT TCC CCG GTA TTC

541/181                          571/191
  S   N   V   P   G   G   P   S   T   K   D   H   D   T   G   V   S   P   V   F
GCG GGC GGT ATC GAG TAT GCT ATC ACC CCT GAA ATC GCA ACC CGT CTG GAA TAC CAG

TGG

A   G   G   I   E   Y   A   I   T   P   E   I   A   T   R   L   E   Y   Q   W

601/201                          631/211
ACT AAC AAC ATC GGT GAT GCC AAC ACC ATC GGC ACC CGT CCG GAC AAC GGC CTG CTG AGC

T   N   N   I   G   D   A   N   T   I   G   T   R   P   D   N   G   L   L   S

661/221                          691/231
GTA GGT GTT TCC TAC CGT TTC GGC CAG CAA GAA GCT GCT CCG GTA GTA GCT CCG GCA CCA

V   G   V   S   Y   R   F   G   Q   Q   E   A   A   P   V   V   A   P   A   P

721/241                          751/251
GCT CCG GCT CCG GAA GTA CAG ACC AAG CAC TTC ACT CTG AAG TCT GAC GTA CTG TTC AAC

A   P   A   P   E   V   Q   T   K   H   F   T   L   K   S   D   V   L   F   N

781/261                          811/271
TTC AAC AAA TCT ACC CTG AAG CCG GAA GGC CAG CAG GCT CTG GAT CAG CTG TAC AGC CAG

F   N   K   S   T   L   K   P   E   G   Q   Q   A   L   D   Q   L   Y   S   Q

841/281                          871/291
CTG AGC AAC CTG GAT CCG AAA GAC GGT TCC GTT GTC GTT CTG GGC TTC ACT GAC CGT ATC

L   S   N   L   D   P   K   D   G   S   V   V   V   L   G   F   T   D   R   I

901/301                          931/311
GGT TCT GAC GCT TAC AAC CAG GGT CTG TCC GAG AAA CGT GCT CAG TCT GTT GTT GAT TAC

G   S   D   A   Y   N   Q   G   L   S   E   K   R   A   Q   S   V   V   D   Y

961/321                          991/331
CTG ATC TCC AAA GGT ATT CCG TCT GAC AAA ATC TCC GCA CGT GGT ATG GGC GAA TCT AAC

L   I   S   K   G   I   P   S   D   K   I   S   A   R   G   M   G   E   S   N

1021/341                         1051/351
CCG GTT ACC GGC AAC ACC TGT GAC AAC GTG AAA CCT CGC GCT GCC CTG ATC GAT GCC CTG

P   V   T   G   N   T   C   D   N   V   K   P   R   A   A   L   I   D   C   L

1081/361                         1111/371
GCT CCG GAT CGT CGC GTA GAG ATC GAA GTT AAA GGC GTT AAA GAC GTG GTA ACT CAG CCG

A   P   D   R   R   V   E   I   E   V   K   G   V   K   D   V   V   T   Q   P

1141/381
CAG GCT TAA (SEQ ID NO: 75 )

Q   A   *   (SEQ ID NO: 76 )

OmpA Δ70-107::Cj1433 aa21-86
                                                              (SEQ ID NO: 77)
ATGAAAAAGACAGCTATCGCGATTGCAGTGGCACTGGCTGGTTTCGCTACCGTAGCGCAGGCCGCTCCGAAAGAT

AACACCTGGTACGCTGGTGCTAAACTGGGCTGGTCTCAGTACCATGACACCGGCTTCATTCACAATGATGGCCCG

ACTCATGAAAACCAACTGGGCGCAGGTGCTTTTGGTGGTTACCAGGTTAACCCGTATGTCGACATCAAAATCGAC

CTGAACAACACCAAAATCGACCTGAACAACACCAAAATCGACCTGAACAACACCAAAATCGACCTGAACAACACC

AAAATCGACCTGAACAACACCAAAATCGACCTGAACAACACCAAAATCGACCTGAACAACACCAAAATCGACCTG

AACAACACCAAAATCGACCTGAACAACACCAAAATCCTGCAGATCACTGACGATCTGGACGTTTATACCCGTCTG

GGTGGTATGGTATGGCGTGCAGACACCAAGTCTAACGTCCCTGGCGGCCCGTCTACTAAAGACCACGACACCGGC

GTTTCCCCGGTATTCGCGGGCGGTATCGAGTATGCTATCACCCCTGAAATCGCAACCCGTCTGGAATACCAGTGG

ACTAACAACATCGGTGATGCCAACACCATCGGCACCCGTCCGGACAACGGCCTGCTGAGCGTAGGTGTTTCCTAC
```

```
-continued
CGTTTCGGCCAGCAAGAAGCTGCTCCGGTAGTAGCTCCGGCACCAGCTCCGGCTCCGGAAGTACAGACCAAGCAC

TTCACTCTGAAGTCTGACGTACTGTTCAACTTCAACAAATCTACCCTGAAGCCGGAAGGCCAGCAGGCTCTGGAT

CAGCTGTACAGCCAGCTGAGCAACCTGGATCCGAAAGACGGTTCCGTTGTCGTTCTGGGCTTCACTGACCGTATC

GGTTCTGACGCTTACAACCAGGGTCTGTCCGAGAAACGTGCTCAGTCTGTTGTTGATTACCTGATCTCCAAAGGT

ATTCCGTCTGACAAAATCTCCGCACGTGGTATGGGCGAATCTAACCCGGTTACCGGCAACACCTGTGACAACGTG

AAACCTCGCGCTGCCCTGATCGATTGCCTGGCTCCGGATCGTCGCGTAGAGATCGAAGTTAAAGGCGTTAAAGAC

GTGGTAACTCAGCCGCAGGCTTAA
```

FIGS. 8A-8B depict the structural aspects of the modified S. Typhimurium OmpA protein with the insertion of the Cj1433c gene encoded sequences specifying the nine repeats to which the *C. jejuni* conserved N-glycan is attached as a consequence of the *C. jejuni* pgl operon and the activity of the *Salmonella* WaaL enzyme. The resulting construct is currently being introduced into a suicide vector that will be used to introduce the sequence encoding this Cj14433c-OmpA fusion into the χ12445 chromosome in place of the wild-type ompA gene. This strain will then be further modified to deliver a lysis plasmid encoding the *C. jeuni* antigens found in earlier studies to be maximally effective in reducing cecal titers of *C. jejuni* challenge strains. Experiments as described above by immunization of white leghorn and broiler chicks will be repeated.

Production of IROMPS and MnOMPs to Enhance Protective Immunity Against *Salmonella* Serotypes and Other Enteric Bacteria.

The $\Delta P_{fur}$::TT araC $P_{BAD}$ fur mutation was inserted into χ12341 to yield χ12396 (Table 2) and the $\Delta P_{mntR}$::TT araC $P_{BAD}$ mntR deletion-insertion mutation (Table 3) will also be inserted to lead to the up-regulation in vivo of all genes needed for iron and manganese uptake. Since immune responses to IROMPs are cross reactive in the Enterobacteriaceae, this strain, as LPS O-antigen synthesis ceases in vivo (due to the pmi mutation and absence of mannose and the araC $P_{araBAD}$ regulated shutoff of the waaL gene) to better expose surface protein antigens, will induce enhanced cross-protective immunity to *Salmonella* serotypes and other enterics.

Example 4: Evaluation of RASV-Cj Strains in White Leghorn Chickens

Evaluation of Ability to Induce Cross Protective Immunity to *Salmonella* Serotypes, to Prevent Organ Colonization, and to Reduce Cecal Titers.

RASV-Cj will be evaluated delivering CjaA specified by the pG8R17 T2SS vector pG8R86 (FIG. 8) comparing χ12341 with the derivative of χ12396 described in Example 2. The protocol described by Hassan and Curtiss (113) will be followed. The CjaA antigen is selected for these comparative studies since in an unpublished study with one of the new RASV strains there was a 3- to 4-log reduction in cecal titers of the *C. jejuni* challenge strain. In addition, CjaA, which has been evaluated in some 23 prior studies, contains a sequence that should permit glycosylation with the *C. jejuni* N-glycan in the RASV-Cj strain. Day-of-hatch white leghorn chicks will be orally immunized and provided a second immunization at 10 days. At six weeks of age, ten immunized chicks and ten unimmunized chicks will each be challenged with 1×10⁶ CFU of each of the eight serotypes of *Salmonella* listed in Table 5 (*Typhimurium, Enteritidis,* Heidelberg, Montevideo, Hadar, *Infantis*, Newport and Kentucky). Four and eleven days after challenge, five birds in each group will be euthanized by $CO_2$ asphyxiation and titers of challenge and vaccine strains in liver, spleen, ovary (if present), bursa of Fabricius and cecum quantitated by direct plating on SS agar and by selenite-cysteine broth enrichment (113). The enrichment broth will detect bacterial titers as low as 5 per gram of tissue or contents. The biological containment features of the RASVs will preclude their detection.

Second Stage Studies.

These studies are repeated with a mixture of the two RASVs each delivering two or three validated protective *C. jejuni* antigens. The same immunization protocol described above will be used. This will serve as an independent repeat of the first experiment and establish the level of repeatability of the initial results. Titers of S. *Typhimurium* and *S. Enteritidis* challenge strains will also be evaluated 10, 20 and 30 days after challenge by immunizing with a combination of the two RASVs each delivering multiple *C. jejuni* protein antigens. Another small study will be directed at determining whether a single immunization is sufficient and determining how soon after primary immunization protective immunity to *Salmonella* serotypes is detectable in challenge studies.

Example 5: Evaluation of RASV-Cj Strains in Broiler Chickens

RASV-Cj strains comprising lysis plasmids encoding each of the *C. jejuni* antigens listed in Table 4 will be evaluated to determine the level of protection against *C. jejuni* colonization and persistence. Initial tests will evaluate whether χ12341 (FIGS. 4A and 4B) or χ12452 (FIG. 5) delivery of the CjaA antigen gives the best results. The best delivery strain will then be used in subsequent evaluations. Protection will be assessed by measuring CFU in cecal contents and the results correlated with antibody responses in both serum and feces. Plasmids encoding *C. jejuni* antigens resulting in the greatest levels of protection will be used to evaluate protection against heterologous challenge using well characterized *C. jejuni* strains, as well as to a cocktail of chicken isolates that are frequently isolated from poultry in the US (listed in Table 5).

Newly hatched day-old broiler chicks will be obtained from hatcheries, and prior to use, chicks will be confirmed negative for *Campylobacter* by culturing cloacal swabs on MH agar plates and by PCR 6 groups of 3-day old broiler chickens (n=10/group) will be immunized with 1×10⁹ CFU/chick orally with different RASV-Cj strains delivering *C. jejuni* antigens (Table 4). Control groups of 10 birds will be inoculated with RASV-Cj with an empty plasmid or be non-vaccinated. Chicks will be re-inoculated with RASVs 10 days after the first inoculation. Two weeks after the boost, chicks will be challenged with *C. jejuni* strain 81-176 orally ($1\times10^5$ CFU/chick in 200 µl of PBS). Our previous work using 81-176 and a chicken *C. jejuni* cocktail indicated that this dose results in 100% colonization (186, 211). One week following challenge, chickens will be killed, cecal contents collected, homogenized in PBS, and plated on MH agar+CSS plates. Plates will be incubated at 42° C. microaerobically for 3 days and CFU/g of cecal contents determined to assess protection against *C. jejuni* challenge comparing titers from the vaccinated groups compared to the non-vaccinated control groups. It is expected that several RASV-Cj constructs will lead to over a 100-fold reduction in cecal *C. jejuni* colonization titers.

Blood, bile and fecal samples will be collected, IgY responses in serum and IgA responses in feces will be measured by indirect ELISA as previously described (212). Briefly, microtiter plates will be coated with purified recombinant *C. jejuni* proteins, washed, blocked with Sea Block blocking buffer (Pierce, Rockford, Ill.). Test samples (serum, bile or feces) will be added, the plates washed and anti-*C. jejuni* antibodies detected with biotinylated goat anti-chicken IgG or IgA antibody (Bethyl Laboratories, Montgomery, Tex.). Plates will be washed and streptavidin-horseradish peroxidase solution (Southern Biotech, Birmingham, Ala.) will be added. Color development will be detected using ABTS (Sigma, St. Louis, Mo.) containing 0.03% $H_2O_2$ in citrate buffer, pH 4.35. After color development, the reaction will be stopped with 1% SDS solution and $OD_{405}$ measured using a microplate reader (Molecular Devices, Sunnyvale, Calif.).

Delivery of multiple *C. jejuni* antigens found to confer reduced challenge titers following immunization are tested. Plasmids encoding the multiple antigens will be constructed and introduced into the RASV-Cj strains. Studies will involve comparing one RASV versus a mixture of the two delivering the same or even different *C. jejuni* antigens. Immunizing with one versus two doses will be compared. If results with a single dose give satisfactory results, lower oral doses will be investigated. Ability of these RASVs to confer protection against *C. jejuni* cecal colonization will be assessed as described above. The protective response will also be correlated with antibody response in sera and feces as above. Control groups of chickens inoculated with a RASV carrying an empty plasmid and challenged and non-vaccinated unchallenged chickens will be used.

RASVs selected from the above studies are tested for whether they confer protection against challenge with heterologous *C. jejuni* strains. RASV-immunized chickens will be challenged with commonly used well-characterized *C. jejuni* strains (NC11168, 81116, RM221 and 81-176). In addition, chickens will be challenged with a cocktail of *C. jejuni* isolates of poultry origin (5 isolates that are frequently isolated from poultry). Chickens (n=10/group) will be vaccinated with selected RASVs ($1\times10^9$ CFU/chicken orally) by the best means as established by the studies described above and challenged with $1\times10^5$ CFU/chick in 200 µl of PBS of *C. jejuni* strains. For the cocktail, equal concentrations of each strain ($1\times10^5$) will be mixed in PBS for challenge. Following challenge, protection against cecal colonization and antibody responses in serum and feces will be assessed as above. Groups of chickens inoculated with RASVs carrying an empty plasmid and challenged with *C. jejuni* as well as a group of non-vaccinated non-challenged chickens will be used as controls.

In regard to safety and utility, multiple mutations in all *S. Typhimurium* strains are included that preclude biofilm formation and inability to colonize gallstones in presence of bile. These same mutations decrease ability for persistence in the intestinal tracts of mice and chickens. *S. Typhi* strains with some of the same mutations in the proposed *S. typhimurium* RASVs were unable to cause bacteremia in humans and were not shed in a viable cultivatable form in stools following oral administration of up to $10^{10}$ CFU (150). *S. typhimurium* strains of the same genotype were safe in newborn (146, 147), pregnant, malnourished and immunocompromised mice. In addition, most of the strains undergo regulated delayed lysis which precludes persistence in vivo and viability if shed in feces (142). Also, infectivity and full virulence of these RASVs requires the presence of the sugars arabinose, mannose and rhamnose and thus inability if shed to infect or immunize animals or humans. New means to evaluate and demonstrate safety and efficacy of RASVs are continually devised, often with productive input from APHIS and FDA. Studies on survival of RASVs in water (with and without chlorination), as a consequence of desiccation, in sewage, in feces, in whole blood, in sera with and without complement inactivation, and in monocyte-derived macrophages have been performed. Such testing of *S. typhimurium* RASVs and in chicken feces, body fluids and cells will ultimately be done.

While *Salmonella* is a category 2 pathogen with research conducted using BSL2 laboratory facilities and procedures and animal studies in ABSL2 facilities, the NIH RAC has reviewed the safety properties of our RASVs and is permitting conduct of all studies with immunization to be done under level 1 containment, in commercial agricultural settings and in outpatient human volunteers. This approval was contingent upon concurrence by the Institutional Biosafety Committee and the UF IBC has given such approval. However, challenge of immunized animals must still be conducted under the level of containment needed for that particular pathogen.

REFERENCES

1. Altekruse S F, Stern N J, Fields P I, Swerdlow D L. 1999. *Campylobacter jejuni*—an emerging foodborne pathogen. Emerg Infect Dis 5:28-35.
2. DuPont H L. 2007. The growing threat of foodborne bacterial enteropathogens of animal origin. Clin Infect Dis 45:1353-1361.
3. Lee M D, Newell D G. 2006. *Campylobacter* in poultry: filling an ecological niche. Avian Dis 50:1-9.
4. Gantois I, Ducatelle R, Pasmans F, Haesebrouck F, Gast R, Humphrey T J, Van Immerseel F. 2009. Mechanisms of egg contamination by *Salmonella Enteritidis*. FEMS Microbiol Rev 33:718-738.
5. Braden C R. 2006. *Salmonella enterica* serotype *Enteritidis* and eggs: a national epidemic in the United States. Clin Infect Dis 43:512-517.
6. Bhaysar A P, Zhao X, Brown E D. 2001. Development and characterization of a xylose-dependent system for expression of cloned genes in *Bacillus subtilis*: conditional complementation of a teichoic acid mutant. Appl Environ Microbiol 67:403-410.
7. Walder R Y, Walder J A. 1986. Oligodeoxynucleotide-directed mutagenesis using the yeast transformation system. Gene 42:133-139.
8. Bauer C E, Hesse S D, Waechter-Brulla D A, Lynn S P, Gumport R I, Gardner J F. 1985. A genetic enrichment for mutations constructed by oligodeoxynucleotide-directed mutagenesis. Gene 37:73-81.
9. Craik C S. 1985. Use Of Oligonucleotides For Site-specific Mutagenesis BIOTECHNIQUES 3:12-19.
10. Smith M, Gillam S. 1981. Constructed Mutants Using Synthetic Oligodeoxyribonucleotides as Site-Specific Mutagens, p 1-32. In Setlow J K, Hollaender A (ed), Genetic Engineering: Principles and Methods Volume 3 doi:10.1007/978-1-4615-7075-2_1. Springer U S, Boston, Mass.
11. Mark D F, Lin L S, Lu S Y. May 21, 1985 1985. Human recombinant interleukin-2 muteins.
12. Mark D F, Lin L S, Lu S D Y. 1988. Structural genes, plasmids and transformed cells for producing cysteine depleted muteins of interferon-β U.S. Pat. No. 4,737,462
13. Nothaft H, Scott N E, Vinogradov E, Liu X, Hu R, Beadle B, Fodor C, Miller W G, Li J, Cordwell S J, Szymanski C M. 2012. Diversity in the protein N-glycosylation pathways within the *Campylobacter* genus. Mol Cell Proteomics 11:1203-1219.
14. Szymanski C M, Michael F S, Jarrell H C, Li J, Gilbert M, Larocque S, Vinogradov E, Brisson J R. 2003. Detection of conserved N-linked glycans and phase-variable lipooligosaccharides and capsules from *campylobacter* cells by mass spectrometry and high resolution magic angle spinning NMR spectroscopy. J Biol Chem 278: 24509-24520.
15. Wacker M, Linton D, Hitchen P G, Nita-Lazar M, Haslam S M, North S J, Panico M, Morris H R, Dell A, Wren B W, Aebi M. 2002. N-linked glycosylation in *Campylobacter jejuni* and its functional transfer into *E. coli*. Science 298:1790-1793.
16. Elhenawy W, Bording-Jorgensen M, Valguarnera E, Haurat M F, Wine E, Feldman M F. 2016. LPS Remodeling Triggers Formation of Outer Membrane Vesicles in *Salmonella*. MBio 7:e00940-00916.
17. Man S M, Hopkins L J, Nugent E, Cox S, Gluck I M, Tourlomousis P, Wright J A, *Cicuta* P, Monie T P, Bryant C E. 2014. Inflammasome activation causes dual recruitment of NLRC4 and NLRP3 to the same macromolecular complex. Proc Natl Acad Sci USA 111:7403-7408.
18. Collins L V, Attridge S, Hackett J. 1991. Mutations at rfc or pmi attenuate *Salmonella typhimurium* virulence for mice. Infect Immun 59:1079-1085.
19. Curtiss R, Ill., Zhang X, Wanda S Y, Kang H Y, Konjufca V, Li Y, Gunn B, Wang S, Scarpellini G, Lee I S. 2007. Induction of host immune responses using *Salmonella*-vectored vaccines, p 297-313. In Brogden K A, Minion F C, Cornick N, Stanton T B, Zhang Q, Nolan L K, Wannemuehler M J (ed), Virulence mechanisms of bacterial pathogens, 4th ed. ASM Press, Washington D.C.
20. Cascales E, Buchanan S K, Duche D, Kleanthous C, Lloubes R, Postle K, Riley M, Slatin S, Cavard D. 2007. Colicin biology. Microbiol Mol Biol Rev 71:158-229.
21. Adak G K, Meakins S M, Yip H, Lopman B A, O'Brien S J. 2005. Disease risks from foods, England and Wales, 1996-2000. Emerg Infect Dis 11:365-372.
22. Allos B M, Moore M R, Griffin P M, Tauxe R V. 2004. Surveillance for sporadic foodborne disease in the 21st century: the FoodNet perspective. Clin Infect Dis 38 Suppl 3:S115-120.
23. Mead P S, Slutsker L, Dietz V, McCaig L F, Bresee J S, Shapiro C, Griffin P M, Tauxe R V. 1999. Food-related illness and death in the United States. Emerg Infect Dis 5:607-625.
24. Scallan E, Hoekstra R M, Angulo F J, Tauxe R V, Widdowson M A, Roy S L, Jones J L, Griffin P M. 2011. Foodborne illness acquired in the United States—major pathogens. Emerg Infect Dis 17:7-15.
25. Nachamkin I, Allos B M, Ho T. 1998. *Campylobacter* species and Guillain-Barre syndrome. Clin Microbiol Rev 11:555-567.
26. Doorduyn Y, Van Den Brandhof W E, Van Duynhoven Y T, Breukink B J, Wagenaar J A, Van Pelt W. 2010. Risk factors for indigenous *Campylobacter jejuni* and *Campylobacter coli* infections in The Netherlands: a case-control study. Epidemiol Infect 138:1391-1404.
27. Ge B, Girard W, Zhao S, Friedman S, Gaines S A, Meng J. 2006. Genotyping of *Campylobacter* spp. from retail meats by pulsed-field gel electrophoresis and ribotyping. J Appl Microbiol 100:175-184.
28. Mullner P, Collins-Emerson J M, Midwinter A C, Carter P, Spencer S E, van der Logt P, Hathaway S, French N P. 2010. Molecular epidemiology of *Campylobacter jejuni* in a geographically isolated country with a uniquely structured poultry industry. Appl Environ Microbiol 76:2145-2154.
29. Mullner P, Shadbolt T, Collins-Emerson J M, Midwinter A C, Spencer S E, Marshall J, Carter P E, Campbell D M, Wilson D J, Hathaway S, Pirie R, French N P. 2010. Molecular and spatial epidemiology of human campylobacteriosis: source association and genotype-related risk factors. Epidemiol Infect 138:1372-1383.
30. Wilson D J, Gabriel E, Leatherbarrow A J, Cheesbrough J, Gee S, Bolton E, Fox A, Fearnhead P, Hart C A, Diggle P J. 2008. Tracing the source of campylobacteriosis. PLoS Genet 4:e1000203.
31. Friedman C R, Hoekstra R M, Samuel M, Marcus R, Bender J, Shiferaw B, Reddy S, Ahuja S D, Helfrick D L, Hardnett F, Carter M, Anderson B, Tauxe R V, Emerging Infections Program FoodNet Working G. 2004. Risk factors for sporadic *Campylobacter* infection in the United States: A case-control study in FoodNet sites. Clin Infect Dis 38 Suppl 3:S285-296.
32. Friedman C R, Niemann J, Wegener H C, Tauxe R V. 2000. Epidemiology of *Campylobacter jejuni* infections in the United States and other industrialized nations, p 121-138. In Nachamkin I, Blaser M J (ed), *Campylobacter*, 2nd ed. ASM Press, Washington, D.C.
33. Guerin M T, Sir C, Sargeant J M, Waddell L, O'Connor A M, Wills R W, Bailey R H, Byrd J A. 2010. The change in prevalence of *Campylobacter* on chicken carcasses during processing: a systematic review. Poult Sci 89:1070-1084.
34. Strachan N J, Gormley F J, Rotariu O, Ogden I D, Miller G, Dunn G M, Sheppard S K, Dallas J F, Reid T $_M$, Howie H, Maiden M C, Forbes K J. 2009. Attribution of *Campylobacter* infections in northeast Scotland to specific sources by use of multilocus sequence typing. J Infect Dis 199:1205-1208.
35. Corry J E, Atabay H I. 2001. Poultry as a source of *Campylobacter* and related organisms. Symp Ser Soc Appl Microbiol:96S-1145.
36. Sahin O, Kobalka P, Zhang Q. 2003. Detection and survival of *Campylobacter* in chicken eggs. J Appl Microbiol 95:1070-1079.
37. Shane S M. 1992. The significance of *Campylobacter jejuni* infection in poultry: a review. Avian Pathol 21:189-213.
38. Newell D G, Fearnley C. 2003. Sources of *Campylobacter* colonization in broiler chickens. Appl Environ Microbiol 69:4343-4351.
39. Zhang Q, P. P. 2008. Mechanisms of antibiotic resistance in *Campylobacter*, p 263-276. In Nachamkin I, Szymanski C M, Blaser M J (ed), *Campylobacter* vol III. ASM Press; Washington D.C., USA.
40. Stern N J, Fedorka-Cray P, Bailey J S, Cox N A, Craven S E, Hiett K L, Musgrove M T, Ladely S, Cosby D, Mead G C. 2001. Distribution of Campylobacterspp. in selected U.S. poultry production and processing operations. J Food Prot 64:1705-1710.
41. Luangtongkum T, Morishita T Y, Ison A J, Huang S, McDermott P F, Zhang Q. 2006. Effect of conventional and organic production practices on the prevalence and antimicrobial resistance of *Campylobacter* spp. in poultry. Appl Environ Microbiol 72:3600-3607.
42. Food Standards Agency U K. 2008. A critical review of interventions and strategies (both biosecurity and non-biosecurity) to reduce *Campylobacter* on the poultry farm. B15025
43. Gregory E, Barnhart H, Dreesen D W, Stern N J, Corn J L. 1997. Epidemiological study of *Campylobacter* spp. in broilers: source, time of colonization, and prevalence. Avian Dis 41:890-898.
44. Cardinale E, Tall F, Gueye E F, Cisse M, Salvat G. 2004. Risk factors for *Campylobacter* spp. infection in Senegalese broiler-chicken flocks. Prev Vet Med 64:15-25.
45. Berndtson E, Danielsson-Tham M L, Engvall A. 1996. *Campylobacter* incidence on a chicken farm and the spread of *Campylobacter* during the slaughter process. Int J Food Microbiol 32:35-47.
46. Barrios P R, Reiersen J, Lowman R, Bisaillon J R, Michel P, Fridriksdottir V, Gunnarsson E, Stern N, Berke O, McEwen S, Martin W. 2006. Risk factors for *Campylobacter* spp. colonization in broiler flocks in Iceland. Prev Vet Med 74:264-278.
47. Stern N J, Pretanik S. 2006. Counts of *Campylobacter-*spp. on U.S. broiler carcasses. J Food Prot 69:1034-1039.
48. Wempe J M, Genigeorgis C A, Farver T B, Yusufu H I. 1983. Prevalence of *Campylobacter jejuni* in two California chicken processing plants. Appl Environ Microbiol 45:355-359.
49. Richardson L J, Cox N A, Bailey J S, Berrang M E, Cox J M, Buhr R J, Fedorka-Cray P J, Harrison M A. 2009. Evaluation of TECRA broth, Bolton broth, and direct plating for recovery of *Campylobacter* spp, from broiler carcass rinsates from commercial processing plants. J Food Prot 72:972-977.
50. Logue C M, Sherwood J S, Elijah L M, Olah P A, Dockter M R. 2003. The incidence of *Campylobacter* spp. on processed turkey from processing plants in the midwestern United States. J Appl Microbiol 95:234-241.
51. Hue O, Le Bouquin S, Laisney M J, Allain V, Lalande F, Petetin I, Rouxel S, Quesne S, Gloaguen P Y, Picherot M, Santolini J, Salvat G, Bougeard S, Chemaly M. 2010. Prevalence of and risk factors for *Campylobacter* spp. contamination of broiler chicken carcasses at the slaughterhouse. Food Microbiol 27:992-999.
52. EFSA. 2011. Annual report 2011.
53. Berrang M E, Bailey J S, Altekruse S F, Patel B, Shaw W K, Jr., Meinersmann R J, Fedorka-Cray P J. 2007. Prevalence and numbers of *Campylobacter* on broiler carcasses collected at rehang and postchill in 20 U.S. processing plants. J Food Prot 70:1556-1560.
54. Nannapaneni R, Story R, Wiggins K C, Johnson M G. 2005. Concurrent quantitation of total *campylobacter* and total ciprofloxacin-resistant *campylobacter* loads in rinses from retail raw chicken carcasses from 2001 to 2003 by direct plating at 42 degrees C. Appl Environ Microbiol 71:4510-4515.
55. Byrd J A, Sams A R, Hargis B M, Caldwell D J. 2011. Effect of selected modified atmosphere packaging on *Campylobacter* survival in raw poultry. Poult Sci 90:1324-1328.
56. Rosenquist H, Sommer H M, Nielsen N L, Christensen B B. 2006. The effect of slaughter operations on the contamination of chicken carcasses with thermotolerant *Campylobacter*. Int J Food Microbiol 108:226-232.
57. Jeon B, Muraoka W T, Zhang Q. 2010. Advances in *Campylobacter* biology and implications for biotechnological applications. Microb Biotechnol 3:242-258.
58. Hue O, Allain V, Laisney M J, Le Bouquin S, Lalande F, Petetin I, Rouxel S, Quesne S, Gloaguen P Y, Picherot M, Santolini J, Bougeard S, Salvat G, Chemaly M. 2011. *Campylobacter* contamination of broiler caeca and carcasses at the slaughterhouse and correlation with *Salmonella* contamination. Food Microbiol 28:862-868.
59. Berrang M E, Smith D P, Windham W R, Feldner P W. 2004. Effect of intestinal content contamination on broiler carcass *Campylobacter* counts. J Food Prot 67:235-238.
60. Allen V M, Bull S A, Corry J E, Domingue G, Jorgensen F, Frost J A, Whyte R, Gonzalez A, Elviss N, Humphrey T J. 2007. *Campylobacter* spp. contamination of chicken carcasses during processing in relation to flock colonisation. Int J Food Microbiol 113:54-61.
61. Andrews-Polymenis H L, Baumler A J, McCormick B A, Fang F C. 2010. Taming the elephant: *Salmonella* biology, pathogenesis, and prevention. Infect Immun 78:2356-2369.
62. Hoffmann S, Batz M B, Morris J G, Jr. 2012. Annual cost of illness and quality-adjusted life year losses in the United States due to 14 foodborne pathogens. J Food Prot 75:1292-1302.
63. Schleifer J H, Juven B J, Beard C W, Cox N A. 1984. The susceptibility of chicks to *Salmonella montevideo* in artificially contaminated poultry feed. Avian Dis 28:497-503.
64. Williams J E, Benson S T. 1978. Survival of *Salmonella typhimurium* in poultry feed and litter at three temperatures. Avian Dis 22:742-747.
65. CDC. 1997. *Salmonella* serotype Montevideo infections associated with chicks—Idaho, Washington, and Oregon, spring 1995 and 1996. MMWR Morb Mortal Wkly Rep 46:237-239.
66. Batz M B, Doyle M P, Morris G, Jr., Painter J, Singh R, Tauxe R V, Taylor M R, Lo Fo Wong D M, Food Attribution Working G. 2005. Attributing illness to food. Emerg Infect Dis 11:993-999.
67. Morris Jr J G, Hoffmann S, Batz B. 2011. Ranking the Risks: The 10 Pathogen-Food Combinations With the Greatest Burden on Public Health.
68. Batz M B, Hoffmann S, Morris Jr J G. 2012. Ranking the disease burden of 14 pathogens in food sources in the United States using attribution data from outbreak investigations and expert elicitation. Journal of Food Protection 75:1278-1291.
69. CDC. 2009. Multistate outbreaks of *Salmonella* infections associated with live poultry—United States, 2007. MMWR Morb Mortal Wkly Rep 58:25-29.
70. CDC. 2007. Three outbreaks of *salmonellosis* associated with baby poultry from three hatcheries—United States, 2006. MMWR Morb Mortal Wkly Rep 56:273-276.
71. Altekruse S F, Bauer N, Chanlongbutra A, DeSagun R, Naugle A, Schlosser W, Umholtz R, White P. 2006. *Salmonella enteritidis* in broiler chickens, United States, 2000-2005. Emerg Infect Dis 12:1848-1852.

72. Patrick M E, Adcock P M, Gomez T$_M$, Altekruse S F, Holland B H, Tauxe R V, Swerdlow D L. 2004. *Salmonella enteritidis* infections, United States, 1985-1999. Emerg Infect Dis 10:1-7.
73. Linam W M, Gerber M A. 2007. Changing epidemiology and prevention of *Salmonella* infections. Pediatr Infect Dis J 26:747-748.
74. CDC. 2014. Foodborne Diseases Active Surveillance Network (FoodNet): FoodNet Surveillance Report for 2012. (Final Report). U.S. Department of Health and Human Services, CDC., Atlanta, Ga.
75. CDC. 2016. National Enteric Disease Surveillance: *Salmonella* Annual Report, 2013. U.S. Department of Health and Human Services, CDC., Atlanta, Ga.
76. CDC. 2012. Foodborne Diseases Active Surveillance Network (FoodNet): FoodNet Surveillance Report for 2011 (Final Report). U.S. Department of Health and Human Services, CDC., Atlanta, Ga.:
77. Roy P, Dhillon A S, Lauerman L H, Schaberg D M, Bandli D, Johnson S. 2002. Results of *Salmonella* isolation from poultry products, poultry, poultry environment, and other characteristics. Avian Dis 46:17-24.
78. Kuehn B M. 2010. *Salmonella* cases traced to egg producers: findings trigger recall of more than 500 million eggs. JAMA 304:1316.
79. Hennessy T W, Cheng L H, Kassenborg H, Ahuja S D, Mohle-Boetani J, Marcus R, Shiferaw B, Angulo F J, Emerging Infections Program FoodNet Working G. 2004. Egg consumption is the principal risk factor for sporadic *Salmonella* serotype Heidelberg infections: a case-control study in FoodNet sites. Clin Infect Dis 38 Suppl 3:S237-243.
80. Elson R, Little C L, Mitchell R T. 2005. *Salmonella* and raw shell eggs: results of a cross-sectional study of contamination rates and egg safety practices in the United Kingdom catering sector in 2003. J Food Prot 68:256-264.
81. Hennessy T W, Hedberg C W, Slutsker L, White K E, Besser-Wiek J M, Moen M E, Feldman J, Coleman W W, Edmonson L M, MacDonald K L, Osterholm M T. 1996. A national outbreak of *Salmonella enteritidis* infections from ice cream. The Investigation Team. N Engl J Med 334:1281-1286.
82. Han J, David D E, Deck J, Lynne A M, Kaldhone P, Nayak R, Stefanova R, Foley S L. 2011. Comparison of *Salmonella enterica* serovar Heidelberg isolates from human patients with those from animal and food sources. J Clin Microbiol 49:1130-1133.
83. Le Hello S, Hendriksen R S, Doublet B, Fisher I, Nielsen E M, Whichard J M, Bouchrif B, Fashae K, Granier S A, Jourdan-Da Silva N, Cloeckaert A, Threlfall E J, Angulo F J, Aarestrup F M, Wain J, Weill F X. 2011. International spread of an epidemic population of *Salmonella enterica* serotype Kentucky ST198 resistant to ciprofloxacin. J Infect Dis 204:675-684.
84. Ladely S R, Meinersmann R J, Ball T A, Fedorka-Cray P J. 2016. Antimicrobial Susceptibility and Plasmid Replicon Typing of *Salmonella enterica* Serovar Kentucky Isolates Recovered from Broilers. Foodborne Pathog Dis 13:309-315.
85. Jones D R, Guard J, Gast R K, Buhr R J, Fedorka-Cray P J, Abdo Z, Plumblee J R, Bourassa D V, Cox N A, Rigsby L L, Robison C I, Regmi P, Karcher D M. 2016. Influence of commercial laying hen housing systems on the incidence and identification of *Salmonella* and *Campylobacter*. Poult Sci 95:1116-1124.
86. Bailar J C, 3rd, Travers K. 2002. Review of assessments of the human health risk associated with the use of antimicrobial agents in agriculture. Clin Infect Dis 34 Suppl 3:S135-143.
87. Cohen M L, Tauxe R V. 1986. Drug-resistant *Salmonella* in the United States: an epidemiologic perspective. Science 234:964-969.
88. Kumarasamy K K, Toleman M A, Walsh T R, Bagaria J, Butt F, Balakrishnan R, Chaudhary U, Doumith M, Giske C G, Irfan S, Krishnan P, Kumar A V, Maharjan S, Mushtaq S, Noorie T, Paterson D L, Pearson A, Perry C, Pike R, Rao B, Ray U, Sarma J B, Sharma M, Sheridan E, Thirunarayan M A, Turton J, Upadhyay S, Warner M, Welfare W, Livermore D M, Woodford N. 2010. Emergence of a new antibiotic resistance mechanism in India, Pakistan, and the UK: a molecular, biological, and epidemiological study. Lancet Infect Dis 10:597-602.
89. Bebell L M, Muiru A N. 2014. Antibiotic use and emerging resistance: how can resource-limited countries turn the tide? Glob Heart 9:347-358.
90. Founou L L, Founou R C, Essack S Y. 2016. Antibiotic Resistance in the Food Chain: A Developing Country-Perspective. Front Microbiol 7:1881.
91. Founou R C, Founou L L, Essack S Y. 2017. Clinical and economic impact of antibiotic resistance in developing countries: A systematic review and meta-analysis. PLoS One 12:e0189621.
92. Prestinaci F, Pezzotti P, Pantosti A. 2015. Antimicrobial resistance: a global multifaceted phenomenon. Pathog Glob Health 109:309-318.
93. O'Brien T F. 1997. The global epidemic nature of antimicrobial resistance and the need to monitor and manage it locally. Clin Infect Dis 24 Suppl 1:S2-8.
94. Centres for Disease Control and Prevention UDoHaHS. 2013. Antibiotic resistance threats in the United States. https://www.cdc.gov/drugresistance/pdf/ar-threats-2013-508.pdf. Accessed
95. Organization WH. 2001. WHO global strategy for containment of antimicrobial resistance. Accessed
96. Organization WH. 2012. The evolving threat of antimicrobial resistance. Options for action. Accessed
97. Organization WH. 2014. Antimicrobial resistance: global report on surveillance 2014. Accessed
98. Casewell M, Friis C, Marco E, McMullin P, Phillips I. 2003. The European ban on growth-promoting antibiotics and emerging consequences for human and animal health. J Antimicrob Chemother 52:159-161.
99. Lin J. 2009. Novel approaches for *Campylobacter* control in poultry. Foodborne Pathog Dis 6:755-765.
100. Hermans D, Van Deun K, Messens W, Martel A, Van Immerseel F, Haesebrouck F, Rasschaert G, Heyndrickx M, Pasmans F. 2011. *Campylobacter* control in poultry by current intervention measures ineffective: urgent need for intensified fundamental research. Vet Microbiol 152:219-228.
101. Doyle M P, Erickson M C. 2006. Reducing the carriage of foodborne pathogens in livestock and poultry. Poult Sci 85:960-973.
102. Ridley A M, Morris V K, Cawthraw S A, Ellis-Iversen J, Harris J A, Kennedy E M, Newell D G, Allen V M. 2011. Longitudinal molecular epidemiological study of thermophilic campylobacters on one conventional broiler chicken farm. Appl Environ Microbiol 77:98-107.
103. Ridley A, Morris V, Gittins J, Cawthraw S, Harris J, Edge S, Allen V. 2011. Potential sources of *Campylobacter* infection on chicken farms: contamination and 103. control of broiler-harvesting equipment, vehicles and personnel. J Appl Microbiol 111:233-244.
104. Arsenault J, Letellier A, Quessy S, Normand V, Boulianne M. 2007. Prevalence and risk factors for *Salmonella* spp. and *Campylobacter* spp. caecal colonization in broiler chicken and turkey flocks slaughtered in Quebec, Canada. Prev Vet Med 81:250-264.
105. Nather G, Alter T, Martin A, Ellerbroek L. 2009. Analysis of risk factors for *Campylobacter* species infection in broiler flocks. Poult Sci 88:1299-1305.
106. Hermans D, Van Deun K, Martel A, Van Immerseel F, Messens W, Heyndrickx M, Haesebrouck F, Pasmans F. 2011. Colonization factors of *Campylobacter jejuni* in the chicken gut. Vet Res 42:82.
107. Layton S L, Morgan M J, Cole K, Kwon Y M, Donoghue D J, Hargis B M, Pumford N R. 2011. Evaluation of *Salmonella*-vectored *Campylobacter* peptide epitopes for reduction of *Campylobacter jejuni* in broiler chickens. Clin Vaccine Immunol 18:449-454.
108. Buckley A M, Wang J, Hudson D L, Grant A J, Jones M A, Maskell D J, Stevens M P. 2010. Evaluation of live-attenuated *Salmonella* vaccines expressing *Campylobacter* antigens for control of *C. jejuni* in poultry. Vaccine 28:1094-1105.
109. Cawthraw S, Ayling R, Nuijten P, Wassenaar T, Newell D G. 1994. Isotype, specificity, and kinetics of systemic and mucosal antibodies to *Campylobacter jejuni* antigens, including flagellin, during experimental oral infections of chickens. Avian Dis 38:341-349.
110. Myszewski M A, Stern N J. 1990. Influence of *Campylobacter jejuni* cecal colonization on immunoglobulin response in chickens. Avian Dis 34:588-594.
111. Noor S M, Husband A J, Widders P R. 1995. In ovo oral vaccination with *Campylobacter jejuni* establishes early development of intestinal immunity in chickens. Br Poult Sci 36:563-573.
112. Sahin O, Zhang Q, Meitzler J C, Harr B S, Morishita T Y, Mohan R. 2001. Prevalence, antigenic specificity, and bactericidal activity of poultry anti-*Campylobacter* maternal antibodies. Appl Environ Microbiol 67:3951-3957.
113. Hassan J O, Curtiss R, III. 1994. Development and evaluation of an experimental vaccination program using a live avirulent *Salmonella typhimurium* strain to protect immunized chickens against challenge with homologous and heterologous *Salmonella* serotypes. Infect Immun 62:5519-5527.
114. Dorea F C, Cole D J, Hofacre C, Zamperini K, Mathis D, Doyle M P, Lee M D, Maurer J J. 2010. Effect of *Salmonella* vaccination of breeder chickens on contamination of broiler chicken carcasses in integrated poultry operations. Appl Environ Microbiol 76:7820-7825.
115. Gantois I, Ducatelle R, Timbermont L, Boyen F, Bohez L, Haesebrouck F, Pasmans F, van Immerseel F. 2006. Oral immunisation of laying hens with the live vaccine strains of TAD *Salmonella* Vac® E and TAD *Salmonella* Vac® T reduces internal egg contamination with *Salmonella Enteritidis*. Vaccine 24:6250-6255.
116. Cooper G L, Venables L M, Woodward M J, Hormaeche C E. 1994. Vaccination of chickens with strain CVL30, a genetically defined *Salmonella enteritidis* aroA live oral vaccine candidate. Infect Immun 62:4747-4754.
117. Cerquetti M C, Gherardi M M. 2000. Vaccination of chickens with a temperature-sensitive mutant of *Salmonella enteritidis*. Vaccine 18:1140-1145.
118. Springer S, Lindner T, Ahrens M, Woitow G, Prandini F, Selbitz H J. 2011. Duration of immunity induced in chickens by an attenuated live *Salmonella enteritidis* vaccine and an inactivated *Salmonella enteritidis/typhimurium* vaccine. Berl Munch Tierarztl Wochenschr 124:89-93.
119. Methner U, Barrow P A, Berndt A, Rychlik I. 2011. *Salmonella Enteritidis* with double deletion in phoP-fliC—a potential live *Salmonella* vaccine candidate with novel characteristics for use in chickens. Vaccine 29:3248-3253.
120. Nandre R M, Matsuda K, Chaudhari A A, Kim B, Lee J H. 2012. A genetically engineered derivative of *Salmonella Enteritidis* as a novel live vaccine candidate for salmonellosis in chickens. Res Vet Sci 93:596-603.
121. Matulova M, Havlickova H, Sisak F, Rychlik I. 2012. Vaccination of chickens with *Salmonella* Pathogenicity Island (SPI) 1 and SPI2 defective mutants of *Salmonella enterica* serovar *Enteritidis*. Vaccine 30:2090-2097.
122. Tan S, Gyles C L, Wilkie B N. 1997. Evaluation of an aroA mutant *Salmonella typhimurium* vaccine in chickens using modified semisolid Rappaport Vassiliadis medium to monitor faecal shedding. Vet Microbiol 54:247-254.
123. Barrow P A. 2007. *Salmonella* infections: immune and non-immune protection with vaccines. Avian Pathol 36:1-13.
124. Gast R K. 2007. Serotype-specific and serotype-independent strategies for preharvest control of food-borne *Salmonella* in poultry. Avian Dis 51:817-828.
125. Desin T S, Koster W, Potter A A. 2013. *Salmonella* vaccines in poultry: past, present and future. Expert Rev Vaccines 12:87-96.
126. Kaniuk N A, Monteiro M A, Parker C T, Whitfield C. 2002. Molecular diversity of the genetic loci responsible for lipopolysaccharide core oligosaccharide assembly within the genus *Salmonella*. Mol Microbiol 46:1305-1318.
127. Malik M, Butchaiah G, Bansal M P, Siddiqui M Z, Bakshi C S, Singh R K. 2002. Antigenic relationships within the genus *Salmonella* as revealed by anti-*Salmonella enteritidis* monoclonal antibodies. Vet Res Commun 26:179-188.
128. Earhart C F. 1996. Uptake and metabolism of iron and molybdenum, p 1075-1090. In Neidhardt F C, Curtiss I I I R, Ingraham J L, Lin E C C, Low K B, Magasanik B, Reznikoff W S, Riley M, Schaechter M, Umbarger H E (ed), *Escherichia coli* and *Salmonella* Cellular and Molecular Biology, 2nd ed, vol 1. ASM Press, Washington, D.C.
129. Curtiss R, III., Wanda S Y, Gunn B M, Zhang X, Tinge S A, Ananthnarayan V, Mo H, Wang S, Kong W. 2009. *Salmonella enterica* serovar *Typhimurium* strains with regulated delayed attenuation in vivo. Infect Immun 77:1071-1082.
130. Bolin C A, Jensen A E. 1987. Passive immunization with antibodies against iron-regulated outer membrane proteins protects turkeys from *Escherichia coli* septicemia. Infect Immun 55:1239-1242.
131. Lin J, Hogan J S, Smith K L. 1999. Antigenic homology of the inducible ferric citrate receptor (FecA) of coliform bacteria isolated from herds with naturally occurring bovine intramammary infections. Clin Diagn Lab Immunol 6:966-969.
132. Wilmes-Riesenberg M R, Bearson B, Foster J W, Curtiss I I I R. 1996. Role of the acid tolerance response in virulence of *Salmonella typhimurium*. Infect Immun 64:1085-1092.
133. Łaniewski P, Mitra A, Karaca K, Khan A, Prasad R, Curtiss R, III, Roland K L. 2014. Evaluation of protective efficacy of live attenuated *Salmonella enterica* serovar *Gallinarum* vaccine strains against fowl typhoid in chickens. Clin Vaccine Immunol 21:1267-1276.

134. Li Y, Wang S, Scarpellini G, Gunn B, Xin W, Wanda S Y, Roland K L, Curtiss R, III. 2009. Evaluation of new generation *Salmonella enterica* serovar *Typhimurium* vaccines with regulated delayed attenuation to induce immune responses against PspA. Proc Natl Acad Sci USA 106:593-598.

135. Shi H, Santander J, Brenneman K E, Wanda S Y, Wang S, Senechal P, Sun W, Roland K L, Curtiss R, III. 2010. Live recombinant *Salmonella Typhi* vaccines constructed to investigate the role of rpoS in eliciting immunity to a heterologous antigen. PLoS One 5:e11142.

136. Shi H, Wang S, Curtiss R, III. 2013. Evaluation of regulated delayed attenuation strategies for *Salmonella enterica* serovar *Typhi* vaccine vectors in neonatal and infant mice. Clin Vaccine Immunol 20:931-944.

137. Wang S, Li Y, Scarpellini G, Kong W, Shi H, Baek C H, Gunn B, Wanda S Y, Roland K L, Zhang X, Senechal-Willis P, Curtiss R, III. 2010. *Salmonella* vaccine vectors displaying delayed antigen synthesis in vivo to enhance immunogenicity. Infect Immun 78:3969-3980.

138. Wang S, Li Y, Shi H, Sun W, Roland K L, Curtiss R, III. 2011. Comparison of a regulated delayed antigen synthesis system with in vivo-inducible promoters for antigen delivery by live attenuated *Salmonella* vaccines. Infect Immun 79:937-949.

139. Xin W, Wanda S Y, Li Y, Wang S, Mo H, Curtiss R, III. 2008. Analysis of type II secretion of recombinant pneumococcal PspA and PspC in a *Salmonella enterica* serovar *Typhimurium* vaccine with regulated delayed antigen synthesis. Infect Immun 76:3241-3254.

140. Juarez-Rodriguez M D, Yang J, Kader R, Alamuri P, Curtiss R, Ill, Clark-Curtiss J E. 2012. Live attenuated *Salmonella* vaccines displaying regulated delayed lysis and delayed antigen synthesis to confer protection against *Mycobacterium tuberculosis*. Infect Immun 80:815-831.

141. Kong W, Brovold M, Koeneman B A, Clark-Curtiss J, Curtiss R, III. 2012. Turning self-destructing *Salmonella* into a universal DNA vaccine delivery platform. Proc Natl Acad Sci USA 109:19414-19419.

142. Kong W, Wanda S Y, Zhang X, Bollen W, Tinge S A, Roland K L, Curtiss R, III. 2008. Regulated programmed lysis of recombinant *Salmonella* in host tissues to release protective antigens and confer biological containment. Proc Natl Acad Sci USA 105:9361-9366.

143. Germanier R, Furer E. 1971. Immunity in experimental *salmonellosis*. II. Basis for the avirulence and protective capacity of gal E mutants of *Salmonella typhimurium*. Infect Immun 4:663-673.

144. Kong Q, Liu Q, Roland K L, Curtiss R, III. 2009. Regulated delayed expression of rfaH in an attenuated *Salmonella enterica* serovar *Typhimurium* vaccine enhances immunogenicity of outer membrane proteins and a heterologous antigen. Infect Immun 77:5572-5582.

145. Li Y, Wang S, Xin W, Scarpellini G, Shi Z, Gunn B, Roland K L, Curtiss R, III. 2008. A sopB deletion mutation enhances the immunogenicity and protective efficacy of a heterologous antigen delivered by live attenuated *Salmonella enterica* vaccines. Infect Immun 76:5238-5246.

146. Gunn B M, Wanda S Y, Burshell D, Wang C, Curtiss R, III. 2010. Construction of recombinant attenuated *Salmonella enterica* serovar *Typhimurium* vaccine vector strains for safety in newborn and infant mice. Clin Vaccine Immunol 17:354-362.

147. Shi H, Wang S, Roland K L, Gunn B M, Curtiss R, III. 2010. Immunogenicity of a live recombinant *Salmonella enterica* serovar *Typhimurium* vaccine expressing pspA in neonates and infant mice born from naive and immunized mothers. Clin Vaccine Immunol 17:363-371.

148. Hassan J O, Curtiss R, III. 1996. Effect of vaccination of hens with an avirulent strain of *Salmonella typhimurium* on immunity of progeny challenged with wild-type *Salmonella* strains. Infection and Immunity 64:938-944.

149. Juarez-Rodriguez M D, Arteaga-Cortes L T, Kader R, Curtiss R, III, Clark-Curtiss J E. 2012. Live attenuated *Salmonella* vaccines against *Mycobacterium tuberculosis* with antigen delivery via the type III secretion system. Infect Immun 80:798-814.

150. Frey S E, Lottenbach K R, Hill H, Blevins T P, Yu Y, Zhang Y, Brenneman K E, Kelly-Aehle S M, McDonald C, Jansen A, Curtiss R, III. 2013. A Phase I, dose-escalation trial in adults of three recombinant attenuated *Salmonella Typhi* vaccine vectors producing *Streptococcus pneumoniae* surface protein antigen PspA. Vaccine 31:4874-4880.

151. Konjufca V, Jenkins M, Wang S, Juarez-Rodriguez M D, Curtiss R, Ill. 2008. Immunogenicity of recombinant attenuated *Salmonella enterica* serovar *Typhimurium* vaccine strains carrying a gene that encodes *Eimeria tenella* antigen SO7. Infect Immun 76:5745-5753.

152. Konjufca V, Wanda S Y, Jenkins M C, Curtiss R, III. 2006. A recombinant attenuated *Salmonella enterica* serovar *Typhimurium* vaccine encoding *Eimeria acervulina* antigen offers protection against *E. acervulina* challenge. Infect Immun 74:6785-6796.

153. Zekarias B, Mo H, Curtiss R, III. 2008. Recombinant attenuated *Salmonella enterica* serovar typhimurium expressing the carboxy-terminal domain of alpha toxin from *Clostridium perfringens* induces protective responses against necrotic enteritis in chickens. Clin Vaccine Immunol 15:805-816.

154. Jiang Y, Mo H, Willingham C, Wang S, Park J Y, Kong W, Roland K L, Curtiss R, III. 2015. Protection Against Necrotic Enteritis in Broiler Chickens by Regulated Delayed Lysis *Salmonella* Vaccines. Avian Dis 59:475-485.

155. Ashraf S, Kong W, Wang S, Yang J, Curtiss R, III. 2011. Protective cellular responses elicited by vaccination with influenza nucleoprotein delivered by a live recombinant attenuated *Salmonella* vaccine. Vaccine 29:3990-4002.

156. Ameiss K, Ashraf S, Kong W, Pekosz A, Wu W H, Milich D, Billaud J N, Curtiss R, III. 2010. Delivery of woodchuck hepatitis virus-like particle presented influenza M2e by recombinant attenuated *Salmonella* displaying a delayed lysis phenotype. Vaccine 28:6704-6713.

157. Nakayama K, Kelly S M, Curtiss R, III 1988. Construction of an Asd+ expression-cloning Vector: stable maintenance and high level expression of cloned genes in a *Salmonella* vaccine strain. Nat Biotech 6:693-697.

158. Branger C G, Sun W, Torres-Escobar A, Perry R, Roland K L, Fetherston J, Curtiss R, III. 2010. Evaluation of Psn, HmuR and a modified LcrV protein delivered to mice by live attenuated *Salmonella* as a vaccine against bubonic and pneumonic *Yersinia pestis* challenge. Vaccine 29:274-282.

159. Kang H Y, Srinivasan J, Curtiss R, III. 2002. Immune responses to recombinant pneumococcal PspA antigen delivered by live attenuated *Salmonella enterica* serovar *Typhimurium* vaccine. Infect Immun 70:1739-1749.

160. Muralinath M, Kuehn M J, Roland K L, Curtiss R, III. 2011. Immunization with *Salmonella enterica* serovar 160. *Typhimurium*-derived outer membrane vesicles delivering the pneumococcal protein PspA confers protection against challenge with *Streptococcus pneumoniae*. Infect Immun 79:887-894.
161. Kaniuk N A, Vinogradov E, Whitfield C. 2004. Investigation of the structural requirements in the lipopolysaccharide core acceptor for ligation of 0 antigens in the genus *Salmonella*: WaaL "ligase" is not the sole determinant of acceptor specificity. J Biol Chem 279:36470-36480.
162. Curtiss R, III, Wanda S Y, Gunn B M, Zhang X, Tinge S A, Ananthnarayan V, Mo H, Wang S, Kong W. 2009. *Salmonella enterica* serovar *Typhimurium* strains with regulated delayed attenuation in vivo. Infect Immun 77:1071-1082.
163. Brosius J, Erfle M, Storella J. 1985. Spacing of the −10 and −35 regions in the tac promoter. Effect on its in vivo activity. J Biol Chem 260:3539-3541.
164. Pizarro-Cerda J, Tedin K. 2004. The bacterial signal molecule, ppGpp, regulates *Salmonella* virulence gene expression. Mol Microbiol 52:1827-1844.
165. Vander Byl C, Kropinski A M. 2000. Sequence of the genome of *Salmonella* bacteriophage P22. J Bacteriol 182:6472-6481.
166. Brown E D, Vivas El, Walsh C T, Kolter R. 1995. MurA (MurZ), the enzyme that catalyzes the first committed step in peptidoglycan biosynthesis, is essential in *Escherichia coli*. J Bacteriol 177:4194-4197.
167. Black S, Wright N G. 1955. Aspartic β-semialdehyde dehydrogenase and aspartic β-semialdehyde. J Biol Chem 213:39-50.
168. Stevenson G, Andrianopoulos K, Hobbs M, Reeves $P_R$. 1996. Organization of the *Escherichia coli* K-12 gene cluster responsible for production of the extracellular polysaccharide colanic acid. J Bacteriol 178:4885-4893.
169. Whitfield C. 2006. Biosynthesis and assembly of capsular polysaccharides in *Escherichia coli*. Annu Rev Biochem 75:39-68.
170. Beuzón C R, Méresse S, Unsworth K E, Ruiz-Albert J, Garvis S, Waterman S R, Ryder T A, Boucrot E, Holden D W. 2000. *Salmonella* maintains the integrity of its intracellular vacuole through the action of SifA. EMBO J 19:3235-3249.
171. Cohen A, Laban A. 1983. Plasmidic recombination in *Escherichia coli* K-12: the role of recF gene function. Mol Gen Genet 189:471-474.
172. Kolodner R, Fishel R A, Howard M. 1985. Genetic recombination of bacterial plasmid DNA: effect of RecF pathway mutations on plasmid recombination in *Escherichia coli*. J Bacteriol 163:1060-1066.
173. Zhang X, Wanda S Y, Brenneman K, Kong W, Roland K, Curtiss R, III. 2011. Improving *Salmonella* vector with rec mutation to stabilize the DNA cargoes. BMC Microbiol 11:31.
174. Link C, Ebensen T, Standner L, Dejosez M, Reinhard E, Rharbaoui F, Guzman C A. 2006. An SopB-mediated immune escape mechanism of *Salmonella enterica* can be subverted to optimize the performance of live attenuated vaccine carrier strains. Microbes Infect 8:2262-2269.
175. Norris F A, Wilson M P, Wallis T S, Galyov E E, Majerus P W. 1998. SopB, a protein required for virulence of *Salmonella dublin*, is an inositol phosphate phosphatase. Proc Natl Acad Sci USA 95:14057-14059.
176. Reis B P, Zhang S, Tsolis R M, Baumler A J, Adams L G, Santos R L. 2003. The attenuated sopB mutant of *Salmonella enterica* serovar *Typhimurium* has the same tissue distribution and host chemokine response as the wild type in bovine Peyer's patches. Vet Microbiol 97:269-277.
177. Singh S P, Williams Y U, Miller S, Nikaido H. 2003. The C-terminal domain of *Salmonella enterica* serovar *typhimurium* OmpA is an immunodominant antigen in mice but appears to be only partially exposed on the bacterial cell surface. Infect Immun 71:3937-3946.
178. Chart H, Rowe B. 1991. Antibodies to lipopolysaccharide and outer membrane proteins of *Salmonella enteritidis* PT4 are not involved in protection from experimental infection. FEMS Microbiol Lett 68:345-350.
179. Curtiss R, I I I., S. B. Porter, M. Munson, S. A. Tinge, J. O. Hassan, C. Gentry-Weeks, Kelly. SM. 1991. Non-recombinant and recombinant avirulent *Salmonella* live vaccines for poultry, p 169-198. In L. C. Blankenship, J. H. S. Bailey, N. A. Cox, Stern N J, Meinersmann R J (ed), Colonization control of human bacterial enteropathogens in poultry. Academic Press New York
180. Poppe C, Gyles C L. 1987. Relation of plasmids to virulence and other properties of salmonellae from avian sources. Avian Dis 31:844-854.
181. Black R E, Levine M M, Clements M L, Hughes T P, Blaser M J. 1988. Experimental *Campylobacter-Jejuni* Infection in Humans. Journal of Infectious Diseases 157:472-479.
182. Parkhill J, Wren B W, Mungall K, Ketley J M, Churcher C, Basham D, Chillingworth T, Davies R M, Feltwell T, Holroyd S, Jagels K, Karlyshev A V, Moule S, Pallen M J, Penn C W, Quail M A, Rajandream M A, Rutherford K M, van Vliet A H, Whitehead S, Barrell B G. 2000. The genome sequence of the food-borne pathogen *Campylobacter jejuni* reveals hypervariable sequences. Nature 403:665-668.
183. Pearson B M, Gaskin D J, Segers R P, Wells J M, Nuijten P J, van Vliet A H. 2007. The complete genome sequence of *Campylobacter jejuni* strain 81116 (NCTC11828). J Bacteriol 189:8402-8403.
184. Fouts D E, Mongodin E F, Mandrell R E, Miller W G, Rasko D A, Ravel J, Brinkac L M, DeBoy R T, Parker C T, Daugherty S C, Dodson R J, Durkin A S, Madupu R, Sullivan S A, Shetty J U, Ayodeji M A, Shvartsbeyn A, Schatz M C, Badger J H, Fraser C M, Nelson K E. 2005. Major structural differences and novel potential virulence mechanisms from the genomes of multiple *campylobacter* species. PLoS Biol 3:e15.
185. Parker C T, Quinones B, Miller W G, Horn S T, Mandrell R E. 2006. Comparative genomic analysis of *Campylobacter jejuni* strains reveals diversity due to genomic elements similar to those present in *C. jejuni* strain RM1221. J Clin Microbiol 44:4125-4135.
186. Issmat I. Kassem, Gbenga K, Kumar A, Chandrashekhar K, Pina-Mimbela R, Rajashekara G. 2014. An evaluation of the impact of litter chemical amendments on reducing *Campylobacter jejuni* in broilers, abstr Conference of research workers in animal disease (CRWAD), Chicago, Ill., December 6-8.
187. Zhang X, Kelly S M, Bollen W S, Curtiss R, III. 1997. Characterization and immunogenicity of *Salmonella typhimurium* SL1344 and UK-1 Δcrp and Δcdt deletion mutants. Infect Immun 65:5381-5387.
188. Kong Q, Liu Q, Jansen A, Curtiss R, III. 2010. Regulated delayed expression of rfc enhances the immunogenicity and protective efficacy of a heterologous antigen delivered by live attenuated *Salmonella enterica* vaccines. Vaccine 28:6094-6103.

189. Bertani G. 1951. Studies on lysogenesis. I. The mode of phage liberation by lysogenic *Escherichia coli*. J Bacteriol 62:293-300.
190. Pardee A B, Jacob F, Monod J. 1959. The genetic control and cytoplasmic expression of "Inducibility" in the synthesis of β-galactosidase by *E. coli*. Journal of Molecular Biology 1:165-178.
191. Sambrook J, Russell D W. 2001. Molecular cloning: a laboratory manual, 3rd ed. Cold Spring Harbor Laboratory Press, Cold Spring Harbor, N.Y.
192. Ehretsmann C P, Carpousis A J, Krisch H M. 1992. Specificity of *Escherichia coli* endoribonuclease RNase E: in vivo and in vitro analysis of mutants in a bacteriophage T4 mRNA processing site. Genes Dev 6:149-159.
193. McDowall K J, Kaberdin V R, Wu S W, Cohen S N, Lin-Chao S. 1995. Site-specific RNase E cleavage of oligonucleotides and inhibition by stem-loops. Nature 374:287-290.
194. Lin-Chao S, Wong T T, McDowall K J, Cohen S N. 1994. Effects of nucleotide sequence on the specificity of rne-dependent and RNase E-mediated cleavages of RNA I encoded by the pBR322 plasmid. J Biol Chem 269: 10797-10803.
195. Edwards R A, Keller L H, Schifferli D M. 1998. Improved allelic exchange vectors and their use to analyze 987P fimbria gene expression. Gene 207:149-157.
196. Kaniga K, Compton M S, Curtiss R, III., Sundaram P. 1998. Molecular and functional characterization of *Salmonella enterica* serovar *Typhimurium* poxA gene: effect on attenuation of virulence and protection. Infect Immun 66:5599-5606.
197. Maloy S R, and W. D. Nunn. 1981. Selection for loss of tetracycline resistance by *Escherichia coli*. J Bacteriol 145:1110-1112.
198. Miller V L, and J. J. Mekalanos. 1988. A novel suicide vector and its use in construction of insertion mutations: osmoregulation of outer membrane proteins and virulence determinants in *Vibrio cholerae* requires toxR. J Bacteriol 170:2575-2583.
199. Ried J, and A. Collmer. 1987. An nptl-sacB-sacR cartridge for constructing directed unmarked mutations in gram-negative bacteria by marker exchange-eviction mutagenesis. Gene 57:239-246.
200. Roland K, Curtiss R, III., Sizemore D. 1999. Construction and evaluation of a Δcya Δcrp *Salmonella typhimurium* strain expressing avian pathogenic *Escherichia coli* O78 LPS as a vaccine to prevent airsacculitis in chickens. Avian Dis 43:429-441.
201. Schmieger H. 1972. Phage P22-mutants with increased or decreased transduction abilities. Mol Gen Genet 119: 75-88.
202. Schmieger H, Backhaus H. 1976. Altered cotransduction frequencies exhibited by HT-mutants of Salmonella-phage P22. Mol Gen Genet 143:307-309.
203. Quandt J, Hynes M F. 1993. Versatile suicide vectors which allow direct selection for gene replacement in gram-negative bacteria. Gene 127:15-21.
204. Hitchcock P J, Brown $T_M$. 1983. Morphological heterogeneity among *Salmonella* lipopolysaccharide chemotypes in silver-stained polyacrylamide gels. J Bacteriol 154:269-277.
205. Kang H Y, Dozois C M, Tinge S A, Lee T H, Curtiss R, III. 2002. Transduction-mediated transfer of unmarked deletion and point mutations through use of counterselectable suicide vectors. J Bacteriol 184:307-312.
206. Young N M, Brisson J R, Kelly J, Watson D C, Tessier L, Lanthier P H, Jarrell H C, Cadotte N, St Michael F, Aberg E, Szymanski C M. 2002. Structure of the N-linked glycan present on multiple glycoproteins in the Gram-negative bacterium, *Campylobacter jejuni*. J Biol Chem 277:42530-42539.
207. Hobbs M, Reeves $P_R$. 1994. The JUMPstart sequence: a 39 bp element common to several polysaccharide gene clusters. Mol Microbiol 12:855-856.
208. Nieto J M, Bailey M J, Hughes C, Koronakis V. 1996. Suppression of transcription polarity in the *Escherichia coli* haemolysin operon by a short upstream element shared by polysaccharide and DNA transfer determinants. Mol Microbiol 19:705-713.
209. Nothaft H, Davis B, Lock Y Y, Perez-Munoz M E, Vinogradov E, Walter J, Coros C, Szymanski C M. 2016. Engineering the *Campylobacter jejuni* N-glycan to create an effective chicken vaccine. Sci Rep 6:26511.
210. Price N L, Goyette-Desjardins G, Nothaft H, Valguarnera E, Szymanski C M, Segura M, Feldman M F. 2016. Glycoengineered Outer Membrane Vesicles: A Novel Platform for Bacterial Vaccines. Sci Rep 6:24931.
211. Gangaiah D, Liu Z, Arcos J, Kassem, I I, Sanad Y, Torrelles J B, Rajashekara G. 2010. Polyphosphate kinase 2: a novel determinant of stress responses and pathogenesis in *Campylobacter jejuni*. PLoS One 5:e12142.
212. Annamalai T, Pina-Mimbela R, Kumar A, Binjawadagi B, Liu Z, Renukaradhya G J, Rajashekara G. 2013. Evaluation of nanoparticle-encapsulated outer membrane proteins for the control of *Campylobacter jejuni* colonization in chickens. Poult Sci 92:2201-2211.
213. Reusch R N. 2013. The role of short-chain conjugated poly-(R)-3-hydroxybutyrate (cPHB) in protein folding. Int J Mol Sci 14:10727-10748.
214. Pautsch A, Schulz G E. 1998. Structure of the outer membrane protein A transmembrane domain. Nat Struct Biol 5:1013-1017.
215. Vogel H, Jahnig F. 1986. Models for the structure of outer-membrane proteins of *Escherichia coli* derived from raman spectroscopy and prediction methods. J Mol Biol 190:191-199.

What is claimed is:

1. A recombinant derivative of a *Salmonella enterica* pathogenic bacterium comprising:
   (a) a regulated-delayed attenuation conferred by a Δpmi mutation;
   (b) a regulated-delayed expression of an antigen of interest conferred by a ΔrelA::araC $P_{BAD}$ lacI TT deletion-insertion mutation;
   (c) a regulated-delayed lysis in vivo phenotype conferred by a ΔP$_{murA}$::TT araC $P_{BAD}$ murA deletion-insertion mutation and a ΔasdA::TT araC $P_{BAD}$ c2 deletion-insertion mutation; and
   (d) a nucleic acid sequence encoding one or more protein antigens of *Eimeria*.

2. The bacterium of claim 1, wherein the one or more protein antigens of *Eimeria* is SO7.

3. The bacterium of claim 1, wherein the bacterium further comprises a ΔsifA mutation.

4. A pharmaceutical composition comprising the recombinant bacterium of claim 1, and a pharmaceutically acceptable carrier.

5. The pharmaceutical composition of claim 4, further comprising a second recombinant derivative of a pathogenic bacterium, wherein said bacterium comprises a nucleic acid encoding a second antigen of interest.

6. The pharmaceutical composition of claim 5, wherein the second antigen of interest is a *Salmonella* antigen.

7. A method for inducing protective immunity in an avian, the method comprising administering to the avian an effective amount of a pharmaceutical composition of claim 4.

8. The recombinant bacterium of claim 1, wherein the Δpmi mutation is Δpmi-2426.

9. The recombinant bacterium of claim 1, wherein the ΔrelA::araC $P_{BAD}$ lacI TT deletion-insertion mutation is ΔrelA197::araC $P_{BAD}$ lacI TT or ΔrelA198::araC $P_{BAD}$ lacI TT.

10. The recombinant bacterium of claim 1, wherein the ΔP$_{murA}$::TT araC $P_{BAD}$ murA deletion-insertion mutation is ΔP$_{murA25}$::TT araC $P_{BAD}$ murA.

11. The recombinant bacterium of claim 1, wherein the ΔasdA::TT araC $P_{BAD}$ c2 deletion-insertion mutation is ΔasdA27::TT araC $P_{BAD}$ c2.

12. The recombinant bacterium of claim 1, where in the bacterium comprises
   (a) Δpmi-2426, ΔP$_{murA25}$::TT araC $P_{BAD}$ murA, ΔasdA27::TT araC $P_{BAD}$ c2 and ΔrelA197::araC $P_{BAD}$ lacI TT;
   (b) Δpmi-2426, ΔP$_{murA25}$::TT araC $P_{BAD}$ murA, ΔasdA27::TT araC $P_{BAD}$ c2 and ΔrelA198::araC $P_{BAD}$ lacI TT;
   (c) Δpmi-2426, ΔP$_{murA25}$::TT araC $P_{BAD}$ murA, ΔasdA27::TT araC $P_{BAD}$ c2, ΔrelA197::araC $P_{BAD}$ lacI TT, and ΔsifA26; or
   (d) Δpmi-2426, ΔP$_{murA25}$::TT araC $P_{BAD}$ murA, ΔasdA27::TT araC $P_{BAD}$ c2, ΔrelA198::araC $P_{BAD}$ lacI TT, and ΔsifA26.

13. The recombinant bacterium of claim 3, wherein the ΔsifA mutation is ΔsifA26.

* * * * *